(12) United States Patent
Schreiber et al.

(10) Patent No.: US 10,927,159 B2
(45) Date of Patent: *Feb. 23, 2021

(54) TIGIT- AND LIGHT-BASED CHIMERIC PROTEINS

(71) Applicant: Shattuck Labs, Inc., Austin, TX (US)

(72) Inventors: Taylor Schreiber, Austin, TX (US); George Fromm, Austin, TX (US); Suresh De Silva, Austin, TX (US)

(73) Assignee: Shattuck Labs, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/017,108

(22) Filed: Sep. 10, 2020

(65) Prior Publication Data

US 2020/0399342 A1 Dec. 24, 2020

Related U.S. Application Data

(63) Continuation of application No. 16/857,787, filed on Apr. 24, 2020, which is a continuation of application No. 16/484,850, filed as application No. PCT/US2018/020037 on Feb. 27, 2018.

(60) Provisional application No. 62/464,002, filed on Feb. 27, 2017.

(51) Int. Cl.
| | |
|---|---|
| *C07K 14/705* | (2006.01) |
| *C07K 14/525* | (2006.01) |
| *A61K 38/17* | (2006.01) |
| *A61P 35/00* | (2006.01) |
| *A61K 38/00* | (2006.01) |

(52) U.S. Cl.
CPC .......... *C07K 14/705* (2013.01); *A61K 38/177* (2013.01); *A61K 38/1774* (2013.01); *A61K 38/1793* (2013.01); *A61P 35/00* (2018.01); *C07K 14/525* (2013.01); *C07K 14/70578* (2013.01); *C07K 14/70596* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,844,095 A | 12/1998 | Linsley et al. | |
| 7,569,663 B2 | 8/2009 | Tykocinski et al. | |
| 7,696,168 B2 | 4/2010 | Kuliopulos et al. | |
| 8,039,437 B2 | 10/2011 | Tykocinski et al. | |
| 8,080,246 B2 | 12/2011 | Lin et al. | |
| 8,263,081 B2 | 9/2012 | Fu | |
| 8,329,657 B2 | 12/2012 | Tykocinski et al. | |
| 8,450,460 B2 | 5/2013 | Hill et al. | |
| 8,921,519 B2 | 12/2014 | Hill et al. | |
| 9,029,315 B2 | 5/2015 | Chen et al. | |
| 9,061,073 B2 | 6/2015 | Fu | |
| 9,221,895 B2 | 12/2015 | Tykocinski | |
| 9,388,230 B2 | 7/2016 | Elhalel | |
| 9,623,116 B2 | 4/2017 | Fu | |
| 9,657,082 B2 | 5/2017 | Tykocinski | |
| 10,259,880 B2 | 4/2019 | Campbell et al. | |
| 2007/0036783 A1 | 2/2007 | Humeau et al. | |
| 2009/0226435 A1 | 9/2009 | Khare | |
| 2011/0041190 A1 | 2/2011 | Tykocinski et al. | |
| 2013/0039911 A1 | 2/2013 | Bedi et al. | |
| 2013/0065815 A1 | 3/2013 | Tykocinski et al. | |
| 2013/0243697 A1 | 9/2013 | Tykocinski et al. | |
| 2014/0154252 A1 | 6/2014 | Thompson et al. | |
| 2014/0227315 A1 | 8/2014 | Tykocinski et al. | |
| 2014/0242077 A1 | 8/2014 | Choi et al. | |
| 2014/0286858 A1 | 9/2014 | Zimmerman et al. | |
| 2015/0098942 A1 | 4/2015 | Curti et al. | |
| 2015/0139943 A1 | 5/2015 | Campana et al. | |
| 2015/0174268 A1 | 6/2015 | Li | |
| 2015/0183881 A1 | 7/2015 | Bedi et al. | |
| 2015/0190506 A1 | 7/2015 | Cheung et al. | |
| 2015/0191525 A1 | 7/2015 | Epstein et al. | |
| 2015/0353642 A1 | 12/2015 | Tykocinski | |
| 2015/0368350 A1 | 12/2015 | Tykocinski et al. | |
| 2015/0376260 A1 | 12/2015 | Elhalel et al. | |
| 2016/0024176 A1 | 1/2016 | Damschroder et al. | |
| 2016/0166685 A1 | 6/2016 | Cheung et al. | |
| 2016/0177276 A1 | 6/2016 | Lo et al. | |
| 2016/0340409 A1 | 11/2016 | Dranitzki-Elhalel | |
| 2016/0347846 A1 | 12/2016 | Tykocinski | |

FOREIGN PATENT DOCUMENTS

| | | |
|---|---|---|
| WO | WO 01/49318 A1 | 7/2001 |
| WO | WO 2010/003118 A1 | 1/2010 |
| WO | WO 2010/005519 A1 | 1/2010 |
| WO | WO 2010/105068 A1 | 9/2010 |
| WO | WO 2012/042480 A1 | 4/2012 |
| WO | WO 2013/019615 A2 | 2/2013 |
| WO | WO 2013/164694 A1 | 11/2013 |

(Continued)

OTHER PUBLICATIONS

Stanietsky et al. (Eur. J. Innnnunol., 43(8): 2138-2150, 2013).*
Del Rio et al. (Transplantation, 98(11): 1165-1174, 2014).*
Anderson, et al., "Lag-3, Tim-3, and TIGIT: Co-Inhibitory Receptors with Specialized Functions in Immune Regulation," Immunity vol. 44, 2016, pp. 989-1004.
Bartkowiak, et al., "4-1BB agonists: Multi-Potent Potentiators of Tumor Immunity," Frontiers in Oncology, 2015, vol. 5, Article 117, pp. 1-16.
Batlevi, et al., "Novel Immunotherapies in Lymphoid Malignancies," Nature Reviews, Clinical Oncology, vol. 13, 2016, pp. 25-40.
Callahan, et al., "Targeting T Cell Co-receptors for Cancer Therapy," Immunity, vol. 44, 2016, pp. 1069-1078.

(Continued)

*Primary Examiner* — Nelson B Moseley, II
(74) *Attorney, Agent, or Firm* — Morgan, Lewis & Bockius LLP

(57) ABSTRACT

The present invention relates, inter alia, to compositions and methods, including TIGIT- and/or LIGHT-based chimeric proteins that find use in the treatment of disease, such as cancer and an inflammatory disease.

26 Claims, 53 Drawing Sheets

Specification includes a Sequence Listing.

(56) References Cited

FOREIGN PATENT DOCUMENTS

| | | |
|---|---|---|
| WO | WO 2013/173820 A2 | 11/2013 |
| WO | WO 2014/094122 A1 | 6/2014 |
| WO | WO 2014/106839 A1 | 7/2014 |
| WO | WO 2014/121085 A1 | 8/2014 |
| WO | WO 2014/121093 A1 | 8/2014 |
| WO | WO 2014/121099 A1 | 8/2014 |
| WO | WO 2014/134165 A1 | 9/2014 |
| WO | WO 2014/164427 A1 | 10/2014 |
| WO | WO 2015/095423 A2 | 6/2015 |
| WO | WO 2015/104406 A2 | 7/2015 |
| WO | WO 2015/112534 A2 | 7/2015 |
| WO | WO 2015/116178 A1 | 8/2015 |
| WO | WO 2015/183902 A1 | 12/2015 |
| WO | WO 2015/200828 A1 | 12/2015 |
| WO | WO 2016/025385 A1 | 2/2016 |
| WO | WO 2016/126608 A1 | 8/2016 |
| WO | WO 2017/059168 A1 | 4/2017 |

OTHER PUBLICATIONS

Curran, et al., "Editorial: Advances in Combination Tumor Immunotherapy," Frontiers in Oncology, 2015, vol. 5, Article 198, pp. 1-2.
De Visser, et al., "Paradoxical Roles of the Immune System During Cancer Development," Nature Reviews Cancer, (2006) 6:24-37.
Fromm, et al., "Agonist redirected checkpoint, PD1-Fc-OX40L, for cancer immunotherapy," Journal for ImmunoTherapy of Cancer, (2018) 6:149.
Guo, et al., "PD-1 Blockade and OX40 Triggering Synergistically Protects Against Tumor Growth in a Murine Model of Ovarian Cancer," PLOS One, 2014, vol. 9, issue 2, pp. 1-10.
Huang, et al., "CTLA-4-FAS ligand functions as a trans signal converter protein in bridging antigen-presenting cells and T cells," International Immunology, vol. 13, No. 4, 2001, pp. 529-539.
International Search Report and Written Opinion, International Application No. PCT/US2016/054598, dated Jan. 9, 2017, 17 pages.
Karman, et al., "Ligation of Cytotoxic T Lymphocyte Antigen-4 to T Cell Receptor Inhibits T Cell Activation and Directs Differentiation into Foxp3+ Regulatory T Cells," The Journal of Biological Chemistry, vol. 287, No. 14, 2012, pp. 11098-11107.
Kermer, et al., "An Antibody Fusion Protein for Cancer Immunotherapy Mimicking IL-15 trans-Presentation at the Tumor Site," Molecular Cancer Therapeutics, vol. 11, No. 6, 2012, pp. 1279-1288.
Khalil, et al., "The Future of Cancer Treatment: Immunomodulation, CARs and Combination Immunotherapy," Nature Reviews Clinical Oncology, 2016, pp. 1-18.
Ledford, "The Perfect Blend," Nature, vol. 532, 2016, pp. 162-164.
Linch, et al., "OX40 Agonists and Combination Immunotherapy: Putting the Pedal to the Metal," Frontiers in Oncology, vol. 5, article 34, 2015, pp. 1-14.
Mahoney, "Combination Cancer Immunotherapy and New Immunomodulatory Targets," Nature Reviews Drug Discovery (2015)14; 561-585.
Mortarini, et al., "Constitutive Expression and Costimulatory Function of LIGHT/TNFSF14 on Human Melanoma Cells and Melanoma-Derived Microvesicles," Cancer Res, 65:8, Apr. 15, 2005.
Orbach, et al., "CD40•FasL and CTLA-4•FasL Fusion Proteins Induce Apoptosis in Malignant Cell Lines by Dual Signaling," The American Journal of Pathology, vol. 177, No. 6, 2010, pp. 3159-3168.
Pardoll, "The Blockade of Immune Checkpoints in Cancer Immunotherapy," Nature Reviews Cancer, vol. 12, 2012, pp. 252-264.
Schildberg, et al., "Coinhibitory Pathways in the B7-CD28 Ligand-Receptor Family," Immunity, vol. 44, 2016, pp. 955-972.
Scott, et al., "Antibody Therapy of Cancer," Nature Reviews Cancer, vol. 12, 2012, pp. 278-287.
Spiess, et al., "Alternative Molecular Formats and Therapeutic Applications for Bispecific Antibodies," Molecular Immunology, vol. 67, 2015, pp. 95-106.
Ward-Kavanagh, et al., "The TNF Receptor Superfamily in Co-stimulating and Co-inhibitory Responses," Immunity, vol. 44, 2016, pp. 1005-1019.
Zhang, et al., "Targeted and Untargeted CD137L Fusion Proteins for the Immunotherapy of Experimental Solid Tumors," Clin Cancer Res 2007, vol. 13 No. 9, pp. 2758-2767.
Zhao, et al., "A Bispecific Protein Capable of Engaging CTLA-4 and MHCII Protects Non-Obese Diabetic Mice from Autoimmune Diabetes," PLOS One, vol. 8, issue 5, 2013, pp. 1-11.
Li, et al., "T-cell Immunoglobulin and ITIM Domain (TIGIT) Receptor/Poliovirus Receptor (PVR) Ligand Engagement Suppresses Interferon-$\gamma$ Production of Natural Killer Cells via $\beta$-Arrestin 2-mediated Negative Signaling," The Journal of Biochemistry, vol. 282, No. 25, May 9, 2014, pp. 17647-17657.
International Search Report & Written Opinion PCT Application No. PCT/US18/20037, dated Jul. 23, 2018, 15 pages.

* cited by examiner

FIG. 7

| | Gene Id | Protein Name | Accession | Primary Screen | | Confirmation Screen | | Comment |
|---|---|---|---|---|---|---|---|---|
| TIGIT-Fc-OX40L | NECTIN4 | Nectin Cell Adhesion Molecule 4 | BC010293 | v. weak | v. weak | weak | weak | |
| | PVR | Poliovirus Receptor | BC015529 | strong | strong | strong | strong | |
| | OX40 | TNF Receptor Superfamily Member 4 | | n/a | n/a | strong | strong | |
| | TNFRSF4 | TNF Receptor Superfamily Member 4 | NM_003327.3 | n/a | n/a | medium | med/strong | canonical isoform |
| | LGALS1 | Galectin 1 | BC001693 | med/strong | med/strong | weak | weak | soluble; seen with other Fc fusion proteins |

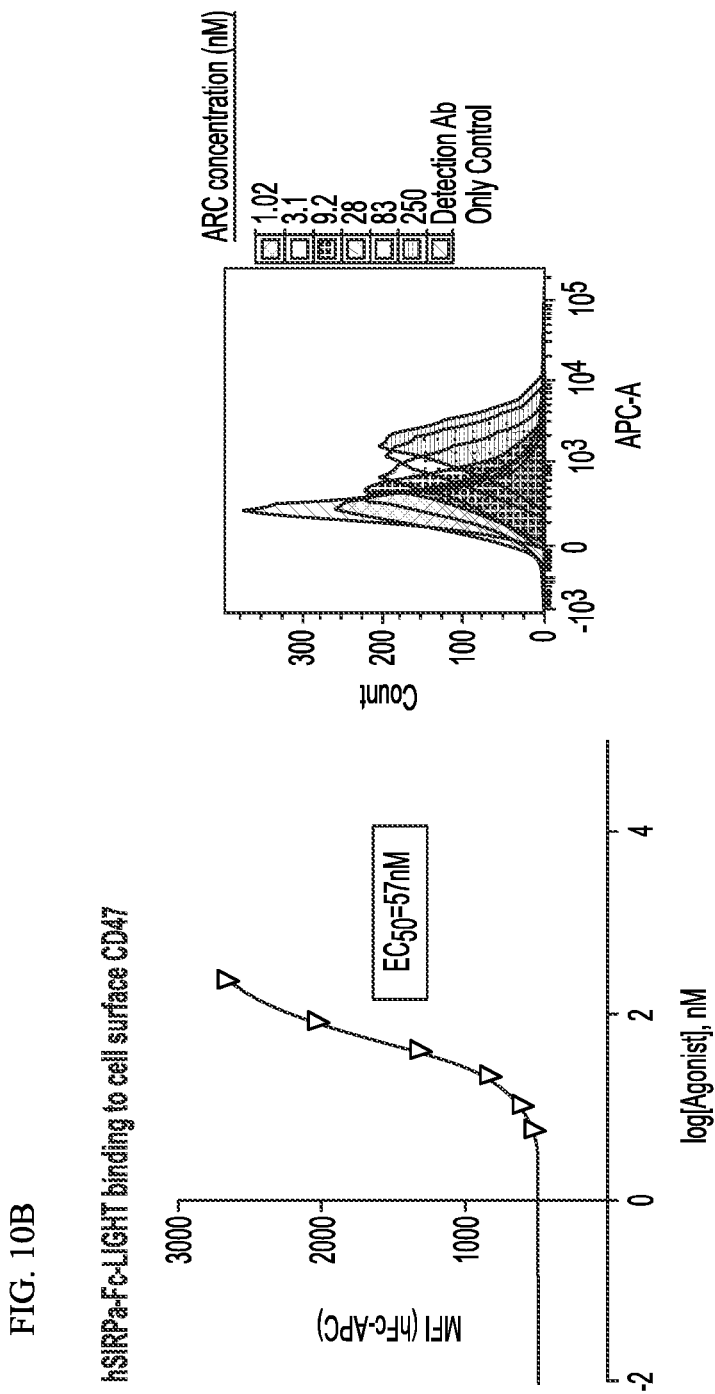

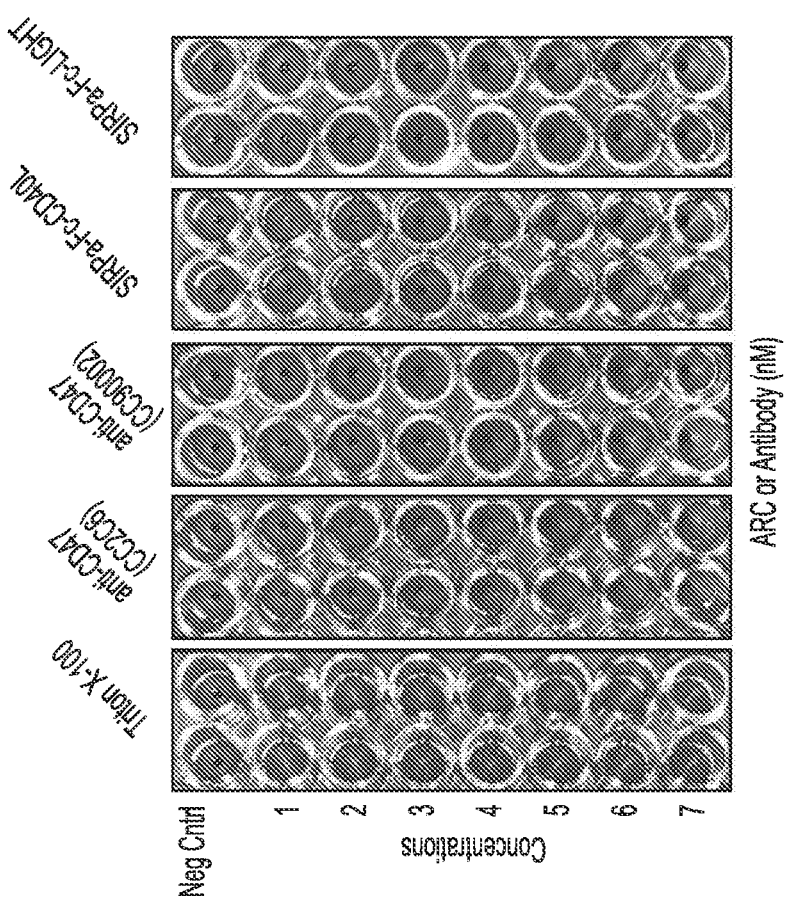
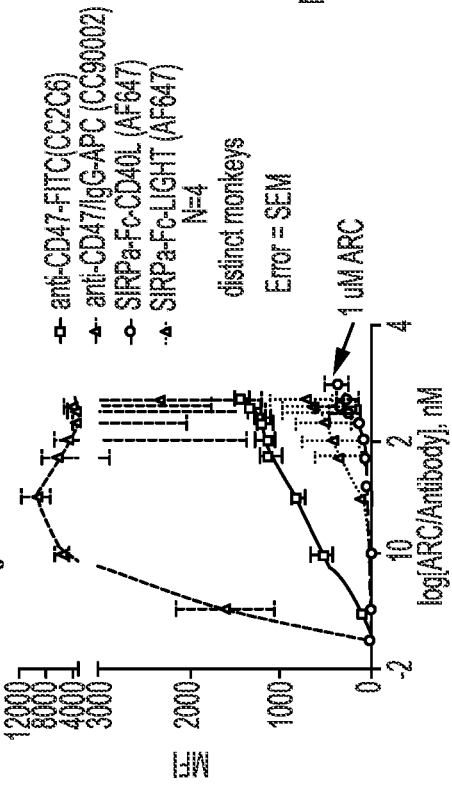
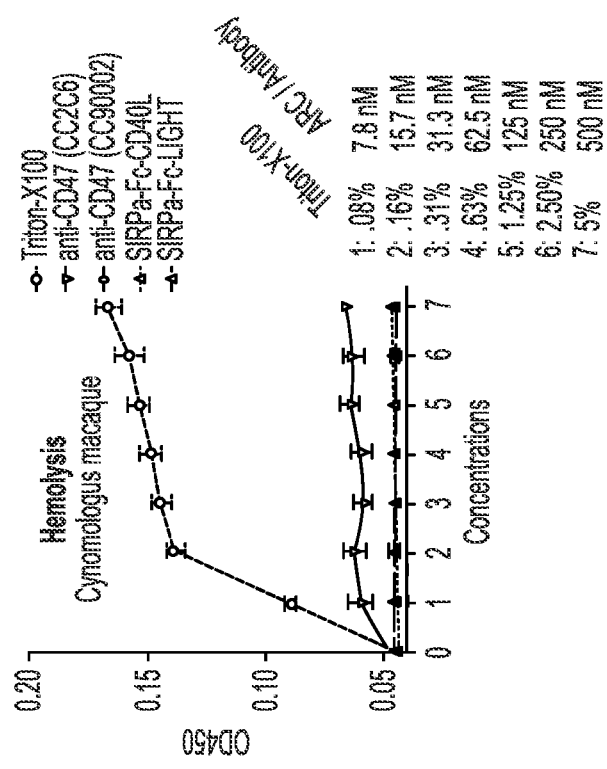
FIG. 11A

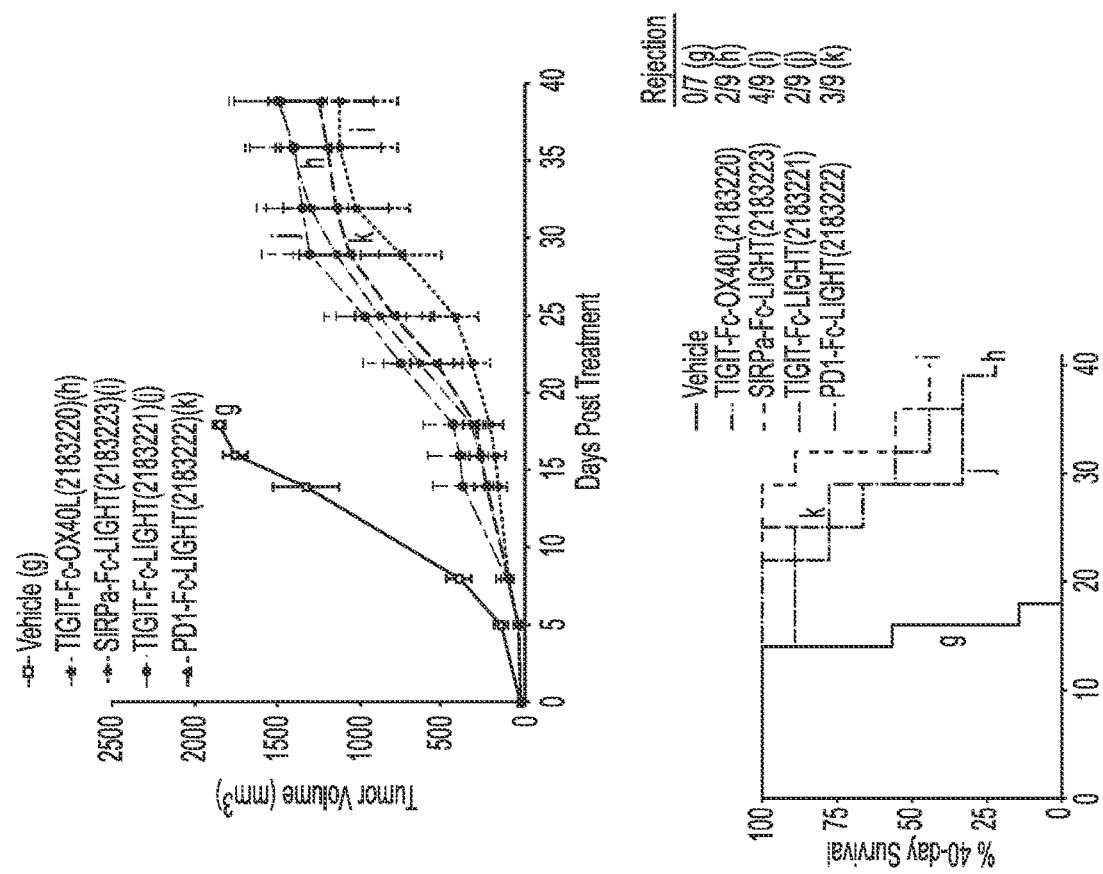
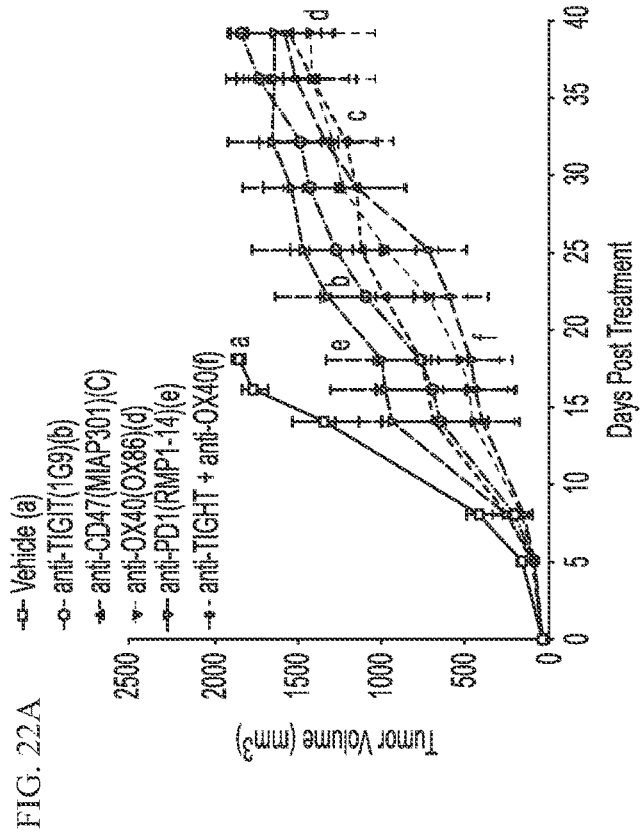
FIG. 22A
FIG. 22B

*Native-Page*

FIG. 32

| Joining Linker 1 | Fc | Joining Linker 2 | Linker Module = Joining Linker 1 + Fc + Joining Linker 2 |
|---|---|---|---|
| SKYGPPCPSCP (SEQ ID NO: 49) | APEFLGGPSVFLFPPKPKDTLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSRWQEGNVFSC SVMHEALHNHYTQKSLSLSLGK (SEQ ID NO: 46) | IEGRMD (SEQ ID NO: 52) | SKYGPPCPSCPAPEFLGGPSVLFPPKPKDTLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVMHEALHNHYTQKSLSLSLGKIEGRMD (SEQ ID NO: 96) |
| SKYGPPCPSCP (SEQ ID NO: 49) | APEFLGGPSVFLFPPKPKDQLMISRTPEVTCVVVDVSQE DPEVQFNWYVDGVEVHNAKTKPREEQFNSTYRVVSVLTT PHSDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSSWQEGNVFSC SVLHEALHNHYTQKSLSLSLGK (SEQ ID NO: 47) | IEGRMD (SEQ ID NO: 52) | SKYGPPCPSCPAPEFLGGPSVLFPPKPKDQLMISRTPEVTCVVVDVS QEDPEVQFNWYVDGVEVHNAKTKPREEQFNSTYRVVSVLTTPHSDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVLHEALHNHYTQKSLSLSLGKIEGRMD (SEQ ID NO: 97) |
| SKYGPPCPSCP (SEQ ID NO: 49) | APEFLGGPSVFLFPPKPKDQLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSRWQEGNVFSC SVLHEALHNHYTQKSLSLSLGK (SEQ ID NO: 48) | IEGRMD (SEQ ID NO: 52) | SKYGPPCPSCPAPEFLGGPSVLFPPKPKDQLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSRWQEGNVFSCSVLHEALHNHYTQKSLSLSLGKIEGRMD (SEQ ID NO: 98) |
| SKYGPPCPPCP (SEQ ID NO: 50) | APEFLGGPSVFLFPPKPKDTLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSRWQEGNVFSC SVMHEALHNHYTQKSLSLSLGK (SEQ ID NO: 46) | IEGRMD (SEQ ID NO: 52) | SKYGPPCPPCPAPEFLGGPSVLFPPKPKDTLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVMHEALHNHYTQKSLSLSLGKIEGRMD (SEQ ID NO: 99) |
| SKYGPPCPPCP (SEQ ID NO: 50) | APEFLGGPSVFLFPPKPKDQLMISRTPEVTCVVVDVSQE DPEVQFNWYVDGVEVHNAKTKPREEQFNSTYRVVSVLTT PHSDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSSWQEGNVFSC SVLHEALHNHYTQKSLSLSLGK (SEQ ID NO: 47) | IEGRMD (SEQ ID NO: 52) | SKYGPPCPPCPAPEFLGGPSVLFPPKPKDQLMISRTPEVTCVVVDVS QEDPEVQFNWYVDGVEVHNAKTKPREEQFNSTYRVVSVLTTPHSDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSSWQEGNVFSCSVLHEALHNHYTQKSLSLSLGKIEGRMD (SEQ ID NO: 100) |
| SKYGPPCPPCP (SEQ ID NO: 50) | APEFLGGPSVFLFPPKPKDQLMISRTPEVTCVVVDVSQE DPEVQFNWYVDGVEVHNAKTKPREEQFNSTYRVVSVLTV LHQDWLSGKEYKCKVSSKGLPSSIEKTISNATGQPREPQ VYTLPPSQEEMTKNQVSLTCLVKGFYPSDIAVEWESNGQ PENNYKTTPPVLDSDGSFFLYSRLTVDKSRWQEGNVFSC SVLHEALHNHYTQKSLSLSLGK (SEQ ID NO: 48) | IEGRMD (SEQ ID NO: 52) | SKYGPPCPPCPAPEFLGGPSVLFPPKPKDQLMISRTPEVTCVVVDVS QEDPEVQFNWYVDGVEVHNAKTKPREEQFNSTYRVVSVLTVLHQDWLS GKEYKCKVSSKGLPSSIEKTISNATGQPREPQVYTLPPSQEEMTKNQV SLTCLVKGFYPSDIAVEWESNGQPENNYKTTPPVLDSDGSFFLYSRLT VDKSRWQEGNVFSCSVLHEALHNHYTQKSLSLSLGKIEGRMD (SEQ ID NO: 101) |

```
                        SEQUENCE LISTING

<160> NUMBER OF SEQ ID NOS: 101

<210> SEQ ID NO 1
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 1

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 2
<211> LENGTH: 182
<212> TYPE: PRT
<213> ORGANISM: Artificial Sequence
<220> FEATURE:
<223> OTHER INFORMATION: Synthetic Polypeptide

<400> SEQUENCE: 2
```

```
Leu Gln Leu His Trp Arg Leu Gly Glu Met Val Thr Arg Leu Pro Asp
1               5                   10                  15

Gly Pro Ala Gly Ser Trp Glu Gln Leu Ile Gln Glu Arg Arg Ser His
            20                  25                  30

Glu Val Asn Pro Ala Ala His Leu Thr Gly Ala Asn Ser Ser Leu Thr
        35                  40                  45

Gly Ser Gly Gly Pro Leu Leu Trp Glu Thr Gln Leu Gly Leu Ala Phe
    50                  55                  60

Leu Arg Gly Leu Ser Tyr His Asp Gly Ala Leu Val Val Thr Lys Ala
65                  70                  75                  80

Gly Tyr Tyr Tyr Ile Tyr Ser Lys Val Gln Leu Gly Gly Val Gly Cys
                85                  90                  95

Pro Leu Gly Leu Ala Ser Thr Ile Thr His Gly Leu Tyr Lys Arg Thr
            100                 105                 110

Pro Arg Tyr Pro Glu Glu Leu Glu Leu Leu Val Ser Gln Gln Ser Pro
            115                 120                 125

Cys Gly Arg Ala Thr Ser Ser Arg Val Trp Trp Asp Ser Ser Phe
            130                 135                 140

Leu Gly Gly Val Val His Leu Glu Ala Gly Glu Lys Val Val Val Arg
145                 150                 155                 160

Val Leu Asp Glu Arg Leu Val Arg Leu Arg Asp Gly Thr Arg Ser Tyr
                165                 170                 175

Phe Gly Ala Phe Met Val
            180

<210> SEQ ID NO 3
<211> LENGTH: 167
<212> TYPE: PRT
<213> ORGANISM: Artificial Sequence
<220> FEATURE:
<223> OTHER INFORMATION: Synthetic Polypeptide

<400> SEQUENCE: 3

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
            130                 135                 140

Thr Glu Arg Arg Ala Glu Val Pro Thr Ala His Pro Ser Pro Ser Pro
145                 150                 155                 160

Arg Pro Ala Gly Gln Phe Gln
            165
```

<210> SEQ ID NO 4
<211> LENGTH: 147
<212> TYPE: PRT
<213> ORGANISM: Artificial Sequence
<220> FEATURE:
<223> OTHER INFORMATION: Synthetic Polypeptide

<400> SEQUENCE: 4

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln
145
```

<210> SEQ ID NO 5
<211> LENGTH: 559
<212> TYPE: PRT
<213> ORGANISM: Artificial Sequence
<220> FEATURE:
<223> OTHER INFORMATION: Synthetic Polypeptide

<400> SEQUENCE: 5

```
Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
            20                  25                  30

Ser Asn Thr Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln Ser
    130                 135                 140

Lys Tyr Gly Pro Pro Cys Pro Cys Pro Ala Pro Glu Phe Leu Gly
145                 150                 155                 160
```

Gly Pro Ser Val Phe Leu Phe Pro Pro Lys Pro Lys Asp Gln Leu Met
            165                 170                 175

Ile Ser Arg Thr Pro Glu Val Thr Cys Val Val Val Asp Val Ser Gln
            180                 185                 190

Glu Asp Pro Glu Val Gln Phe Asn Trp Tyr Val Asp Gly Val Glu Val
            195                 200                 205

His Asn Ala Lys Thr Lys Pro Arg Glu Glu Gln Phe Asn Ser Thr Tyr
            210                 215                 220

Arg Val Val Ser Val Leu Thr Val Leu His Gln Asp Trp Leu Ser Gly
225                 230                 235                 240

Lys Glu Tyr Lys Cys Lys Val Ser Ser Lys Gly Leu Pro Ser Ser Ile
            245                 250                 255

Glu Lys Thr Ile Ser Asn Ala Thr Gly Gln Pro Arg Glu Pro Gln Val
            260                 265                 270

Tyr Thr Leu Pro Pro Ser Gln Glu Glu Met Thr Lys Asn Gln Val Ser
            275                 280                 285

Leu Thr Cys Leu Val Lys Gly Phe Tyr Pro Ser Asp Ile Ala Val Glu
            290                 295                 300

Trp Glu Ser Asn Gly Gln Pro Glu Asn Asn Tyr Lys Thr Thr Pro Pro
305                 310                 315                 320

Val Leu Asp Ser Asp Gly Ser Phe Phe Leu Tyr Ser Arg Leu Thr Val
            325                 330                 335

Asp Lys Ser Arg Trp Gln Glu Gly Asn Val Phe Ser Cys Ser Val Leu
            340                 345                 350

His Glu Ala Leu His Asn His Tyr Thr Gln Lys Ser Leu Ser Leu Ser
            355                 360                 365

Leu Gly Lys Ile Glu Gly Arg Met Asp Leu Gln Leu His Trp Arg Leu
            370                 375                 380

Gly Glu Met Val Thr Arg Leu Pro Asp Gly Pro Ala Gly Ser Trp Glu
385                 390                 395                 400

Gln Leu Ile Gln Glu Arg Arg Ser His Glu Val Asn Pro Ala Ala His
            405                 410                 415

Leu Thr Gly Ala Asn Ser Ser Leu Thr Gly Ser Gly Gly Pro Leu Leu
            420                 425                 430

Trp Glu Thr Gln Leu Gly Leu Ala Phe Leu Arg Gly Leu Ser Tyr His
            435                 440                 445

Asp Gly Ala Leu Val Val Thr Lys Ala Gly Tyr Tyr Tyr Ile Tyr Ser
            450                 455                 460

Lys Val Gln Leu Gly Gly Val Gly Cys Pro Leu Gly Leu Ala Ser Thr
465                 470                 475                 480

Ile Thr His Gly Leu Tyr Lys Arg Thr Pro Arg Tyr Pro Glu Glu Leu
            485                 490                 495

Glu Leu Leu Val Ser Gln Gln Ser Pro Cys Gly Arg Ala Thr Ser Ser
            500                 505                 510

Ser Arg Val Trp Trp Asp Ser Ser Phe Leu Gly Gly Val Val His Leu
            515                 520                 525

Glu Ala Gly Glu Lys Val Val Val Arg Val Leu Asp Glu Arg Leu Val
            530                 535                 540

Arg Leu Arg Asp Gly Thr Arg Ser Tyr Phe Gly Ala Phe Met Val
545                 550                 555

<210> SEQ ID NO 6
<211> LENGTH: 373

-continued

```
<212> TYPE: PRT
<213> ORGANISM: Artificial Sequence
<220> FEATURE:
<223> OTHER INFORMATION: Synthetic Polypeptide

<400> SEQUENCE: 6

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
    50                  55                  60

Pro Ile Gln Trp Phe Arg Gly Ala Gly Pro Gly Arg Glu Leu Ile Tyr
65                  70                  75                  80

Asn Gln Lys Glu Gly His Phe Pro Arg Val Thr Thr Val Ser Asp Leu
                85                  90                  95

Thr Lys Arg Asn Asn Met Asp Phe Ser Ile Arg Ile Gly Asn Ile Thr
            100                 105                 110

Pro Ala Asp Ala Gly Thr Tyr Tyr Cys Val Lys Phe Arg Lys Gly Ser
        115                 120                 125

Pro Asp Asp Val Glu Phe Lys Ser Gly Ala Gly Thr Glu Leu Ser Val
    130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
        195                 200                 205

Ile His Ser Thr Ala Lys Val Val Leu Thr Arg Glu Asp Val His Ser
    210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
            260                 265                 270

Cys Gln Val Arg Lys Phe Tyr Pro Gln Arg Leu Gln Leu Thr Trp Leu
        275                 280                 285

Glu Asn Gly Asn Val Ser Arg Thr Glu Thr Ala Ser Thr Val Thr Glu
    290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
        355                 360                 365

Glu Arg Asn Ile Tyr
    370
```

-continued

```
<210> SEQ ID NO 7
<211> LENGTH: 343
<212> TYPE: PRT
<213> ORGANISM: Artificial Sequence
<220> FEATURE:
<223> OTHER INFORMATION: Synthetic Polypeptide

<400> SEQUENCE: 7

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
    130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
    210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
    290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr
            340

<210> SEQ ID NO 8
<211> LENGTH: 759
```

```
<212> TYPE: PRT
<213> ORGANISM: Artificial Sequence
<220> FEATURE:
<223> OTHER INFORMATION: Synthetic Polypeptide

<400> SEQUENCE: 8

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Pro Val Val Ser Gly Pro Ala Ala
        115                 120                 125

Arg Ala Thr Pro Gln His Thr Val Ser Phe Thr Cys Glu Ser His Gly
130                 135                 140

Phe Ser Pro Arg Asp Ile Thr Leu Lys Trp Phe Lys Asn Gly Asn Glu
145                 150                 155                 160

Leu Ser Asp Phe Gln Thr Asn Val Asp Pro Val Gly Glu Ser Val Ser
                165                 170                 175

Tyr Ser Ile His Ser Thr Ala Lys Val Val Leu Thr Arg Glu Asp Val
            180                 185                 190

His Ser Gln Val Ile Cys Glu Val Ala His Val Thr Leu Gln Gly Asp
        195                 200                 205

Pro Leu Arg Gly Thr Ala Asn Leu Ser Glu Thr Ile Arg Val Pro Pro
210                 215                 220

Thr Leu Glu Val Thr Gln Gln Pro Val Arg Ala Glu Asn Gln Val Asn
225                 230                 235                 240

Val Thr Cys Gln Val Arg Lys Phe Tyr Pro Gln Arg Leu Gln Leu Thr
                245                 250                 255

Trp Leu Glu Asn Gly Asn Val Ser Arg Thr Glu Thr Ala Ser Thr Val
            260                 265                 270

Thr Glu Asn Lys Asp Gly Thr Tyr Asn Trp Met Ser Trp Leu Leu Val
        275                 280                 285

Asn Val Ser Ala His Arg Asp Asp Val Lys Leu Thr Cys Gln Val Glu
290                 295                 300

His Asp Gly Gln Pro Ala Val Ser Lys Ser His Asp Leu Lys Val Ser
305                 310                 315                 320

Ala His Pro Lys Glu Gln Gly Ser Asn Thr Ala Ala Glu Asn Thr Gly
                325                 330                 335

Ser Asn Glu Arg Asn Ile Tyr Ser Lys Tyr Gly Pro Pro Cys Pro Pro
            340                 345                 350

Cys Pro Ala Pro Glu Phe Leu Gly Gly Pro Ser Val Phe Leu Phe Pro
        355                 360                 365

Pro Lys Pro Lys Asp Gln Leu Met Ile Ser Arg Thr Pro Glu Val Thr
370                 375                 380
```

```
Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
            405                 410                 415

Glu Glu Gln Phe Asn Ser Thr Tyr Arg Val Val Ser Val Leu Thr Val
            420                 425                 430

Leu His Gln Asp Trp Leu Ser Gly Lys Glu Tyr Lys Cys Lys Val Ser
        435                 440                 445

Ser Lys Gly Leu Pro Ser Ser Ile Glu Lys Thr Ile Ser Asn Ala Thr
450                 455                 460

Gly Gln Pro Arg Glu Pro Gln Val Tyr Thr Leu Pro Pro Ser Gln Glu
465                 470                 475                 480

Glu Met Thr Lys Asn Gln Val Ser Leu Thr Cys Leu Val Lys Gly Phe
            485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Arg Leu Thr Val Asp Lys Ser Arg Trp Gln Glu Gly
530                 535                 540

Asn Val Phe Ser Cys Ser Val Leu His Glu Ala Leu His Asn His Tyr
545                 550                 555                 560

Thr Gln Lys Ser Leu Ser Leu Ser Leu Gly Lys Ile Glu Gly Arg Met
            565                 570                 575

Asp Leu Gln Leu His Trp Arg Leu Gly Glu Met Val Thr Arg Leu Pro
            580                 585                 590

Asp Gly Pro Ala Gly Ser Trp Glu Gln Leu Ile Gln Glu Arg Arg Ser
        595                 600                 605

His Glu Val Asn Pro Ala Ala His Leu Thr Gly Ala Asn Ser Ser Leu
610                 615                 620

Thr Gly Ser Gly Gly Pro Leu Leu Trp Glu Thr Gln Leu Gly Leu Ala
625                 630                 635                 640

Phe Leu Arg Gly Leu Ser Tyr His Asp Gly Ala Leu Val Val Thr Lys
            645                 650                 655

Ala Gly Tyr Tyr Tyr Ile Tyr Ser Lys Val Gln Leu Gly Gly Val Gly
            660                 665                 670

Cys Pro Leu Gly Leu Ala Ser Thr Ile Thr His Gly Leu Tyr Lys Arg
        675                 680                 685

Thr Pro Arg Tyr Pro Glu Glu Leu Glu Leu Leu Val Ser Gln Gln Ser
690                 695                 700

Pro Cys Gly Arg Ala Thr Ser Ser Ser Arg Val Trp Trp Asp Ser Ser
705                 710                 715                 720

Phe Leu Gly Gly Val Val His Leu Glu Ala Gly Glu Lys Val Val Val
            725                 730                 735

Arg Val Leu Asp Glu Arg Leu Val Arg Leu Arg Asp Gly Thr Arg Ser
            740                 745                 750

Tyr Phe Gly Ala Phe Met Val
            755
```

<210> SEQ ID NO 9
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 9

Met Arg Trp Cys Leu Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
        35                  40                  45

Ser Thr Thr Ala Gln Val Thr Gln Val Asn Trp Glu Gln Gln Asp Gln
    50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
        115                 120                 125

Ser Ser Val Ala Glu His Gly Ala Arg Phe Gln Ile Pro
    130                 135                 140

<210> SEQ ID NO 10
<211> LENGTH: 120
<212> TYPE: PRT
<213> ORGANISM: Artificial Sequence
<220> FEATURE:
<223> OTHER INFORMATION: Synthetic Polypeptide

<400> SEQUENCE: 10

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro
        115                 120

<210> SEQ ID NO 11
<211> LENGTH: 536
<212> TYPE: PRT
<213> ORGANISM: Artificial Sequence
<220> FEATURE:
<223> OTHER INFORMATION: Synthetic Polypeptide

<400> SEQUENCE: 11

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

```
Val Thr Gln Val Asn Trp Glu Gln Gln Asp Gln Leu Ala Ile Cys
         35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
             100                 105                 110

His Gly Ala Arg Phe Gln Ile Pro Ser Lys Tyr Gly Pro Pro Cys Pro
         115                 120                 125

Pro Cys Pro Ala Pro Glu Phe Leu Gly Gly Pro Ser Val Phe Leu Phe
     130                 135                 140

Pro Pro Lys Pro Lys Asp Gln Leu Met Ile Ser Arg Thr Pro Glu Val
145                 150                 155                 160

Thr Cys Val Val Val Asp Val Ser Gln Glu Asp Pro Glu Val Gln Phe
                 165                 170                 175

Asn Trp Tyr Val Asp Gly Val Glu Val His Asn Ala Lys Thr Lys Pro
             180                 185                 190

Arg Glu Glu Gln Phe Asn Ser Thr Tyr Arg Val Val Ser Val Leu Thr
         195                 200                 205

Val Leu His Gln Asp Trp Leu Ser Gly Lys Glu Tyr Lys Cys Lys Val
     210                 215                 220

Ser Ser Lys Gly Leu Pro Ser Ser Ile Glu Lys Thr Ile Ser Asn Ala
225                 230                 235                 240

Thr Gly Gln Pro Arg Glu Pro Gln Val Tyr Thr Leu Pro Pro Ser Gln
                 245                 250                 255

Glu Glu Met Thr Lys Asn Gln Val Ser Leu Thr Cys Leu Val Lys Gly
             260                 265                 270

Phe Tyr Pro Ser Asp Ile Ala Val Glu Trp Glu Ser Asn Gly Gln Pro
         275                 280                 285

Glu Asn Asn Tyr Lys Thr Thr Pro Pro Val Leu Asp Ser Asp Gly Ser
     290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Leu His Glu Ala Leu His Asn His
                 325                 330                 335

Tyr Thr Gln Lys Ser Leu Ser Leu Ser Leu Gly Lys Ile Glu Gly Arg
             340                 345                 350

Met Asp Leu Gln Leu His Trp Arg Leu Gly Glu Met Val Thr Arg Leu
         355                 360                 365

Pro Asp Gly Pro Ala Gly Ser Trp Glu Gln Leu Ile Gln Glu Arg Arg
     370                 375                 380

Ser His Glu Val Asn Pro Ala Ala His Leu Thr Gly Ala Asn Ser Ser
385                 390                 395                 400

Leu Thr Gly Ser Gly Gly Pro Leu Leu Trp Glu Thr Gln Leu Gly Leu
                 405                 410                 415

Ala Phe Leu Arg Gly Leu Ser Tyr His Asp Gly Ala Leu Val Val Thr
             420                 425                 430

Lys Ala Gly Tyr Tyr Tyr Ile Tyr Ser Lys Val Gln Leu Gly Gly Val
         435                 440                 445
```

```
Gly Cys Pro Leu Gly Leu Ala Ser Thr Ile Thr His Gly Leu Tyr Lys
    450                 455                 460

Arg Thr Pro Arg Tyr Pro Glu Leu Glu Leu Leu Val Ser Gln Gln
465                 470                 475                 480

Ser Pro Cys Gly Arg Ala Thr Ser Ser Arg Val Trp Trp Asp Ser
                485                 490                 495

Ser Phe Leu Gly Gly Val Val His Leu Glu Ala Gly Glu Lys Val Val
                500                 505                 510

Val Arg Val Leu Asp Glu Arg Leu Val Arg Leu Arg Asp Gly Thr Arg
                515                 520                 525

Ser Tyr Phe Gly Ala Phe Met Val
            530                 535

<210> SEQ ID NO 12
<211> LENGTH: 254
<212> TYPE: PRT
<213> ORGANISM: Artificial Sequence
<220> FEATURE:
<223> OTHER INFORMATION: Synthetic Polypeptide

<400> SEQUENCE: 12

Met Glu Tyr Ala Ser Asp Ala Ser Leu Asp Pro Glu Ala Pro Trp Pro
1               5                   10                  15

Pro Ala Pro Arg Ala Arg Ala Cys Arg Val Leu Pro Trp Ala Leu Val
                20                  25                  30

Ala Gly Leu Leu Leu Leu Leu Leu Ala Ala Ala Cys Ala Val Phe
            35                  40                  45

Leu Ala Cys Pro Trp Ala Val Ser Gly Ala Arg Ala Ser Pro Gly Ser
    50                  55                  60

Ala Ala Ser Pro Arg Leu Arg Glu Gly Pro Glu Leu Ser Pro Asp Asp
65                  70                  75                  80

Pro Ala Gly Leu Leu Asp Leu Arg Gln Gly Met Phe Ala Gln Leu Val
                85                  90                  95

Ala Gln Asn Val Leu Leu Ile Asp Gly Pro Leu Ser Trp Tyr Ser Asp
                100                 105                 110

Pro Gly Leu Ala Gly Val Ser Leu Thr Gly Gly Leu Ser Tyr Lys Glu
            115                 120                 125

Asp Thr Lys Glu Leu Val Val Ala Lys Ala Gly Val Tyr Tyr Val Phe
130                 135                 140

Phe Gln Leu Glu Leu Arg Arg Val Val Ala Gly Glu Gly Ser Gly Ser
145                 150                 155                 160

Val Ser Leu Ala Leu His Leu Gln Pro Leu Arg Ser Ala Ala Gly Ala
                165                 170                 175

Ala Ala Leu Ala Leu Thr Val Asp Leu Pro Pro Ala Ser Ser Glu Ala
            180                 185                 190

Arg Asn Ser Ala Phe Gly Phe Gln Gly Arg Leu Leu His Leu Ser Ala
                195                 200                 205

Gly Gln Arg Leu Gly Val His Leu His Thr Glu Ala Arg Ala Arg His
            210                 215                 220

Ala Trp Gln Leu Thr Gln Gly Ala Thr Val Leu Gly Leu Phe Arg Val
225                 230                 235                 240

Thr Pro Glu Ile Pro Ala Gly Leu Pro Ser Pro Arg Ser Glu
                245                 250

<210> SEQ ID NO 13
<211> LENGTH: 205
```

```
<212> TYPE: PRT
<213> ORGANISM: Artificial Sequence
<220> FEATURE:
<223> OTHER INFORMATION: Synthetic Polypeptide

<400> SEQUENCE: 13

Ala Cys Pro Trp Ala Val Ser Gly Ala Arg Ala Ser Pro Gly Ser Ala
1               5                   10                  15

Ala Ser Pro Arg Leu Arg Glu Gly Pro Glu Leu Ser Pro Asp Asp Pro
            20                  25                  30

Ala Gly Leu Leu Asp Leu Arg Gln Gly Met Phe Ala Gln Leu Val Ala
        35                  40                  45

Gln Asn Val Leu Leu Ile Asp Gly Pro Leu Ser Trp Tyr Ser Asp Pro
    50                  55                  60

Gly Leu Ala Gly Val Ser Leu Thr Gly Leu Ser Tyr Lys Glu Asp
65                  70                  75                  80

Thr Lys Glu Leu Val Val Ala Lys Ala Gly Val Tyr Tyr Val Phe Phe
                85                  90                  95

Gln Leu Glu Leu Arg Arg Val Val Ala Gly Glu Gly Ser Gly Ser Val
            100                 105                 110

Ser Leu Ala Leu His Leu Gln Pro Leu Arg Ser Ala Ala Gly Ala Ala
        115                 120                 125

Ala Leu Ala Leu Thr Val Asp Leu Pro Pro Ala Ser Ser Glu Ala Arg
    130                 135                 140

Asn Ser Ala Phe Gly Phe Gln Gly Arg Leu Leu His Leu Ser Ala Gly
145                 150                 155                 160

Gln Arg Leu Gly Val His Leu His Thr Glu Ala Arg Ala Arg His Ala
                165                 170                 175

Trp Gln Leu Thr Gln Gly Ala Thr Val Leu Gly Leu Phe Arg Val Thr
            180                 185                 190

Pro Glu Ile Pro Ala Gly Leu Pro Ser Pro Arg Ser Glu
        195                 200                 205

<210> SEQ ID NO 14
<211> LENGTH: 559
<212> TYPE: PRT
<213> ORGANISM: Artificial Sequence
<220> FEATURE:
<223> OTHER INFORMATION: Synthetic Polypeptide

<400> SEQUENCE: 14

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
        35                  40                  45

Asn Ala Asp Leu Gly Trp His Ile Ser Pro Ser Phe Lys Asp Arg Val
    50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
            100                 105                 110

His Gly Ala Arg Phe Gln Ile Pro Ser Lys Tyr Gly Pro Pro Cys Pro
        115                 120                 125
```

```
Pro Cys Pro Ala Pro Glu Phe Leu Gly Gly Pro Ser Val Phe Leu Phe
    130                 135                 140

Pro Pro Lys Pro Lys Asp Gln Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
        195                 200                 205

Val Leu His Gln Asp Trp Leu Ser Gly Lys Glu Tyr Lys Cys Lys Val
    210                 215                 220

Ser Ser Lys Gly Leu Pro Ser Ser Ile Glu Lys Thr Ile Ser Asn Ala
225                 230                 235                 240

Thr Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
        275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Leu His Glu Ala Leu His Asn His
                325                 330                 335

Tyr Thr Gln Lys Ser Leu Ser Leu Ser Leu Gly Lys Ile Glu Gly Arg
            340                 345                 350

Met Asp Ala Cys Pro Trp Ala Val Ser Gly Ala Arg Ala Ser Pro Gly
        355                 360                 365

Ser Ala Ala Ser Pro Arg Leu Arg Glu Gly Pro Glu Leu Ser Pro Asp
    370                 375                 380

Asp Pro Ala Gly Leu Leu Asp Leu Arg Gln Gly Met Phe Ala Gln Leu
385                 390                 395                 400

Val Ala Gln Asn Val Leu Leu Ile Asp Gly Pro Leu Ser Trp Tyr Ser
                405                 410                 415

Asp Pro Gly Leu Ala Gly Val Ser Leu Thr Gly Gly Leu Ser Tyr Lys
            420                 425                 430

Glu Asp Thr Lys Glu Leu Val Val Ala Lys Ala Gly Val Tyr Tyr Val
        435                 440                 445

Phe Phe Gln Leu Glu Leu Arg Arg Val Val Ala Gly Glu Gly Ser Gly
    450                 455                 460

Ser Val Ser Leu Ala Leu His Leu Gln Pro Leu Arg Ser Ala Ala Gly
465                 470                 475                 480

Ala Ala Ala Leu Ala Leu Thr Val Asp Leu Pro Pro Ala Ser Ser Glu
                485                 490                 495

Ala Arg Asn Ser Ala Phe Gly Phe Gln Gly Arg Leu Leu His Leu Ser
            500                 505                 510

Ala Gly Gln Arg Leu Gly Val His Leu His Thr Glu Ala Arg Ala Arg
        515                 520                 525

His Ala Trp Gln Leu Thr Gln Gly Ala Thr Val Leu Gly Leu Phe Arg
    530                 535                 540
```

Val Thr Pro Glu Ile Pro Ala Gly Leu Pro Ser Pro Arg Ser Glu
545                 550                 555

<210> SEQ ID NO 15
<211> LENGTH: 199
<212> TYPE: PRT
<213> ORGANISM: Artificial Sequence
<220> FEATURE:
<223> OTHER INFORMATION: Synthetic Polypeptide

<400> SEQUENCE: 15

Met Thr Leu His Pro Ser Pro Ile Thr Cys Glu Phe Leu Phe Ser Thr
1               5                   10                  15

Ala Leu Ile Ser Pro Lys Met Cys Leu Ser His Leu Glu Asn Met Pro
            20                  25                  30

Leu Ser His Ser Arg Thr Gln Gly Ala Gln Arg Ser Ser Trp Lys Leu
        35                  40                  45

Trp Leu Phe Cys Ser Ile Val Met Leu Leu Phe Leu Cys Ser Phe Ser
50                  55                  60

Trp Leu Ile Phe Ile Phe Leu Gln Leu Glu Thr Ala Lys Glu Pro Cys
65                  70                  75                  80

Met Ala Lys Phe Gly Pro Leu Pro Ser Lys Trp Gln Met Ala Ser Ser
                85                  90                  95

Glu Pro Pro Cys Val Asn Lys Val Ser Asp Trp Lys Leu Glu Ile Leu
            100                 105                 110

Gln Asn Gly Leu Tyr Leu Ile Tyr Gly Gln Val Ala Pro Asn Ala Asn
        115                 120                 125

Tyr Asn Asp Val Ala Pro Phe Glu Val Arg Leu Tyr Lys Asn Lys Asp
130                 135                 140

Met Ile Gln Thr Leu Thr Asn Lys Ser Lys Ile Gln Asn Val Gly Gly
145                 150                 155                 160

Thr Tyr Glu Leu His Val Gly Asp Thr Ile Asp Leu Ile Phe Asn Ser
                165                 170                 175

Glu His Gln Val Leu Lys Asn Asn Thr Tyr Trp Gly Ile Ile Leu Leu
            180                 185                 190

Ala Asn Pro Gln Phe Ile Ser
        195

<210> SEQ ID NO 16
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 16

Gln Leu Glu Thr Ala Lys Glu Pro Cys Met Ala Lys Phe Gly Pro Leu
1               5                   10                  15

Pro Ser Lys Trp Gln Met Ala Ser Ser Glu Pro Pro Cys Val Asn Lys
            20                  25                  30

Val Ser Asp Trp Lys Leu Glu Ile Leu Gln Asn Gly Leu Tyr Leu Ile
        35                  40                  45

Tyr Gly Gln Val Ala Pro Asn Ala Asn Tyr Asn Asp Val Ala Pro Phe
50                  55                  60

Glu Val Arg Leu Tyr Lys Asn Lys Asp Met Ile Gln Thr Leu Thr Asn
65                  70                  75                  80

Lys Ser Lys Ile Gln Asn Val Gly Gly Thr Tyr Glu Leu His Val Gly
                85                  90                  95

```
Asp Thr Ile Asp Leu Ile Phe Asn Ser Glu His Gln Val Leu Lys Asn
            100                 105                 110
Asn Thr Tyr Trp Gly Ile Ile Leu Leu Ala Asn Pro Gln Phe Ile Ser
            115                 120                 125

<210> SEQ ID NO 17
<211> LENGTH: 482
<212> TYPE: PRT
<213> ORGANISM: Artificial Sequence
<220> FEATURE:
<223> OTHER INFORMATION: Synthetic Polypeptide

<400> SEQUENCE: 17

Met Met Thr Gly Thr Ile Glu Thr Thr Gly Asn Ile Ser Ala Glu Lys
1               5                   10                  15
Gly Gly Ser Ile Ile Leu Gln Cys His Leu Ser Ser Thr Thr Ala Gln
            20                  25                  30
Val Thr Gln Val Asn Trp Glu Gln Gln Asp Gln Leu Leu Ala Ile Cys
        35                  40                  45
Asn Ala Asp Leu Gly Trp His Ile Ser Pro Ser Phe Lys Asp Arg Val
    50                  55                  60
Ala Pro Gly Pro Gly Leu Gly Leu Thr Leu Gln Ser Leu Thr Val Asn
65                  70                  75                  80
Asp Thr Gly Glu Tyr Phe Cys Ile Tyr His Thr Tyr Pro Asp Gly Thr
                85                  90                  95
Tyr Thr Gly Arg Ile Phe Leu Glu Val Leu Glu Ser Ser Val Ala Glu
            100                 105                 110
His Gly Ala Arg Phe Gln Ile Pro Ser Lys Tyr Gly Pro Pro Cys Pro
        115                 120                 125
Pro Cys Pro Ala Pro Glu Phe Leu Gly Gly Pro Ser Val Phe Leu Phe
    130                 135                 140
Pro Pro Lys Pro Lys Asp Gln Leu Met Ile Ser Arg Thr Pro Glu Val
145                 150                 155                 160
Thr Cys Val Val Val Asp Val Ser Gln Glu Asp Pro Glu Val Gln Phe
                165                 170                 175
Asn Trp Tyr Val Asp Gly Val Glu Val His Asn Ala Lys Thr Lys Pro
            180                 185                 190
Arg Glu Glu Gln Phe Asn Ser Thr Tyr Arg Val Val Ser Val Leu Thr
        195                 200                 205
Val Leu His Gln Asp Trp Leu Ser Gly Lys Glu Tyr Lys Cys Lys Val
    210                 215                 220
Ser Ser Lys Gly Leu Pro Ser Ser Ile Glu Lys Thr Ile Ser Asn Ala
225                 230                 235                 240
Thr Gly Gln Pro Arg Glu Pro Gln Val Tyr Thr Leu Pro Pro Ser Gln
                245                 250                 255
Glu Glu Met Thr Lys Asn Gln Val Ser Leu Thr Cys Leu Val Lys Gly
            260                 265                 270
Phe Tyr Pro Ser Asp Ile Ala Val Glu Trp Glu Ser Asn Gly Gln Pro
        275                 280                 285
Glu Asn Asn Tyr Lys Thr Thr Pro Pro Val Leu Asp Ser Asp Gly Ser
    290                 295                 300
Phe Phe Leu Tyr Ser Arg Leu Thr Val Asp Lys Ser Arg Trp Gln Glu
305                 310                 315                 320
Gly Asn Val Phe Ser Cys Ser Val Leu His Glu Ala Leu His Asn His
                325                 330                 335
```

-continued

```
Tyr Thr Gln Lys Ser Leu Ser Leu Ser Leu Gly Lys Ile Glu Gly Arg
            340                 345                 350

Met Asp Gln Leu Glu Thr Ala Lys Glu Pro Cys Met Ala Lys Phe Gly
            355                 360                 365

Pro Leu Pro Ser Lys Trp Gln Met Ala Ser Ser Glu Pro Pro Cys Val
            370                 375                 380

Asn Lys Val Ser Asp Trp Lys Leu Glu Ile Leu Gln Asn Gly Leu Tyr
385                 390                 395                 400

Leu Ile Tyr Gly Gln Val Ala Pro Asn Ala Asn Tyr Asn Asp Val Ala
                405                 410                 415

Pro Phe Glu Val Arg Leu Tyr Lys Asn Lys Asp Met Ile Gln Thr Leu
                420                 425                 430

Thr Asp Lys Ser Lys Ile Gln Asn Val Gly Gly Thr Tyr Glu Leu His
            435                 440                 445

Val Gly Asp Thr Ile Asp Leu Ile Phe Asn Ser Glu His Gln Val Leu
        450                 455                 460

Lys Asn Asn Thr Tyr Trp Gly Ile Ile Leu Leu Ala Asn Pro Gln Phe
465                 470                 475                 480

Ile Ser

<210> SEQ ID NO 18
<211> LENGTH: 251
<212> TYPE: PRT
<213> ORGANISM: Artificial Sequence
<220> FEATURE:
<223> OTHER INFORMATION: Synthetic Polypeptide

<400> SEQUENCE: 18

Met Ala Glu Asp Leu Gly Leu Ser Phe Gly Glu Thr Ala Ser Val Glu
1               5                   10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
    50                  55                  60

Ala Cys Val Gln Phe Gln Ala Leu Lys Gly Gln Glu Phe Ala Pro Ser
65                  70                  75                  80

His Gln Gln Val Tyr Ala Pro Leu Arg Ala Asp Gly Asp Lys Pro Arg
                85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205
```

Phe Gln Pro Ile Tyr Leu Gly Ala Met Phe Ser Leu Gln Glu Gly Asp
    210                 215                 220
Lys Leu Met Val Asn Val Ser Asp Ile Ser Leu Val Asp Tyr Thr Lys
225                 230                 235                 240
Glu Asp Lys Thr Phe Phe Gly Ala Phe Leu Leu
                245                 250

<210> SEQ ID NO 19
<211> LENGTH: 192
<212> TYPE: PRT
<213> ORGANISM: Artificial Sequence
<220> FEATURE:
<223> OTHER INFORMATION: Synthetic Polypeptide

<400> SEQUENCE: 19

Arg Ala Gln Gly Glu Ala Cys Val Gln Phe Gln Ala Leu Lys Gly Gln
1               5                   10                  15
Glu Phe Ala Pro Ser His Gln Gln Val Tyr Ala Pro Leu Arg Ala Asp
                20                  25                  30
Gly Asp Lys Pro Arg Ala His Leu Thr Val Val Arg Gln Thr Pro Thr
            35                  40                  45
Gln His Phe Lys Asn Gln Phe Pro Ala Leu His Trp Glu His Glu Leu
        50                  55                  60
Gly Leu Ala Phe Thr Lys Asn Arg Met Asn Tyr Thr Asn Lys Phe Leu
65                  70                  75                  80
Leu Ile Pro Glu Ser Gly Asp Tyr Phe Ile Tyr Ser Gln Val Thr Phe
                85                  90                  95
Arg Gly Met Thr Ser Glu Cys Ser Glu Ile Arg Gln Ala Gly Arg Pro
            100                 105                 110
Asn Lys Pro Asp Ser Ile Thr Val Val Ile Thr Lys Val Thr Asp Ser
        115                 120                 125
Tyr Pro Glu Pro Thr Gln Leu Leu Met Gly Thr Lys Ser Val Cys Glu
    130                 135                 140
Val Gly Ser Asn Trp Phe Gln Pro Ile Tyr Leu Gly Ala Met Phe Ser
145                 150                 155                 160
Leu Gln Glu Gly Asp Lys Leu Met Val Asn Val Ser Asp Ile Ser Leu
                165                 170                 175
Val Asp Tyr Thr Lys Glu Asp Lys Thr Phe Phe Gly Ala Phe Leu Leu
            180                 185                 190

<210> SEQ ID NO 20
<211> LENGTH: 549
<212> TYPE: PRT
<213> ORGANISM: Artificial Sequence
<220> FEATURE:
<223> OTHER INFORMATION: Synthetic Polypeptide

<400> SEQUENCE: 20

Met Met Thr Gly Thr Ile Glu Thr Thr Gly Asn Ile Ser Ala Glu Lys
1               5                   10                  15
Gly Gly Ser Ile Ile Leu Gln Cys His Leu Ser Ser Thr Thr Ala Gln
                20                  25                  30
Val Thr Gln Val Asn Trp Glu Gln Gln Asp Gln Leu Leu Ala Ile Cys
            35                  40                  45
Asn Ala Asp Leu Gly Trp His Ile Ser Pro Ser Phe Lys Asp Arg Val
        50                  55                  60
Ala Pro Gly Pro Gly Leu Gly Leu Thr Leu Gln Ser Leu Thr Val Asn
65                  70                  75                  80

```
Asp Thr Gly Glu Tyr Phe Cys Ile Tyr His Thr Tyr Pro Asp Gly Thr
                85                  90                  95

Tyr Thr Gly Arg Ile Phe Leu Glu Val Leu Glu Ser Ser Val Ala Glu
                100                 105                 110

His Gly Ala Arg Phe Gln Ile Pro Ser Lys Tyr Gly Pro Pro Cys Pro
            115                 120                 125

Pro Cys Pro Ala Pro Glu Phe Leu Gly Gly Pro Ser Val Phe Leu Phe
    130                 135                 140

Pro Pro Lys Pro Lys Asp Gln Leu Met Ile Ser Arg Thr Pro Glu Val
145                 150                 155                 160

Thr Cys Val Val Val Asp Val Ser Gln Glu Asp Pro Glu Val Gln Phe
                165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
            195                 200                 205

Val Leu His Gln Asp Trp Leu Ser Gly Lys Glu Tyr Lys Cys Lys Val
    210                 215                 220

Ser Ser Lys Gly Leu Pro Ser Ser Ile Glu Lys Thr Ile Ser Asn Ala
225                 230                 235                 240

Thr Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Leu His Glu Ala Leu His Asn His
                325                 330                 335

Tyr Thr Gln Lys Ser Leu Ser Leu Ser Leu Gly Lys Ile Glu Gly Arg
            340                 345                 350

Met Asp Ser Gln Leu Arg Ala Gln Gly Glu Ala Cys Val Gln Phe Gln
            355                 360                 365

Ala Leu Lys Gly Gln Glu Phe Ala Pro Ser His Gln Gln Val Tyr Ala
    370                 375                 380

Pro Leu Arg Ala Asp Gly Asp Lys Pro Arg Ala His Leu Thr Val Val
385                 390                 395                 400

Arg Gln Thr Pro Thr Gln His Phe Lys Asn Gln Phe Pro Ala Leu His
                405                 410                 415

Trp Glu His Glu Leu Gly Leu Ala Phe Thr Lys Asn Arg Met Asn Tyr
            420                 425                 430

Thr Asn Lys Phe Leu Leu Ile Pro Glu Ser Gly Asp Tyr Phe Ile Tyr
    435                 440                 445

Ser Gln Val Thr Phe Arg Gly Met Thr Ser Glu Cys Ser Glu Ile Arg
450                 455                 460

Gln Ala Gly Arg Pro Asn Lys Pro Asp Ser Ile Thr Val Val Ile Thr
465                 470                 475                 480

Lys Val Thr Asp Ser Tyr Pro Glu Pro Thr Gln Leu Leu Met Gly Thr
                485                 490                 495
```

```
Lys Ser Val Cys Glu Val Gly Ser Asn Trp Phe Gln Pro Ile Tyr Leu
                500                 505                 510
Gly Ala Met Phe Ser Leu Gln Glu Gly Asp Lys Leu Met Val Asn Val
            515                 520                 525
Ser Asp Ile Ser Leu Val Asp Tyr Thr Lys Glu Asp Lys Thr Phe Phe
530                 535                 540
Gly Ala Phe Leu Leu
545
```

```
<210> SEQ ID NO 21
<211> LENGTH: 183
<212> TYPE: PRT
<213> ORGANISM: Artificial Sequence
<220> FEATURE:
<223> OTHER INFORMATION: Synthetic Polypeptide

<400> SEQUENCE: 21

Met Glu Arg Val Gln Pro Leu Glu Glu Asn Val Gly Asn Ala Ala Arg
1               5                   10                  15
Pro Arg Phe Glu Arg Asn Lys Leu Leu Leu Val Ala Ser Val Ile Gln
            20                  25                  30
Gly Leu Gly Leu Leu Cys Phe Thr Tyr Ile Cys Leu His Phe Ser
        35                  40                  45
Ala Leu Gln Val Ser His Arg Tyr Pro Arg Ile Gln Ser Ile Lys Val
50                  55                  60
Gln Phe Thr Glu Tyr Lys Lys Glu Lys Gly Phe Ile Leu Thr Ser Gln
65                  70                  75                  80
Lys Glu Asp Glu Ile Met Lys Val Gln Asn Asn Ser Val Ile Ile Asn
                85                  90                  95
Cys Asp Gly Phe Tyr Leu Ile Ser Leu Lys Gly Tyr Phe Ser Gln Glu
            100                 105                 110
Val Asn Ile Ser Leu His Tyr Gln Lys Asp Glu Glu Pro Leu Phe Gln
        115                 120                 125
Leu Lys Lys Val Arg Ser Val Asn Ser Leu Met Val Ala Ser Leu Thr
130                 135                 140
Tyr Lys Asp Lys Val Tyr Leu Asn Val Thr Thr Asp Asn Thr Ser Leu
145                 150                 155                 160
Asp Asp Phe His Val Asn Gly Gly Glu Leu Ile Leu Ile His Gln Asn
                165                 170                 175
Pro Gly Glu Phe Cys Val Leu
            180
```

```
<210> SEQ ID NO 22
<211> LENGTH: 133
<212> TYPE: PRT
<213> ORGANISM: Artificial Sequence
<220> FEATURE:
<223> OTHER INFORMATION: Synthetic Polypeptide

<400> SEQUENCE: 22

Gln Val Ser His Arg Tyr Pro Arg Ile Gln Ser Ile Lys Val Gln Phe
1               5                   10                  15
Thr Glu Tyr Lys Lys Glu Lys Gly Phe Ile Leu Thr Ser Gln Lys Glu
            20                  25                  30
Asp Glu Ile Met Lys Val Gln Asn Asn Ser Val Ile Ile Asn Cys Asp
        35                  40                  45
Gly Phe Tyr Leu Ile Ser Leu Lys Gly Tyr Phe Ser Gln Glu Val Asn
50                  55                  60
```

```
Ile Ser Leu His Tyr Gln Lys Asp Glu Glu Pro Leu Phe Gln Leu Lys
 65                  70                  75                  80

Lys Val Arg Ser Val Asn Ser Leu Met Val Ala Ser Leu Thr Tyr Lys
                 85                  90                  95

Asp Lys Val Tyr Leu Asn Val Thr Thr Asp Asn Thr Ser Leu Asp Asp
             100                 105                 110

Phe His Val Asn Gly Gly Glu Leu Ile Leu Ile His Gln Asn Pro Gly
         115                 120                 125

Glu Phe Cys Val Leu
        130

<210> SEQ ID NO 23
<211> LENGTH: 487
<212> TYPE: PRT
<213> ORGANISM: Artificial Sequence
<220> FEATURE:
<223> OTHER INFORMATION: Synthetic Polypeptide

<400> SEQUENCE: 23

Met Met Thr Gly Thr Ile Glu Thr Thr Gly Asn Ile Ser Ala Glu Lys
 1               5                  10                  15

Gly Gly Ser Ile Ile Leu Gln Cys His Leu Ser Ser Thr Thr Ala Gln
                 20                  25                  30

Val Thr Gln Val Asn Trp Glu Gln Gln Asp Gln Leu Leu Ala Ile Cys
             35                  40                  45

Asn Ala Asp Leu Gly Trp His Ile Ser Pro Ser Phe Lys Asp Arg Val
 50                  55                  60

Ala Pro Gly Pro Gly Leu Gly Leu Thr Leu Gln Ser Leu Thr Val Asn
 65                  70                  75                  80

Asp Thr Gly Glu Tyr Phe Cys Ile Tyr His Thr Tyr Pro Asp Gly Thr
                 85                  90                  95

Tyr Thr Gly Arg Ile Phe Leu Glu Val Leu Glu Ser Ser Val Ala Glu
             100                 105                 110

His Gly Ala Arg Phe Gln Ile Pro Ser Lys Tyr Gly Pro Pro Cys Pro
         115                 120                 125

Pro Cys Pro Ala Pro Glu Phe Leu Gly Gly Pro Ser Val Phe Leu Phe
     130                 135                 140

Pro Pro Lys Pro Lys Asp Gln Leu Met Ile Ser Arg Thr Pro Glu Val
145                 150                 155                 160

Thr Cys Val Val Val Asp Val Ser Gln Glu Asp Pro Glu Val Gln Phe
                 165                 170                 175

Asn Trp Tyr Val Asp Gly Val Glu Val His Asn Ala Lys Thr Lys Pro
             180                 185                 190

Arg Glu Glu Gln Phe Asn Ser Thr Tyr Arg Val Val Ser Val Leu Thr
         195                 200                 205

Val Leu His Gln Asp Trp Leu Ser Gly Lys Glu Tyr Lys Cys Lys Val
     210                 215                 220

Ser Ser Lys Gly Leu Pro Ser Ser Ile Glu Lys Thr Ile Ser Asn Ala
225                 230                 235                 240

Thr Gly Gln Pro Arg Glu Pro Gln Val Tyr Thr Leu Pro Pro Ser Gln
                 245                 250                 255

Glu Glu Met Thr Lys Asn Gln Val Ser Leu Thr Cys Leu Val Lys Gly
             260                 265                 270

Phe Tyr Pro Ser Asp Ile Ala Val Glu Trp Glu Ser Asn Gly Gln Pro
         275                 280                 285
```

```
Glu Asn Asn Tyr Lys Thr Thr Pro Pro Val Leu Asp Ser Asp Gly Ser
    290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Leu His Glu Ala Leu His Asn His
                325                 330                 335

Tyr Thr Gln Lys Ser Leu Ser Leu Ser Leu Gly Lys Ile Glu Gly Arg
            340                 345                 350

Met Asp Gln Val Ser His Arg Tyr Pro Arg Ile Gln Ser Ile Lys Val
        355                 360                 365

Gln Phe Thr Glu Tyr Lys Lys Glu Lys Gly Phe Ile Leu Thr Ser Gln
    370                 375                 380

Lys Glu Asp Glu Ile Met Lys Val Gln Asn Asn Ser Val Ile Ile Asn
385                 390                 395                 400

Cys Asp Gly Phe Tyr Leu Ile Ser Leu Lys Gly Tyr Phe Ser Gln Glu
                405                 410                 415

Val Asn Ile Ser Leu His Tyr Gln Lys Asp Glu Pro Leu Phe Gln
            420                 425                 430

Leu Lys Lys Val Arg Ser Val Asn Ser Leu Met Val Ala Ser Leu Thr
        435                 440                 445

Tyr Lys Asp Lys Val Tyr Leu Asn Val Thr Thr Asp Asn Thr Ser Leu
    450                 455                 460

Asp Asp Phe His Val Asn Gly Gly Glu Leu Ile Leu Ile His Gln Asn
465                 470                 475                 480

Pro Gly Glu Phe Cys Val Leu
                485

<210> SEQ ID NO 24
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 24

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Glu Lys Asn Ile Ser
                85                  90                  95

Phe Phe Ile Leu His Phe Glu Pro Val Leu Pro Asn Asp Asn Gly Ser
            100                 105                 110

Tyr Arg Cys Ser Ala Asn Phe Gln Ser Asn Leu Ile Glu Ser His Ser
        115                 120                 125

Thr Thr Leu Tyr Val Thr Asp Val Lys Ser Ala Ser Glu Arg Pro Ser
    130                 135                 140

Lys Asp Glu Met Ala Ser
145                 150
```

<210> SEQ ID NO 25
<211> LENGTH: 127
<212> TYPE: PRT
<213> ORGANISM: Artificial Sequence
<220> FEATURE:
<223> OTHER INFORMATION: Synthetic Polypeptide

<400> SEQUENCE: 25

```
Lys Glu Ser Cys Asp Val Gln Leu Tyr Ile Lys Arg Gln Ser Glu His
1               5                   10                  15

Ser Ile Leu Ala Gly Asp Pro Phe Glu Leu Glu Cys Pro Val Lys Tyr
            20                  25                  30

Cys Ala Asn Arg Pro His Val Thr Trp Cys Lys Leu Asn Gly Thr Thr
        35                  40                  45

Cys Val Lys Leu Glu Asp Arg Gln Thr Ser Trp Lys Glu Glu Lys Asn
    50                  55                  60

Ile Ser Phe Phe Ile Leu His Phe Glu Pro Val Leu Pro Asn Asp Asn
65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg
        115                 120                 125
```

<210> SEQ ID NO 26
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 26

```
Met Asp Pro Gly Leu Gln Gln Ala Leu Asn Gly Met Ala Pro Pro Gly
1               5                   10                  15

Asp Thr Ala Met His Val Pro Ala Gly Ser Val Ala Ser His Leu Gly
            20                  25                  30

Thr Thr Ser Arg Ser Tyr Phe Tyr Leu Thr Thr Ala Thr Leu Ala Leu
        35                  40                  45

Cys Leu Val Phe Thr Val Ala Thr Ile Met Val Leu Val Val Gln Arg
    50                  55                  60

Thr Asp Ser Ile Pro Asn Ser Pro Asp Asn Val Pro Leu Lys Gly Gly
65                  70                  75                  80

Asn Cys Ser Glu Asp Leu Leu Cys Ile Leu Lys Arg Ala Pro Phe Lys
                85                  90                  95

Lys Ser Trp Ala Tyr Leu Gln Val Ala Lys His Leu Asn Lys Thr Lys
            100                 105                 110

Leu Ser Trp Asn Lys Asp Gly Ile Leu His Gly Val Arg Tyr Gln Asp
        115                 120                 125

Gly Asn Leu Val Ile Gln Phe Pro Gly Leu Tyr Phe Ile Ile Cys Gln
    130                 135                 140

Leu Gln Phe Leu Val Gln Cys Pro Asn Asn Ser Val Asp Leu Lys Leu
145                 150                 155                 160

Glu Leu Leu Ile Asn Lys His Ile Lys Lys Gln Ala Leu Val Thr Val
                165                 170                 175

Cys Glu Ser Gly Met Gln Thr Lys His Val Tyr Gln Asn Leu Ser Gln
```

```
                    180                 185                 190
Phe Leu Leu Asp Tyr Leu Gln Val Asn Thr Thr Ile Ser Val Asn Val
            195                 200                 205

Asp Thr Phe Gln Tyr Ile Asp Thr Ser Thr Phe Pro Leu Glu Asn Val
    210                 215                 220

Leu Ser Ile Phe Leu Tyr Ser Asn Ser Asp
225                 230

<210> SEQ ID NO 27
<211> LENGTH: 172
<212> TYPE: PRT
<213> ORGANISM: Artificial Sequence
<220> FEATURE:
<223> OTHER INFORMATION: Synthetic Polypeptide

<400> SEQUENCE: 27

Gln Arg Thr Asp Ser Ile Pro Asn Ser Pro Asp Asn Val Pro Leu Lys
1               5                   10                  15

Gly Gly Asn Cys Ser Glu Asp Leu Leu Cys Ile Leu Lys Arg Ala Pro
            20                  25                  30

Phe Lys Lys Ser Trp Ala Tyr Leu Gln Val Ala Lys His Leu Asn Lys
        35                  40                  45

Thr Lys Leu Ser Trp Asn Lys Asp Gly Ile Leu His Gly Val Arg Tyr
    50                  55                  60

Gln Asp Gly Asn Leu Val Ile Gln Phe Pro Gly Leu Tyr Phe Ile Ile
65                  70                  75                  80

Cys Gln Leu Gln Phe Leu Val Gln Cys Pro Asn Asn Ser Val Asp Leu
                85                  90                  95

Lys Leu Glu Leu Leu Ile Asn Lys His Ile Lys Lys Gln Ala Leu Val
            100                 105                 110

Thr Val Cys Glu Ser Gly Met Gln Thr Lys His Val Tyr Gln Asn Leu
        115                 120                 125

Ser Gln Phe Leu Leu Asp Tyr Leu Gln Val Asn Thr Thr Ile Ser Val
    130                 135                 140

Asn Val Asp Thr Phe Gln Tyr Ile Asp Thr Ser Thr Phe Pro Leu Glu
145                 150                 155                 160

Asn Val Leu Ser Ile Phe Leu Tyr Ser Asn Ser Asp
                165                 170

<210> SEQ ID NO 28
<211> LENGTH: 261
<212> TYPE: PRT
<213> ORGANISM: Artificial Sequence
<220> FEATURE:
<223> OTHER INFORMATION: Synthetic Polypeptide

<400> SEQUENCE: 28

Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80
```

```
Leu Leu Asn Cys Glu Glu Ile Lys Ser Gln Phe Glu Gly Phe Val Lys
                85                  90                  95
Asp Ile Met Leu Asn Lys Glu Glu Thr Lys Lys Glu Asn Ser Phe Glu
            100                 105                 110
Met Gln Lys Gly Asp Gln Asn Pro Gln Ile Ala Ala His Val Ile Ser
        115                 120                 125
Glu Ala Ser Ser Lys Thr Thr Ser Val Leu Gln Trp Ala Glu Lys Gly
    130                 135                 140
Tyr Tyr Thr Met Ser Asn Asn Leu Val Thr Leu Glu Asn Gly Lys Gln
145                 150                 155                 160
Leu Thr Val Lys Arg Gln Gly Leu Tyr Tyr Ile Tyr Ala Gln Val Thr
                165                 170                 175
Phe Cys Ser Asn Arg Glu Ala Ser Ser Gln Ala Pro Phe Ile Ala Ser
            180                 185                 190
Leu Cys Leu Lys Ser Pro Gly Arg Phe Glu Arg Ile Leu Leu Arg Ala
        195                 200                 205
Ala Asn Thr His Ser Ser Ala Lys Pro Cys Gly Gln Gln Ser Ile His
    210                 215                 220
Leu Gly Gly Val Phe Glu Leu Gln Pro Gly Ala Ser Val Phe Val Asn
225                 230                 235                 240
Val Thr Asp Pro Ser Gln Val Ser His Gly Thr Gly Phe Thr Ser Phe
                245                 250                 255
Gly Leu Leu Lys Leu
            260

<210> SEQ ID NO 29
<211> LENGTH: 215
<212> TYPE: PRT
<213> ORGANISM: Artificial Sequence
<220> FEATURE:
<223> OTHER INFORMATION: Synthetic Polypeptide

<400> SEQUENCE: 29

His Arg Arg Leu Asp Lys Ile Glu Asp Glu Arg Asn Leu His Glu Asp
1               5                   10                  15
Phe Val Phe Met Lys Thr Ile Gln Arg Cys Asn Thr Gly Glu Arg Ser
                20                  25                  30
Leu Ser Leu Leu Asn Cys Glu Glu Ile Lys Ser Gln Phe Glu Gly Phe
            35                  40                  45
Val Lys Asp Ile Met Leu Asn Lys Glu Glu Thr Lys Lys Glu Asn Ser
        50                  55                  60
Phe Glu Met Gln Lys Gly Asp Gln Asn Pro Gln Ile Ala Ala His Val
65                  70                  75                  80
Ile Ser Glu Ala Ser Ser Lys Thr Thr Ser Val Leu Gln Trp Ala Glu
                85                  90                  95
Lys Gly Tyr Tyr Thr Met Ser Asn Asn Leu Val Thr Leu Glu Asn Gly
            100                 105                 110
Lys Gln Leu Thr Val Lys Arg Gln Gly Leu Tyr Tyr Ile Tyr Ala Gln
        115                 120                 125
Val Thr Phe Cys Ser Asn Arg Glu Ala Ser Ser Gln Ala Pro Phe Ile
    130                 135                 140
Ala Ser Leu Cys Leu Lys Ser Pro Gly Arg Phe Glu Arg Ile Leu Leu
145                 150                 155                 160
Arg Ala Ala Asn Thr His Ser Ser Ala Lys Pro Cys Gly Gln Gln Ser
                165                 170                 175
```

```
Ile His Leu Gly Gly Val Phe Glu Leu Gln Pro Gly Ala Ser Val Phe
            180                 185                 190

Val Asn Val Thr Asp Pro Ser Gln Val Ser His Gly Thr Gly Phe Thr
            195                 200                 205

Ser Phe Gly Leu Leu Lys Leu
    210             215

<210> SEQ ID NO 30
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 30

Met Gln Gln Pro Phe Asn Tyr Pro Tyr Pro Gln Ile Tyr Trp Val Asp
1               5                   10                  15

Ser Ser Ala Ser Ser Pro Trp Ala Pro Pro Gly Thr Val Leu Pro Cys
            20                  25                  30

Pro Thr Ser Val Pro Arg Arg Pro Gly Gln Arg Arg Pro Pro Pro Pro
            35                  40                  45

Pro Pro Pro Pro Pro Leu Pro Pro Pro Pro Pro Pro Pro Pro Leu Pro
        50                  55                  60

Pro Leu Pro Leu Pro Pro Leu Lys Lys Arg Gly Asn His Ser Thr Gly
65                  70                  75                  80

Leu Cys Leu Leu Val Met Phe Phe Met Val Leu Val Ala Leu Val Gly
                85                  90                  95

Leu Gly Leu Gly Met Phe Gln Leu Phe His Leu Gln Lys Glu Leu Ala
            100                 105                 110

Glu Leu Arg Glu Ser Thr Ser Gln Met His Thr Ala Ser Ser Leu Glu
            115                 120                 125

Lys Gln Ile Gly His Pro Ser Pro Pro Pro Glu Lys Lys Glu Leu Arg
        130                 135                 140

Lys Val Ala His Leu Thr Gly Lys Ser Asn Ser Arg Ser Met Pro Leu
145                 150                 155                 160

Glu Trp Glu Asp Thr Tyr Gly Ile Val Leu Leu Ser Gly Val Lys Tyr
                165                 170                 175

Lys Lys Gly Gly Leu Val Ile Asn Glu Thr Gly Leu Tyr Phe Val Tyr
            180                 185                 190

Ser Lys Val Tyr Phe Arg Gly Gln Ser Cys Asn Asn Leu Pro Leu Ser
            195                 200                 205

His Lys Val Tyr Met Arg Asn Ser Lys Tyr Pro Gln Asp Leu Val Met
        210                 215                 220

Met Glu Gly Lys Met Met Ser Tyr Cys Thr Thr Gly Gln Met Trp Ala
225                 230                 235                 240

Arg Ser Ser Tyr Leu Gly Ala Val Phe Asn Leu Thr Ser Ala Asp His
                245                 250                 255

Leu Tyr Val Asn Val Ser Glu Leu Ser Leu Val Asn Phe Glu Glu Ser
            260                 265                 270

Gln Thr Phe Phe Gly Leu Tyr Lys Leu
        275                 280

<210> SEQ ID NO 31
<211> LENGTH: 179
<212> TYPE: PRT
<213> ORGANISM: Artificial Sequence
<220> FEATURE:
```

<223> OTHER INFORMATION: Synthetic Polypeptide

<400> SEQUENCE: 31

```
Gln Leu Phe His Leu Gln Lys Glu Leu Ala Glu Leu Arg Glu Ser Thr
1               5                   10                  15
Ser Gln Met His Thr Ala Ser Ser Leu Glu Lys Gln Ile Gly His Pro
            20                  25                  30
Ser Pro Pro Glu Lys Lys Glu Leu Arg Lys Val Ala His Leu Thr
        35                  40                  45
Gly Lys Ser Asn Ser Arg Ser Met Pro Leu Glu Trp Glu Asp Thr Tyr
    50                  55                  60
Gly Ile Val Leu Leu Ser Gly Val Lys Tyr Lys Lys Gly Gly Leu Val
65                  70                  75                  80
Ile Asn Glu Thr Gly Leu Tyr Phe Val Tyr Ser Lys Val Tyr Phe Arg
                85                  90                  95
Gly Gln Ser Cys Asn Asn Leu Pro Leu Ser His Lys Val Tyr Met Arg
            100                 105                 110
Asn Ser Lys Tyr Pro Gln Asp Leu Val Met Met Glu Gly Lys Met Met
            115                 120                 125
Ser Tyr Cys Thr Thr Gly Gln Met Trp Ala Arg Ser Ser Tyr Leu Gly
    130                 135                 140
Ala Val Phe Asn Leu Thr Ser Ala Asp His Leu Tyr Val Asn Val Ser
145                 150                 155                 160
Glu Leu Ser Leu Val Asn Phe Glu Glu Ser Gln Thr Phe Phe Gly Leu
                165                 170                 175
Tyr Lys Leu
```

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35

<400> SEQUENCE: 35

000

<210> SEQ ID NO 36
<211> LENGTH: 202
<212> TYPE: PRT
<213> ORGANISM: Artificial Sequence
<220> FEATURE:
<223> OTHER INFORMATION: Synthetic Polypeptide

<400> SEQUENCE: 36

```
Met Phe Ser His Leu Pro Phe Asp Cys Val Leu Leu Leu Leu Leu Leu
1               5                   10                  15
```

Leu Leu Thr Arg Ser Ser Glu Val Glu Tyr Arg Ala Glu Val Gly Gln
        20                  25                  30

Asn Ala Tyr Leu Pro Cys Phe Tyr Thr Pro Ala Ala Pro Gly Asn Leu
            35                  40                  45

Val Pro Val Cys Trp Lys Gly Ala Cys Pro Val Phe Glu Cys Gly
 50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
            100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Arg Gln Arg Asp Phe
130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
            180                 185                 190

Arg Asp Ser Gly Ala Thr Ile Arg Ile Gly
            195                 200

<210> SEQ ID NO 37
<211> LENGTH: 181
<212> TYPE: PRT
<213> ORGANISM: Artificial Sequence
<220> FEATURE:
<223> OTHER INFORMATION: Synthetic Polypeptide

<400> SEQUENCE: 37

Ser Glu Val Glu Tyr Arg Ala Glu Val Gly Gln Asn Ala Tyr Leu Pro
1               5                   10                  15

Cys Phe Tyr Thr Pro Ala Ala Pro Gly Asn Leu Val Pro Val Cys Trp
            20                  25                  30

Gly Lys Gly Ala Cys Pro Val Phe Glu Cys Gly Asn Val Val Leu Arg
        35                  40                  45

Thr Asp Glu Arg Asp Val Asn Tyr Trp Thr Ser Arg Tyr Trp Leu Asn
 50                  55                  60

Gly Asp Phe Arg Lys Gly Asp Val Ser Leu Thr Ile Glu Asn Val Thr
 65                  70                  75                  80

Leu Ala Asp Ser Gly Ile Tyr Cys Cys Arg Ile Gln Ile Pro Gly Ile
                85                  90                  95

Met Asn Asp Glu Lys Phe Asn Leu Lys Leu Val Ile Lys Pro Ala Lys
            100                 105                 110

Val Thr Pro Ala Pro Thr Arg Gln Arg Asp Phe Thr Ala Ala Phe Pro
            115                 120                 125

Arg Met Leu Thr Thr Arg Gly His Gly Pro Ala Glu Thr Gln Thr Leu
130                 135                 140

Gly Ser Leu Pro Asp Ile Asn Leu Thr Gln Ile Ser Thr Leu Ala Asn
145                 150                 155                 160

Glu Leu Arg Asp Ser Arg Leu Ala Asn Asp Leu Arg Asp Ser Gly Ala
                165                 170                 175

Thr Ile Arg Ile Gly
          180

<210> SEQ ID NO 38
<211> LENGTH: 150
<212> TYPE: PRT
<213> ORGANISM: Artificial Sequence
<220> FEATURE:
<223> OTHER INFORMATION: Synthetic Polypeptide

<400> SEQUENCE: 38

Met Gly Ser Pro Gly Met Val Leu Gly Leu Leu Val Gln Ile Trp Ala
1               5                   10                  15

Leu Gln Glu Ala Ser Ser Leu Ser Val Gln Gln Gly Pro Asn Leu Leu
            20                  25                  30

Gln Val Arg Gln Gly Ser Gln Ala Thr Leu Val Cys Gln Val Asp Gln
        35                  40                  45

Ala Thr Ala Trp Glu Arg Leu Arg Val Lys Trp Thr Lys Asp Gly Ala
    50                  55                  60

Ile Leu Cys Gln Pro Tyr Ile Thr Asn Gly Ser Leu Ser Leu Gly Val
65                  70                  75                  80

Cys Gly Pro Gln Gly Arg Leu Ser Trp Gln Ala Pro Ser His Leu Thr
                85                  90                  95

Leu Gln Leu Asp Pro Val Ser Leu Asn His Ser Gly Ala Tyr Val Cys
            100                 105                 110

Trp Ala Ala Val Glu Ile Pro Glu Leu Glu Glu Ala Glu Gly Asn Ile
        115                 120                 125

Thr Arg Leu Phe Val Asp Pro Asp Pro Thr Gln Asn Arg Asn Arg
    130                 135                 140

Ile Ala Ser Phe Pro Gly
145                 150

<210> SEQ ID NO 39
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 39

Leu Ser Val Gln Gln Gly Pro Asn Leu Leu Gln Val Arg Gln Gly Ser
1               5                   10                  15

Gln Ala Thr Leu Val Cys Gln Val Asp Gln Ala Thr Ala Trp Glu Arg
            20                  25                  30

Leu Arg Val Lys Trp Thr Lys Asp Gly Ala Ile Leu Cys Gln Pro Tyr
        35                  40                  45

Ile Thr Asn Gly Ser Leu Ser Leu Gly Val Cys Gly Pro Gln Gly Arg
    50                  55                  60

Leu Ser Trp Gln Ala Pro Ser His Leu Thr Leu Gln Leu Asp Pro Val
65                  70                  75                  80

Ser Leu Asn His Ser Gly Ala Tyr Val Cys Trp Ala Ala Val Glu Ile
                85                  90                  95

Pro Glu Leu Glu Glu Ala Glu Gly Asn Ile Thr Arg Leu Phe Val Asp
            100                 105                 110

Pro Asp Asp Pro Thr Gln Asn Arg Asn Arg Ile Ala Ser Phe Pro Gly
        115                 120                 125

```
<210> SEQ ID NO 40
<211> LENGTH: 281
<212> TYPE: PRT
<213> ORGANISM: Artificial Sequence
<220> FEATURE:
<223> OTHER INFORMATION: Synthetic Polypeptide

<400> SEQUENCE: 40

Met Ala Met Met Glu Val Gln Gly Gly Pro Ser Leu Gly Gln Thr Cys
1               5                   10                  15

Val Leu Ile Val Ile Phe Thr Val Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 41
<211> LENGTH: 243
<212> TYPE: PRT
<213> ORGANISM: Artificial Sequence
<220> FEATURE:
<223> OTHER INFORMATION: Synthetic Polypeptide

<400> SEQUENCE: 41

Thr Asn Glu Leu Lys Gln Met Gln Asp Lys Tyr Ser Lys Ser Gly Ile
1               5                   10                  15

Ala Cys Phe Leu Lys Glu Asp Asp Ser Tyr Trp Asp Pro Asn Asp Glu
                20                  25                  30
```

Glu Ser Met Asn Ser Pro Cys Trp Gln Val Lys Trp Gln Leu Arg Gln
            35                  40                  45

Leu Val Arg Lys Met Ile Leu Arg Thr Ser Glu Glu Thr Ile Ser Thr
 50                  55                  60

Val Gln Glu Lys Gln Gln Asn Ile Ser Pro Leu Val Arg Glu Arg Gly
 65                  70                  75                  80

Pro Gln Arg Val Ala Ala His Ile Thr Gly Thr Arg Gly Arg Ser Asn
                85                  90                  95

Thr Leu Ser Ser Pro Asn Ser Lys Asn Glu Lys Ala Leu Gly Arg Lys
            100                 105                 110

Ile Asn Ser Trp Glu Ser Ser Arg Ser Gly His Ser Phe Leu Ser Asn
            115                 120                 125

Leu His Leu Arg Asn Gly Glu Leu Val Ile His Glu Lys Gly Phe Tyr
130                 135                 140

Tyr Ile Tyr Ser Gln Thr Tyr Phe Arg Phe Gln Glu Glu Ile Lys Glu
145                 150                 155                 160

Asn Thr Lys Asn Asp Lys Gln Met Val Gln Tyr Ile Tyr Lys Tyr Thr
                165                 170                 175

Ser Tyr Pro Asp Pro Ile Leu Leu Met Lys Ser Ala Arg Asn Ser Cys
            180                 185                 190

Trp Ser Lys Asp Ala Glu Tyr Gly Leu Tyr Ser Ile Tyr Gln Gly Gly
            195                 200                 205

Ile Phe Glu Leu Lys Glu Asn Asp Arg Ile Phe Val Ser Val Thr Asn
210                 215                 220

Glu His Leu Ile Asp Met Asp His Glu Ala Ser Phe Phe Gly Ala Phe
225                 230                 235                 240

Leu Val Gly

<210> SEQ ID NO 42
<211> LENGTH: 543
<212> TYPE: PRT
<213> ORGANISM: Artificial Sequence
<220> FEATURE:
<223> OTHER INFORMATION: Synthetic Polypeptide

<400> SEQUENCE: 42

Lys Glu Ser Cys Asp Val Gln Leu Tyr Ile Lys Arg Gln Ser Glu His
 1               5                  10                  15

Ser Ile Leu Ala Gly Asp Pro Phe Glu Leu Glu Cys Pro Val Lys Tyr
                20                  25                  30

Cys Ala Asn Arg Pro His Val Thr Trp Cys Lys Leu Asn Gly Thr Thr
            35                  40                  45

Cys Val Lys Leu Glu Asp Arg Gln Thr Ser Trp Lys Glu Glu Lys Asn
 50                  55                  60

Ile Ser Phe Phe Ile Leu His Phe Glu Pro Val Leu Pro Asn Asp Asn
 65                  70                  75                  80

Gly Ser Tyr Arg Cys Ser Ala Asn Phe Gln Ser Asn Leu Ile Glu Ser
                85                  90                  95

His Ser Thr Thr Leu Tyr Val Thr Asp Val Lys Ser Ala Ser Glu Arg
            100                 105                 110

Pro Ser Lys Asp Glu Met Ala Ser Arg Pro Trp Leu Leu Tyr Arg Ser
            115                 120                 125

Lys Tyr Gly Pro Pro Cys Pro Pro Cys Pro Ala Pro Glu Phe Leu Gly
130                 135                 140

Gly Pro Ser Val Phe Leu Phe Pro Pro Lys Pro Lys Asp Gln Leu Met

```
            145                 150                 155                 160
Ile Ser Arg Thr Pro Glu Val Thr Cys Val Val Asp Val Ser Gln
                165                 170                 175

Glu Asp Pro Glu Val Gln Phe Asn Trp Tyr Val Asp Gly Val Glu Val
                180                 185                 190

His Asn Ala Lys Thr Lys Pro Arg Glu Glu Gln Phe Asn Ser Thr Tyr
                195                 200                 205

Arg Val Val Ser Val Leu Thr Val Leu His Gln Asp Trp Leu Ser Gly
            210                 215                 220

Lys Glu Tyr Lys Cys Lys Val Ser Ser Lys Gly Leu Pro Ser Ser Ile
225                 230                 235                 240

Glu Lys Thr Ile Ser Asn Ala Thr Gly Gln Pro Arg Glu Pro Gln Val
                245                 250                 255

Tyr Thr Leu Pro Pro Ser Gln Glu Glu Met Thr Lys Asn Gln Val Ser
                260                 265                 270

Leu Thr Cys Leu Val Lys Gly Phe Tyr Pro Ser Asp Ile Ala Val Glu
                275                 280                 285

Trp Glu Ser Asn Gly Gln Pro Glu Asn Asn Tyr Lys Thr Thr Pro Pro
290                 295                 300

Val Leu Asp Ser Asp Gly Ser Phe Phe Leu Tyr Ser Arg Leu Thr Val
305                 310                 315                 320

Asp Lys Ser Arg Trp Gln Glu Gly Asn Val Phe Ser Cys Ser Val Leu
                325                 330                 335

His Glu Ala Leu His Asn His Tyr Thr Gln Lys Ser Leu Ser Leu Ser
                340                 345                 350

Leu Gly Lys Ile Glu Gly Arg Met Asp Leu Gln Leu His Trp Arg Leu
            355                 360                 365

Gly Glu Met Val Thr Arg Leu Pro Asp Gly Pro Ala Gly Ser Trp Glu
            370                 375                 380

Gln Leu Ile Gln Glu Arg Arg Ser His Glu Val Asn Pro Ala Ala His
385                 390                 395                 400

Leu Thr Gly Ala Asn Ser Ser Leu Thr Gly Ser Gly Gly Pro Leu Leu
                405                 410                 415

Trp Glu Thr Gln Leu Gly Leu Ala Phe Leu Arg Gly Leu Ser Tyr His
                420                 425                 430

Asp Gly Ala Leu Val Val Thr Lys Ala Gly Tyr Tyr Tyr Ile Tyr Ser
            435                 440                 445

Lys Val Gln Leu Gly Gly Val Gly Cys Pro Leu Gly Leu Ala Ser Thr
450                 455                 460

Ile Thr His Gly Leu Tyr Lys Arg Thr Pro Arg Tyr Pro Glu Glu Leu
465                 470                 475                 480

Glu Leu Leu Val Ser Gln Gln Ser Pro Cys Gly Arg Ala Thr Ser Ser
                485                 490                 495

Ser Arg Val Trp Trp Asp Ser Ser Phe Leu Gly Gly Val Val His Leu
                500                 505                 510

Glu Ala Gly Glu Lys Val Val Val Arg Val Leu Asp Glu Arg Leu Val
            515                 520                 525

Arg Leu Arg Asp Gly Thr Arg Ser Tyr Phe Gly Ala Phe Met Val
            530                 535                 540

<210> SEQ ID NO 43
<211> LENGTH: 838
<212> TYPE: PRT
<213> ORGANISM: Artificial Sequence
```

<220> FEATURE:
<223> OTHER INFORMATION: Synthetic Polypeptide

<400> SEQUENCE: 43

```
Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly Gln Ala Ser Met Thr
    130                 135                 140

Ala Ser Pro Pro Gly Ser Leu Arg Ala Ser Asp Trp Val Ile Leu Asn
145                 150                 155                 160

Cys Ser Phe Ser Arg Pro Asp Arg Pro Ala Ser Val His Trp Phe Arg
                165                 170                 175

Asn Arg Gly Gln Gly Arg Val Pro Val Arg Glu Ser Pro His His His
            180                 185                 190

Leu Ala Glu Ser Phe Leu Phe Leu Pro Gln Val Ser Pro Met Asp Ser
        195                 200                 205

Gly Pro Trp Gly Cys Ile Leu Thr Tyr Arg Asp Gly Phe Asn Val Ser
    210                 215                 220

Ile Met Tyr Asn Leu Thr Val Leu Gly Leu Glu Pro Pro Thr Pro Leu
225                 230                 235                 240

Thr Val Tyr Ala Gly Ala Gly Ser Arg Val Gly Leu Pro Cys Arg Leu
                245                 250                 255

Pro Ala Gly Val Gly Thr Arg Ser Phe Leu Thr Ala Lys Trp Thr Pro
            260                 265                 270

Pro Gly Gly Gly Pro Asp Leu Leu Val Thr Gly Asp Asn Gly Asp Phe
        275                 280                 285

Thr Leu Arg Leu Glu Asp Val Ser Gln Ala Gln Ala Gly Thr Tyr Thr
    290                 295                 300

Cys His Ile His Leu Gln Glu Gln Gln Leu Asn Ala Thr Val Thr Leu
305                 310                 315                 320

Ala Ile Ile Thr Val Thr Pro Lys Ser Phe Gly Ser Pro Gly Ser Leu
                325                 330                 335

Gly Lys Leu Leu Cys Glu Val Thr Pro Val Ser Gly Gln Glu Arg Phe
            340                 345                 350

Val Trp Ser Ser Leu Asp Thr Pro Ser Gln Arg Ser Phe Ser Gly Pro
        355                 360                 365

Trp Leu Glu Ala Gln Glu Ala Gln Leu Leu Ser Gln Pro Trp Gln Cys
    370                 375                 380

Gln Leu Tyr Gln Gly Glu Arg Leu Leu Gly Ala Ala Val Tyr Phe Thr
385                 390                 395                 400
```

-continued

Glu Leu Ser Ser Pro Gly Ala Gln Arg Ser Gly Arg Ala Pro Gly Ala
            405                 410                 415

Leu Pro Ala Gly His Leu Ser Lys Tyr Gly Pro Cys Pro Pro Cys
        420                 425                 430

Pro Ala Pro Glu Phe Leu Gly Gly Pro Ser Val Phe Leu Phe Pro Pro
            435                 440                 445

Lys Pro Lys Asp Gln Leu Met Ile Ser Arg Thr Pro Glu Val Thr Cys
450                 455                 460

Val Val Val Asp Val Ser Gln Glu Asp Pro Glu Val Gln Phe Asn Trp
465                 470                 475                 480

Tyr Val Asp Gly Val Glu Val His Asn Ala Lys Thr Lys Pro Arg Glu
            485                 490                 495

Glu Gln Phe Asn Ser Thr Tyr Arg Val Val Ser Val Leu Thr Val Leu
            500                 505                 510

His Gln Asp Trp Leu Ser Gly Lys Glu Tyr Lys Cys Lys Val Ser Ser
            515                 520                 525

Lys Gly Leu Pro Ser Ser Ile Glu Lys Thr Ile Ser Asn Ala Thr Gly
        530                 535                 540

Gln Pro Arg Glu Pro Gln Val Tyr Thr Leu Pro Pro Ser Gln Glu Glu
545                 550                 555                 560

Met Thr Lys Asn Gln Val Ser Leu Thr Cys Leu Val Lys Gly Phe Tyr
            565                 570                 575

Pro Ser Asp Ile Ala Val Glu Trp Glu Ser Asn Gly Gln Pro Glu Asn
            580                 585                 590

Asn Tyr Lys Thr Thr Pro Pro Val Leu Asp Ser Asp Gly Ser Phe Phe
        595                 600                 605

Leu Tyr Ser Arg Leu Thr Val Asp Lys Ser Arg Trp Gln Gln Gly Asn
        610                 615                 620

Val Phe Ser Cys Ser Val Leu His Glu Ala Leu His Asn His Tyr Thr
625                 630                 635                 640

Gln Lys Ser Leu Ser Leu Ser Leu Gly Lys Ile Glu Gly Arg Met Asp
            645                 650                 655

Leu Gln Leu His Trp Arg Leu Gly Glu Met Val Thr Arg Leu Pro Asp
            660                 665                 670

Gly Pro Ala Gly Ser Trp Glu Gln Leu Ile Gln Glu Arg Arg Ser His
        675                 680                 685

Glu Val Asn Pro Ala Ala His Leu Thr Gly Ala Asn Ser Ser Leu Thr
690                 695                 700

Gly Ser Gly Gly Pro Leu Leu Trp Glu Thr Gln Leu Gly Leu Ala Phe
705                 710                 715                 720

Leu Arg Gly Leu Ser Tyr His Asp Gly Ala Leu Val Val Thr Lys Ala
            725                 730                 735

Gly Tyr Tyr Tyr Ile Tyr Ser Lys Val Gln Leu Gly Gly Val Gly Cys
            740                 745                 750

Pro Leu Gly Leu Ala Ser Thr Ile Thr His Gly Leu Tyr Lys Arg Thr
        755                 760                 765

Pro Arg Tyr Pro Glu Glu Leu Glu Leu Leu Val Ser Gln Gln Ser Pro
770                 775                 780

Cys Gly Arg Ala Thr Ser Ser Arg Val Trp Trp Asp Ser Ser Phe
785                 790                 795                 800

Leu Gly Gly Val Val His Leu Glu Ala Gly Glu Lys Val Val Val Arg
            805                 810                 815

```
Val Leu Asp Glu Arg Leu Val Arg Leu Arg Asp Gly Thr Arg Ser Tyr
            820                 825                 830
Phe Gly Ala Phe Met Val
            835

<210> SEQ ID NO 44
<211> LENGTH: 597
<212> TYPE: PRT
<213> ORGANISM: Artificial Sequence
<220> FEATURE:
<223> OTHER INFORMATION: Synthetic Polypeptide

<400> SEQUENCE: 44

Ser Glu Val Glu Tyr Arg Ala Glu Val Gly Gln Asn Ala Tyr Leu Pro
1               5                   10                  15
Cys Phe Tyr Thr Pro Ala Ala Pro Gly Asn Leu Val Pro Val Cys Trp
            20                  25                  30
Gly Lys Gly Ala Cys Pro Val Phe Glu Cys Gly Asn Val Val Leu Arg
        35                  40                  45
Thr Asp Glu Arg Asp Val Asn Tyr Trp Thr Ser Arg Tyr Trp Leu Asn
50                  55                  60
Gly Asp Phe Arg Lys Gly Asp Val Ser Leu Thr Ile Glu Asn Val Thr
65                  70                  75                  80
Leu Ala Asp Ser Gly Ile Tyr Cys Cys Arg Ile Gln Ile Pro Gly Ile
                85                  90                  95
Met Asn Asp Glu Lys Phe Asn Leu Lys Leu Val Ile Lys Pro Ala Lys
            100                 105                 110
Val Thr Pro Ala Pro Thr Arg Gln Arg Asp Phe Thr Ala Ala Phe Pro
        115                 120                 125
Arg Met Leu Thr Thr Arg Gly His Gly Pro Ala Glu Thr Gln Thr Leu
130                 135                 140
Gly Ser Leu Pro Asp Ile Asn Leu Thr Gln Ile Ser Thr Leu Ala Asn
145                 150                 155                 160
Glu Leu Arg Asp Ser Arg Leu Ala Asn Asp Leu Arg Asp Ser Gly Ala
                165                 170                 175
Thr Ile Arg Ile Gly Ser Lys Tyr Gly Pro Pro Cys Pro Pro Cys Pro
            180                 185                 190
Ala Pro Glu Phe Leu Gly Gly Pro Ser Val Phe Leu Phe Pro Pro Lys
        195                 200                 205
Pro Lys Asp Gln Leu Met Ile Ser Arg Thr Pro Glu Val Thr Cys Val
210                 215                 220
Val Val Asp Val Ser Gln Glu Asp Pro Glu Val Gln Phe Asn Trp Tyr
225                 230                 235                 240
Val Asp Gly Val Glu Val His Asn Ala Lys Thr Lys Pro Arg Glu Glu
                245                 250                 255
Gln Phe Asn Ser Thr Tyr Arg Val Val Ser Val Leu Thr Val Leu His
            260                 265                 270
Gln Asp Trp Leu Ser Gly Lys Glu Tyr Lys Cys Lys Val Ser Ser Lys
        275                 280                 285
Gly Leu Pro Ser Ser Ile Glu Lys Thr Ile Ser Asn Ala Thr Gly Gln
290                 295                 300
Pro Arg Glu Pro Gln Val Tyr Thr Leu Pro Pro Ser Gln Glu Glu Met
305                 310                 315                 320
Thr Lys Asn Gln Val Ser Leu Thr Cys Leu Val Lys Gly Phe Tyr Pro
                325                 330                 335
```

```
Ser Asp Ile Ala Val Glu Trp Glu Ser Asn Gly Gln Pro Glu Asn Asn
            340                 345                 350

Tyr Lys Thr Thr Pro Pro Val Leu Asp Ser Asp Gly Ser Phe Phe Leu
        355                 360                 365

Tyr Ser Arg Leu Thr Val Asp Lys Ser Arg Trp Gln Glu Gly Asn Val
    370                 375                 380

Phe Ser Cys Ser Val Leu His Glu Ala Leu His Asn His Tyr Thr Gln
385                 390                 395                 400

Lys Ser Leu Ser Leu Ser Leu Gly Lys Ile Glu Gly Arg Met Asp Leu
                405                 410                 415

Gln Leu His Trp Arg Leu Gly Glu Met Val Thr Arg Leu Pro Asp Gly
            420                 425                 430

Pro Ala Gly Ser Trp Glu Gln Leu Ile Gln Glu Arg Arg Ser His Glu
        435                 440                 445

Val Asn Pro Ala Ala His Leu Thr Gly Ala Asn Ser Ser Leu Thr Gly
    450                 455                 460

Ser Gly Gly Pro Leu Leu Trp Glu Thr Gln Leu Gly Leu Ala Phe Leu
465                 470                 475                 480

Arg Gly Leu Ser Tyr His Asp Gly Ala Leu Val Val Thr Lys Ala Gly
                485                 490                 495

Tyr Tyr Tyr Ile Tyr Ser Lys Val Gln Leu Gly Gly Val Gly Cys Pro
            500                 505                 510

Leu Gly Leu Ala Ser Thr Ile Thr His Gly Leu Tyr Lys Arg Thr Pro
        515                 520                 525

Arg Tyr Pro Glu Glu Leu Glu Leu Leu Val Ser Gln Gln Ser Pro Cys
    530                 535                 540

Gly Arg Ala Thr Ser Ser Ser Arg Val Trp Trp Asp Ser Ser Phe Leu
545                 550                 555                 560

Gly Gly Val Val His Leu Glu Ala Gly Glu Lys Val Val Arg Val
                565                 570                 575

Leu Asp Glu Arg Leu Val Arg Leu Arg Asp Gly Thr Arg Ser Tyr Phe
        580                 585                 590

Gly Ala Phe Met Val
        595

<210> SEQ ID NO 45
<211> LENGTH: 569
<212> TYPE: PRT
<213> ORGANISM: Artificial Sequence
<220> FEATURE:
<223> OTHER INFORMATION: Synthetic Polypeptide

<400> SEQUENCE: 45

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
                20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
        50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
                85                  90                  95
```

-continued

```
Tyr Thr Gly Arg Ile Phe Leu Glu Val Leu Glu Ser Ser Val Ala Glu
            100                 105                 110

His Gly Ala Arg Phe Gln Ile Pro Ser Lys Tyr Gly Pro Pro Cys Pro
            115                 120                 125

Pro Cys Pro Ala Pro Glu Phe Leu Gly Gly Pro Ser Val Phe Leu Phe
            130                 135                 140

Pro Pro Lys Pro Lys Asp Gln Leu Met Ile Ser Arg Thr Pro Glu Val
145                 150                 155                 160

Thr Cys Val Val Val Asp Val Ser Gln Glu Asp Pro Glu Val Gln Phe
                    165                 170                 175

Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
            195                 200                 205

Val Leu His Gln Asp Trp Leu Ser Gly Lys Glu Tyr Lys Cys Lys Val
            210                 215                 220

Ser Ser Lys Gly Leu Pro Ser Ser Ile Glu Lys Thr Ile Ser Asn Ala
225                 230                 235                 240

Thr Gly Gln Pro Arg Glu Pro Gln Val Tyr Thr Leu Pro Pro Ser Gln
                    245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Leu His Glu Ala Leu His Asn His
                    325                 330                 335

Tyr Thr Gln Lys Ser Leu Ser Leu Ser Leu Gly Lys Ile Glu Gly Arg
            340                 345                 350

Met Asp His Arg Arg Leu Asp Lys Ile Glu Asp Glu Arg Asn Leu His
            355                 360                 365

Glu Asp Phe Val Phe Met Lys Thr Ile Gln Arg Cys Asn Thr Gly Glu
            370                 375                 380

Arg Ser Leu Ser Leu Leu Asn Cys Glu Glu Ile Lys Ser Gln Phe Glu
385                 390                 395                 400

Gly Phe Val Lys Asp Ile Met Leu Asn Lys Glu Glu Thr Lys Lys Glu
                    405                 410                 415

Asn Ser Phe Glu Met Gln Lys Gly Asp Gln Asn Pro Gln Ile Ala Ala
            420                 425                 430

His Val Ile Ser Glu Ala Ser Ser Lys Thr Thr Ser Val Leu Gln Trp
            435                 440                 445

Ala Glu Lys Gly Tyr Tyr Thr Met Ser Asn Asn Leu Val Thr Leu Glu
            450                 455                 460

Asn Gly Lys Gln Leu Thr Val Lys Arg Gln Gly Leu Tyr Tyr Ile Tyr
465                 470                 475                 480

Ala Gln Val Thr Phe Cys Ser Asn Arg Glu Ala Ser Ser Gln Ala Pro
                    485                 490                 495

Phe Ile Ala Ser Leu Cys Leu Lys Ser Pro Gly Arg Phe Glu Arg Ile
            500                 505                 510

Leu Leu Arg Ala Ala Asn Thr His Ser Ser Ala Lys Pro Cys Gly Gln
```

```
                    515                 520                 525
Gln Ser Ile His Leu Gly Gly Val Phe Glu Leu Gln Pro Gly Ala Ser
            530                 535                 540

Val Phe Val Asn Val Thr Asp Pro Ser Gln Val Ser His Gly Thr Gly
545                 550                 555                 560

Phe Thr Ser Phe Gly Leu Leu Lys Leu
                565

<210> SEQ ID NO 46
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 46

Ala Pro Glu Phe Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser Gln Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Tyr Arg Val Val Ser Val Leu Thr Val Leu His
65                  70                  75                  80

Gln Asp Trp Leu Ser Gly Lys Glu Tyr Lys Cys Lys Val Ser Ser Lys
                85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Met His Glu Ala Leu His Asn His Tyr Thr Gln
        195                 200                 205

Lys Ser Leu Ser Leu Ser Leu Gly Lys
    210                 215

<210> SEQ ID NO 47
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 47

Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30
```

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Thr Pro His
 65                  70                  75                  80

Ser Asp Trp Leu Ser Gly Lys Glu Tyr Lys Cys Lys Val Ser Ser Lys
                 85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Ser Trp Gln Glu Gly Asn Val
            180                 185                 190

Phe Ser Cys Ser Val Leu His Glu Ala Leu His Asn His Tyr Thr Gln
            195                 200                 205

Lys Ser Leu Ser Leu Ser Leu Gly Lys
            210                 215

<210> SEQ ID NO 48
<211> LENGTH: 217
<212> TYPE: PRT
<213> ORGANISM: Artificial Sequence
<220> FEATURE:
<223> OTHER INFORMATION: Synthetic Polypeptide

<400> SEQUENCE: 48

Ala Pro Glu Phe Leu Gly Gly Pro Ser Val Phe Leu Phe Pro Pro Lys
1               5                   10                  15

Pro Lys Asp Gln Leu Met Ile Ser Arg Thr Pro Glu Val Thr Cys Val
            20                  25                  30

Val Val Asp Val Ser Gln Glu Asp Pro Glu Val Gln Phe Asn Trp Tyr
            35                  40                  45

Val Asp Gly Val Glu Val His Asn Ala Lys Thr Lys Pro Arg Glu Glu
 50                  55                  60

Gln Phe Asn Ser Thr Tyr Arg Val Val Ser Val Leu Thr Val Leu His
 65                  70                  75                  80

Gln Asp Trp Leu Ser Gly Lys Glu Tyr Lys Cys Lys Val Ser Ser Lys
                 85                  90                  95

Gly Leu Pro Ser Ser Ile Glu Lys Thr Ile Ser Asn Ala Thr Gly Gln
            100                 105                 110

Pro Arg Glu Pro Gln Val Tyr Thr Leu Pro Pro Ser Gln Glu Glu Met
            115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Arg Leu Thr Val Asp Lys Ser Arg Trp Gln Glu Gly Asn Val
            180                 185                 190

Phe Ser Cys Ser Val Leu His Glu Ala Leu His Asn His Tyr Thr Gln
        195                 200                 205

Lys Ser Leu Ser Leu Ser Leu Gly Lys
    210                 215

<210> SEQ ID NO 49
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 49

Ser Lys Tyr Gly Pro Pro Cys Pro Ser Cys Pro
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 50

Ser Lys Tyr Gly Pro Pro Cys Pro Pro Cys Pro
1               5                   10

<210> SEQ ID NO 51
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 51

Ser Lys Tyr Gly Pro Pro
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 52

Ile Glu Gly Arg Met Asp
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 53

Gly Gly Gly Val Pro Arg Asp Cys Gly
1               5

<210> SEQ ID NO 54
<211> LENGTH: 15
<212> TYPE: PRT
<213> ORGANISM: Artificial Sequence

```
<220> FEATURE:
<223> OTHER INFORMATION: Synthetic Polypeptide

<400> SEQUENCE: 54

Ile Glu Gly Arg Met Asp Gly Gly Gly Ala Gly Gly Gly
1               5                   10                  15

<210> SEQ ID NO 55
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 55

Gly Gly Gly Ser Gly Gly Gly Ser
1               5

<210> SEQ ID NO 56
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 56

Gly Gly Gly Ser Gly Gly Gly Gly Ser Gly Gly Gly
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 57

Glu Gly Lys Ser Ser Gly Ser Gly Ser Glu Ser Lys Ser Thr
1               5                   10

<210> SEQ ID NO 58
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 58

Gly Gly Ser Gly
1

<210> SEQ ID NO 59
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 59

Gly Gly Ser Gly Gly Gly Ser Gly Gly Gly Ser Gly
1               5                   10

<210> SEQ ID NO 60
<211> LENGTH: 15
<212> TYPE: PRT
<213> ORGANISM: Artificial Sequence
<220> FEATURE:
```

<223> OTHER INFORMATION: Synthetic Polypeptide

<400> SEQUENCE: 60

Glu Ala Ala Ala Lys Glu Ala Ala Ala Lys Glu Ala Ala Ala Lys
1               5                   10                  15

<210> SEQ ID NO 61
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 61

Glu Ala Ala Ala Arg Glu Ala Ala Ala Arg Glu Ala Ala Ala Arg Glu
1               5                   10                  15

Ala Ala Ala Arg
            20

<210> SEQ ID NO 62
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 62

Gly Gly Gly Gly Ser Gly Gly Gly Gly Ser Gly Gly Gly Gly Ser Ala
1               5                   10                  15

Ser

<210> SEQ ID NO 63
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 63

Gly Gly Gly Gly Ala Gly Gly Gly Gly
1               5

<210> SEQ ID NO 64

<400> SEQUENCE: 64

000

<210> SEQ ID NO 65
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 65

Gly Ser Gly Ser Gly Ser
1               5

<210> SEQ ID NO 66
<211> LENGTH: 10
<212> TYPE: PRT
<213> ORGANISM: Artificial Sequence
<220> FEATURE:
<223> OTHER INFORMATION: Synthetic Polypeptide

```
<400> SEQUENCE: 66

Gly Ser Gly Ser Gly Ser Gly Ser Gly Ser
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 67

Gly Gly Gly Gly Ser Ala Ser
1               5

<210> SEQ ID NO 68
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 68

Ala Pro Ala Pro Ala Pro Ala Pro Ala Pro Ala Pro Ala Pro Ala Pro
1               5                   10                  15

Ala Pro Ala Pro
            20

<210> SEQ ID NO 69
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 69

Cys Pro Pro Cys
1

<210> SEQ ID NO 70
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 70

Gly Gly Gly Gly Ser
1               5

<210> SEQ ID NO 71
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 71

Gly Gly Gly Gly Ser Gly Gly Gly Gly Ser
1               5                   10

<210> SEQ ID NO 72
<211> LENGTH: 15
<212> TYPE: PRT
<213> ORGANISM: Artificial Sequence
<220> FEATURE:
```

<223> OTHER INFORMATION: Synthetic Polypeptide

<400> SEQUENCE: 72

Gly Gly Gly Gly Ser Gly Gly Gly Gly Ser Gly Gly Gly Gly Ser
1               5                   10                  15

<210> SEQ ID NO 73
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 73

Gly Gly Gly Gly Ser Gly Gly Gly Gly Ser Gly Gly Gly Gly Ser Gly
1               5                   10                  15

Gly Gly Gly Ser
            20

<210> SEQ ID NO 74
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 74

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 75
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 75

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 76
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 76

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 77
<211> LENGTH: 40
<212> TYPE: PRT
<213> ORGANISM: Artificial Sequence

```
<220> FEATURE:
<223> OTHER INFORMATION: Synthetic Polypeptide

<400> SEQUENCE: 77

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
                20                  25                  30

Gly Gly Ser Gly Gly Gly Gly Ser
        35                  40

<210> SEQ ID NO 78
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 78

Gly Gly Ser Gly Gly Ser Gly Gly Gly Ser Gly Gly Gly Ser
1               5                   10                  15

<210> SEQ ID NO 79
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 79

Gly Gly Gly Gly Gly Gly Gly Gly
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 80

Gly Gly Gly Gly Gly Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 81

Glu Ala Ala Ala Lys
1               5

<210> SEQ ID NO 82
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 82

Glu Ala Ala Ala Lys Glu Ala Ala Ala Lys
1               5                   10
```

<210> SEQ ID NO 83
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 83

Glu Ala Ala Ala Lys Glu Ala Ala Ala Lys Glu Ala Ala Ala Lys
1               5                   10                  15

<210> SEQ ID NO 84
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 84

Ala Glu Ala Ala Ala Lys Glu Ala Ala Ala Lys Ala
1               5                   10

<210> SEQ ID NO 85
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 85

Ala Glu Ala Ala Ala Lys Glu Ala Ala Ala Lys Glu Ala Ala Ala Lys
1               5                   10                  15

Ala

<210> SEQ ID NO 86
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 86

Ala Glu Ala Ala Ala Lys Glu Ala Ala Ala Lys Glu Ala Ala Ala Lys
1               5                   10                  15

Glu Ala Ala Ala Lys Ala
            20

<210> SEQ ID NO 87
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 87

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 88
<211> LENGTH: 46
<212> TYPE: PRT
<213> ORGANISM: Artificial Sequence
<220> FEATURE:

<223> OTHER INFORMATION: Synthetic Polypeptide

<400> SEQUENCE: 88

Ala Glu Ala Ala Ala Lys Glu Ala Ala Lys Glu Ala Ala Ala Lys
1               5                   10                  15
Glu Ala Ala Ala Lys Ala Leu Glu Ala Glu Ala Ala Lys Glu Ala
            20                  25                  30
Ala Ala Lys Glu Ala Ala Lys Glu Ala Ala Ala Lys Ala
        35                  40                  45

<210> SEQ ID NO 89
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 89

Pro Ala Pro Ala Pro
1               5

<210> SEQ ID NO 90
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 90

Lys Glu Ser Gly Ser Val Ser Ser Glu Gln Leu Ala Gln Phe Arg Ser
1               5                   10                  15
Leu Asp

<210> SEQ ID NO 91
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 91

Gly Ser Ala Gly Ser Ala Ala Gly Ser Gly Glu Phe
1               5                   10

<210> SEQ ID NO 92
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 92

Gly Gly Gly Ser Glu
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 93

Gly Ser Glu Ser Gly
1               5

<210> SEQ ID NO 94
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 94

Gly Ser Glu Gly Ser
1               5

<210> SEQ ID NO 95
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 95

Gly Glu Gly Gly Ser Gly Glu Gly Ser Ser Gly Glu Gly Ser Ser Ser
1               5                   10                  15

Glu Gly Gly Ser Glu Gly Gly Gly Ser Glu Gly Gly Gly Ser Glu
            20                  25                  30

Gly Gly Ser
        35

<210> SEQ ID NO 96
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 96

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
            195                 200                 205

Met His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 97
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 97

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
        195                 200                 205

Leu His Glu Ala Leu His Asn His Tyr Thr Gln Lys Ser Leu Ser Leu
    210                 215                 220

Ser Leu Gly Lys Ile Glu Gly Arg Met Asp
225                 230

<210> SEQ ID NO 98
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 98

Ser Lys Tyr Gly Pro Pro Cys Pro Ser Cys Pro Ala Pro Glu Phe Leu
1               5                   10                  15

Gly Gly Pro Ser Val Phe Leu Phe Pro Pro Lys Pro Lys Asp Gln Leu
            20                  25                  30

```
Met Ile Ser Arg Thr Pro Glu Val Thr Cys Val Val Val Asp Val Ser
         35                  40                  45

Gln Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Tyr Arg Val Val Ser Val Leu Thr Val Leu His Gln Asp Trp Leu Ser
                 85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
210                 215                 220

Ser Leu Gly Lys Ile Glu Gly Arg Met Asp
225                 230
```

<210> SEQ ID NO 99
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 99

```
Ser Lys Tyr Gly Pro Pro Cys Pro Pro Cys Pro Ala Pro Glu Phe Leu
 1               5                  10                  15

Gly Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
         35                  40                  45

Gln Glu Asp Pro Glu Val Gln Phe Asn Trp Tyr Val Asp Gly Val Glu
 50                  55                  60

Val His Asn Ala Lys Thr Lys Pro Arg Glu Glu Gln Phe Asn Ser Thr
 65                  70                  75                  80

Tyr Arg Val Val Ser Val Leu Thr Val Leu His Gln Asp Trp Leu Ser
                 85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
        115                 120                 125

Val Tyr Thr Leu Pro Pro Ser Gln Glu Glu Met Thr Lys Asn Gln Val
130                 135                 140

Ser Leu Thr Cys Leu Val Lys Gly Phe Tyr Pro Ser Asp Ile Ala Val
145                 150                 155                 160
```

Glu Trp Glu Ser Asn Gly Gln Pro Glu Asn Asn Tyr Lys Thr Thr Pro
            165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
            195                 200                 205

Met His Glu Ala Leu His Asn His Tyr Thr Gln Lys Ser Leu Ser Leu
            210                 215                 220

Ser Leu Gly Lys Ile Glu Gly Arg Met Asp
225                 230

<210> SEQ ID NO 100
<211> LENGTH: 234
<212> TYPE: PRT
<213> ORGANISM: Artificial Sequence
<220> FEATURE:
<223> OTHER INFORMATION: Synthetic Polypeptide

<400> SEQUENCE: 100

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Thr Pro His Ser Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
            165                 170                 175

Pro Val Leu Asp Ser Asp Gly Ser Phe Phe Leu Tyr Ser Arg Leu Thr
            180                 185                 190

Val Asp Lys Ser Ser Trp Gln Glu Gly Asn Val Phe Ser Cys Ser Val
            195                 200                 205

Leu His Glu Ala Leu His Asn His Tyr Thr Gln Lys Ser Leu Ser Leu
            210                 215                 220

Ser Leu Gly Lys Ile Glu Gly Arg Met Asp
225                 230

<210> SEQ ID NO 101
<211> LENGTH: 234
<212> TYPE: PRT
<213> ORGANISM: Artificial Sequence
<220> FEATURE:
<223> OTHER INFORMATION: Synthetic Polypeptide

```
<400> SEQUENCE: 101

Ser Lys Tyr Gly Pro Pro Cys Pro Pro Cys Pro Ala Pro Glu Phe Leu
1               5                   10                  15

Gly Gly Pro Ser Val Phe Leu Phe Pro Pro Lys Pro Lys Asp Gln Leu
            20                  25                  30

Met Ile Ser Arg Thr Pro Glu Val Thr Cys Val Val Val Asp Val Ser
            35                  40                  45

Gln Glu Asp Pro Glu Val Gln Phe Asn Trp Tyr Val Asp Gly Val Glu
        50                  55                  60

Val His Asn Ala Lys Thr Lys Pro Arg Glu Glu Gln Phe Asn Ser Thr
65                  70                  75                  80

Tyr Arg Val Val Ser Val Leu Thr Val Leu His Gln Asp Trp Leu Ser
                85                  90                  95

Gly Lys Glu Tyr Lys Cys Lys Val Ser Ser Lys Gly Leu Pro Ser Ser
            100                 105                 110

Ile Glu Lys Thr Ile Ser Asn Ala Thr Gly Gln Pro Arg Glu Pro Gln
            115                 120                 125

Val Tyr Thr Leu Pro Pro Ser Gln Glu Glu Met Thr Lys Asn Gln Val
        130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Leu His Glu Ala Leu His Asn His Tyr Thr Gln Lys Ser Leu Ser Leu
        210                 215                 220

Ser Leu Gly Lys Ile Glu Gly Arg Met Asp
225                 230
```

TIGIT- AND LIGHT-BASED CHIMERIC PROTEINS

PRIORITY

This application is a continuation of U.S. application Ser. No. 16/857,787, filed Apr. 24, 2020. U.S. application Ser. No. 16/857,787 is a continuation of U.S. application Ser. No. 16/484,850, filed Aug. 9, 2019. U.S. application Ser. No. 16/484,850 is the 371 National Stage Entry of PCT/US18/20037, filed Feb. 27, 2018, which claims the benefit of, and priority to, U.S. Provisional Application No. 62/464,002, filed Feb. 27, 2017, the contents of each of which are hereby incorporated by reference in their entireties.

DESCRIPTION OF THE TEXT FILE SUBMITTED ELECTRONICALLY

This application contains a sequence listing. It has been submitted electronically via EFS-Web as an ASCII text file entitled "SHK-001US1C2_SequenceListing_ST25". The sequence listing is 143,360 bytes in size, and was created on Sep. 3, 2020. The sequence listing is hereby incorporated by reference in its entirety.

TECHNICAL FIELD

The present invention relates to, inter alia, compositions and methods, including chimeric proteins that find use in the treatment of disease, such as immunotherapies for cancer and autoimmunity.

BACKGROUND

The immune system is central to the body's response to foreign entities that can cause disease. However, many cancers have developed mechanisms to avoid the immune system by, for instance, delivering or propagating immune inhibitory signals. Thus, there remains a need to develop therapeutics that are endowed with multiple functionalities—for instance, reversing immune inhibitory signal and stimulating an anti-cancer immune response.

SUMMARY

Accordingly, in various aspects, the present invention provides for compositions and methods that are useful for cancer immunotherapy. For instance, the present invention, in part, relates to specific chimeric proteins that reverse or suppresses immune inhibitory signals while providing immune activating or co-stimulatory signals. Importantly, inter alia, the present invention provides for improved chimeric proteins that can maintain a stable and producible multimeric state based on, without wishing to be bound by theory, stabilization in a linker region including one or more disulfide bonds. Accordingly, the present compositions and methods overcome various deficiencies in producing bispecific agents.

In some aspects, the chimeric protein is of a general structure of: N terminus-(a)-(b)-(c)-C terminus, where (a) is a first domain comprising an extracellular domain of a Type I transmembrane protein, (b) is a linker comprising at least one cysteine residue capable of forming a disulfide bond (including without limitation, hinge-CH2-CH3 Fc domain is derived from human IgG4), and (c) is a second domain comprising an extracellular domain of Type II transmembrane protein, where the linker connects the first domain and the second domain and optionally comprises one or more joining linkers as described herein.

For instance, in embodiments, the extracellular domain of a Type I transmembrane protein is from TIGIT (VSIG9, VSTM3).

In embodiments, the chimeric protein is of a general structure of: N terminus-(a)-(b)-(c)-C terminus, where (a) is a first domain comprising an extracellular domain of a Type I transmembrane protein, the transmembrane protein being TIGIT, (b) is a linker comprising at least one cysteine residue capable of forming a disulfide bond (including without limitation, hinge-CH2-CH3 Fc domain is derived from human IgG4), and (c) is a second domain comprising an extracellular domain of Type II transmembrane protein, the transmembrane protein being selected from 4-1BBL (TNFSF9), GITRL (TNFSF18), TL1A (TNFSF15), and LIGHT (TNFSF14), where the linker connects the first domain and the second domain and optionally comprises one or more joining linkers as described herein.

For instance, in embodiments, the extracellular domain of a Type II transmembrane protein is from LIGHT.

In embodiments, the chimeric protein is of a general structure of: N terminus-(a)-(b)-(c)-C terminus, where (a) is a first domain comprising an extracellular domain of a Type I transmembrane protein, the transmembrane protein being selected from PD-1, CD172a(SIRPa), and TIGIT, (b) is a linker comprising at least one cysteine residue capable of forming a disulfide bond (including without limitation, hinge-CH2-CH3 Fc domain is derived from human IgG4), and (c) is a second domain comprising an extracellular domain of Type II transmembrane protein, the transmembrane protein being LIGHT, where the linker connects the first domain and the second domain and optionally comprises one or more joining linkers as described herein.

In some aspects, there is provided a method for treating cancer or an inflammatory disease comprising administering an effective amount of a pharmaceutical composition of the afore-mentioned chimeric proteins. In embodiments, the subject's T cells are activated when bound by the second domain of the chimeric protein and (a) one or more tumor cells are prevented from transmitting an immunosuppressive signal when bound by the first domain of the chimeric protein, (b) a quantifiable cytokine response in the peripheral blood of the subject is achieved, and/or (c) tumor growth is reduced in the subject in need thereof as compared to a subject treated with antibodies directed to the Type I or Type II protein, or their respective ligands or receptors. In embodiments, the method stimulates signaling of one or more of LIGHT, 4-1BBL, GITRL, and TL1A and activates antigen-presenting cells. In embodiments, the method reduces the amount or activity of regulatory T cells (Tregs) as compared to untreated subjects or subjects treated with antibodies directed to the Type I or Type II protein, or their respective ligands or receptors. In embodiments, the method increases priming of effector T cells in draining lymph nodes of the subject as compared to untreated subjects or subjects treated with antibodies directed to the Type I or Type II protein, or their respective ligands or receptors. In embodiments, the method causes an overall decrease in immunosuppressive cells and a shift toward a more inflammatory tumor environment as compared to untreated subjects or subjects treated with antibodies directed to the Type I or Type II protein, or their respective ligands or receptors.

Any aspect or embodiment described herein can be combined with any other aspect or embodiment as disclosed herein.

BRIEF DESCRIPTION OF THE DRAWINGS

FIG. 1B depicts the linkage of a Type I and Type II membrane protein by removal of the transmembrane and intracellular domains of each protein, and where the liberated extracellular domains (ECD) from each protein have been adjoined by a linker sequence. The ECD in this depiction may include the entire amino acid sequence of a candidate Type I or Type II protein which is typically localized outside the cell membrane, or any portion thereof which retains binding to the intended receptor or ligand. FIG. 1D depicts adjoined extracellular domains in a linear construct wherein the extracellular domain of the Type I membrane protein faces the "left" side of the construct and the extracellular domain of the Type II membrane protein faces the "right" side of the construct.

FIG. 2A to FIG. 2C illustrate the mechainsms through which a PD-1-Fc-OX40L chimeric protein binds to its target molecules to creates a synapse between cells; thus, PD-1-Fc-OX40L is illustrative of the mechanism through which chimeric proteins of the present invention operate.

FIG. 7 is a table of results showing the identified binding partners of human TIGIT-Fc-OX40L from a microarray containing approximately 6,000 human membrane proteins. In each case, the expected binding partners for each candidate molecule were identified by the screen. There was no evidence of non-specific binding to other human proteins, and binding to Galectin-1 is seen in the screen for all Fc-containing fusion proteins.

FIG. 10B are graphs showing binding of human CD172a(SIRPα)-Fc-LIGHT to CHO-K1 cells expressing mouse CD47 (Detection Ab Only Control peak is far left, remainder of peak distribute left to righty by increasing concentration (i.e. 250 is far right)).

FIG. 11A are graphs showing binding of human CD172a (SIRPα)-Fc-LIGHT and CD172a(SIRPα)-Fc-CD40L to cynomolgus macaque red blood cells in comparison to CD47 specific antibodies (clone CC2C6 or CC900002), top left. Lysis of cynomolgus macaque red blood cells following each treatment is shown over a titration curve in the bottom left and an example plate is shown on right. Triton-X was used as a positive control to cause lysis of cynomolgus macaque red blood cells (for reference, in the top panel, at X-axis point 2 nM, curves top to bottom are anti-CD47/

IgG-APC, anti-CD47-FITC, SIRPα-Fc-LIGHT, and SIRPα-Fc-CD40L while in the bottom panel at X-axis point 2, curves top to bottom are Triton-X100, anti-CD47 (CC2C6) and anti-CD47 (CC9002), SIRPα-Fc-LIGHT, and SIRPα-Fc-CD40L all overlay).

FIG. 20A assays IL2 secretion and FIG. 20B assays TNFα secretion. For FIG. 20A and FIG. 20B, the order of conditions for each concentration of SEB mirrors from left to right, the conditions listed in the legends from top to bottom (e.g. α-PD-1 (RMP1-14) is the third from the top in the legends and is therefore third from the left in the graphs, PD-1-Fc-LIGHT (10 nM) is the third from the bottom in the legends and is therefore third from the right in the graphs, and so forth).

FIG. 22A to FIG. 22B shows results from in vivo tumor studies demonstrating the anti-tumor efficacy of mTIGIT-Fc-OX40L, mCD172a(SIRPα)-Fc-LIGHT, mTIGIT-Fc-LIGHT, and mPD-1-Fc-LIGHT chimeric proteins in comparison with monoclonal antibodies to TIGIT, CD47, OX40, PD-1 or a combination of TIGIT and OX40. A CT26 tumor was implanted into Balb/c mice prior to treatment with the indicated regimens. FIG. 22A shows the evolution of tumor size over forty days after tumor inoculation for each group. FIG. 22B shows the overall survival percentage of mice through forty days after tumor inoculation and the number of complete tumor rejectors are indicate in the embedded table. In FIG. 22A and FIG. 22B, the treatment conditions are identified by letters.

FIG. 32 is a table showing joining linkers and Fc linkers that can be combined into illustrative modular linkers. The illustrative modular linkers shown can be combined with any herein-described Type I and Type II proteins and/or extracellular domains of a herein-described Type I and Type II proteins to form a chimeric protein of the present invention.

DETAILED DESCRIPTION

Figure 1B:
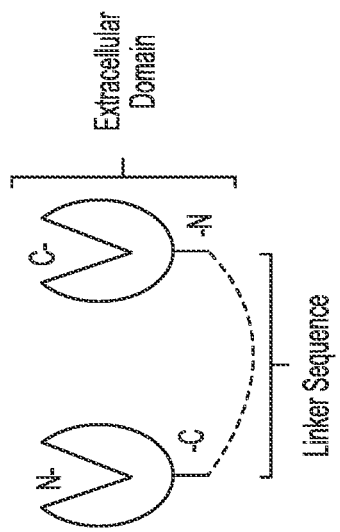
FIG. 1A to FIG. 1D show schematic illustrations of how a Type I and Type II membrane protein (FIG. 1A and FIG. 1C) may be engineered with transmembrane and intracellular domains removed and adjoined using a linker sequence (FIG. 1B) to generate a single chimeric protein wherein the extracellular domains of the Type I and Type II membrane proteins each face outward in a single chimeric protein.

The present invention is based, in part, on the discovery that chimeric proteins can be engineered from the extracellular, or effector, regions of immune-modulating transmembrane proteins in a manner that exploits the orientations of these proteins (e.g. Type I versus Type II) and therefore allows the delivery of immune stimulatory and/or immune inhibitory signals, including, for example, masking an immune inhibitory signal and replacing it with an immune stimulatory signal in the treatment of cancer, specifically, that LIGHT- and/or TIGIT-based chimeric proteins have medical uses.

Chimeric Proteins

In some aspects, the chimeric protein is of a general structure of: N terminus-(a)-(b)-(c)-C terminus, where (a) is a first domain comprising an extracellular domain of a Type I transmembrane protein, (b) is a linker having at least one cysteine residue capable of forming a disulfide bond (including without limitation, hinge-CH2-CH3 Fc domain is derived from human IgG4), and (c) is a second domain comprising an extracellular domain of Type II transmembrane protein, where the linker connects the first domain and the second domain and optionally comprises one or more joining linkers as described herein, where one of the first and second extracellular domains is an immune inhibitory signal and one of the first and second extracellular domains is an immune stimulatory signal.

In embodiments, chimeric protein refers to a recombinant fusion protein, e.g. a single polypeptide having the extracellular domains described herein. For example, in embodiments, the chimeric protein is translated as a single unit in a cell. In embodiments, chimeric protein refers to a recombinant protein of multiple polypeptides, e.g. multiple extracellular domains described herein, that are linked to yield a single unit, e.g. in vitro (e.g. with one or more synthetic linkers described herein).

In embodiments, the chimeric protein is chemically synthesized as one polypeptide or each domain may be chemically synthesized separately and then combined. In embodiments, a portion of the chimeric protein is translated and a portion is chemically synthesized.

In embodiments, an extracellular domain refers to a portion of a transmembrane protein which is capable of interacting with the extracellular environment. In embodiments, an extracellular domain refers to a portion of a transmembrane protein which is sufficient to bind to a ligand or receptor and effective transmit a signal to a cell. In embodiments, an extracellular domain is the entire amino acid sequence of a transmembrane protein which is external of a cell or the cell membrane. In embodiments, an extracellular domain is the that portion of an amino acid sequence of a transmembrane protein which is external of a cell or the cell membrane and is needed for signal transduction and/or ligand binding as may be assayed using methods know in the art (e.g. in vitro ligand binding and/or cellular activation assays).

In embodiments, an immune inhibitory signal refers to a signal that diminishes or eliminates an immune response. For example, in the context of oncology, such signals may diminish or eliminate antitumor immunity. Under normal physiological conditions, inhibitory signals are useful in the maintenance of self-tolerance (e.g. prevention of autoimmunity) and also to protect tissues from damage when the immune system is responding to pathogenic infection. For instance, without limitation, immune inhibitory signal may be identified by detecting an increase in cellular proliferation, cytokine production, cell killing activity or phagocytic activity when such an inhibitory signal is blocked.

In embodiments, an immune stimulatory signal refers to a signal that enhances an immune response. For example, in the context of oncology, such signals may enhance antitumor immunity. For instance, without limitation, immune stimulatory signal may be identified by directly stimulating proliferation, cytokine production, killing activity or phagocytic activity of leukocytes. Specific examples include direct stimulation of TNF superfamily receptors such as OX40, LTbR, 4-1BB or TNFRSF25 using either receptor agonist antibodies or using chimeric proteins encoding the ligands for such receptors (OX40L, LIGHT, 4-1BBL, TL1A, respectively). Stimulation from any one of these receptors may directly stimulate the proliferation and cytokine production of individual T cell subsets. Another example includes direct stimulation of an immune inhibitory cell with through a receptor that inhibits the activity of such an immune suppressor cell. This would include, for example, stimulation of CD4+FoxP3+ regulatory T cells with a GITR agonist antibody or GITRL containing chimeric protein, which would reduce the ability of those regulatory T cells to suppress the proliferation of conventional CD4+ or CD8+ T cells. In another example, this would include stimulation of CD40 on the surface of an antigen presenting cell using a CD40 agonist antibody or a chimeric protein containing CD40L, causing activation of antigen presenting cells including enhanced ability of those cells to present antigen in the context of appropriate native costimulatory molecules, including those in the B7 or TNF superfamily. In another example, this would include stimulation of LTBR on the surface of a lymphoid or stromal cell using a LIGHT containing chimeric protein, causing activation of the lymphoid cell and/or production of pro-inflammatory cytokines or chemokines to further stimulate an immune response, optionally within a tumor.

Membrane proteins typically consist of an extracellular domain, one or a series of transmembrane domains, and an intracellular domain. Without wishing to be bound by theory, the extracellular domain of a membrane protein is responsible for interacting with a soluble or membrane bound receptor or ligand. Without wishing to be bound by theory, the trans-membrane domain(s) are responsible for localizing a protein to the plasma membrane. Without wishing to be bound by theory, the intracellular domain of a membrane protein is responsible for coordinating interactions with cellular signaling molecules to coordinate intracellular responses with the extracellular environment (or visa-versa). There are two types of single-pass membrane proteins, those with an extracellular amino terminus and intracellular carboxy terminus (Type I) and those with an extracellular carboxy terminus and intracellular amino terminus (Type II). Both Type I and Type II membrane proteins can be either receptors or ligands. For Type I membrane proteins, the amino terminus of the protein faces outside the cell, and therefore contains the functional domains that are responsible for interacting with other binding partners (either ligands or receptors) in the extracellular environment. For Type II membrane proteins, the carboxy terminus of the protein faces outside the cell, and therefore contains the functional domains that are responsible for interacting with other binding partners (either ligands or receptors) in the extracellular environment. Thus, these two types of proteins have opposite orientations to each other.

Figure 1D:
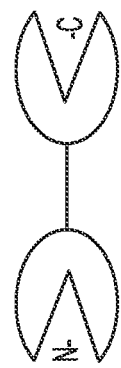
Figure 1A:
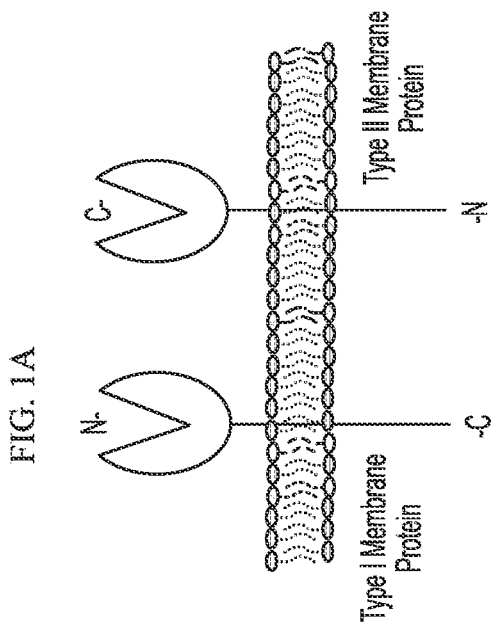
Figure 1C:
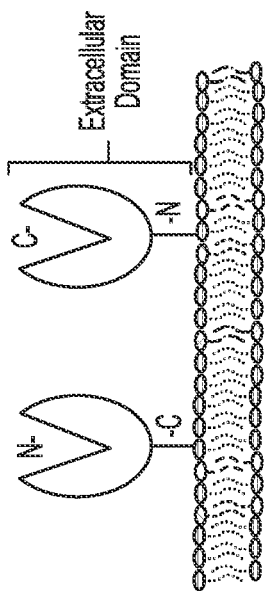
Figure 2A:
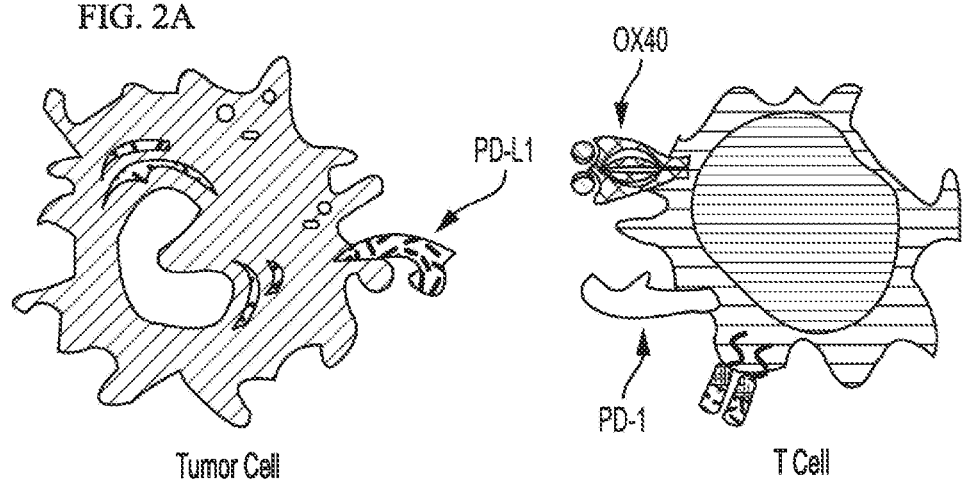
FIG. 2A, using an PD-1-Fc-OX40L chimeric protein as an example, shows that tumor cells may express PD-L1 on the cell surface, which can bind to PD-1 expressed by a T cell (FIG. 2B). This interaction suppresses activation of T cells. A chimeric protein comprising the extracellular domain of PD-1, adjoined to the extracellular domain of OX40L may bind to PD-L1 on the surface of a tumor cell, preventing binding to PD-1 on the surface of a T cell (FIG. 2C). The chimeric protein may then "dangle" from the surface of the tumor cell, and the OX40L portion of the chimeric protein may then bind to OX40 expressed on the surface of the T cell. This would result in replacement of an inhibitory PD-L1 signal with a co-stimulatory OX40L signal to enhance the anti-tumor activity of T cells.
Figure 2B:
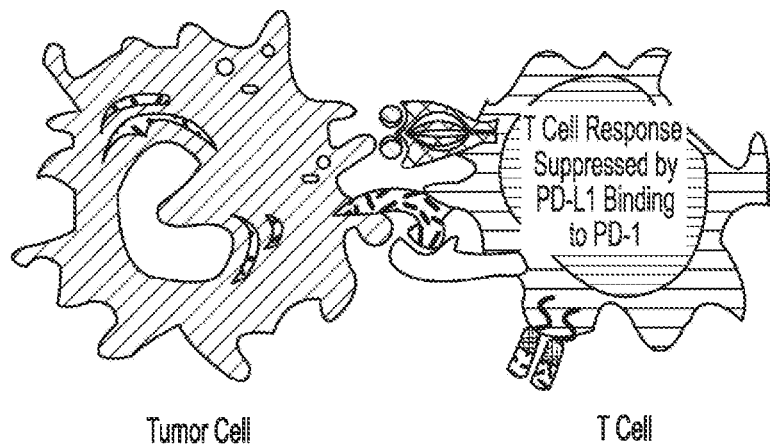
Figure 2C:
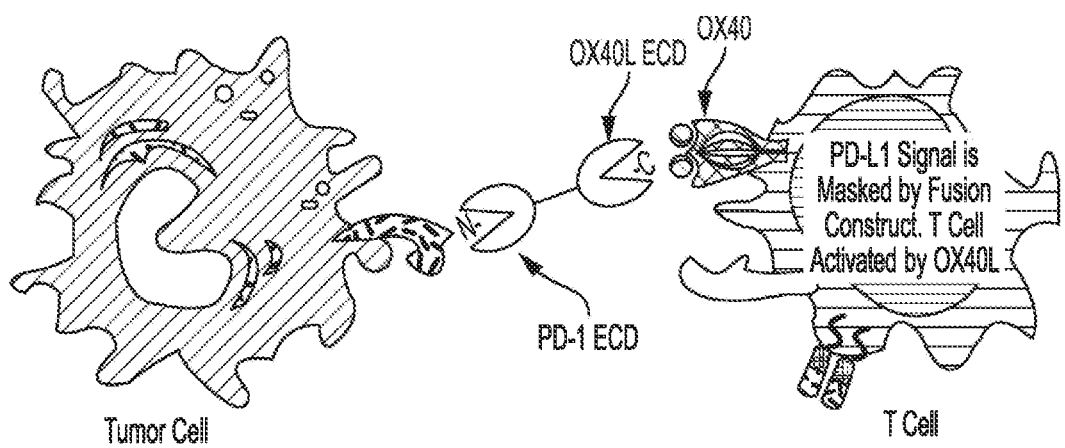
Figure 2D:
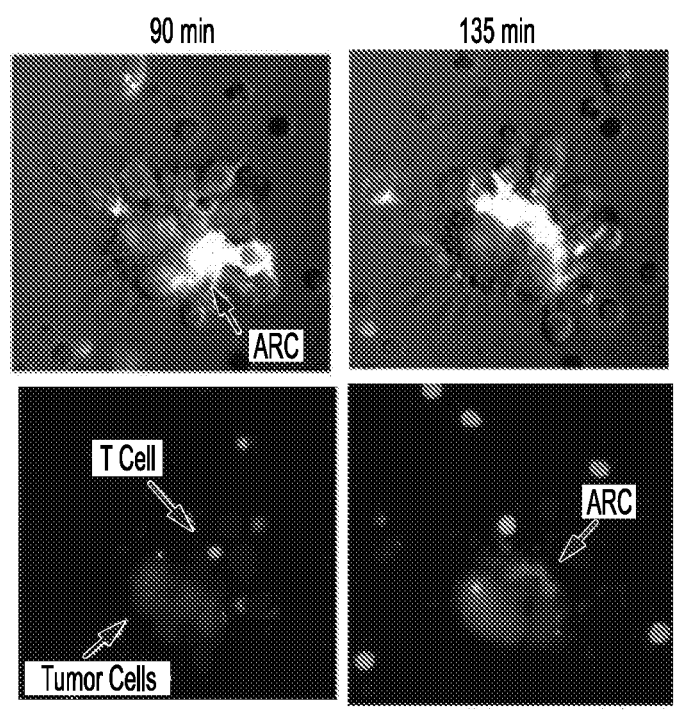
FIG. 2D shows a synapse that has formed by a chimeric protein between a tumor cell and a T cell.

Because the outward facing domains of Type I and Type II membrane proteins are opposite, it is possible to link the extracellular domains of a Type I and Type II membrane protein such that the 'outward facing' domains of the molecules are also in opposing orientation to each other (FIG. 1D). The resulting construct would therefore consist of the extracellular domain of a Type I membrane protein on the 'left' side of the molecule, connected to the extracellular domain of a Type 11 membrane protein on the 'right' side of the molecule using a linker sequence. This construct could be produced by cloning of these three fragments (the extracellular domain of a Type 1 protein, followed by a linker sequence, followed by the extracellular domain of a Type 11 protein) into a vector (plasmid, viral or other) wherein the amino terminus of the complete sequence corresponded to the 'left' side of the molecule containing the Type 1 protein and the carboxy terminus of the complete sequence corresponded to the 'right' side of the molecule containing the Type 11 protein. Accordingly, in embodiments, the present chimeric proteins are engineered as such.

In embodiments, the extracellular domain may be used to produce a soluble protein to competitively inhibit signaling by that receptor's ligand. In embodiments, the extracellular domain may be used to provide artificial signaling.

In embodiments, the extracellular domain of a Type I transmembrane protein is an immune inhibitory signal. In embodiments, the extracellular domain of a Type II transmembrane protein is an immune stimulatory signal.

In embodiments, the present chimeric proteins comprise an extracellular domain of a Type I transmembrane protein, or a functional fragment thereof. In embodiments, the present chimeric proteins comprise an extracellular domain of a Type II transmembrane protein, or a functional fragment thereof. In embodiments, the present chimeric proteins comprise an extracellular domain of a Type I transmembrane protein, or a functional fragment thereof, and an extracellular domain of a Type II transmembrane protein, or a functional fragment thereof.

In embodiments, the present chimeric proteins may be engineered to target one or more molecules that reside on human leukocytes including, without limitation, the extracellular domains (where applicable) of SLAMF4, IL-2 R α, 4-1BB/TNFRSF9, IL-2 R β, ALCAM, BTLA, B7-1, IL-4 R, B7-H3, BLAME/SLAMFS, CEACAM1, IL-6 R, IL-7 Rα, IL-10R α, IL-I 0 R β, IL-12 R β 1, IL-12 R β 2, CD2, IL-13 R α 1, IL-13, CD3, CD4, ILT2/CDS5j, ILT3/CDS5k, ILT4/CDS5d, ILT5/CDS5a, lutegrin α 4/CD49d, CDS, Integrin α E/CD103, CD6, Integrin α M/CD 11 b, CDS, Integrin α X/CD11c, Integrin β 2/CDIS, KIR/CD15S, CD27/TNFRSF7, KIR2DL1, CD2S, KIR2DL3, CD30/TNFRSFS, KIR2DL4/CD15Sd, CD31/PECAM-1, KIR2DS4, CD40 Ligand/TNFSF5, CD43, LAIR1, CD45, LAIR2, CDS3, Leukotriene B4-R1, CDS4/SLAMF5, NCAM-L1, CD94, NKG2A, CD97, NKG2C, CD229/SLAMF3, NKG2D, CD2F-10/SLAMF9, NT-4, CD69, NTB-A/SLAMF6, Common γ Chain/IL-2 R γ, Osteopontin, CRACC/SLAMF7, PD-1, CRTAM, PSGL-1, CTLA-4, RANK/TNFRSF11A, CX3CR1, CX3CL1, L-Selectin, SIRP β 1, SLAM, TCCR/WSX-1, DNAM-1, Thymopoietin, EMMPRIN/CD147, TIM-1, EphB6, TIM-2, Fas/TNFRSF6, TIM-3, Fas Ligand/TNFSF6, TIM-4, Fcγ RIII/CD16, TIM-6, TNFR1/TNFRSF1A, Granulysin, TNF RIII/TNFRSF1B, TRAIL RI/TNFRSFIOA, ICAM-1/CD54, TRAIL R2/TNFRSF10B, ICAM-2/CD102, TRAILR3/TNFRSF10C, IFN-γR1, TRAILR4/TNFRSF10D, IFN-γ R2, TSLP, IL-1 R1, LIGHT, LTBR (TNFRSF3) and TSLP R.

The activation of regulatory T cells is critically influenced by costimulatory and coinhibitory signals. Two major families of costimulatory molecules include the B7 and the tumor necrosis factor (TNF) families. These molecules bind to receptors on T cells belonging to the CD28 or TNF receptor families, respectively. Many well-defined coinhibitors and their receptors belong to the B7 and CD28 families.

In embodiments, the present chimeric proteins may be engineered to target one or more molecules involved in immune inhibition, including for example TIGIT.

In embodiments, the chimeric protein of the present invention comprises an extracellular domain of an immune inhibitory agent, including for example TIGIT.

In embodiments, the chimeric protein of the present invention comprises an extracellular domain of a Type I membrane protein which has immune inhibitory properties. In embodiments, the chimeric protein is engineered to disrupt, block, reduce, and/or inhibit the transmission of an immune inhibitory signal.

In embodiments, the chimeric protein of the present invention comprises an extracellular domain of an immune stimulatory signal is LIGHT (CD258).

In embodiments, the chimeric protein simulates binding of an inhibitory signal ligand to its cognate receptor (e.g. TIGIT to CD155/PVR, Nectin-2, Nectin-3 and/or Nectin-4) but inhibits the inhibitory signal transmission to an immune cell (e.g. a T cell, macrophage or other leukocyte).

In embodiments, the chimeric protein comprises an immune inhibitory receptor extracellular domain and an immune stimulatory ligand extracellular domain which can, without limitation, deliver an immune stimulation to a T cell while masking a tumor cell's immune inhibitory signals. In embodiments, the chimeric protein delivers a signal that has the net result of T cell activation.

In embodiments, the chimeric protein comprises an immune inhibitory signal which is an ECD of a receptor of an immune inhibitory signal and this acts on a tumor cell that bears a cognate ligand of the immune inhibitory signal. In embodiments, the chimeric protein comprises an immune stimulatory signal which is an ECD of a ligand of an immune stimulatory signal and this acts on a T cell that bears a cognate receptor of the immune stimulatory signal. In embodiments, the chimeric protein comprises both (i) an immune inhibitory signal which is a receptor of an immune inhibitory signal and this acts on a tumor cell that bears a cognate ligand of the immune inhibitory signal and (ii) an immune stimulatory signal which is a ligand of an immune stimulatory signal and this acts on a T cell that bears a cognate receptor of the immune stimulatory signal.

In embodiments, the chimeric protein of the present invention comprises an extracellular domain of one or more of the immune-modulating agents described in Mahoney, Nature Reviews Drug Discovery 2015:14; 561-585, the entire contents of which are hereby incorporated by reference.

In embodiments, a chimeric protein is capable of binding murine ligand(s)/receptor(s).

In embodiments, a chimeric protein is capable of binding human ligand(s)/receptor(s).

In embodiments, the chimeric protein of the present invention comprises an extracellular domain of a Type II membrane protein which has immune stimulatory properties. In embodiments, the chimeric protein is engineered to enhance, increase, and/or stimulate the transmission of an immune stimulatory signal.

For instance, in embodiments, the extracellular domain of a Type I transmembrane protein is from TIGIT.

TIGIT is a poliovirus receptor (PVR)-like protein, an immunoreceptor expressed on T cells that contains immunoglobulin and immunoreceptor tyrosine-based inhibitory motif (ITIM) domains. As such, TIGIT acts as an inhibitory immune checkpoint on both T cells and natural killer (NK) cells, providing an opportunity to target both the adaptive and innate arms of the immune system.

TIGIT is expressed on NK cells and subsets of activated, memory and regulatory T cells, and particularly on follicular helper T cells within secondary lymphoid organs CD155/PVR is up-regulated on endothelial cells by IFN-gamma and is highly expressed on immature thymocytes, lymph node dendritic cells, and tumor cells of epithelial and neuronal origin. In embodiments, the present chimeric proteins (e.g. comprising the TIGIT ECD) modulate any of the cells described immediately above (e.g. in the context of an immune synapse).

TIGIT binds CD155/PVR, Nectin-2, Nectin-3 and Nectin-4. In embodiments, the present chimeric proteins (e.g. comprising the TIGIT ECD) modulate the binding of TIGIT to CD155/PVR (e.g. reduce or disrupt the binding or signal transmission). In embodiments, the present chimeric proteins (e.g. comprising the TIGIT ECD) modulate the binding of TIGIT to Nectin-2 (e.g. reduce or disrupt the binding or signal transmission). In embodiments, the present chimeric proteins (e.g. comprising the TIGIT ECD) modulate the binding of TIGIT to Nectin-3 (e.g. reduce or disrupt the binding or signal transmission). In embodiments, the present chimeric proteins (e.g. comprising the TIGIT ECD) modulate the binding of TIGIT to Nectin-4 (e.g. reduce or disrupt the binding or signal transmission).

In embodiments, the chimeric protein is of a general structure of: N terminus-(a)-(b)-(c)-C terminus, where (a) is a first domain comprising an extracellular domain of a Type I transmembrane protein, the transmembrane protein being TIGIT, (b) is a linker comprising at least one cysteine residue capable of forming a disulfide bond (including without limitation, hinge-CH2-CH3 Fc domain is derived from human IgG4), and (c) is a second domain comprising an extracellular domain of Type II transmembrane protein, the transmembrane protein being selected from 4-1BBL, GITRL, TL1A, and LIGHT, where the linker connects the first domain and the second domain and optionally comprises one or more joining linkers as described herein.

In embodiments, the chimeric protein comprises the extracellular domain of the immune inhibitory agent TIGIT and is paired with an immune stimulatory agent as follows: TIGIT/OX-40L; TIGIT/4-1BBL, TIGIT/LIGHT; TIGIT/GITRL; TIGIT/CD70; TIGIT/CD30L; TIGIT/CD40L; TIGIT/CD137L; TIGIT/TL1A; and TIGIT/OX40L. In embodiments the chimeric protein is TIGIT-Fc-4-1BBL, TIGIT-Fc-GITRL, TIGIT-Fc-LIGHT, TIGIT-Fc-OX40L, or TIGIT-Fc-TL1A, in which the Fc represents a linker that comprises at least a portion of an Fc domain of an antibody and which comprises at least one cysteine residue capable of forming a disulfide bond.

For instance, in embodiments, the extracellular domain of a Type II transmembrane protein is from LIGHT.

LIGHT (HVEM-L, TNFSF14, or CD258), an entity homologous to lymphotoxins, with inducible nature, and able to compete with herpes simplex virus glycoprotein D for herpes virus entry mediator (HVEM)/tumor necrosis factor (TNF)-related 2 is a member of the TNF superfamily. It is a 29-kDa Type II transmembrane protein, is expressed as a homotrimer on activated T cells as well as DCs, and has three receptors, namely, HVEM, LT-β receptor (LTβR, TNFRSF3) and decoy receptor 3 (DcR3). Without wishing to be bound by theory, three receptors with distinct cellular expression patterns have been known to interact with LIGHT: HVEM (TNFRSF14, CD270) detected on activated DCs, T and B cells, NK cells, monocytes, and endothelial cells; LTβR found on follicular DCs and stromal cells and binds LIGHT; and the soluble entity decoy receptor 3 (DcR3) detected on diverse cancer cells such as multiple myeloma and diffuse large B-cell lymphoma. In embodiments, the present chimeric proteins can disrupt or decrease the interaction of LIGHT with one or more of these three receptors.

LIGHT binds LTBR, and potentially HVEM as well as DcR3. In embodiments, the present chimeric proteins (e.g.

comprising the LIGHT ECD) modulate the binding of LIGHT to LTBR (e.g. increase or promote the binding or signal transmission). LTBR is expressed by visceral, lymphoid, and other stroma, epithelia and myeloid cells, but not lymphocytes. In embodiments, the present chimeric proteins (e.g. comprising the LIGHT ECD) modulate one or more of visceral, lymphoid, and other stroma, epithelia and myeloid cells. In embodiments, the present chimeric proteins (e.g. comprising the LIGHT ECD) modulate the binding of LIGHT to HVEM (e.g. increase or promote the binding or signal transmission). In embodiments, the present chimeric proteins (e.g. comprising the LIGHT ECD) modulate the binding of LIGHT to DcR3 (e.g. increase or promote the binding or signal transmission).

In embodiments, the chimeric protein is of a general structure of: N terminus-(a)-(b)-(c)-C terminus, where (a) is a first domain comprising an extracellular domain of a Type I transmembrane protein, the transmembrane protein being selected from PD-1, CD172a(SIRPα), and TIGIT, (b) is a linker comprising at least one cysteine residue capable of forming a disulfide bond (including without limitation, hinge-CH2-CH3 Fc domain is derived from human IgG4), and (c) is a second domain comprising an extracellular domain of Type II transmembrane protein, the transmembrane protein being LIGHT, where the linker connects the first domain and the second domain and optionally comprises one or more joining linkers as described herein.

In embodiments, the chimeric protein comprises the extracellular domain of the immune stimulatory agent LIGHT and is paired with an immune inhibitory agent as follows: PD-1/LIGHT, CD172a(SIRPα)/LIGHT, and TIGIT/LIGHT. In embodiments the chimeric protein is PD-1-Fc-LIGHT, CD172a(SIRPα)-Fc-LIGHT, and TIGIT-Fc-LIGHT, in which the Fc represents a linker that comprises at least a portion of an Fc domain of an antibody and which comprises at least one cysteine residue capable of forming a disulfide bond.

In an embodiment, the chimeric protein comprises the extracellular domain of the immune inhibitory agent and is paired with the immune stimulatory agent. In embodiments, the chimeric protein binds to a cognate receptor or ligand with a $K_D$ of about 1 nM to about 5 nM, for example, about 1 nM, about 1.5 nM, about 2 nM, about 2.5 nM, about 3 nM, about 3.5 nM, about 4 nM, about 4.5 nM, or about 5 nM. In embodiments, the chimeric protein binds to a cognate receptor or ligand with a $K_D$ of about 5 nM to about 15 nM, for example, about 5 nM, about 5.5 nM, about 6 nM, about 6.5 nM, about 7 nM, about 7.5 nM, about 8 nM, about 8.5 nM, about 9 nM, about 9.5 nM, about 10 nM, about 10.5 nM, about 11 nM, about 11.5 nM, about 12 nM, about 12.5 nM, about 13 nM, about 13.5 nM, about 14 nM, about 14.5 nM, or about 15 nM.

In embodiments, the chimeric protein exhibits enhanced stability and protein half-life. In embodiments, the chimeric protein binds to FcRn with high affinity. In embodiments, the chimeric protein may bind to FcRn with a $K_D$ of about 1 nM to about 80 nM. For example, the chimeric protein may bind to FcRn with a $K_D$ of about 1 nM, about 2 nM, about 3 nM, about 4 nM, about 5 nM, about 6 nM, about 7 nM, about 8 nM, about 9 nM, about 10 nM, about 15 nM, about 20 nM, about 25 nM, about 30 nM, about 35 nM, about 40 nM, about 45 nM, about 50 nM, about 55 nM, about 60 nM, about 65 nM, about 70 nM, about 71 nM, about 72 nM, about 73 nM, about 74 nM, about 75 nM, about 76 nM, about 77 nM, about 78 nM, about 79 nM, or about 80 nM. In an embodiment, the chimeric protein may bind to FcRn with a $K_D$ of about 9 nM. In embodiments, the chimeric protein does not substantially bind to other Fc receptors (i.e. other than FcRn) with effector function.

In embodiments, there is provided a method of treating a cancer and/or inflammatory disease (e.g. any one of those described elsewhere herein) by administering to a subject one or more of a PD-1-Fc-LIGHT, CD172a(SIRPα)-Fc-LIGHT, and TIGIT-Fc-LIGHT chimeric protein, in which the Fc represents a linker that comprises at least a portion of an Fc domain of an antibody and which comprises at least one cysteine residue capable of forming a disulfide bond. In embodiments, the method generates a memory response which may, e.g. be capable of preventing relapse. In embodiments, the method includes a sustained therapeutic effect of the one or more of a PD-1-Fc-LIGHT, CD172a(SIRPα)-Fc-LIGHT, and TIGIT-Fc-LIGHT, e.g. due to binding of the extracellular domain components to their respective binding partners with slow off rates ($K_d$ or $K_{off}$) to optionally provide sustained negative signal masking effect and/or a longer positive signal effect, e.g. to allow an effector cell to be adequately stimulated for an anti-tumor effect.

In embodiments, there is provided a method of treating a cancer or an inflammatory disease (e.g. any one of those described elsewhere herein) by administering to a subject one or more of a TIGIT-Fc-4-1BBL, TIGIT-Fc-GITRL, TIGIT-Fc-TL1A, and TIGIT-Fc-LIGHT chimeric protein, in which the Fc represents a linker that comprises at least a portion of an Fc domain of an antibody and which comprises at least one cysteine residue capable of forming a disulfide bond. In embodiments, the method generates a memory response which may, e.g. be capable of preventing relapse. In embodiments, the method includes a sustained therapeutic effect of the one or more of a TIGIT-Fc-4-1BBL, TIGIT-Fc-GITRL, TIGIT-Fc-TL1A, and TIGIT-Fc-LIGHT, e.g. due to binding of the extracellular domain components to their respective binding partners with slow off rates ($K_d$ or $K_{off}$) to optionally provide sustained negative signal masking effect and/or a longer positive signal effect, e.g. to allow an effector cell to be adequately stimulated for an anti-tumor effect.

In embodiments, the present chimeric proteins may comprises variants of the extracellular domains described herein, for instance, a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the known amino acid or nucleic acid sequence of any of the disclosed extracellular domains, e.g. human extracellular domains, e.g. one or more of SEQ IDs NOs: 2, 4, 7, 10, 13, 16, 19, 22, 25, 27, 29, 31, 37, or 41.

In embodiments, the chimeric protein of the present invention comprises an extracellular domain of LIGHT (SEQ ID NO: 2).

In embodiments, the chimeric protein of the present invention comprises an extracellular domain of PD-1 (SEQ ID NO: 4).

In embodiments, the chimeric protein of the present invention comprises an extracellular domain of TIGIT (SEQ ID NO: 10).

In embodiments, the chimeric protein of the present invention comprises an extracellular domain of CD172a (SIRPα) (SEQ ID NO: 7).

In embodiments, the chimeric protein of the present invention comprises an extracellular domain of LIGHT (SEQ ID NO: 2) and the extracellular domain of PD-1 (SEQ ID NO: 4).

In embodiments, the chimeric protein of the present invention comprises an extracellular domain of LIGHT (SEQ ID NO: 2) and the extracellular domain of TIGIT (SEQ ID NO: 10).

In embodiments, the chimeric protein of the present invention comprises an extracellular domain of LIGHT (SEQ ID NO: 2) and the extracellular domain of CD172a (SIRPα) (SEQ ID NO: 7).

In embodiments, the chimeric protein of the present invention comprises the hinge-CH2-CH3 domain from a human IgG4 antibody sequence (SEQ ID NO: 46, 47, or 48).

In embodiments, the chimeric protein of the present invention comprises the hinge-CH2-CH3 domain from a human IgG4 antibody sequence (SEQ ID NO: 46, 47, or 48) and this sequence is flanked by at least one joining linker selected from SKYGPPCPSCP (SEQ ID NO: 49), SKYGPPCPPCP (SEQ ID NO: 50), IEGRMD SEQ ID NO: 52 (optionally SKYGPPCPSCP (SEQ ID NO: 49) or SKYGPPCPPCP (SEQ ID NO: 50) is N terminal and one of IEGRMD SEQ ID NO: 52 is C terminal).

In embodiments, a chimeric protein comprises a modular linker as shown in FIG. 32.

In embodiments, the chimeric protein of the present invention comprises an extracellular domain of LIGHT and the extracellular domain of PD-1, using the hinge-CH2-CH3 domain from a human IgG4 antibody sequence as a linker (this PD-1-Fc-LIGHT chimera is SEQ ID NO: 5).

In embodiments, the chimeric protein of the present invention comprises an extracellular domain of LIGHT and the extracellular domain of TIGIT, using the hinge-CH2-CH3 domain from a human IgG4 antibody sequence as a linker (this TIGIT-Fc-LIGHT chimera is SEQ ID NO: 11).

In embodiments, the chimeric protein of the present invention comprises an extracellular domain of LIGHT and the extracellular domain of CD172a(SIRPα), using the hinge-CH2-CH3 domain from a human IgG4 antibody sequence as a linker (this CD172a(SIRPα)-Fc-LIGHT chimera is SEQ ID NO: 8).

In embodiments, the chimeric protein of the present invention comprises an extracellular domain of TIGIT (SEQ ID NO: 10).

In embodiments, the chimeric protein of the present invention comprises an extracellular domain of 4-1BBL (SEQ ID NO: 13).

In embodiments, the chimeric protein of the present invention comprises an extracellular domain of GITRL (SEQ ID NO: 16).

In embodiments, the chimeric protein of the present invention comprises an extracellular domain of TL1A (SEQ ID NO: 19).

In embodiments, the chimeric protein of the present invention comprises an extracellular domain of LIGHT (SEQ ID NO: 2).

In embodiments, the chimeric protein of the present invention comprises an extracellular domain of OX40L (SEQ ID NO: 22).

In embodiments, the chimeric protein of the present invention comprises an extracellular domain of TIGIT (SEQ ID NO: 10) and the extracellular domain of 4-1BBL (SEQ ID NO: 13).

In embodiments, the chimeric protein of the present invention comprises an extracellular domain of TIGIT (SEQ ID NO: 10) and the extracellular domain of GITRL (SEQ ID NO: 16).

In embodiments, the chimeric protein of the present invention comprises an extracellular domain of TIGIT (SEQ ID NO: 10) and the extracellular domain of TL1A (SEQ ID NO: 19).

In embodiments, the chimeric protein of the present invention comprises an extracellular domain of TIGIT (SEQ ID NO: 10) and the extracellular domain of LIGHT (SEQ ID NO: 2).

In embodiments, the chimeric protein of the present invention comprises an extracellular domain of TIGIT (SEQ ID NO: 10) and the extracellular domain of OX40L (SEQ ID NO: 22).

In embodiments, the chimeric protein of the present invention comprises the hinge-CH2-CH3 domain from a human IgG4 antibody sequence (SEQ ID NO: 46, 47, or 48).

In embodiments, the chimeric protein of the present invention comprises the hinge-CH2-CH3 domain from a human IgG4 antibody sequence (SEQ ID NO: 46, 47, or 48) and this sequence is flanked by at least one joining linker selected from SKYGPPCPSCP (SEQ ID NO: 49), SKYGPPCPPCP (SEQ ID NO: 50), IEGRMD SEQ ID NO: 52 (optionally SKYGPPCPSCP (SEQ ID NO: 49) or SKYGPPCPPCP (SEQ ID NO: 50) is N terminal and one of IEGRMD SEQ ID NO: 52 is C terminal).

In embodiments, the chimeric protein of the present invention comprises an extracellular domain of TIGIT and the extracellular domain of 4-1BBL, using the hinge-CH2-CH3 domain from a human IgG4 antibody sequence as a linker (this TIGIT-Fc-4-1BBL chimera is SEQ ID NO: 14).

In embodiments, the chimeric protein of the present invention comprises an extracellular domain of TIGIT and the extracellular domain of GITRL, using the hinge-CH2-CH3 domain from a human IgG4 antibody sequence as a linker (this TIGIT-Fc-GITRL chimera is SEQ ID NO: 17).

In embodiments, the chimeric protein of the present invention comprises an extracellular domain of TIGIT and the extracellular domain of TL1A, using the hinge-CH2-CH3 domain from a human IgG4 antibody sequence as a linker (this TIGIT-Fc-TL1A chimera is SEQ ID NO: 20).

In embodiments, the chimeric protein of the present invention comprises an extracellular domain of TIGIT and the extracellular domain of LIGHT, using the hinge-CH2-CH3 domain from a human IgG4 antibody sequence as a linker (this TIGIT-Fc-LIGHT chimera is SEQ ID NO: 11).

In embodiments, the chimeric protein of the present invention comprises an extracellular domain of TIGIT and the extracellular domain of OX40L, using the hinge-CH2-CH3 domain from a human IgG4 antibody sequence as a linker (this TIGIT-Fc-OX40L chimera is SEQ ID NO: 23).

In embodiments, a chimeric protein can comprise an extracellular domain from a sequence identified herein combined with an extracellular domain from another sequence identified herein. For example, the sequence of a TIGIT-Fc-TL1A chimeric protein could include the extracellular domain of TIGIT as disclosed above in SEQ ID NO: 10 and the extracellular domain of TL1A as disclosed above in SEQ ID NO: 19.

In embodiments, additional chimeric proteins and methods using the additional chimeric proteins (e.g., in treating a cancer and/or treating an inflammatory disease): TIGIT-Fc-4-1BBL, TIGIT-Fc-CD30L, TIGIT-Fc-FasL, TIGIT-Fc-GITRL, TIGIT-Fc-TL1A, and TIGIT-Fc-TRAIL. The amino acid sequence for 4-1BBL, CD30L, FasL, GITRL, TL1A, and TRAIL, respectively, comprises SEQ ID NO: 12, 26, 30, 15, 18, and 40. The amino acid sequence for extracellular domain of 4-1BBL, CD30L, FasL, GITRL, TL1A, and TRAIL, respectively, are SEQ ID NO: 13, 27, 31, 16, 19, and 41.

In embodiments, the present chimeric proteins may be variants described herein, for instance, the present chimeric proteins may have a sequence having at least about 60%, or at least about 61%, or at least about 62%, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%) sequence identity with the amino acid sequence of the present chimeric proteins, e.g. one or more of SEQ IDs NOs: 5, 8, 11, 14, 17, 20, 23, 42, 43, 44, or 45.

In embodiments, the present chimeric proteins comprise an extracellular domain of a human Type I transmembrane protein as recited in TABLE 1 of PCT/US2016/054598, or a functional fragment thereof. In embodiments, the present chimeric proteins comprise an extracellular domain of a human Type II transmembrane protein as recited in TABLE 2 of PCT/US2016/054598, or a functional fragment thereof. In embodiments, the present chimeric proteins comprise an extracellular domain of a Type I transmembrane protein as recited in TABLE 1 of PCT/US2016/054598, or a functional fragment thereof, and an extracellular domain of a Type II transmembrane protein as recited in TABLE 2 of PCT/US2016/054598, or a functional fragment thereof. The entire contents of PCT/US2016/054598 are hereby incorporated by reference.

In embodiments, the chimeric protein may comprise an amino acid sequence having one or more amino acid mutations relative to any of the protein sequences described herein. In embodiments, the one or more amino acid mutations may be independently selected from substitutions, insertions, deletions, and truncations.

In embodiments, the amino acid mutations are amino acid substitutions, and may include conservative and/or non-conservative substitutions.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups: (1) hydrophobic: Met, Ala, Val, Leu, Ile; (2) neutral hydrophilic: Cys, Ser, Thr; Asn, Gln; (3) acidic: Asp, Glu; (4) basic: His, Lys, Arg; (5) residues that influence chain orientation: Gly, Pro; and (6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices.

As used herein, "non-conservative substitutions" are defined as exchanges of an amino acid by another amino acid listed in a different group of the six standard amino acid groups (1) to (6) shown above.

In embodiments, the substitutions may also include non-classical amino acids (e.g. selenocysteine, pyrrolysine, N-formylmethionine β-alanine, GABA and δ-Aminolevulinic acid, 4-aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as β methyl amino acids, C α-methyl amino acids, N α-methyl amino acids, and amino acid analogs in general).

Mutations may also be made to the nucleotide sequences of the chimeric proteins by reference to the genetic code, including taking into account codon degeneracy.

In embodiments, the chimeric protein comprises a linker. In embodiments, the linker comprising at least one cysteine residue capable of forming a disulfide bond. As described elsewhere herein, such at least one cysteine residue capable of forming a disulfide bond is, without wishing to be bound by theory, responsible for maintain a proper multimeric state of the chimeric protein and allowing for efficient production.

In embodiments, the linker may be derived from naturally-occurring multi-domain proteins or are empirical linkers as described, for example, in Chichili et al., (2013), Protein Sci. 22(2):153-167, Chen et al., (2013), Adv Drug Deliv Rev. 65(10):1357-1369, the entire contents of which are hereby incorporated by reference. In embodiments, the linker may be designed using linker designing databases and computer programs such as those described in Chen et al., (2013), Adv Drug Deliv Rev. 65(10):1357-1369 and Crasto et. al., (2000), Protein Eng. 13(5):309-312, the entire contents of which are hereby incorporated by reference.

In embodiments, the linker is a synthetic linker such as PEG.

In embodiments, the linker is a polypeptide. In embodiments, the linker is less than about 500 amino acids long, about 450 amino acids long, about 400 amino acids long, about 350 amino acids long, about 300 amino acids long, about 250 amino acids long, about 200 amino acids long, about 150 amino acids long, or about 100 amino acids long. For example, the linker may be less than about 100, about 95, about 90, about 85, about 80, about 75, about 70, about 65, about 60, about 55, about 50, about 45, about 40, about 35, about 30, about 25, about 20, about 19, about 18, about 17, about 16, about 15, about 14, about 13, about 12, about 11, about 10, about 9, about 8, about 7, about 6, about 5, about 4, about 3, or about 2 amino acids long. In embodiments, the linker is flexible. In another embodiment, the linker is rigid.

In embodiments, the linker is substantially comprised of glycine and serine residues (e.g. about 30%, or about 40%, or about 50%, or about 60%, or about 70%, or about 80%, or about 90%, or about 95%, or about 97%, or about 98%, or about 99%, or about 100% glycines and serines).

In embodiments, the linker is a hinge region of an antibody (e.g., of IgG, IgA, IgD, and IgE, inclusive of subclasses (e.g. IgG1, IgG2, IgG3, and IgG4, and IgA1 and IgA2)). The hinge region, found in IgG, IgA, IgD, and IgE class antibodies, acts as a flexible spacer, allowing the Fab portion to move freely in space. In contrast to the constant regions, the hinge domains are structurally diverse, varying in both sequence and length among immunoglobulin classes and subclasses. For example, the length and flexibility of the hinge region varies among the IgG subclasses. The hinge region of IgG1 encompasses amino acids 216-231 and, because it is freely flexible, the Fab fragments can rotate about their axes of symmetry and move within a sphere centered at the first of two inter-heavy chain disulfide bridges. IgG2 has a shorter hinge than IgG1, with 12 amino acid residues and four disulfide bridges. The hinge region of IgG2 lacks a glycine residue, is relatively short, and contains a rigid poly-proline double helix, stabilized by extra inter-heavy chain disulfide bridges. These properties restrict the flexibility of the IgG2 molecule. IgG3 differs from the other subclasses by its unique extended hinge region (about four times as long as the IgG1 hinge), containing 62 amino acids (including 21 prolines and 11 cysteines), forming an inflexible poly-proline double helix. In IgG3, the Fab fragments are relatively far away from the Fc fragment, giving the molecule a greater flexibility. The elongated hinge in IgG3 is also responsible for its higher molecular weight compared to the other subclasses. The hinge region of IgG4 is shorter than that of IgG1 and its flexibility is intermediate between that of IgG1 and IgG2. The flexibility of the hinge regions reportedly decreases in the order IgG3>IgG1>IgG4>IgG2. In embodiments, the linker may be derived from human IgG4 and contain one or more mutations to enhance dimerization (including S228P) or FcRn binding.

According to crystallographic studies, the immunoglobulin hinge region can be further subdivided functionally into three regions: the upper hinge region, the core region, and the lower hinge region. See Shin et al., 1992 Immunological Reviews 130:87. The upper hinge region includes amino acids from the carboxyl end of CH1 to the first residue in the hinge that restricts motion, generally the first cysteine residue that forms an interchain disulfide bond between the two heavy chains. The length of the upper hinge region correlates with the segmental flexibility of the antibody. The core hinge region contains the inter-heavy chain disulfide bridges, and the lower hinge region joins the amino terminal end of the $C_{H2}$ domain and includes residues in $C_{H2}$. Id. The core hinge region of wild-type human IgG1 contains the sequence Cys-Pro-Pro-Cys which, when dimerized by disulfide bond formation, results in a cyclic octapeptide believed to act as a pivot, thus conferring flexibility. In embodiments, the present linker comprises, one, or two, or three of the upper hinge region, the core region, and the lower hinge region of any antibody (e.g., of IgG, IgA, IgD, and IgE, inclusive of subclasses (e.g. IgG1, IgG2, IgG3, and IgG4, and IgA1 and IgA2)). The hinge region may also contain one or more glycosylation sites, which include a number of structurally distinct types of sites for carbohydrate attachment. For example, IgA1 contains five glycosylation sites within a 17-amino-acid segment of the hinge region, conferring resistance of the hinge region polypeptide to intestinal proteases, considered an advantageous property for a secretory immunoglobulin. In embodiments, the linker of the present invention comprises one or more glycosylation sites.

In embodiments, the linker comprises an Fc domain of an antibody (e.g., of IgG, IgA, IgD, and IgE, inclusive of subclasses (e.g. IgG1, IgG2, IgG3, and IgG4, and IgA1 and IgA2)). In embodiments, the linker comprises a hinge-CH2-CH3 Fc domain derived from a human IgG4 antibody. In embodiments, the linker comprises a hinge-CH2-CH3 Fc domain derived from a human IgG1 antibody. In embodiments, the Fc domain exhibits increased affinity for and enhanced binding to the neonatal Fc receptor (FcRn). In embodiments, the Fc domain includes one or more mutations that increases the affinity and enhances binding to FcRn. Without wishing to be bound by theory, it is believed that increased affinity and enhanced binding to FcRn increases the in vivo half-life of the present chimeric proteins.

In embodiments, the Fc domain linker contains one or more amino acid substitutions at amino acid residue 250, 252, 254, 256, 308, 309, 311, 416, 428, 433 or 434 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference), or equivalents thereof. In an embodiment, the amino acid substitution at amino acid residue 250 is a substitution with glutamine. In an embodiment, the amino acid substitution at amino acid residue 252 is a substitution with tyrosine, phenylalanine, tryptophan or threonine. In an embodiment, the amino acid substitution at amino acid residue 254 is a substitution with threonine. In an embodiment, the amino acid substitution at amino acid residue 256 is a substitution with serine, arginine, glutamine, glutamic acid, aspartic acid, or threonine. In an embodiment, the amino acid substitution at amino acid residue 308 is a substitution with threonine. In an embodiment, the amino acid substitution at amino acid residue 309 is a substitution with proline. In an embodiment, the amino acid substitution at amino acid residue 311 is a substitution with serine. In an embodiment, the amino acid substitution at amino acid residue 385 is a substitution with arginine, aspartic acid, serine, threonine, histidine, lysine, alanine or glycine. In an embodiment, the amino acid substitution at amino acid residue 386 is a substitution with threonine, proline, aspartic acid, serine, lysine, arginine, isoleucine, or methionine. In an embodiment, the amino acid substitution at amino acid residue 387 is a substitution with arginine, proline, histidine, serine, threonine, or alanine. In an embodiment, the amino acid substitution at amino acid residue 389 is a substitution with proline, serine or asparagine. In an embodiment, the amino acid substitution at amino acid residue 416 is a substitution with leucine. In an embodiment, the amino acid substitution at amino acid residue 428 is a substitution with serine. In an embodiment, the amino acid substitution at amino acid residue 433 is a substitution with arginine, serine, isoleucine, proline, or glutamine. In an embodiment, the amino acid substitution at amino acid residue 434 is a substitution with histidine, phenylalanine, or tyrosine.

In embodiments, the Fc domain linker (e.g., comprising an IgG constant region) comprises one or more mutations such as substitutions at amino acid residue 252, 254, 256, 433, 434, or 436 (in accordance with Kabat numbering, as in as in Kabat, et al., Sequences of Proteins of Immunological Interest, 5th Ed. Public Health Service, National Institutes of Health, Bethesda, Md. (1991) expressly incorporated herein by reference). In an embodiment, the IgG constant region includes a triple M252Y/S254T/T256E mutation or YTE mutation. In another embodiment, the IgG constant region includes a triple H433K/N434F/Y436H mutation or KFH mutation. In a further embodiment, the IgG constant region includes an YTE and KFH mutation in combination.

In embodiments, the modified humanized antibodies of the invention comprise an IgG constant region that contains one or more mutations at amino acid residues 250, 253, 307, 310, 380, 416, 428, 433, 434, and 435. Illustrative mutations include T250Q, M428L, T307A, E380A, I253A, H310A, R416S, M428L, H433K, N434A, N434F, N434S, and H435A. In an embodiment, the IgG constant region comprises a M428UN434S mutation or LS mutation. In another embodiment, the IgG constant region comprises a T250Q/M428L mutation or QL mutation. In another embodiment, the IgG constant region comprises an N434A mutation. In another embodiment, the IgG constant region comprises a T307A/E380A/N434A mutation or MA mutation. In another embodiment, the IgG constant region comprises an I253A/H310A/H435A mutation or IHH mutation. In another embodiment, the IgG constant region comprises a H433K/N434F mutation. In another embodiment, the IgG constant region comprises a M252Y/S254T/T256E and a H433K/N434F mutation in combination.

Additional illustrative mutations in the IgG constant region are described, for example, in Robbie, et al., Antimicrobial Agents and Chemotherapy (2013), 57(12):6147-6153, Dall'Acqua et al., JBC (2006), 281(33):23514-24, Dall'Acqua et al., Journal of Immunology (2002), 169:5171-80, Ko et al. Nature (2014) 514:642-645, Grevys et al. Journal of Immunology. (2015), 194(11):5497-508, and U.S. Pat. No. 7,083,784, the entire contents of which are hereby incorporated by reference.

In embodiments, the linker comprises the amino acid sequence of SEQ ID NO: 46, or at least 90%, or 93%, or 95%, or 97%, or 98%, or 99% identity thereto. In embodiments, mutations are made to SEQ ID NO: 46 to increase stability and/or half-life. For instance, in embodiments, the linker has the amino acid sequence of SEQ ID NO: 47, or at least 90%, or 93%, or 95%, or 97%, or 98%, or 99% identity thereto. In embodiments, the linker comprises the amino acid sequence of SEQ ID NO: 48, or at least 90%, or 93%, or 95%, or 97%, or 98%, or 99% identity thereto.

Without wishing to be bound by theory, including a linker comprising at least a part of an Fc domain in a chimeric protein, helps avoid formation of insoluble and, likely, non-functional protein concatamers and/or aggregates. This is in part due to the presence of cysteines in the Fc domain which are capable of forming disulfide bonds between chimeric proteins.

An illustrative Fc stabilizing mutant is S228P. Illustrative Fc half-life extending mutants are T250Q, M428L, V308T, L309P, and Q311S and the present linkers may comprise 1, or 2, or 3, or 4, or 5 of these mutants.

Further, one or more joining linkers may be employed to connect an Fc domain in a linker (e.g., one of SEQ ID NO: 46, SEQ ID NO: 47, or SEQ ID NO: 48 or at least 90%, or 93%, or 95%, or 97%, or 98%, or 99% identity thereto) and the extracellular domains. For example, any one of SEQ ID NO: 49, SEQ ID NO: 50, SEQ ID NO: 51, SEQ ID NO: 52, SEQ ID NO: 53, SEQ ID NO: 54, or variants thereof may connect an extracellular domain as described herein and a linker as described herein. Optionally, any one of SEQ ID NO: 49, SEQ ID NO: 50, SEQ ID NO: 51, SEQ ID NO: 52, SEQ ID NO: 53, SEQ ID NO: 54, or variants thereof are displaced between an extracellular domain as described herein and a linker as described herein. Optionally, any one of SEQ ID NOs: 49 to 95, or variants thereof are located between an extracellular domain as described herein and an Fc domain as described herein. In embodiments, a chimeric protein comprises one joining linker preceding an Fc domain and a second joining linker following the Fc domain; thus, a chimeric protein may comprise the following structure:

ECD 1-Joining Linker 1-Fc Domain-Joining Linker 2-ECD 2.

In embodiments, the first and second joining linkers may be different or they may be the same.

The amino acid sequences of illustrative linkers are provided in Table 1 below:

TABLE 1

Illustrative linkers (Fc domain linkers and joining linkers)

| SEQ ID NO. | Sequence |
|---|---|
| 46 | APEFLGGPSVFLFPPKPKDTLMISRTPEVTCVVVDVSQEDPEV QFNWYVDGVEVHNAKTKPREEQFNSTYRVVSVLTVLHQDWLSG KEYKCKVSSKGLPSSIEKTISNATGQPREPQVYTLPPSQEEMT KNQVSLTCLVKGFYPSDIAVEWESNGQPENNYKTTPPVLDSDG SFFLYSRLTVDKSSWQEGNVFSCSVMHEALHNHYTQKSLSLSL GK |
| 47 | APEFLGGPSVFLFPPKPKDQLMISRTPEVTCVVVDVSQEDPEV QFNWYVDGVEVHNAKTKPREEQFNSTYRVVSVLTTPHSDWLSG KEYKCKVSSKGLPSSIEKTISNATGQPREPQVYTLPPSQEEMT KNQVSLTCLVKGFYPSDIAVEWESNGQPENNYKTTPPVLDSDG SFFLYSRLTVDKSSWQEGNVFSCSVLHEALHNHYTQKSLSLSL GK |
| 48 | APEFLGGPSVFLFPPKPKDQLMISRTPEVTCVVVDVSQEDPEV QFNWYVDGVEVHNAKTKPREEQFNSTYRVVSVLTVLHQDWLSG KEYKCKVSSKGLPSSIEKTISNATGQPREPQVYTLPPSQEEMT KNQVSLTCLVKGFYPSDIAVEWESNGQPENNYKTTPPVLDSDG SFFLYSRLTVDKSRWQEGNVFSCSVLHEALHNHYTQKSLSLSL GK |
| 49 | SKYGPPCPSCP |
| 50 | SKYGPPCPPCP |
| 51 | SKYGPP |
| 52 | IEGRMD |
| 53 | GGGVPRDCG |
| 54 | IEGRMDGGGGAGGGG |
| 55 | GGGSGGGS |
| 56 | GGGSGGGGSGGG |
| 57 | EGKSSGSGSESKST |
| 58 | GGSG |
| 59 | GGSGGGSGGGSG |
| 60 | EAAAKEAAAKEAAAK |
| 61 | EAAAREAAAREAAAREAAAR |
| 62 | GGGGSGGGGSGGGGSAS |
| 63 | GGGGAGGGG |
| 64 | GS or GGS or LE |
| 65 | GSGSGS |
| 66 | GSGSGSGSGS |
| 67 | GGGGSAS |
| 68 | APAPAPAPAPAPAPAPAPAP |
| 69 | CPPC |

TABLE 1-continued

Illustrative linkers (Fc domain linkers and joining linkers)

| SEQ ID NO. | Sequence |
|---|---|
| 70 | GGGGS |
| 71 | GGGGSGGGGS |
| 72 | GGGGSGGGGSGGGGS |
| 73 | GGGGSGGGGSGGGGSGGGGS |
| 74 | GGGGSGGGGSGGGGSGGGGSGGGGS |
| 75 | GGGGSGGGGSGGGGSGGGGSGGGGSGGGGS |
| 76 | GGGGSGGGGSGGGGSGGGGSGGGGSGGGGSGGGGS |
| 77 | GGGGSGGGGSGGGGSGGGGSGGGGSGGGGSGGGGSGGGGS |
| 78 | GGSGGGSGGGGSGGGGS |
| 79 | GGGGGGGG |
| 80 | GGGGGG |
| 81 | EAAAK |
| 82 | EAAAKEAAAK |
| 83 | EAAAKEAAAKEAAAK |
| 84 | AEAAAKEAAAKA |
| 85 | AEAAAKEAAAKEAAAKA |
| 86 | AEAAAKEAAAKEAAAKEAAAKA |
| 87 | AEAAAKEAAAKEAAAKEAAAKEAAAKA |
| 88 | AEAAAKEAAAKEAAAKEAAAKALEAEAAAKEAAAKEAAAKEAAAKA |
| 89 | PAPAP |
| 90 | KESGSVSSEQLAQFRSLD |
| 91 | GSAGSAAGSGEF |
| 92 | GGGSE |
| 93 | GSESG |
| 94 | GSEGS |
| 95 | GEGGSGEGSSGEGSSSEGGGSEGGGSEGGGSEGGS |

Additional illustrative joining linkers include, but are not limited to, linkers having the sequence LE, GGGGS (SEQ ID NO: 70), (GGGGS)$_n$ (n=1-4) (SEQ ID NO: 70-73), (Gly)$_8$ (SEQ ID NO: 79), (Gly)$_6$ (SEQ ID NO: 80), (EAAAK)$_n$ (n=1-3) (SEQ ID NO: 81-83), A(EAAAK)$_n$A (n=2-5) (SEQ ID NO: 84-87), AEAAAKEAAAKA (SEQ ID NO: 84), A(EAAAK)$_4$ALEA(EAAAK)$_4$A (SEQ ID NO: 88), PAPAP (SEQ ID NO: 89), KESGSVSSEQLAQFRSLD (SEQ ID NO: 90), EGKSSGSGSESKST (SEQ ID NO: 57), GSAGSAAGSGEF (SEQ ID NO: 91), and (XP)$_n$, with X designating any amino acid, e.g., Ala, Lys, or Glu.

In embodiments, the joining linker is substantially comprised of glycine and serine residues (e.g., about 30%, or about 40%, or about 50%, or about 60%, or about 70%, or about 80%, or about 90%, or about 95%, or about 97%, or about 98%, or about 99%, or about 100% glycines and serines). For example, in embodiments, the joining linker is (Gly$_4$Ser)$_n$, where n is from about 1 to about 8, e.g., 1, 2, 3, 4, 5, 6, 7, or 8 (SEQ ID NO: 70 to SEQ ID NO: 77, respectively). In embodiments, the joining linker sequence is GGSGGSGGGGSGGGGS (SEQ ID NO: 78). Additional illustrative joining linkers include, but are not limited to, linkers having the sequence LE, (Gly)$_8$ (SEQ ID NO: 79), (Gly)$_6$ (SEQ ID NO: 80), (EAAAK)$_n$ (n=1-3) (SEQ ID NO: 81-SEQ ID NO: 83), A(EAAAK)$_n$A (n=2-5) (SEQ ID NO: 84-SEQ ID NO: 87), A(EAAAK)$_4$ALEA(EAAAK)$_4$A (SEQ ID NO: 88), PAPAP (SEQ ID NO: 89), KESGSVSSEQLAQFRSLD (SEQ ID NO: 90), GSAGSAAGSGEF (SEQ ID NO: 91), and (XP)$_n$, with X designating any amino acid, e.g., Ala, Lys, or Glu. In embodiments, the joining linker is GGS.

In embodiments, the joining linker is one or more of GGGSE (SEQ ID NO: 92), GSESG (SEQ ID NO: 93), GSEGS (SEQ ID NO: 94), GEGGSGEGSSGEGSSSEGGGSEGGGSEGGGSEGGS (SEQ ID NO: 95), and a joining linker of randomly placed G, S, and E every 4 amino acid intervals.

In embodiments, a chimeric protein comprises a modular linker as shown in FIG. 32.

In embodiments, the linker may be flexible, including without limitation highly flexible. In embodiments, the linker may be rigid, including without limitation a rigid alpha helix.

In embodiments, the linker may be functional. For example, without limitation, the linker may function to improve the folding and/or stability, improve the expression, improve the pharmacokinetics, and/or improve the bioactivity of the present chimeric protein. In another example, the linker may function to target the chimeric protein to a particular cell type or location.

In embodiments, the present chimeric proteins are capable of, and can be used in methods comprising, promoting immune activation (e.g. against tumors). In embodiments, the present chimeric proteins are capable of, and can be used in methods comprising, suppressing immune inhibition (e.g. that allows tumors to survive). In embodiments, the present chimeric proteins provide improved immune activation and/or improved suppression of immune inhibition due to the proximity of signaling that is provided by the chimeric nature of the constructs.

In embodiments, the present chimeric proteins are capable of, or can be used in methods comprising, modulating the amplitude of an immune response, e.g. modulating the level of effector output. In embodiments, e.g. when used for the treatment of cancer, the present chimeric proteins alter the extent of immune stimulation as compared to immune inhibition to increase the amplitude of a T cell response, including, without limitation, stimulating increased levels of cytokine production, proliferation or target killing potential.

In embodiments the present chimeric proteins, in embodiments are capable of, or find use in methods involving, masking an inhibitory ligand on the surface of a tumor cell and replacing that immune inhibitory ligand with an immune stimulatory ligand. Accordingly, the present chimeric proteins, in embodiments are capable of, or find use in methods involving, reducing or eliminating an inhibitory immune signal and/or increasing or activating an immune stimulatory signal. For example, a tumor cell bearing an inhibitory signal (and thus evading an immune response) may be substituted for a positive signal binding on a T cell that can then attack a tumor cell. Accordingly, in embodiments, an inhibitory immune signal is masked by the present constructs and a stimulatory immune signal is activated. Such beneficial properties are enhanced by the single construct approach of the present chimeric proteins. For instance, the signal replacement can be effected nearly simultaneously and the signal replacement is tailored to be local at a site of clinical importance (e.g. the tumor microenvironment). Further embodiments apply the same principle to other chimeric protein constructs, such as, for example, (i) the extracellular domain of TIGIT and (ii) extracellular domain of 4-1BBL; (i) the extracellular domain of TIGIT and (ii) extracellular domain of GITRL; (i) the extracellular domain of TIGIT and (ii) extracellular domain of TL1A; (i) the extracellular domain of TIGIT and (ii) extracellular domain of LIGHT; and (i) the extracellular domain of PD-1 and (ii) extracellular domain of LIGHT; and (i) the extracellular domain of CD172a(SIRPα) and (ii) extracellular domain of LIGHT; and (i) the extracellular domain of TIGIT and (ii) extracellular domain of LIGHT; among others.

In embodiments, the present chimeric proteins are capable of, or find use in methods comprising, stimulating or enhancing the binding of immune stimulatory receptor/ligand pairs. Illustrative T cell costimulatory receptors and their ligands include OX-40:OX40-L, CD27:CD70, CD30:CD30-L, CD40:CD40-L; CD137:CD137-L, HVEM:LIGHT, GITR:GITR-L, TNFRSF25:TL1A, DR5:TRAIL, and BTLA:HVEM. In embodiments, the present chimeric proteins are capable of, or find use in methods comprising, inhibiting or reducing the binding of immune inhibitory receptor/ligand pairs. Illustrative T cell coinhibitory receptors and their ligands include, for example, CTLA-4:CD80/CD86, PD-1:PD-L1/PD-L2, BTLA:HVEM, TIM-3:galectin-9/phosphatidylserine, TIGIT/CD155 or CD112, VISTANSIG8, CD172a(SIRPα)/CD47, B7H3R/B7H3, B7H4R/B7H4, CD244/CD48, TMIGD2/HHLA2, among others.

In embodiments, the present chimeric protein blocks, reduces and/or inhibits PD-1 and PD-L1 or PD-L2 and/or the binding of PD-1 with PD-L1 or PD-L2. In embodiments, the present chimeric protein blocks, reduces and/or inhibits the activity of CTLA-4 and/or the binding of CTLA-4 with one or more of AP2M1, CD80, CD86, SHP-2, and PPP2R5A. In embodiments, the present chimeric protein increases and/or stimulates GITR and/or the binding of GITR with one or more of GITR ligand. In embodiments, the present chimeric protein increases and/or stimulates OX40 and/or the binding of OX40 with one or more of OX40 ligand.

In embodiments, the present chimeric proteins are capable of, or find use in methods involving, enhancing, restoring, promoting and/or stimulating immune modulation. In embodiments, the present chimeric proteins described herein, restore, promote and/or stimulate the activity or activation of one or more immune cells against tumor cells including, but not limited to: T cells, cytotoxic T lymphocytes, T helper cells, natural killer (NK) cells, natural killer T (NKT) cells, anti-tumor macrophages (e.g. M1 macrophages), B cells, and dendritic cells. In embodiments, the present chimeric proteins enhance, restore, promote and/or stimulate the activity and/or activation of T cells, including, by way of a non-limiting example, activating and/or stimulating one or more T-cell intrinsic signals, including a pro-survival signal; an autocrine or paracrine growth signal; a p38 MAPK-, ERK-, STAT-, JAK-, AKT- or PI3K-mediated signal; an anti-apoptotic signal; and/or a signal promoting and/or necessary for one or more of: proinflammatory cytokine production or T cell migration or T cell tumor infiltration.

In embodiments, the present chimeric proteins are capable of, or find use in methods involving, causing an increase of one or more of T cells (including without limitation cytotoxic T lymphocytes, T helper cells, natural killer T (NKT) cells), B cells, natural killer (NK) cells, natural killer T (NKT) cells, dendritic cells, monocytes, and macrophages (e.g. one or more of M1 and M2) into a tumor or the tumor microenvironment. In embodiments, the present chimeric proteins are capable of, or find use in methods involving, inhibiting and/or causing a decrease in recruitment of immunosuppressive cells (e.g. myeloid-derived suppressor cells (MDSCs), regulatory T cells (Tregs), tumor associated neutrophils (TANs), M2 macrophages, and tumor associated macrophages (TAMs)) to the tumor and/or tumor microenvironment (TME). In embodiments, the present therapies may alter the ratio of M1 versus M2 macrophages in the tumor site and/or TME to favor M1 macrophages.

In embodiments, the present chimeric proteins are capable of, and can be used in methods comprising, inhibiting and/or reducing T cell inactivation and/or immune tolerance to a tumor, comprising administering an effective amount of a chimeric protein described herein to a subject. In embodiments, the present chimeric proteins are able to increase the serum levels of various cytokines including, but not limited to, one or more of IFNγ, TNFα, IL-2, IL-4, IL-5, IL-6, IL-9, IL-10, IL-13, IL-17A, IL-17F, and IL-22. In embodiments, the present chimeric proteins are capable of enhancing IL-2, IL-4, IL-5, IL-10, IL-13, IL-17A, IL-22, TNFα or IFNγ in the serum of a treated subject. In embodiments, administration of the present chimeric protein is capable of enhancing TNFα secretion. In a specific embodiment, administration of the present chimeric protein is capable of enhancing superantigen mediated TNFα secretion by leukocytes. Detection of such a cytokine response may provide a method to determine the optimal dosing regimen for the indicated chimeric protein.

In embodiments, the present chimeric proteins inhibit, block and/or reduce cell death of an anti-tumor CD8+ and/or CD4+ T cell; or stimulate, induce, and/or increase cell death of a pro-tumor T cell. T cell exhaustion is a state of T cell dysfunction characterized by progressive loss of proliferative and effector functions, culminating in clonal deletion. Accordingly, a pro-tumor T cell refers to a state of T cell dysfunction that arises during many chronic infections and cancer. This dysfunction is defined by poor proliferative and/or effector functions, sustained expression of inhibitory receptors and a transcriptional state distinct from that of functional effector or memory T cells. Exhaustion prevents optimal control of infection and tumors. In addition, an anti-tumor CD8+ and/or CD4+ T cell refers to T cells that can mount an immune response to a tumor. Illustrative pro-tumor T cells include, but are not limited to, Tregs, CD4+ and/or CD8+ T cells expressing one or more checkpoint inhibitory receptors, Th2 cells and Th17 cells. Checkpoint inhibitory receptors refers to receptors expressed on immune cells that prevent or inhibit uncontrolled immune responses.

In embodiments, the present chimeric proteins are capable of, and can be used in methods comprising, increasing a ratio of effector T cells to regulatory T cells. Illustrative effector T cells include ICOS+ effector T cells; cytotoxic T cells (e.g. αβ TCR, CD3+, CD8+, CD45RO+); CD4+ effector T cells (e.g. αβ TCR, CD3+, CD4+, CCR7+, CD62Lhi, IL−7R/CD127+); CD8+ effector T cells (e.g. αβ TCR, CD3+, CD8+, CCR7+, CD62Lhi, IL−7R/CD127+); effector memory T cells (e.g. CD62Llow, CD44+, TCR, CD3+, IL−7R/CD127+, IL-15R+, CCR7low); central memory T cells (e.g. CCR7+, CD62L+, CD27+; or CCR7hi, CD44+, CD62Lhi, TCR, CD3+, IL-7R/CD127+, IL-15R+); CD62L+ effector T cells;

CD8$^+$ effector memory T cells (TEM) including early effector memory T cells (CD27$^+$CD62L$^-$) and late effector memory T cells (CD27$^-$ CD62L$^-$) (TemE and TemL, respectively); CD127(+)CD25(low/–) effector T cells; CD127($^-$)CD25($^-$) effector T cells; CD8$^+$ stem cell memory effector cells (TSCM) (e.g. CD44(low)CD62L(high)CD122(high) sca($^+$)); TH1 effector T-cells (e.g. CXCR3$^+$, CXCR6$^+$ and CCR5$^+$; or αβ TCR, CD3$^+$, CD4$^+$, IL-12R$^+$, IFNγR$^+$, CXCR3$^+$), TH2 effector T cells (e.g. CCR3$^+$, CCR4$^+$ and CCR8$^+$; or αβ TCR, CD3$^+$, CD4$^+$, IL-4R$^+$, IL-33R$^+$, CCR4$^+$, IL-17RB$^+$, CRTH2$^+$); TH9 effector T cells (e.g. αβ TCR, CD3$^+$, CD4$^+$); TH17 effector T cells (e.g. αβ TCR, CD3$^+$, CD4$^+$, IL-23R$^+$, CCR6$^+$, IL-1R$^+$); CD4$^+$CD45RO$^+$CCR7$^+$ effector T cells, CD4$^+$CD45RO$^+$CCR7($^-$) effector T cells; and effector T cells secreting IL-2, IL-4 and/or IFN-γ. Illustrative regulatory T cells include ICOS$^+$ regulatory T cells, CD4$^+$CD25$^+$FOXP3$^+$ regulatory T cells, CD4$^+$CD25$^+$ regulatory T cells, CD4$^+$CD25$^-$ regulatory T cells, CD4$^+$CD25high regulatory T cells, TIM-3$^+$PD-1$^+$ regulatory T cells, lymphocyte activation gene-3 (LAG-3)$^+$ regulatory T cells, CTLA-4/CD152$^+$ regulatory T cells, neuropilin-1 (Nrp-1)$^+$ regulatory T cells, CCR4$^+$CCR8$^+$ regulatory T cells, CD62L (L-selectin)$^+$ regulatory T cells, CD45RBlow regulatory T cells, CD127low regulatory T cells, LRRC32/GARP$^+$ regulatory T cells, CD39$^+$ regulatory T cells, GITR$^+$ regulatory T cells, LAP$^+$ regulatory T cells, 1B11$^+$ regulatory T cells, BTLA$^+$ regulatory T cells, type 1 regulatory T cells (Tr1 cells), T helper type 3 (Th3) cells, regulatory cell of natural killer T cell phenotype (NKTregs), CD8$^+$ regulatory T cells, CD8$^+$CD28$^-$ regulatory T cells and/or regulatory T-cells secreting IL-10, IL-35, TGF-β, TNF-α, Galectin-1, IFN-γ and/or MCP1.

In embodiments, the chimeric protein generates a memory response which may, e.g., be capable of preventing relapse or protecting the animal from a rechallenge. Thus, an animal treated with the chimeric protein is later able to attack tumor cells and/or prevent development of tumors when rechallenged after an initial treatment with the chimeric protein. Accordingly, a chimeric protein of the present invention stimulates both active tumor destruction and also immune recognition of tumor antigens, which are essential in programming a memory response capable of preventing relapse.

In embodiments, the present chimeric proteins are capable of, and can be used in methods comprising, transiently stimulating effector T cells for no longer than about 12 hours, about 24 hours, about 48 hours, about 72 hours or about 96 hours or about 1 week or about 2 weeks. In embodiments, the present chimeric proteins are capable of, and can be used in methods comprising, transiently depleting or inhibiting regulatory T cells for no longer than about 12 hours, about 24 hours, about 48 hours, about 72 hours or about 96 hours or about 1 week or about 2 weeks. In embodiments, the transient stimulation of effector T cells and/or transient depletion or inhibition of regulatory T cells occurs substantially in a patient's bloodstream or in a particular tissue/location including lymphoid tissues such as for example, the bone marrow, lymph-node, spleen, thymus, mucosa-associated lymphoid tissue (MALT), non-lymphoid tissues, or in the tumor microenvironment.

In embodiments, the present chimeric proteins provide advantages including, without limitation, ease of use and ease of production. This is because two distinct immunotherapy agents are combined into a single product which allows for a single manufacturing process instead of two independent manufacturing processes. In addition, administration of a single agent instead of two separate agents allows for easier administration and greater patient compliance. Further, in contrast to, for example, monoclonal antibodies, which are large multimeric proteins containing numerous disulfide bonds and post-translational modifications such as glycosylation, the present chimeric proteins are easier and more cost effective to manufacture.

In embodiments, the present chimeric protein is producible in a mammalian host cell as a secretable and fully functional single polypeptide chain.

In embodiments, the present chimeric protein unexpectedly provides binding of the extracellular domain components to their respective binding partners with slow off rates ($K_d$ or $K_{off}$). In embodiments, this provides an unexpectedly long interaction of the receptor to ligand and vice versa. Such an effect allows for a sustained negative signal masking effect. Further, in embodiments, this delivers a longer positive signal effect, e.g. to allow an effector cell to be adequately stimulated for an anti-tumor effect. For example, the present chimeric protein, e.g. via the long off rate binding allows sufficient signal transmission to provide T cell proliferation and allow for anti-tumor attack. By way of further example, the present chimeric protein, e.g. via the long off rate binding allows sufficient signal transmission to provide release of stimulatory signals, such as, for example, cytokines.

The stable synapse of cells promoted by the present agents (e.g. a tumor cell bearing negative signals and a T cell which could attack the tumor) provides spatial orientation to favor tumor reduction—such as positioning the T cells to attack tumor cells and/or sterically preventing the tumor cell from delivering negative signals, including negative signals beyond those masked by the chimeric protein of the invention.

In embodiments, this provides longer on-target (e.g. intratumoral) half-life ($t_{1/2}$) as compared to serum $t_{1/2}$ of the chimeric proteins. Such properties could have the combined advantage of reducing off-target toxicities which may be associated with systemic distribution of the chimeric proteins.

In embodiments, the present agents allow certain immune cells to act, e.g. in an antitumoral manner, by preventing and/or disrupting inhibition of NK cells and/or subsets of activated, memory and/or regulatory T cells, and/or helper T cells by blocking a signal via TIGIT and, optionally, create further immune responses via 4-1BBL-, and/or GITRL-, and/or TL1A-, and/or LIGHT-based stimulatory signaling.

In embodiments, the present agents allow certain immune cells to act, e.g. in an antitumoral manner, by stimulating and/or increasing stimulatory LIGHT-based signaling, e.g. on visceral and/or lymphoid and/or other stroma and/or epithelia and/or myeloid cells and, optionally, create further immune responses via blokckade or reduction of PD-1-, and/or CD172a(SIRPα)-, and/or TIGIT-based inhibitory signaling.

Further, in embodiments, the present chimeric proteins provide synergistic therapeutic effects as it allows for improved site-specific interplay of two immunotherapy agents.

In embodiments, the present chimeric proteins provide the potential for reducing off-site and/or systemic toxicity.

In embodiments, the present chimeric proteins provide reduced side-effects, e.g., GI complications, relative to current immunotherapies, e.g., antibodies directed to checkpoint moleclues as described herein. Illustrative GI complications include abdominal pain, appetite loss, autoimmune effects, constipation, cramping, dehydration, diarrhea, eating problems, fatigue, flatulence, fluid in the abdomen or ascites, gastrointestinal (GI) dysbiosis, GI mucositis, inflammatory bowel disease, irritable bowel syndrome (IBS-D and IBS-C), nausea, pain, stool or urine changes, ulcerative colitis, vomiting, weight gain from retaining fluid, and/or weakness.

Diseases; Methods of Treatment, and Patient Selections

In embodiments, the present invention pertains to cancers and/or tumors; for example, the treatment or prevention of cancers and/or tumors. As described elsewhere herein, the treatment of cancer may involve in embodiments, modulating the immune system with the present chimeric proteins to favor immune stimulation over immune inhibition.

Cancers or tumors refer to an uncontrolled growth of cells and/or abnormal increased cell survival and/or inhibition of apoptosis which interferes with the normal functioning of the bodily organs and systems. Included are benign and malignant cancers, polyps, hyperplasia, as well as dormant tumors or micrometastases. Also, included are cells having abnormal proliferation that is not impeded by the immune system (e.g. virus infected cells). The cancer may be a primary cancer or a metastatic cancer. The primary cancer may be an area of cancer cells at an originating site that becomes clinically detectable, and may be a primary tumor. In contrast, the metastatic cancer may be the spread of a disease from one organ or part to another non-adjacent organ or part. The metastatic cancer may be caused by a cancer cell that acquires the ability to penetrate and infiltrate surrounding normal tissues in a local area, forming a new tumor, which may be a local metastasis. The cancer may also be caused by a cancer cell that acquires the ability to penetrate the walls of lymphatic and/or blood vessels, after which the cancer cell is able to circulate through the bloodstream (thereby being a circulating tumor cell) to other sites and tissues in the body. The cancer may be due to a process such as lymphatic or hematogeneous spread. The cancer may also be caused by a tumor cell that comes to rest at another site, re-penetrates through the vessel or walls, continues to multiply, and eventually forms another clinically detectable tumor. The cancer may be this new tumor, which may be a metastatic (or secondary) tumor.

The cancer may be caused by tumor cells that have metastasized, which may be a secondary or metastatic tumor. The cells of the tumor may be like those in the original tumor. As an example, if a breast cancer or colon cancer metastasizes to the liver, the secondary tumor, while present in the liver, is made up of abnormal breast or colon cells, not of abnormal liver cells. The tumor in the liver may thus be a metastatic breast cancer or a metastatic colon cancer, not liver cancer.

The cancer may have an origin from any tissue. The cancer may originate from melanoma, colon, breast, or prostate, and thus may be made up of cells that were originally skin, colon, breast, or prostate, respectively. The cancer may also be a hematological malignancy, which may be leukemia or lymphoma. The cancer may invade a tissue such as liver, lung, bladder, or intestinal.

Representative cancers and/or tumors of the present invention include, but are not limited to, a basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

In embodiments, the chimeric protein is used to treat a subject that has a treatment-refractory cancer. In embodiments, the chimeric protein is used to treat a subject that is refractory to one or more immune-modulating agents. For example, in embodiments, the chimeric protein is used to treat a subject that presents no response to treatment, or even progress, after 12 weeks or so of treatment. For instance, in embodiments, the subject is refractory to a PD-1 and/or PD-L1 and/or PD-L2 agent, including, for example, nivolumab (ONO-4538/BMS-936558, MDX1106, OPDIVO, BRISTOL MYERS SQUIBB), pembrolizumab (KEYTRUDA, MERCK), pidilizumab (CT-011, CURE TECH), MK-3475 (MERCK), BMS 936559 (BRISTOL MYERS SQUIBB), Ibrutinib (PHARMACYCLICS/ABBVIE), atezolizumab (TECENTRIQ, GENENTECH), and/or MPDL328OA (ROCHE)-refractory patients. For instance, in embodiments, the subject is refractory to an anti-CTLA-4 agent, e.g. ipilimumab (YERVOY)-refractory patients (e.g. melanoma patients). Accordingly, in embodiments the present invention provides methods of cancer treatment that rescue patients that are non-responsive to various therapies, including monotherapy of one or more immune-modulating agents.

In embodiments, the present invention provides chimeric proteins which target a cell or tissue within the tumor microenviroment. In embodiments, the cell or tissue within the tumor microenvironment expresses one or more targets or binding partners of the chimeric protein. The tumor microenvironment refers to the cellular milieu, including cells, secreted proteins, physiological small molecules, and blood vessels in which the tumor exists. In embodiments, the cells or tissue within the tumor microenvironment are one or more of: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor. In embodiments, the present chimeric protein targets a cancer cell. In embodiments, the cancer cell expresses one or more of targets or binding partners of the chimeric protein.

In embodiments, the chimeric protein of the invention may target a cell (e.g., cancer cell or immune cell) that expresses TIGIT. In embodiments, the chimeric protein of the invention may target a cell (e.g., cancer cell or immune cell) that expresses CD155/PVR. In embodiments, the chimeric protein of the invention may target a cell (e.g., cancer cell or immune cell) that expresses Nectin-2. In embodiments, the chimeric protein of the invention may target a cell (e.g., cancer cell or immune cell) that expresses Nectin-3. In embodiments, the chimeric protein of the invention may target a cell (e.g., cancer cell or immune cell) that expresses Nectin-4.

In embodiments, the chimeric protein of the invention may target a cell (e.g., cancer cell or immune cell) that expresses LIGHT. In embodiments, the chimeric protein of the invention may target a cell (e.g., cancer cell or immune cell) that expresses LTBR. In embodiments, the chimeric protein of the invention may target a cell (e.g., cancer cell or immune cell) that expresses HVEM. In embodiments, the chimeric protein of the invention may target a cell (e.g., cancer cell or immune cell) that expresses DcR3.

In embodiments, the present methods provide treatment with the chimeric protein in a patient who is refractory to an additional agent, such "additional agents" being described elsewhere herein, inclusive, without limitation, of the various chemotherapeutic agents described herein.

In embodiments, the chimeric proteins are used to treat, control or prevent one or more inflammatory diseases or conditions. Non-limiting examples of inflammatory diseases include acne vulgaris, acute inflammation, allergic rhinitis, asthma, atherosclerosis, atopic dermatitis, autoimmune disease, autoinflammatory diseases, autosomal recessive spastic ataxia, bronchiectasis, celiac disease, chronic cholecystitis, chronic inflammation, chronic prostatitis, colitis, diverticulitis, familial eosinophilia (fe), glomerulonephritis, glycerol kinase deficiency, hidradenitis suppurativa, hypersensitivities, inflammation, inflammatory bowel diseases, inflammatory pelvic disease, interstitial cystitis, laryngeal inflammatory disease, Leigh syndrome, lichen planus, mast cell activation syndrome, mastocytosis, ocular inflammatory disease, otitis, pain, pelvic inflammatory disease, reperfusion injury, respiratory disease, restenosis, rheumatic fever, rheumatoid arthritis, rhinitis, sarcoidosis, septic shock, silicosis and other pneumoconioses, transplant rejection, tuberculosis, and vasculitis.

In embodiments, the inflammatory disease is an autoimmune disease or condition, such as multiple sclerosis, diabetes mellitus, lupus, celiac disease, Crohn's disease, ulcerative colitis, Guillain-Barre syndrome, scleroderms, Goodpasture's syndrome, Wegener's granulomatosis, autoimmune epilepsy, Rasmussen's encephalitis, Primary biliary sclerosis, Sclerosing cholangitis, Autoimmune hepatitis, Addison's disease, Hashimoto's thyroiditis, Fibromyalgia, Menier's syndrome; transplantation rejection (e.g., prevention of allograft rejection) pernicious anemia, rheumatoid arthritis, systemic lupus erythematosus, dermatomyositis, Sjogren's syndrome, lupus erythematosus, multiple sclerosis, myasthenia gravis, Reiter's syndrome, Grave's disease, and other autoimmune diseases.

In some aspects, the present chimeric agents are used to eliminate intracellular pathogens. In some aspects, the present chimeric agents are used to treat one or more infections. In embodiments, the present chimeric proteins are used in methods of treating viral infections (including, for example, HIV and HCV), parasitic infections (including, for example, malaria), and bacterial infections. In embodiments, the infections induce immunosuppression. For example, HIV infections often result in immunosuppression in the infected subjects. Accordingly, as described elsewhere herein, the treatment of such infections may involve, in embodiments, modulating the immune system with the present chimeric proteins to favor immune stimulation over immune inhibition. Alternatively, the present invention provides methods for treating infections that induce immunoactivation. For example, intestinal helminth infections have been associated with chronic immune activation. In these embodiments, the treatment of such infections may involve modulating the immune system with the present chimeric proteins to favor immune inhibition over immune stimulation.

In embodiments, the present invention provides methods of treating viral infections including, without limitation, acute or chronic viral infections, for example, of the respiratory tract, of papilloma virus infections, of herpes simplex virus (HSV) infection, of human immunodeficiency virus (HIV) infection, and of viral infection of internal organs such as infection with hepatitis viruses. In embodiments, the viral infection is caused by a virus of family Flaviviridae. In embodiments, the virus of family Flaviviridae is selected from Yellow Fever Virus, West Nile virus, Dengue virus, Japanese Encephalitis Virus, St. Louis Encephalitis Virus, and Hepatitis C Virus. In embodiments, the viral infection is caused by a virus of family Picornaviridae, e.g., poliovirus, rhinovirus, coxsackievirus. In embodiments, the viral infection is caused by a member of Orthomyxoviridae, e.g., an influenza virus. In embodiments, the viral infection is caused by a member of Retroviridae, e.g., a lentivirus. In embodiments, the viral infection is caused by a member of Paramyxoviridae, e.g., respiratory syncytial virus, a human parainfluenza virus, rubulavirus (e.g., mumps virus), measles virus, and human metapneumovirus. In embodiments, the viral infection is caused by a member of Bunyaviridae, e.g., hantavirus. In embodiments, the viral infection is caused by a member of Reoviridae, e.g., a rotavirus.

In embodiments, the present invention provides methods of treating parasitic infections such as protozoan or helminths infections. In embodiments, the parasitic infection is by a protozoan parasite. In embodiments, the oritiziab parasite is selected from intestinal protozoa, tissue protozoa, or blood protozoa. Illustrative protozoan parasites include, but are not limited to, *Entamoeba hystolytica, Giardia lamblia, Cryptosporidium muris, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis*, and *Histomonas meleagridis*. In embodiments, the parasitic infection is by a helminthic parasite such as nematodes (e.g., Adenophorea). In embodiments, the parasite is selected from Secementea (e.g., *Trichuris trichiura, Ascaris lumbricoides, Enterobius vermicularis, Ancylostoma duodenale, Necator americanus, Strongyloides stercoralis, Wuchereria bancrofti, Dracunculus medinensis*). In embodiments, the parasite is selected from trematodes (e.g. blood flukes, liver flukes, intestinal flukes, and lung flukes). In embodiments, the parasite is selected from: *Schistosoma mansoni, Schistosoma haematobium, Schistosoma japonicum, Fasciola hepatica, Fasciola gigantica*, Heterophyes, *Paragonimus westermani*. In embodiments, the parasite is selected from cestodes (e.g., *Taenia solium, Taenia saginata, Hymenolepis nana, Echinococcus granulosus*).

In embodiments, the present invention provides methods of treating bacterial infections. In embodiments, the bacterial infection is by gram-positive bacteria, gram-negative bacteria, aerobic and/or anaerobic bacteria. In embodiments, the bacteria is selected from, but not limited to, *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms. In embodiments, the bacteria is selected from, but not limited to, *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis*, or *Staphylococcus saccharolyticus*.

In some aspects, the present chimeric agents are used to treat one or more autoimmune diseases or disorders. In embodiments, the treatment of an autoimmune disease or disorder may involve modulating the immune system with the present chimeric proteins to favor immune inhibition over immune stimulation. Illustrative autoimmune diseases or disorders treatable with the present chimeric proteins include those in which the body's own antigens become targets for an immune response, such as, for example, rheumatoid arthritis, systemic lupus erythematosus, diabetes mellitus, ankylosing spondylitis, Sjögren's syndrome, inflammatory bowel diseases (e.g. colitis ulcerosa, Crohn's disease), multiple sclerosis, sarcoidosis, psoriasis, Grave's disease, Hashimoto's thyroiditis, psoriasis, hypersensitivity reactions (e.g., allergies, hay fever, asthma, and acute edema cause Type I hypersensitivity reactions), and vasculitis.

In still another other aspect, the present invention is directed toward methods of treating and preventing T cell-mediated diseases and disorders, such as, but not limited to diseases or disorders described elsewhere herein and inflammatory disease or disorder, graft-versus-host disease (GVHD), transplant rejection, and T cell proliferative disorder.

In some aspects, the present chimeric agents are used in methods of activating a T cell, e.g. via the extracellular domain having an immune stimulatory signal.

In some aspects, the present chimeric agents are used in methods of preventing the cellular transmission of an immunosuppressive signal.

Combination Therapies and Conjugation

In embodiments, the invention provides for chimeric proteins and methods that further comprise administering an additional agent to a subject. In embodiments, the invention pertains to co-administration and/or co-formulation. Any of the compositions described herein may be co-formulated and/or co-administered.

In embodiments, any chimeric protein described herein acts synergistically when co-administered with another agent and is administered at doses that are lower than the doses commonly employed when such agents are used as monotherapy. In embodiments, any agent referenced herein may be used in combination with any of the chimeric proteins described herein.

In embodiments, inclusive of, without limitation, cancer applications, the present invention pertains to chemotherapeutic agents as additional agents. Examples of chemotherapeutic agents include, but are not limited to, alkylating agents such as thiotepa and CYTOXAN cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (e.g., bullatacin and bullatacinone); a camptothecin (including the synthetic analogue topotecan); bryostatin; cally statin; CC-1065 (including its adozelesin, carzelesin and bizelesin synthetic analogues); cryptophycins (e.g., cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate;

purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as minoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (e.g., T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL paclitaxel (Bristol-Myers Squibb Oncology, Princeton, N.J.), ABRAXANE Cremophor-free, albumin-engineered nanoparticle formulation of paclitaxel (American Pharmaceutical Partners, Schaumberg, 111.), and TAXOTERE doxetaxel (Rhone-Poulenc Rorer, Antony, France); chlorambucil; GEMZAR gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE. vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-α, Raf, H-Ras, EGFR (e.g., erlotinib (Tarceva)) and VEGF-A that reduce cell proliferation and pharmaceutically acceptable salts, acids or derivatives of any of the above. In addition, the methods of treatment can further include the use of radiation. In addition, the methods of treatment can further include the use of photodynamic therapy.

In embodiments, inclusive of, without limitation, cancer applications, the present additional agent is one or more immune-modulating agents selected from an agent that blocks, reduces and/or inhibits PD-1 and PD-L1 or PD-L2 and/or the binding of PD-1 with PD-L1 or PD-L2 (by way of non-limiting example, one or more of nivolumab (ONO-4538/BMS-936558, MDX1106, OPDIVO, BRISTOL MYERS SQUIBB), pembrolizumab (KEYTRUDA, Merck), MK-3475 (MERCK), BMS 936559 (BRISTOL MYERS SQUIBB), atezolizumab (TECENTRIQ, GENENTECH), MPDL328OA (ROCHE)), an agent that increases and/or stimulates CD137 (4-1BB) and/or the binding of CD137 (4-1BB) with one or more of 4-1BB ligand (by way of non-limiting example, urelumab (BMS-663513 and anti-4-1BB antibody), and an agent that blocks, reduces and/or inhibits the activity of CTLA-4 and/or the binding of CTLA-4 with one or more of AP2M1, CD80, CD86, SHP-2, and PPP2R5A and/or the binding of OX40 with OX40L (by way of non-limiting example GBR 830 (GLENMARK), MED16469 (MEDIMMUNE).

In embodiments, inclusive of, without limitation, infectious disease applications, the present invention pertains to anti-infectives as additional agents. In embodiments, the anti-infective is an anti-viral agent including, but not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. In embodiments, the anti-infective is an anti-bacterial agent including, but not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In embodiments, the anti-infectives include anti-malarial agents (e.g., chloroquine, quinine, mefloquine, primaquine, doxycycline, artemether/lumefantrine, atovaquone/proguanil and sulfadoxine/pyrimethamine), metronidazole, tinidazole, ivermectin, pyrantel pamoate, and albendazole.

In embodiments, inclusive, without limitation, of autoimmune applications, the additional agent is an immunosuppressive agent. In embodiments, the immunosuppressive agent is an anti-inflammatory agent such as a steroidal anti-inflammatory agent or a non-steroidal anti-inflammatory agent (NSAID). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluoromethalone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. In embodiments, the immunosupressive agent may be cytostatics such as alkylating agents, antimetabolites (e.g., azathioprine, methotrexate), cytotoxic antibiotics, antibodies (e.g., basiliximab, daclizumab, and muromonab), anti-immunophilins (e.g., cyclosporine, tacrolimus, sirolimus), inteferons, opioids, TNF binding proteins, mycophenolates, and small biological agents (e.g., fingolimod, myriocin).

In embodiments, the chimeric proteins (and/or additional agents) described herein, include derivatives that are modified, i.e., by the covalent attachment of any type of molecule to the composition such that covalent attachment does not prevent the activity of the composition. For example, but not by way of limitation, derivatives include composition that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, metabolic synthesis of turicamycin, etc. Additionally, the derivative can contain one or more non-classical amino acids. In still other embodiments, the chimeric proteins (and/or additional agents) described herein further comprise a cytotoxic agent, comprising, in illustrative embodiments, a toxin, a chemotherapeutic agent, a radioisotope, and an agent that causes apoptosis or cell death. Such agents may be conjugated to a composition described herein.

The chimeric proteins (and/or additional agents) described herein may thus be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Formulations

The chimeric proteins (and/or additional agents) described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts; Properties, Selection, and Use*. P. H. Stahl and C. G. Wermuth (eds.), Verlag, Zurich (Switzerland) 2002, which are hereby incorporated by reference in their entirety.

In embodiments, the compositions described herein are in the form of a pharmaceutically acceptable salt.

Further, any chimeric protein (and/or additional agents) described herein can be administered to a subject as a component of a composition that comprises a pharmaceutically acceptable carrier or vehicle. Such compositions can optionally comprise a suitable amount of a pharmaceutically acceptable excipient so as to provide the form for proper administration. Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Any agent described herein, if desired, can also comprise minor amounts of wetting or emulsifying agents, or pH buffering agents.

In embodiments, the compositions described herein are resuspended in a saline buffer (including, without limitation TBS, PBS, and the like).

In embodiments, the chimeric proteins may by conjugated and/or fused with another agent to extend half-life or otherwise improve pharmacodynamic and pharmacokinetic properties. In embodiments, the chimeric proteins may be fused or conjugated with one or more of PEG, XTEN (e.g., as rPEG), polysialic acid (POLYXEN), albumin (e.g., human serum albumin or HAS), elastin-like protein (ELP), PAS, HAP, GLK, CTP, transferrin, and the like. In embodiments, each of the individual chimeric proteins is fused to one or more of the agents described in BioDrugs (2015) 29:215-239, the entire contents of which are hereby incorporated by reference.

Administration, Dosing, and Treatment Regimens

The present invention includes the described chimeric protein (and/or additional agents) in various formulations. Any chimeric protein (and/or additional agents) described herein can take the form of solutions, suspensions, emulsion, drops, tablets, pills, pellets, capsules, capsules containing liquids, powders, sustained-release formulations, suppositories, emulsions, aerosols, sprays, suspensions, or any other form suitable for use. DNA or RNA constructs encoding the protein sequences may also be used. In one embodiment, the composition is in the form of a capsule (see, e.g., U.S. Pat. No. 5,698,155). Other examples of suitable pharmaceutical excipients are described in Remington's Pharmaceutical Sciences 1447-1676 (Alfonso R. Gennaro eds., 19th ed. 1995), incorporated herein by reference.

Where necessary, the formulations comprising the chimeric protein (and/or additional agents) can also include a solubilizing agent. Also, the agents can be delivered with a suitable vehicle or delivery device as known in the art. Combination therapies outlined herein can be co-delivered in a single delivery vehicle or delivery device. Compositions for administration can optionally include a local anesthetic such as, for example, lignocaine to lessen pain at the site of the injection.

The formulations comprising the chimeric protein (and/or additional agents) of the present invention may conveniently be presented in unit dosage forms and may be prepared by any of the methods well known in the art of pharmacy. Such methods generally include the step of bringing therapeutic agents into association with a carrier, which constitutes one or more accessory ingredients. Typically, the formulations are prepared by uniformly and intimately bringing therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art)

In one embodiment, any chimeric protein (and/or additional agents) described herein is formulated in accordance with routine procedures as a composition adapted for a mode of administration described herein.

Routes of administration include, for example: intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. In embodiments, the administering is effected orally or by parenteral injection. In most instances, administration results in the release of any agent described herein into the bloodstream.

Any chimeric protein (and/or additional agents) described herein can be administered orally. Such chimeric proteins (and/or additional agents) can also be administered by any other convenient route, for example, by intravenous infusion or bolus injection, by absorption through epithelial or mucocutaneous linings (e.g., oral mucosa, rectal and intestinal mucosa, etc.) and can be administered together with another biologically active agent. Administration can be systemic or local. Various delivery systems are known, e.g., encapsulation in liposomes, microparticles, microcapsules, capsules, etc., and can be used to administer.

In specific embodiments, it may be desirable to administer locally to the area in need of treatment. In one embodiment, for instance in the treatment of cancer, the chimeric protein (and/or additional agents) are administered in the tumor microenvironment (e.g. cells, molecules, extracellular matrix and/or blood vessels that surround and/or feed a tumor cell, inclusive of, for example, tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T cells; macrophages; neutrophils; and other immune cells located proximal to a tumor) or lymph node and/or targeted to the tumor microenvironment or lymph node. In embodiments, for instance in the treatment of cancer, the chimeric protein (and/or additional agents) are administered intratumorally.

In the various embodiments, the present chimeric protein allows for a dual effect that provides less side effects than are seen in conventional immunotherapy (e.g. treatments with one or more of OPDIVO, KEYTRUDA, YERVOY, and TECENTRIQ). For example, the present chimeric proteins reduce or prevent commonly observed immune-related adverse events that affect various tissues and organs including the skin, the gastrointestinal tract, the kidneys, peripheral and central nervous system, liver, lymph nodes, eyes, pancreas, and the endocrine system; such as hypophysitis, colitis, hepatitis, pneumonitis, rash, and rheumatic disease. Further, the present local administration, e.g. intratumorally, obviate adverse event seen with standard systemic administration, e.g. IV infusions, as are used with conventional immunotherapy (e.g. treatments with one or more of OPDIVO, KEYTRUDA, YERVOY, and TECENTRIQ).

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents known in the art.

The dosage of any chimeric protein (and/or additional agents) described herein as well as the dosing schedule can depend on various parameters, including, but not limited to, the disease being treated, the subject's general health, and the administering physician's discretion. Any chimeric protein described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concurrently with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an additional agent, to a subject in need thereof. In embodiments any chimeric protein and additional agent described herein are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart.

In embodiments, the present invention relates to the co-administration of a chimeric protein which induces an innate immune response and another chimeric protein which induces an adaptive immune response. In such embodiments, the chimeric protein which induces an innate immune response may be administered before, concurrently with, or subsequent to administration of the chimeric protein which induces an adaptive immune response. For example, the chimeric proteins may be administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, 1 day apart, 2 days apart, 3 days apart, 4 days apart, 5 days apart, 6 days apart, 1 week apart, 2 weeks apart, 3 weeks apart, or 4 weeks apart. In an illustrative embodiment, the chimeric protein which induces an innate immune response and the chimeric protein which induces an adaptive response are administered 1 week apart, or administered on alternate weeks (i.e., administration of the chimeric protein inducing an innate immune response is followed 1 week later with administration of the chimeric protein which induces an adaptive immune response and so forth).

The dosage of any chimeric protein (and/or additional agents) described herein can depend on several factors including the severity of the condition, whether the condition is to be treated or prevented, and the age, weight, and health of the subject to be treated. Additionally, pharmacogenomic (the effect of genotype on the pharmacokinetic, pharmacodynamic or efficacy profile of a therapeutic) information about a particular subject may affect dosage used. Furthermore, the exact individual dosages can be adjusted somewhat depending on a variety of factors, including the specific combination of the agents being administered, the time of administration, the route of administration, the nature of the formulation, the rate of excretion, the particular disease being treated, the severity of the disorder, and the anatomical location of the disorder. Some variations in the dosage can be expected.

For administration of any chimeric protein (and/or additional agents) described herein by parenteral injection, the dosage may be about 0.1 mg to about 250 mg per day, about 1 mg to about 20 mg per day, or about 3 mg to about 5 mg per day. Generally, when orally or parenterally administered, the dosage of any agent described herein may be about 0.1 mg to about 1500 mg per day, or about 0.5 mg to about 10 mg per day, or about 0.5 mg to about 5 mg per day, or about 200 to about 1,200 mg per day (e.g., about 200 mg, about 300 mg, about 400 mg, about 500 mg, about 600 mg, about 700 mg, about 800 mg, about 900 mg, about 1,000 mg, about 1,100 mg, about 1,200 mg per day).

In embodiments, administration of the chimeric protein (and/or additional agents) described herein is by parenteral injection at a dosage of about 0.1 mg to about 1500 mg per treatment, or about 0.5 mg to about 10 mg per treatment, or about 0.5 mg to about 5 mg per treatment, or about 200 to about 1,200 mg per treatment (e.g., about 200 mg, about 300 mg, about 400 mg, about 500 mg, about 600 mg, about 700 mg, about 800 mg, about 900 mg, about 1,000 mg, about 1,100 mg, about 1,200 mg per treatment).

In embodiments, a suitable dosage of the chimeric protein (and/or additional agents) is in a range of about 0.01 mg/kg to about 100 mg/kg of body weight, or about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween.

In another embodiment, delivery can be in a vesicle, in particular a liposome (see Langer, 1990, Science 249:1527-1533; Treat et al., in Liposomes in therapy of Infectious Disease and Cancer, Lopez-Berestein and Fidler (eds.), Liss, New York, pp. 353-365 (1989).

Any chimeric protein (and/or additional agents) described herein can be administered by controlled-release or sustained-release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,556, each of which is incorporated herein by reference in its entirety. Such dosage forms can be useful for providing controlled- or sustained-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Controlled- or sustained-release of an active ingredient can be stimulated by various conditions, including but not limited to, changes in pH, changes in temperature, stimulation by an appropriate wavelength of light, concentration or availability of enzymes, concentration or availability of water, or other physiological conditions or compounds.

In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105).

In another embodiment, a controlled-release system can be placed in proximity of the target area to be treated, thus requiring only a fraction of the systemic dose (see, e.g., Goodson, in *Medical Applications of Controlled Release*, supra, vol. 2, pp. 115-138 (1984)). Other controlled-release systems discussed in the review by Langer, 1990, *Science* 249:1527-1533) may be used.

Administration of any chimeric protein (and/or additional agents) described herein can, independently, be one to four times daily or one to four times per month or one to six times per year or once every two, three, four or five years. Administration can be for the duration of one day or one month, two months, three months, six months, one year, two years, three years, and may even be for the life of the subject.

The dosage regimen utilizing any chimeric protein (and/or additional agents) described herein can be selected in accordance with a variety of factors including type, species, age, weight, sex and medical condition of the subject; the severity of the condition to be treated; the route of administration; the renal or hepatic function of the subject; the pharmacogenomic makeup of the individual; and the specific compound of the invention employed. Any chimeric protein (and/or additional agents) described herein can be administered in a single daily dose, or the total daily dosage can be administered in divided doses of two, three or four times daily. Furthermore, any chimeric protein (and/or additional agents) described herein can be administered continuously rather than intermittently throughout the dosage regimen.

Cells and Nucleic Acids

In embodiments, the present invention provides an expression vector, comprising a nucleic acid encoding the chimeric protein described herein. In embodiments, the expression vector comprises DNA or RNA. In embodiments, the expression vector is a mammalian expression vector.

Both prokaryotic and eukaryotic vectors can be used for expression of the chimeric protein. Prokaryotic vectors include constructs based on *E. coli* sequences (see, e.g., Makrides, *Microbiol Rev* 1996, 60:512-538). Non-limiting examples of regulatory regions that can be used for expression in *E. coli* include lac, trp, Ipp, phoA, recA, tac, T3, T7 and $\lambda P_L$. Non-limiting examples of prokaryotic expression vectors may include the λgt vector series such as λgt11 (Huynh et al., in "DNA Cloning Techniques, Vol. I: A Practical Approach," 1984, (D. Glover, ed.), pp. 49-78, IRL Press, Oxford), and the pET vector series (Studier et al., *Methods Enzymol* 1990, 185:60-89). Prokaryotic host-vector systems cannot perform much of the post-translational processing of mammalian cells, however. Thus, eukaryotic host-vector systems may be particularly useful. A variety of regulatory regions can be used for expression of the chimeric proteins in mammalian host cells. For example, the SV40 early and late promoters, the cytomegalovirus (CMV) immediate early promoter, and the Rous sarcoma virus long terminal repeat (RSV-LTR) promoter can be used. Inducible promoters that may be useful in mammalian cells include, without limitation, promoters associated with the metallothionein II gene, mouse mammary tumor virus glucocorticoid responsive long terminal repeats (MMTV-LTR), the β-interferon gene, and the hsp70 gene (see, Williams et al., *Cancer Res* 1989, 49:2735-42; and Taylor et al., *Mol Cell Biol* 1990, 10:165-75). Heat shock promoters or stress promoters also may be advantageous for driving expression of the chimeric proteins in recombinant host cells.

In embodiments, expression vectors of the invention comprise a nucleic acid encoding the chimeric proteins (and/or additional agents), or a complement thereof, operably linked to an expression control region, or complement thereof, that is functional in a mammalian cell. The expression control region is capable of driving expression of the operably linked blocking and/or stimulating agent encoding nucleic acid such that the blocking and/or stimulating agent is produced in a human cell transformed with the expression vector.

Expression control regions are regulatory polynucleotides (sometimes referred to herein as elements), such as promoters and enhancers, that influence expression of an operably linked nucleic acid. An expression control region of an expression vector of the invention is capable of expressing operably linked encoding nucleic acid in a human cell. In an embodiment, the cell is a tumor cell. In another embodiment, the cell is a non-tumor cell. In an embodiment, the expression control region confers regulatable expression to an operably linked nucleic acid. A signal (sometimes referred to as a stimulus) can increase or decrease expression of a nucleic acid operably linked to such an expression control region. Such expression control regions that increase expression in response to a signal are often referred to as inducible. Such expression control regions that decrease expression in response to a signal are often referred to as repressible. Typically, the amount of increase or decrease conferred by such elements is proportional to the amount of signal present; the greater the amount of signal, the greater the increase or decrease in expression.

In an embodiment, the present invention contemplates the use of inducible promoters capable of effecting high level of expression transiently in response to a cue. For example, when in the proximity of a tumor cell, a cell transformed with an expression vector for the chimeric protein (and/or additional agents) comprising such an expression control sequence is induced to transiently produce a high level of the agent by exposing the transformed cell to an appropriate cue. Illustrative inducible expression control regions include those comprising an inducible promoter that is stimulated with a cue such as a small molecule chemical compound. Particular examples can be found, for example, in U.S. Pat. Nos. 5,989,910, 5,935,934, 6,015,709, and 6,004,941, each of which is incorporated herein by reference in its entirety.

Expression control regions and locus control regions include full-length promoter sequences, such as native promoter and enhancer elements, as well as subsequences or polynucleotide variants which retain all or part of full-length or non-variant function. As used herein, the term "functional" and grammatical variants thereof, when used in reference to a nucleic acid sequence, subsequence or fragment, means that the sequence has one or more functions of native nucleic acid sequence (e.g., non-variant or unmodified sequence).

As used herein, "operable linkage" refers to a physical juxtaposition of the components so described as to permit them to function in their intended manner. In the example of an expression control element in operable linkage with a nucleic acid, the relationship is such that the control element modulates expression of the nucleic acid. Typically, an expression control region that modulates transcription is juxtaposed near the 5' end of the transcribed nucleic acid (i.e., "upstream"). Expression control regions can also be located at the 3' end of the transcribed sequence (i.e., "downstream") or within the transcript (e.g., in an intron). Expression control elements can be located at a distance away from the transcribed sequence (e.g., 100 to 500, 500 to 1000, 2000 to 5000, or more nucleotides from the nucleic acid). A specific example of an expression control element is a promoter, which is usually located 5' of the transcribed sequence. Another example of an expression control element is an enhancer, which can be located 5' or 3' of the transcribed sequence, or within the transcribed sequence.

Expression systems functional in human cells are well known in the art, and include viral systems. Generally, a promoter functional in a human cell is any DNA sequence capable of binding mammalian RNA polymerase and initiating the downstream (3') transcription of a coding sequence into mRNA. A promoter will have a transcription initiating region, which is usually placed proximal to the 5' end of the coding sequence, and typically a TATA box located 25-30 base pairs upstream of the transcription initiation site. The TATA box is thought to direct RNA polymerase II to begin RNA synthesis at the correct site. A promoter will also typically contain an upstream promoter element (enhancer element), typically located within 100 to 200 base pairs upstream of the TATA box. An upstream promoter element determines the rate at which transcription is initiated and can act in either orientation. Of particular use as promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenylation signals include those derived from SV40. Introns may also be included in expression constructs.

There are a variety of techniques available for introducing nucleic acids into viable cells. Techniques suitable for the transfer of nucleic acid into mammalian cells in vitro include the use of liposomes, electroporation, microinjection, cell fusion, polymer-based systems, DEAE-dextran, viral transduction, the calcium phosphate precipitation method, etc. For in vivo gene transfer, a number of techniques and reagents may also be used, including liposomes; natural polymer-based delivery vehicles, such as chitosan and gelatin; viral vectors are also suitable for in vivo transduction. In some situations, it is desirable to provide a targeting agent, such as an antibody or ligand specific for a tumor cell surface membrane protein. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., J. Biol. Chem. 262, 4429-4432 (1987); and Wagner et al., Proc. Natl. Acad. Sci. USA 87, 3410-3414 (1990).

Where appropriate, gene delivery agents such as, e.g., integration sequences can also be employed. Numerous integration sequences are known in the art (see, e.g., Nunes-Duby et al., Nucleic Acids Res. 26:391-406, 1998; Sadwoski, J. Bacteriol., 165:341-357, 1986; Bestor, Cell, 122 (3):322-325, 2005; Plasterk et al., TIG 15:326-332, 1999; Kootstra et al., Ann. Rev. Pharm. Toxicol., 43:413-439, 2003). These include recombinases and transposases. Examples include Cre (Sternberg and Hamilton, J. Mol. Biol., 150:467-486, 1981), lambda (Nash, Nature, 247, 543-545, 1974), Flp (Broach, et al., Cell, 29:227-234, 1982), R (Matsuzaki, et al., J. Bacteriology, 172:610-618, 1990), cpC31 (see, e.g., Groth et al., J. Mol. Biol. 335:667-678, 2004), sleeping beauty, transposases of the mariner family (Plasterk et al., supra), and components for integrating viruses such as AAV, retroviruses, and antiviruses having components that provide for virus integration such as the LTR sequences of retroviruses or lentivirus and the ITR sequences of MV (Kootstra et al., Ann. Rev. Pharm. Toxicol., 43:413-439, 2003). In addition, direct and targeted genetic integration strategies may be used to insert nucleic acid sequences encoding the chimeric fusion proteins including CRISPR/CAS9, zinc finger, TALEN, and meganuclease gene-editing technologies.

In one aspect, the invention provides expression vectors for the expression of the chimeric proteins (and/or additional agents) that are viral vectors. Many viral vectors useful for gene therapy are known (see, e.g., Lundstrom, Trends Biotechnol., 21: 1 17, 122, 2003. Illustrative viral vectors include those selected from Antiviruses (LV), retroviruses (RV), adenoviruses (AV), adeno-associated viruses (AAV), and a viruses, though other viral vectors may also be used. For in vivo uses, viral vectors that do not integrate into the host genome are suitable for use, such as a viruses and adenoviruses. Illustrative types of a viruses include Sindbis virus, Venezuelan equine encephalitis (VEE) virus, and Semliki Forest virus (SFV). For in vitro uses, viral vectors that integrate into the host genome are suitable, such as retroviruses, AAV, and Antiviruses. In one embodiment, the invention provides methods of transducing a human cell in vivo, comprising contacting a solid tumor in vivo with a viral vector of the invention.

In embodiments, the present invention provides a host cell, comprising the expression vector comprising the chimeric protein described herein.

Expression vectors can be introduced into host cells for producing the present chimeric proteins. Cells may be cultured in vitro or genetically engineered, for example. Useful mammalian host cells include, without limitation, cells derived from humans, monkeys, and rodents (see, for example, Kriegler in "Gene Transfer and Expression: A Laboratory Manual," 1990, New York, Freeman & Co.). These include monkey kidney cell lines transformed by SV40 (e.g., COS-7, ATCC CRL 1651); human embryonic kidney lines (e.g., 293, 293-EBNA, or 293 cells subcloned for growth in suspension culture, Graham et al., *J Gen Virol* 1977, 36:59); baby hamster kidney cells (e.g., BHK, ATCC CCL 10); Chinese hamster ovary-cells-DHFR (e.g., CHO, Urlaub and Chasin, *Proc Natl Acad Sci USA* 1980, 77:4216); DG44 CHO cells, CHO-K1 cells, mouse sertoli cells (Mather, *Biol Reprod* 1980, 23:243-251); mouse fibroblast cells (e.g., NIH-3T3), monkey kidney cells (e.g., CV1 ATCC CCL 70); African green monkey kidney cells. (e.g., VERO-76, ATCC CRL-1587); human cervical carcinoma cells (e.g., HELA, ATCC CCL 2); canine kidney cells (e.g., MDCK, ATCC CCL 34); buffalo rat liver cells (e.g., BRL 3A, ATCC CRL 1442); human lung cells (e.g., W138, ATCC CCL 75); human liver cells (e.g., Hep G2, HB 8065); and mouse mammary tumor cells (e.g., MMT 060562, ATCC CCL51). Illustrative cancer cell types for expressing the chimeric proteins described herein include mouse fibroblast cell line, NIH3T3, mouse Lewis lung carcinoma cell line, LLC, mouse mastocytoma cell line, P815, mouse lymphoma cell line, EL4 and its ovalbumin transfectant, E.G7, mouse melanoma cell line, B16F10, mouse fibrosarcoma cell line, MC57, and human small cell lung carcinoma cell lines, SCLC #2 and SCLC #7.

Host cells can be obtained from normal or affected subjects, including healthy humans, cancer patients, and patients with an infectious disease, private laboratory deposits, public culture collections such as the American Type Culture Collection, or from commercial suppliers.

Cells that can be used for production of the present chimeric proteins in vitro, ex vivo, and/or in vivo include, without limitation, epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells (e.g., as obtained from bone marrow), umbilical cord blood, peripheral blood, fetal liver, etc. The choice of cell type depends on the type of tumor or infectious disease being treated or prevented, and can be determined by one of skill in the art.

Production and purification of Fc-containing macromolecules (such as monoclonal antibodies) has become a standardized process, with minor modifications between products. For example, many Fc containing macromolecules are produced by human embryonic kidney (HEK) cells (or variants thereof) or Chinese Hamster Ovary (CHO) cells (or variants thereof) or in some cases by bacterial or synthetic methods. Following production, the Fc containing macromolecules that are secreted by HEK or CHO cells are purified through binding to Protein A columns and subsequently 'polished' using various methods. Generally speaking, purified Fc containing macromolecules are stored in liquid form for some period of time, frozen for extended periods of time or in some cases lyophilized. In embodiments, production of the chimeric proteins contemplated herein may have unique characteristics as compared to traditional Fc containing macromolecules. In certain examples, the chimeric proteins may be purified using specific chromatography resins, or using chromatography methods that do not depend upon Protein A capture. In embodiments, the chimeric proteins may be purified in an oligomeric state, or in multiple oligomeric states, and enriched for a specific oligomeric state using specific methods. Without being bound by theory, these methods could include treatment with specific buffers including specified salt concentrations, pH and additive compositions. In other examples, such methods could include treatments that favor one oligomeric state over another. The chimeric proteins obtained herein may be additionally 'polished' using methods that are specified in the art. In embodiments, the chimeric proteins are highly stable and able to tolerate a wide range of pH exposure (between pH 3-12), are able to tolerate a large number of freeze/thaw stresses (greater than 3 freeze/thaw cycles) and are able to tolerate extended incubation at high temperatures (longer than 2 weeks at 40 degrees C.). In embodiments, the chimeric proteins are shown to remain intact, without evidence of degradation, deamidation, etc. under such stress conditions.

Subjects and/or Animals

In embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In embodiments, the subject and/or animal is a non-mammal, such, for example, a zebrafish. In embodiments, the subject and/or animal may comprise fluorescently-tagged cells (with e.g. GFP). In embodiments, the subject and/or animal is a transgenic animal comprising a fluorescent cell.

In embodiments, the subject and/or animal is a human. In embodiments, the human is a pediatric human. In embodiments, the human is an adult human. In embodiments, the human is a geriatric human. In embodiments, the human may be referred to as a patient.

In certain embodiments, the human has an age in a range of from about 0 months to about 6 months old, from about 6 to about 12 months old, from about 6 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old.

In embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An illustrative kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional agent described herein. In one embodiment, the kit comprises a container containing an effective amount of a composition of the invention and an effective amount of another composition, such those described herein.

Any aspect or embodiment described herein can be combined with any other aspect or embodiment as disclosed herein The invention will be further described in the following examples, which do not limit the scope of the invention described in the claims.

EXAMPLES

Example 1: Characterization of TIGIT-Fc-OX40L Chimeric Proteins

In this example, chimeric proteins comprising TIGIT and OX40L domains were biochemically and functionally characterized.

Figure 3A:
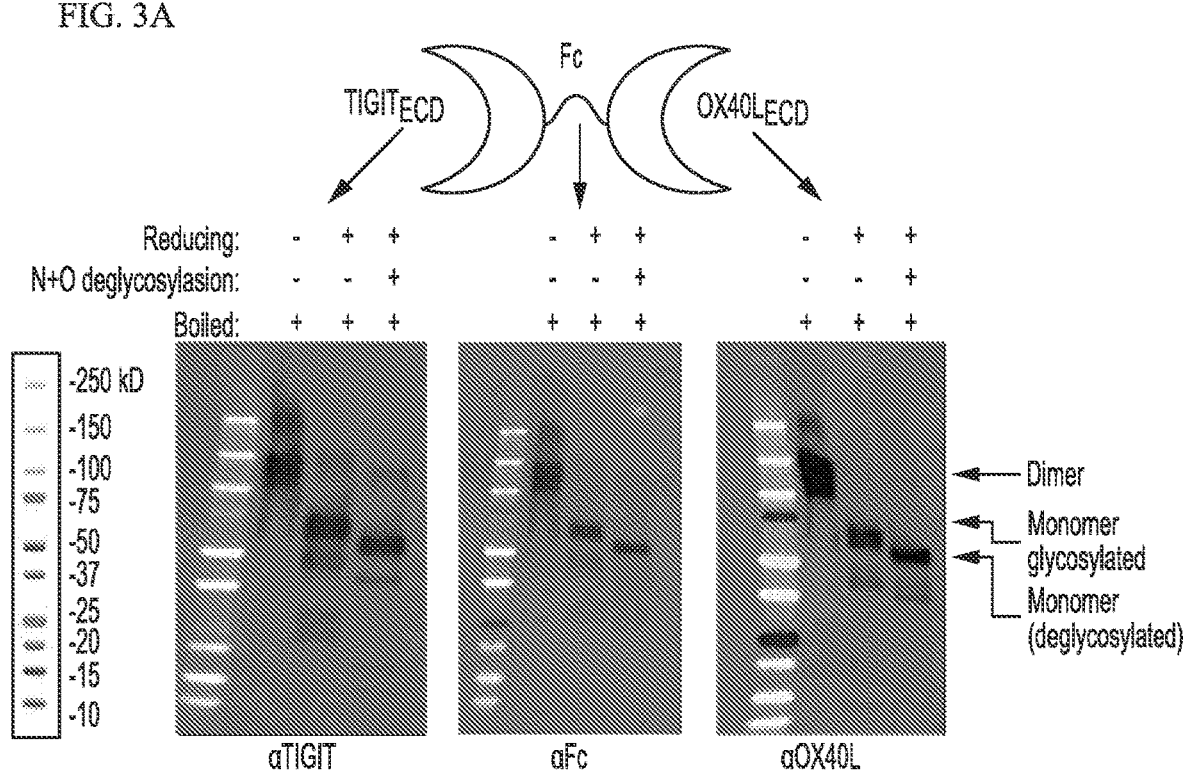
FIG. 3A shows Western blots of murine TIGIT-Fc-OX40L chimeric proteins run on SDS-PAGE under reducing conditions, following treatment with N+O deglycosylating enzyme, and/or after boiling.
Figure 3B:
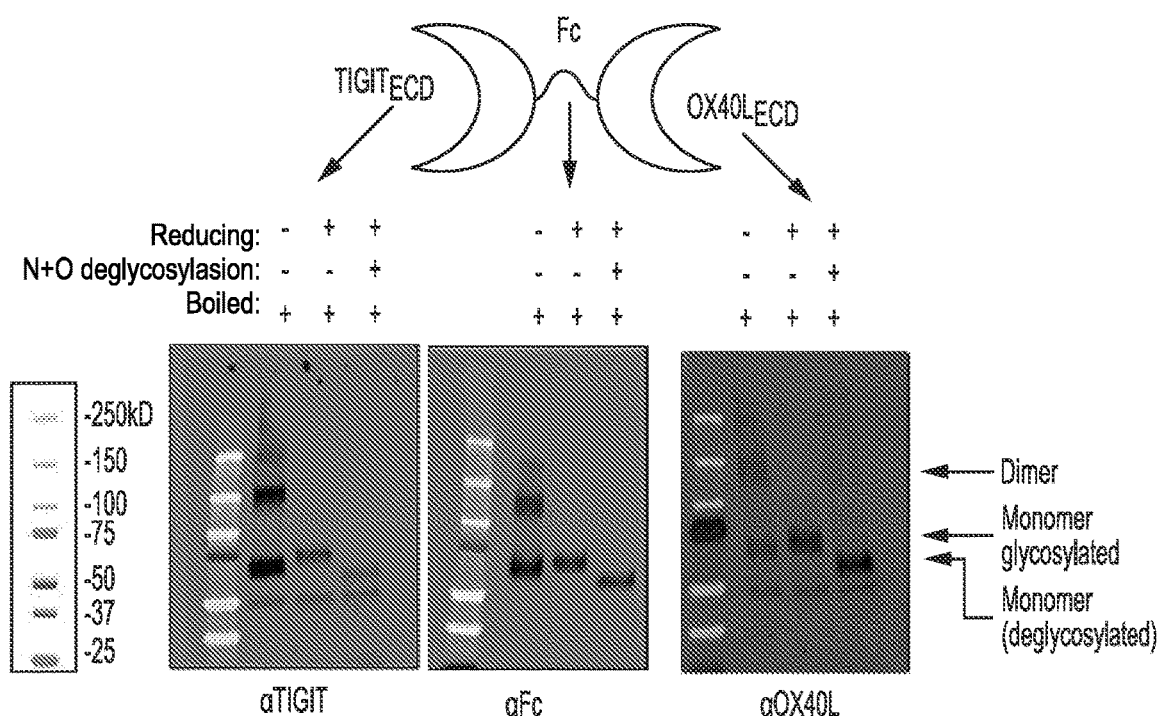
FIG. 3B shows Western blots of human TIGIT-Fc-OX40L chimeric proteins run on SDS-PAGE under reducing conditions, following treatment with N+O deglycosylating enzyme, and/or after boiling. In both cases, specific detection of each domain is indicated by the anti-TIGIT, anti-Fc and anti-OX40L blots.

Murine TIGIT-Fc-OX40L chimeric proteins and human TIGIT-Fc-OX40L chimeric proteins were prepared; their schematics are shown at the top of FIG. 3A and FIG. 3B. The mTIGIT-Fc-OX40L and hTIGIT-Fc-OX40L chimeric proteins were run on SDS-PAGE under reducing conditions, following treatment with N+O deglycosylating enzyme, and/or after boiling. The Western blots of the mTIGIT-Fc-OX40L and hTIGIT-Fc-OX40L chimeric proteins indicated the presence of a dominant dimeric band in the non-reduced lanes (FIG. 3A and FIG. 3B, lane 2 in each blot), which was reduced to a glycosylated monomeric band in the presence of the reducing agent, 3-mercaptoethanol (FIG. 3A and FIG. 3B, lane 3 each blot). As shown in FIGS. 3A and 3B, lane 3 in each bot, the chimeric protein ran as a monomer in the presence of both a reducing agent (3-mercaptoethanol) and an endoglycosidase (PNGase).

Figure 4A:
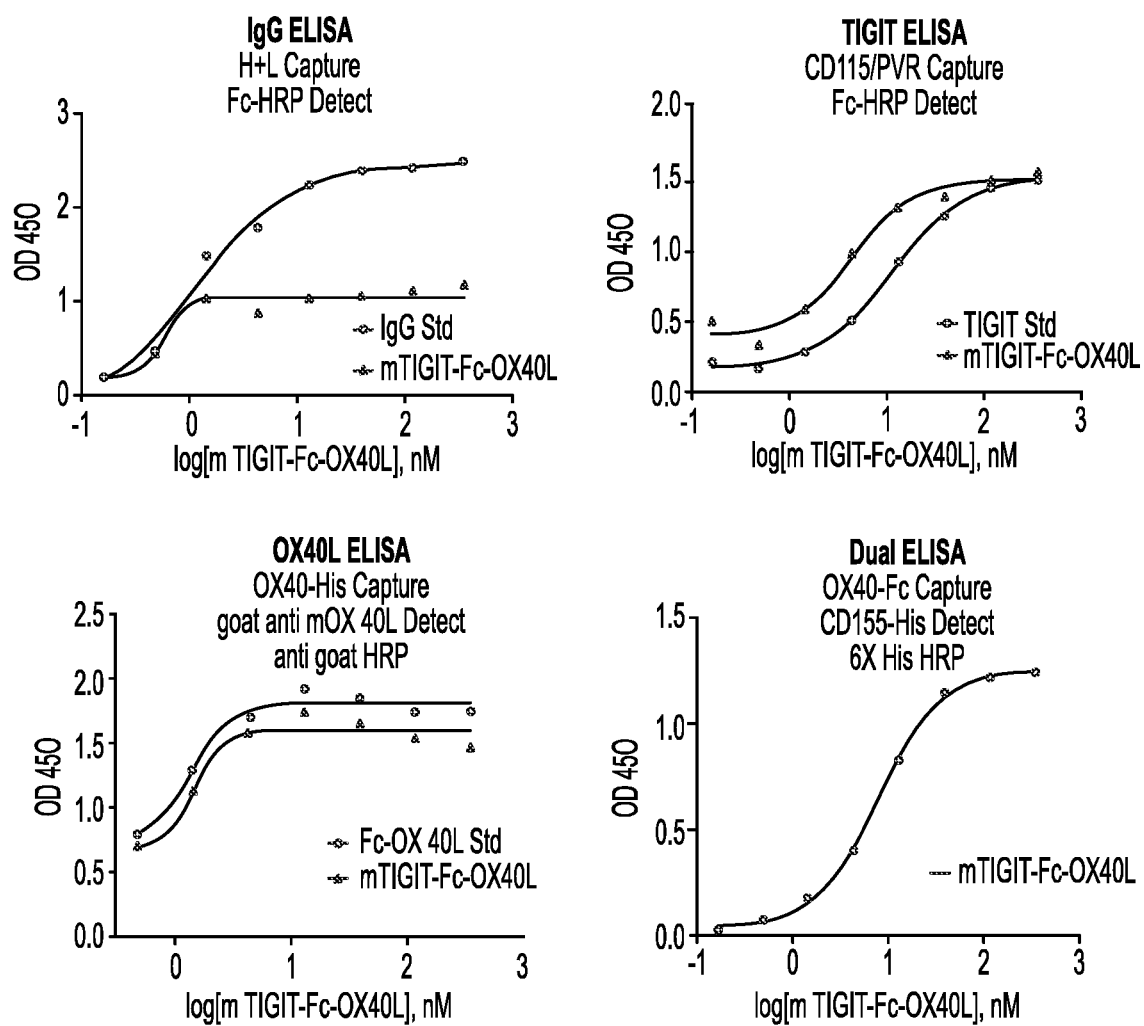
FIG. 4A are graphs showing ELISAs of murine TIGIT-Fc-OX40L chimeric proteins performed under the following conditions: Heavy+Light Chain captured and detected with Fc-HRP (top left), CD155/PVR-His captured and detected with IgG (top right), OX40-His captured and detected with an antibody directed to mOX40L (bottom left), and OX40-Fc captured and detected with a recombinant CD155 (bottom right).
Figure 4B:
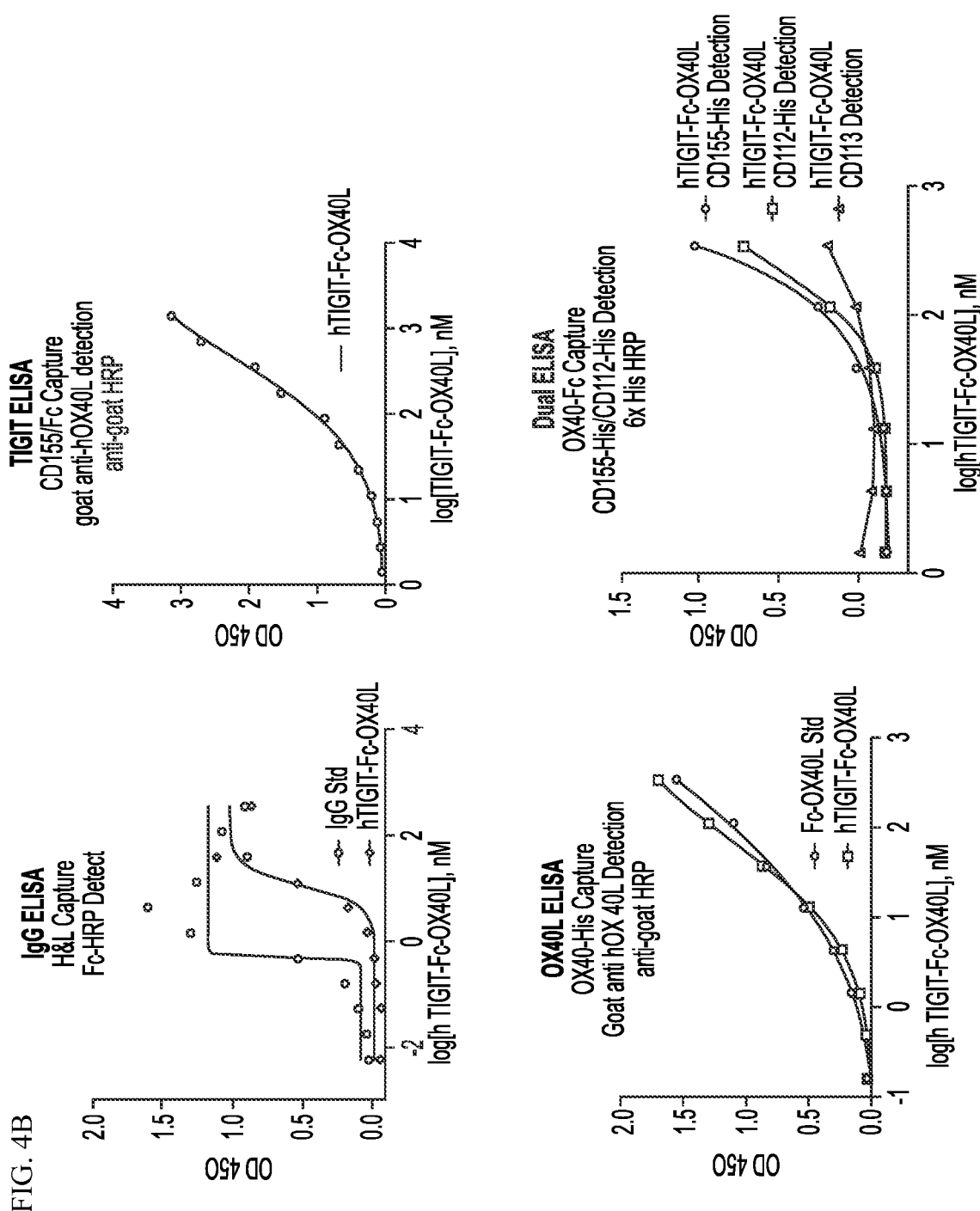
FIG. 4B are graphs showing ELISAs of human TIGIT-Fc-OX40L chimeric proteins performed under the following conditions: Heavy+Light Chain captured and detected with Fc-HRP (top left), CD155/PVR-His captured and detected with IgG (top right), OX40-His captured and detected with an antibody directed to mOX40L (bottom left), and OX40-Fc captured and detected with a recombinant CD155, CD112 or CD113 protein (bottom right).

The binding capabilities of the mTIGIT-Fc-OX40L chimeric proteins and hTIGIT-Fc-OX40L chimeric proteins were then assayed. For each chimeric protein ELISAs were performed under the following conditions: Heavy+Light Chain captured and detected with Fc-HRP (FIG. 4A and FIG. 4B, top left), CD155/PVR-His captured and detected with IgG (FIG. 4A and FIG. 4B, top right), and OX40-His captured and detected with an antibody directed to mOX40L (FIG. 4A and FIG. 4B, bottom left). The mTIGIT-Fc-OX40L chimeric protein was OX40-Fc captured and detected with a recombinant CD155 (FIG. 4A, bottom right, "Dual ELISA") and the hTIGIT-Fc-OX40L chimeric protein was OX40-Fc captured and detected with a recombinant CD155, CD112 or CD113 protein (FIG. 4A, bottom right, "Dual ELISA"). These data indicate that the mTIGIT-Fc-OX40L chimeric protein and the hTIGIT-Fc-OX40L chimeric proteins bind each of their targets and can bind both targets contemporaneously.

Figure 5A:
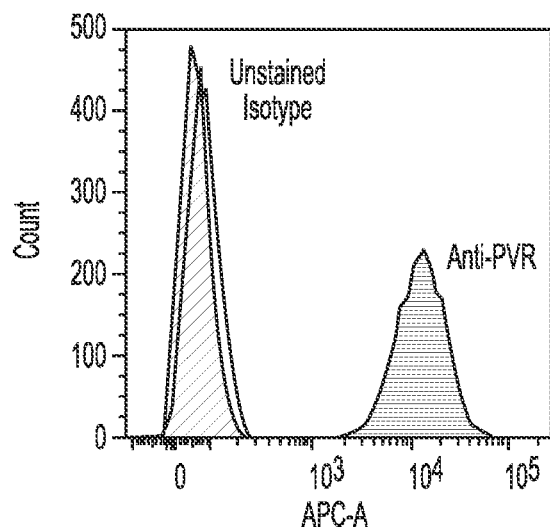
FIG. 5A shows cell lines generated to overexpress human PVR (CHOK1/PVR), which could be used to detect binding via a TIGIT containing construct (in FIG. 5A, unstained and isotype are overlapping).
Figure 5B:
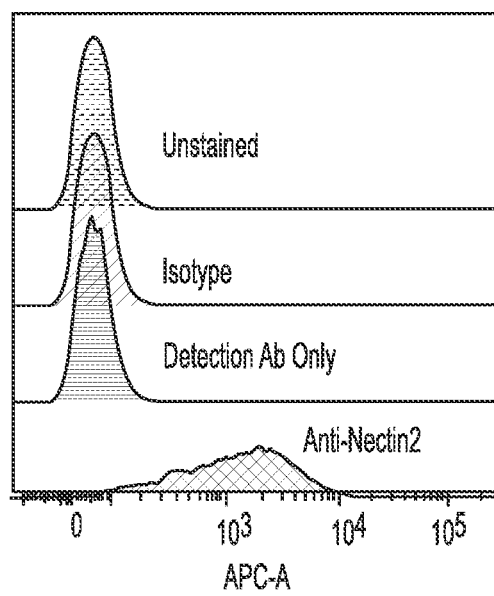
FIG. 5B shows cell lines generated to overexpress Nectin-2, (CHOK1/Nectin2), which could be used to detect binding via a TIGIT containing construct.
Figure 5C:
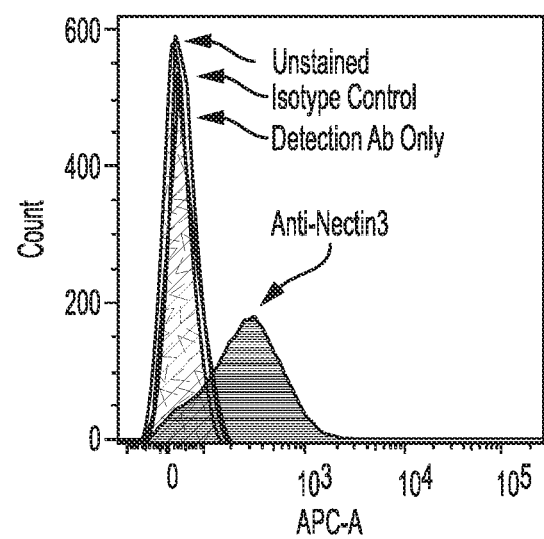
FIG. 5C shows cell lines generated to overexpress Nectin-3 (CHOK1/Nectin3), which could be used to detect binding via a TIGIT containing construct (in FIG. 5C, unstained, isotype, and detection Ab are overlapping).
Figure 6:
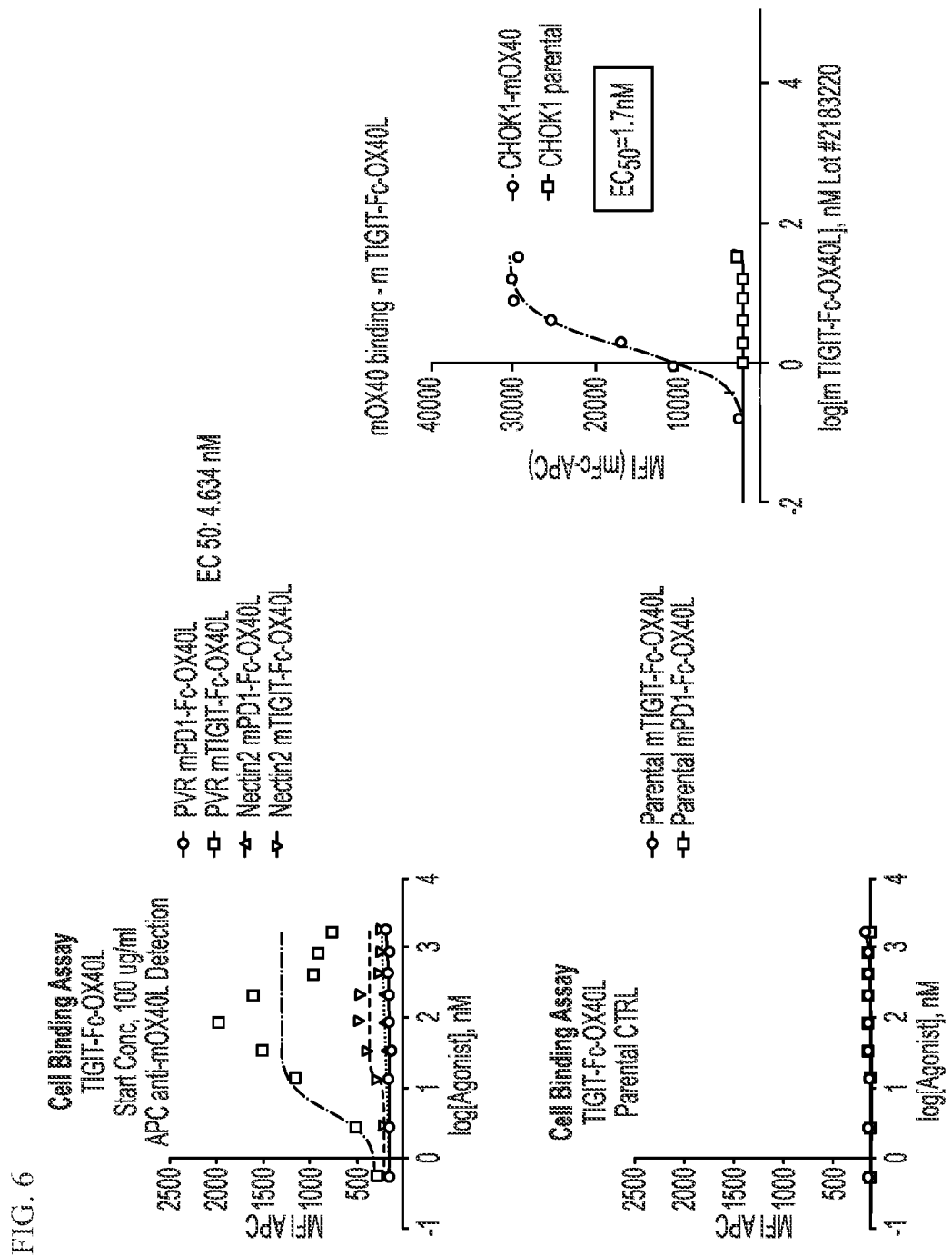
FIG. 6 are graphs showing binding of mouse TIGIT-Fc-OX40L to CHO-K1 cells expressing mouse PVR (top left), to parental CHO-K1 cells lacking PVR (bottom left) or to CHO-K1 cells expressing mouse OX40 (right).

Additional analyses were carried out to determine whether the mTIGIT-Fc-OX40L chimeric protein could bind its targets on the surface of living cells. A cell line was generated to overexpress human PVR (i.e., CHOK1/PVR); these cells are useful for detecting binding of a TIGIT-containing construct to cell membrane-associated PVR. See, FIG. 5A. A cell line was generated to overexpress Nectin-2 (i.e., CHOK1/Nectin2); these cells are useful for detecting binding of a TIGIT-containing construct to cell membrane-associated Nectin-2. See, FIG. 5B. A cell line was generated to overexpress Nectin-3 (i.e., CHOK1/Nectin3); these cells are useful for detecting binding of a TIGIT-containing construct to cell membrane-associated Nectin-3. See, FIG. 5C. Another cell line was prepared that overexpresses mOX40 (i.e., CHOK1-mOX40). Each of the cell lines were based on Chinese hamster ovary K1 (CHOK1).

mTIGIT-Fc-OX40L chimeric protein or mPD-1-Fc-OX40L chimeric protein was incubated with the parental and over-expressing cell lines for 2 hours. Cells were collected, washed, and stained with antibodies for the detection of the chimeric protein binding by flow cytometry. As shown in FIG. 6 (bottom left and right), and as expected, the chimeric proteins did not bind the parental cell line and at any concentration of chimeric protein. However, the mTIGIT-Fc-OX40L bound the CHOK1/PVR engineered cell line in a concentration-dependent manner; based on this data an $EC_{50}$ value of 4.634 nM was calculated. See, FIG. 6 (top left). In contrast, the mPD-1-Fc-OX40L bound to neither engineered cell line. As with the CHOK1/PVR engineered cell line, the mTIGIT-Fc-OX40L chimeric protein also bound the CHOK1-mOX40 engineered cell line in a concentration-dependent manner; based on this data an $EC_{50}$ value of 1.7 nM was calculated. See, FIG. 6 (right). These data indicate that the different components of the chimeric protein are each capable of binding its respective receptor/ligands on living cells.

Next a microarray screen was conducted to identify further binding partners of the hTIGIT-Fc-OX40L. FIG. 7 is a table of results showing the identified binding partners of the hTIGIT-Fc-OX40L from a microarray (containing about 6,000 human membrane proteins). Each expected binding partner for hTIGIT-Fc-OX40L was identified by the screen. There was no evidence of non-specific binding to other human proteins, and binding to Galectin-1 is seen in the screen for all Fc-containing fusion proteins.

Example 2: Characterization of CD172a(SIRPα)-Fc-LIGHT Chimeric Proteins

In this example, chimeric proteins comprising LIGHT and CD172a(SIRPα) domains were biochemically and functionally characterized.

Figure 8A:
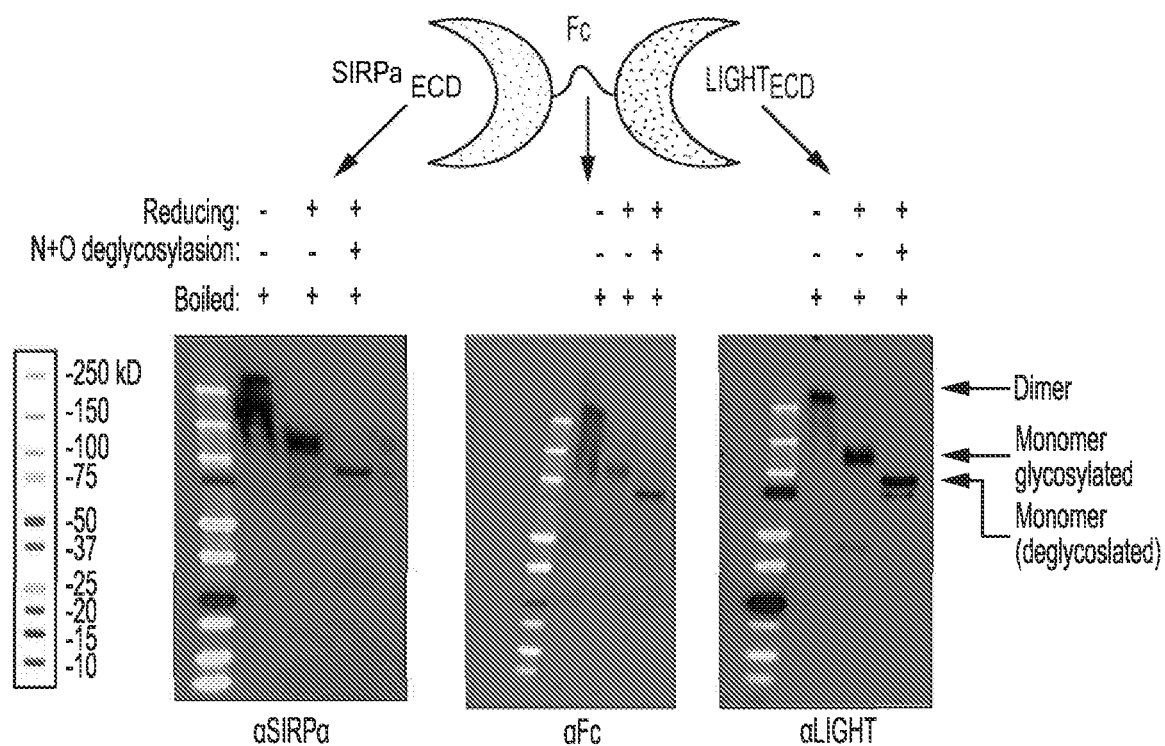
FIG. 8A shows Western blots of murine mCD172a (SIRPα)-Fc-LIGHT chimeric proteins run on SDS-PAGE under reducing conditions, following treatment with N+O deglycosylating enzyme, and/or after boiling.
Figure 8B:
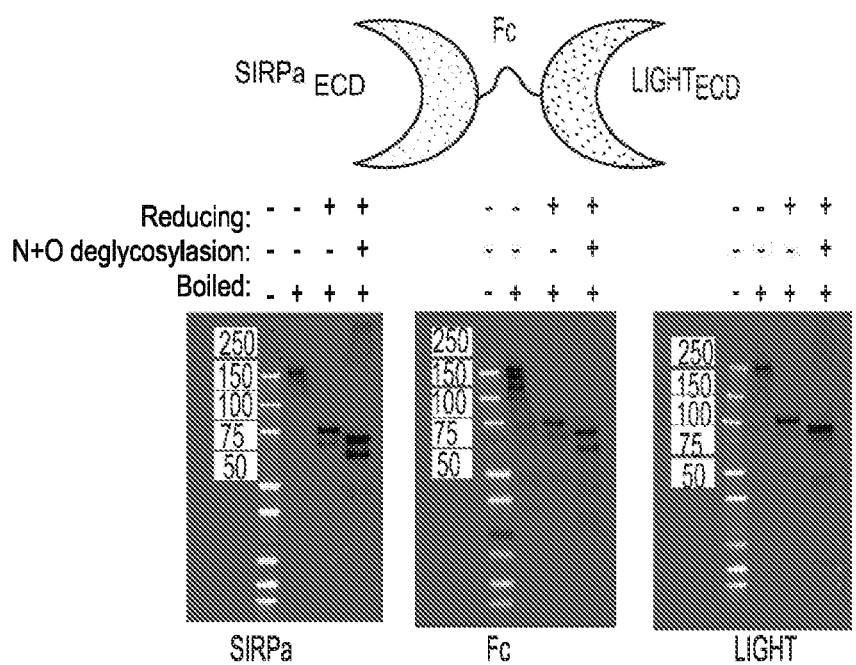
FIG. 8B shows Western blots of human CD172a(SIRPα)-Fc-LIGHT chimeric proteins run on SDS-PAGE under reducing conditions, following treatment with N+O deglycosylating enzyme, and/or after boiling.

Murine CD172a(SIRPα)-Fc-LIGHT chimeric proteins and human CD172a(SIRPα)-Fc-LIGHT chimeric proteins were prepared; their schematics are shown at the top of FIG. 8A and FIG. 8B. The mCD172a(SIRPα)-Fc-LIGHT and hCD172a(SIRPα)-Fc-LIGHT chimeric proteins were run on SDS-PAGE under reducing conditions, following treatment with N+O deglycosylating enzyme, and/or after boiling. The Western blots of the mCD172a(SIRPα)-Fc-LIGHT and hCD172a(SIRPα)-Fc-LIGHT chimeric proteins indicated the presence of a dominant dimeric band in the non-reduced lanes (FIG. 8A and FIG. 8B, lane 2 in each blot), which was reduced to a glycosylated monomeric band in the presence of the reducing agent, 3-mercaptoethanol (FIG. 8A and FIG. 8B, lane 3 each blot). As shown in FIGS. 8A and 8B, lane 3 in each bot, the chimeric protein ran as a monomer in the presence of both a reducing agent (3-mercaptoethanol) and an endoglycosidase (PNGase).

Figure 9A:
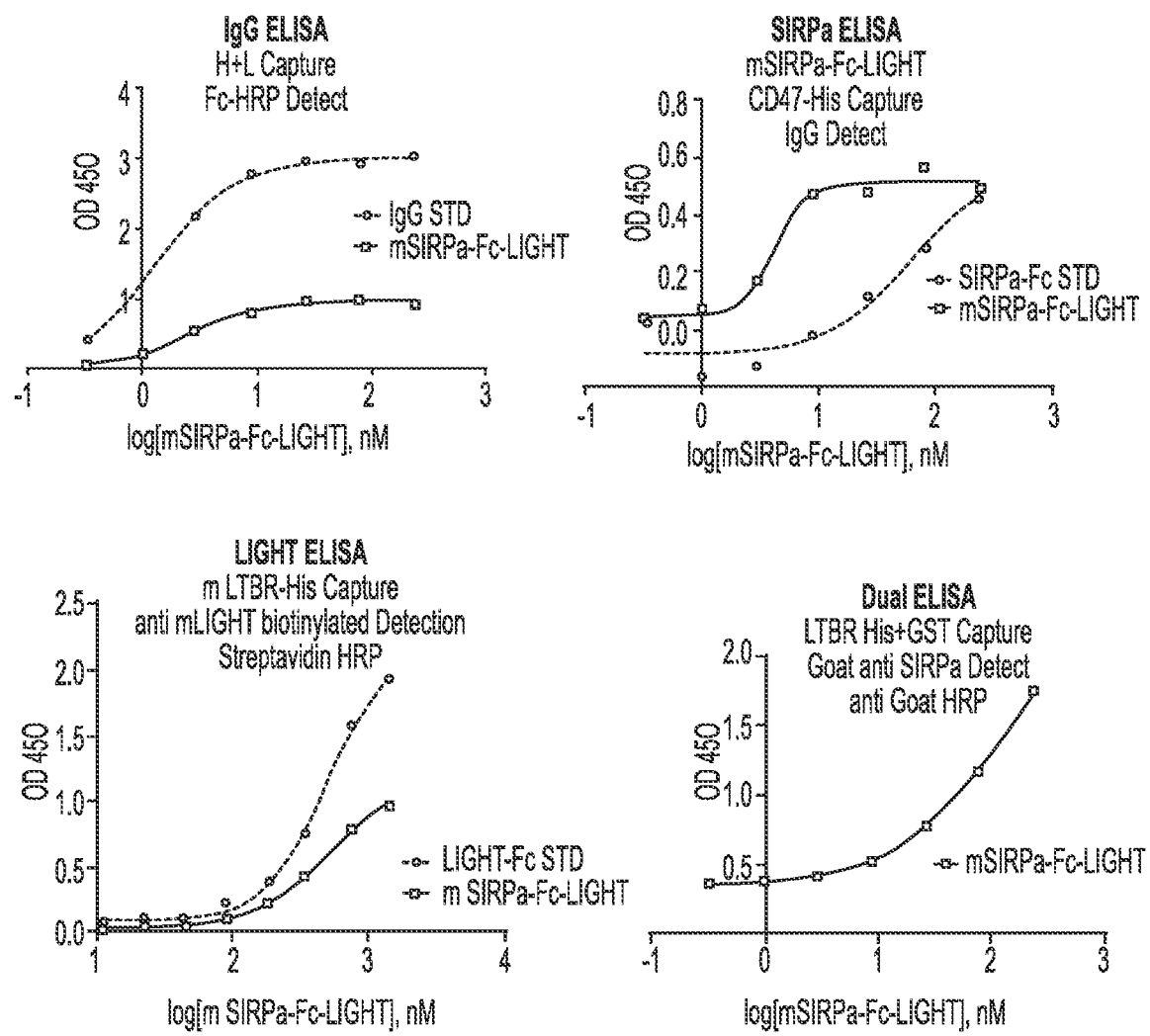
FIG. 9A are graphs showing ELISAs of murine mCD172a (SIRPα)-Fc-LIGHT chimeric proteins performed under the following conditions: Heavy+Light Chain captured and detected with Fc-HRP (top left), CD47-His captured and detected with IgG (top right), mLTBR-His captured and detected with an antibody directed to mLIGHT (bottom left), and LTBR His+GST captured and detected with an antibody directed to SIRPa (bottom right).
Figure 9B:
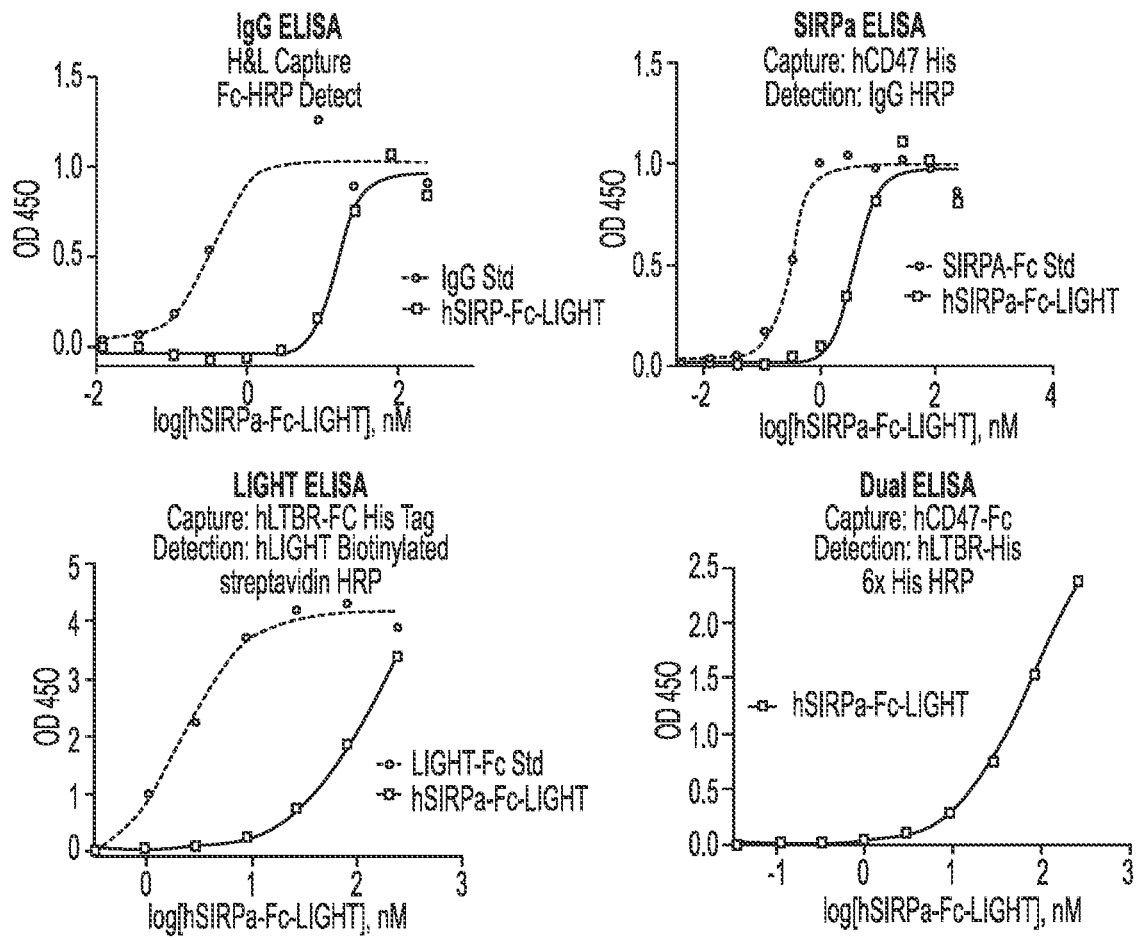
FIG. 9B are graphs showing ELISAs of human CD172a(SIRPα)-Fc-LIGHT chimeric proteins performed under the following conditions: Heavy+Light Chain captured and detected with Fc-HRP (top left), CD47-His captured and detected with IgG (top right), human LTBR-His captured and detected with an antibody directed to human LIGHT (bottom left), and LTBR His+GST captured and detected with an antibody directed to SIRPa (bottom right).

The binding capabilities of the mCD172a(SIRPα)-Fc-LIGHT chimeric proteins and hCD172a(SIRPα)-Fc-LIGHT chimeric proteins were then assayed. For each chimeric protein ELISAs were performed under the following conditions: Heavy+Light Chain captured and detected with Fc-HRP (FIG. 9A and FIG. 9B, top left), CD47-His captured and detected with IgG (FIG. 9A and FIG. 9B, top right), a murine LTBR-His captured and detected with an antibody directed to murine LIGHT (FIG. 9A, bottom left) or human LTBR-His captured and detected with an antibody directed to human LIGHT (FIG. 9B, bottom left), and LTBR His+ GST captured and detected with an antibody directed to SIRPa (FIG. 9A and FIG. 9B, bottom right, "Dual ELISA"). These data indicate that the mCD172a(SIRPα)-Fc-LIGHT chimeric protein and the hCD172a(SIRPα)-Fc-LIGHT chimeric proteins bind each of their targets and can bind both targets contemporaneously.

Figure 10A:
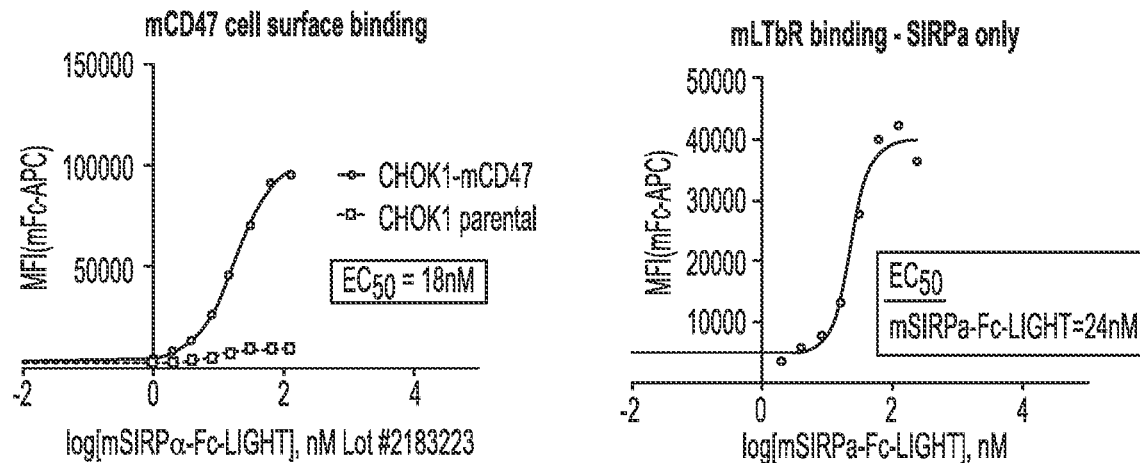
FIG. 10A are graphs showing binding of mouse CD172a (SIRPα)-Fc-LIGHT to CHO-K1 cells expressing mouse CD47 (left) or to CHO-K1 cells expressing mouse LTbR (right).

Additional analyses were carried out to determine whether the mCD172a(SIRPα)-Fc-LIGHT chimeric protein could bind its targets on the surface of living cells. CHO-K1 cells expressing murine CD47 (FIG. 10A, left) or to CHO-K1 cells expressing murine LTbR (FIG. 10A, right) were prepared.

mCD172a(SIRPα)-Fc-LIGHT chimeric protein was incubated with the parental and over-expressing cell lines for 2 hours. Cells were collected, washed, and stained with antibodies for the detection of the chimeric protein binding by flow cytometry. As shown in FIG. 10A (left), and as expected, the chimeric protein did not bind the parental cell line and at any concentration of chimeric protein. However, the mCD172a(SIRPα)-Fc-LIGHT bound the mCD47 engineered cell line (FIG. 10A, left) and the mLTbR engineered cell line (FIG. 10A, right) in concentration-dependent manners; based on this data an $EC_{50}$ value for CD47 of 18 nM and for mCD172a(SIRPα) of 24 nM were calculated. Additionally, hCD172a(SIRPα)-Fc-LIGHT chimeric protein was incubated with the mCD47 over-expressing cell line. The hCD172a(SIRPα)-Fc-LIGHT bound the mCD47 engineered cell line (FIG. 10B) in concentration-dependent manner; based on this data an $EC_{50}$ value of 57 nM was calculated. These data indicate that the different components of the chimeric protein are each capable of binding its respective receptor/ligands on living cells.

Figure 11B:
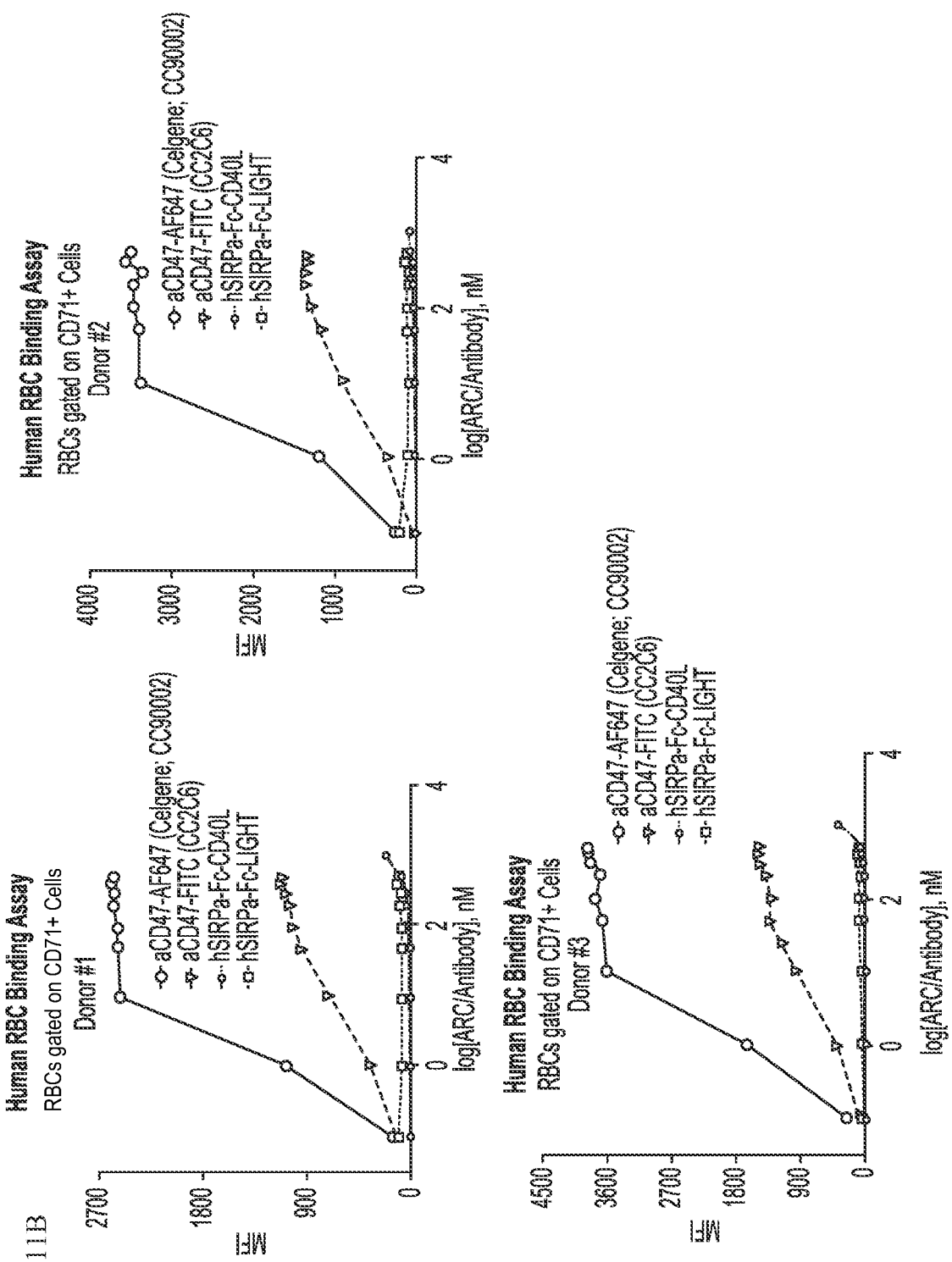
FIG. 11B are graphs showing binding of human CD172a(SIRPα)-Fc-LIGHT and CD172a (SIRPα)-Fc-CD40L to human red blood cells in comparison to CD47 specific antibodies (clone CC2C6 or CC900002), from each of 3 different human blood donors.
Figure 11C:
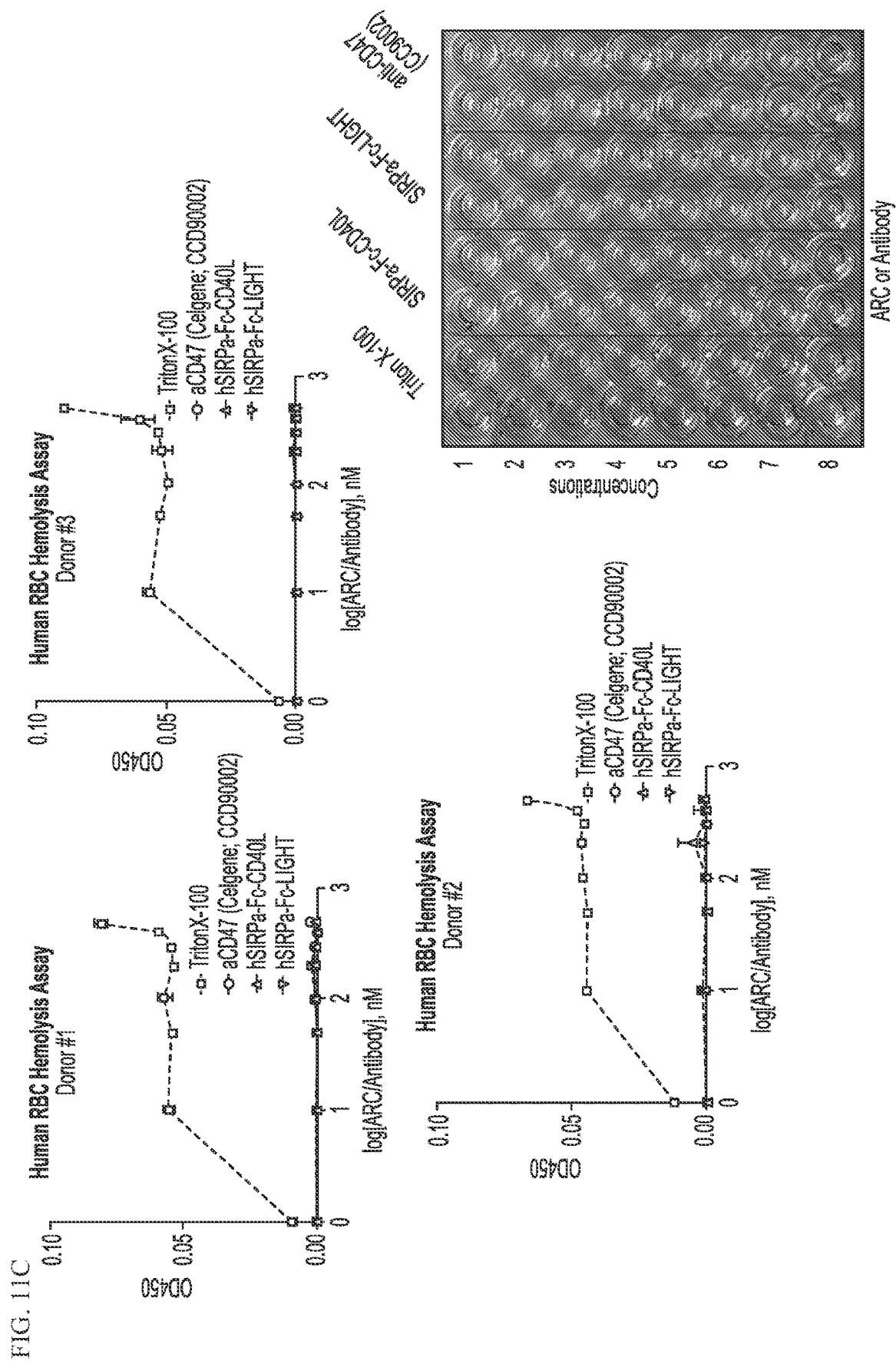
FIG. 11C, lysis of human red blood cells following each treatment is shown over a titration curve in the left and an example plate is shown on right. Triton-X was used as a positive control to cause lysis of cynomolgus macaque red blood cells. Data are shown for 3 human red blood cell donors.

The inability of the human TIGIT-Fc-OX40L chimeric protein to bind to red blood cells and, thereby, causing hemolysis was then tested. Here, hCD172a(SIRPα)-Fc-LIGHT, hCD172a(SIRPα)-Fc-CD40, or CD47 specific antibodies (clone CC2C6 or CC900002) were contacted with cynomolgus macaque red blood cells (RBCs; FIG. 11A, left top and bottom) or human RBCs (FIG. 11B and FIG. 11C, all panels). When compared to treatments with Triton-X (as a positive control), neither hCD172a(SIRPα)-Fc-LIGHT nor hCD172a(SIRPα)-Fc-CD40 caused significant lysis of cynomolgus macaque RBCs (FIG. 11A, bottom left); an example plate is shown (FIG. 11A, right). Neither hCD172a (SIRPα)-Fc-LIGHT nor hCD172a(SIRPα)-Fc-CD40 significantly bound to human RBCs (FIG. 11B, all panels). When compared to treatments with Triton-X (as a positive control), hCD172a(SIRPα)-Fc-LIGHT or hCD172a (SIRPα)-Fc-CD40 caused nearly undetectable levels of lysis of human RBCs (FIG. 11C, all panels); an example plate is shown (FIG. 11C, right). These data indicate that hCD172a (SIRPα)-Fc-LIGHT and hCD172a(SIRPα)-Fc-CD40 do not cause hemolysis of human RBCs as an unwanted side effect.

Example 3: Characterization of PD-1-Fc-LIGHT Chimeric Proteins

In this example, chimeric proteins comprising LIGHT and PD-1 domains were biochemically and functionally characterized.

Figure 12A:
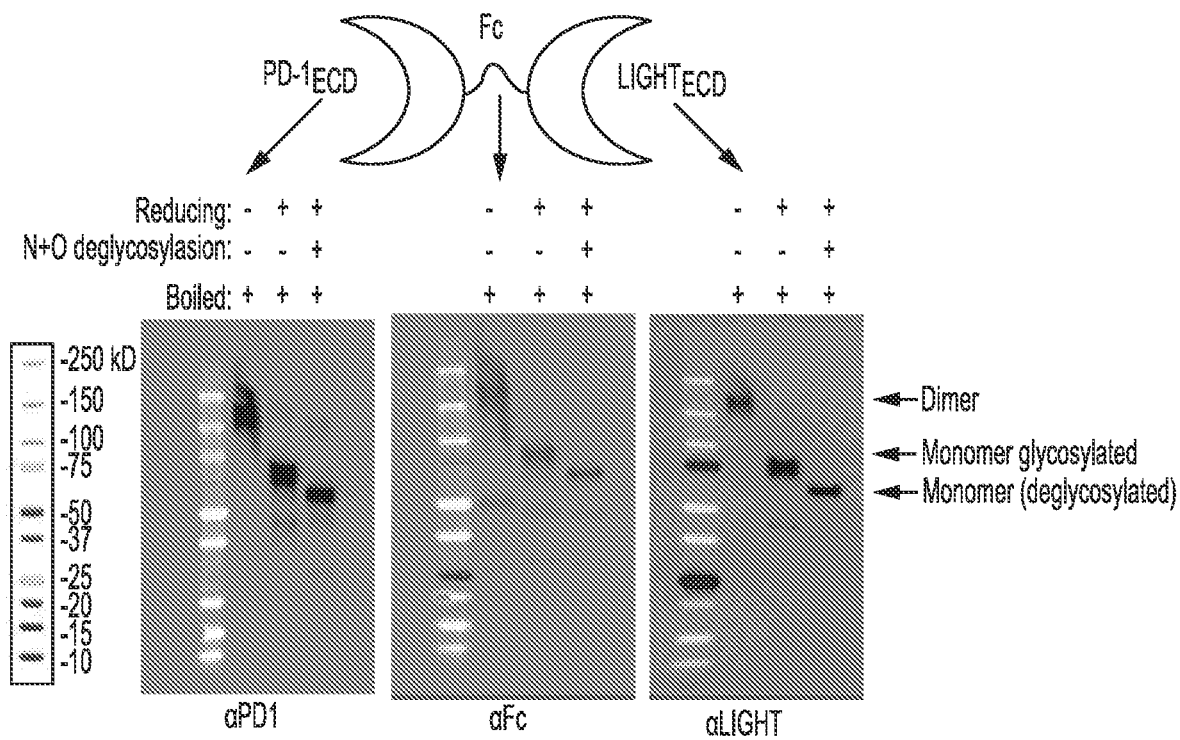
FIG. 12A shows Western blots of murine PD-1-Fc-LIGHT chimeric proteins run on SDS-PAGE under reducing conditions, following treatment with N+O deglycosylating enzyme, and/or after boiling.
Figure 12B:
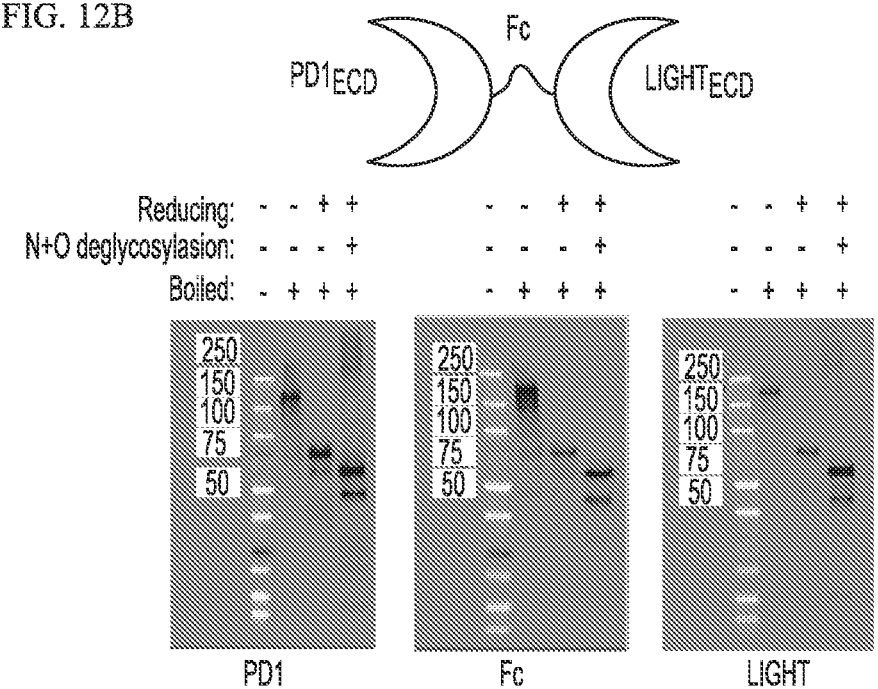
FIG. 12B shows Western blots of human PD-1-Fc-LIGHT chimeric proteins run on SDS-PAGE under reducing conditions, following treatment with N+O deglycosylating enzyme, and/or after boiling.

Murine PD-1-Fc-LIGHT chimeric proteins and human PD-1-Fc-LIGHT chimeric proteins were prepared; their schematics are shown at the top of FIG. 12A and FIG. 12B. The mPD-1-Fc-LIGHT and hPD-1-Fc-LIGHT chimeric proteins were run on SDS-PAGE under reducing conditions, following treatment with N+O deglycosylating enzyme, and/or after boiling. The Western blots of the mPD-1-Fc-LIGHT and hPD-1-Fc-LIGHT chimeric proteins indicated the presence of a dominant dimeric band in the non-reduced lanes (FIG. 12A and FIG. 12B, lane 2 in each blot), which was reduced to a glycosylated monomeric band in the presence of the reducing agent, 3-mercaptoethanol (FIG. 12A and FIG. 12B, lane 3 each blot). As shown in FIGS. 12A and 12B, lane 3 in each bot, the chimeric protein ran as a monomer in the presence of both a reducing agent (3-mercaptoethanol) and an endoglycosidase (PNGase).

Figure 13A:
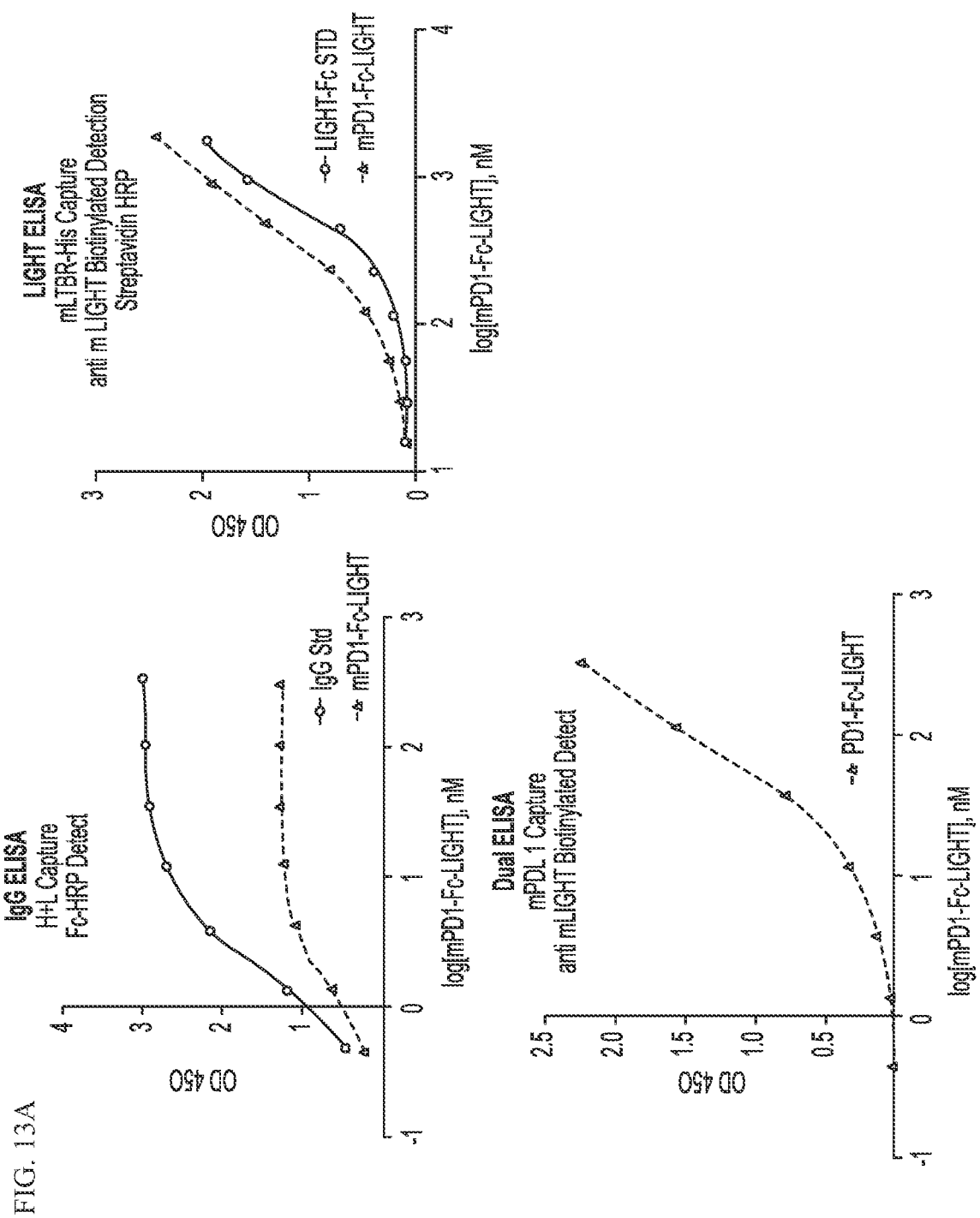
FIG. 13A are graphs showing ELISAs of murine PD-1-Fc-LIGHT chimeric proteins performed under the following conditions: Heavy+Light Chain captured and detected with Fc-HRP (left), mLTBR-His captured and detected with an antibody directed to mLIGHT (middle), and mPD-L1 captured and detected with an antibody directed to mLIGHT (right).
Figure 13B:
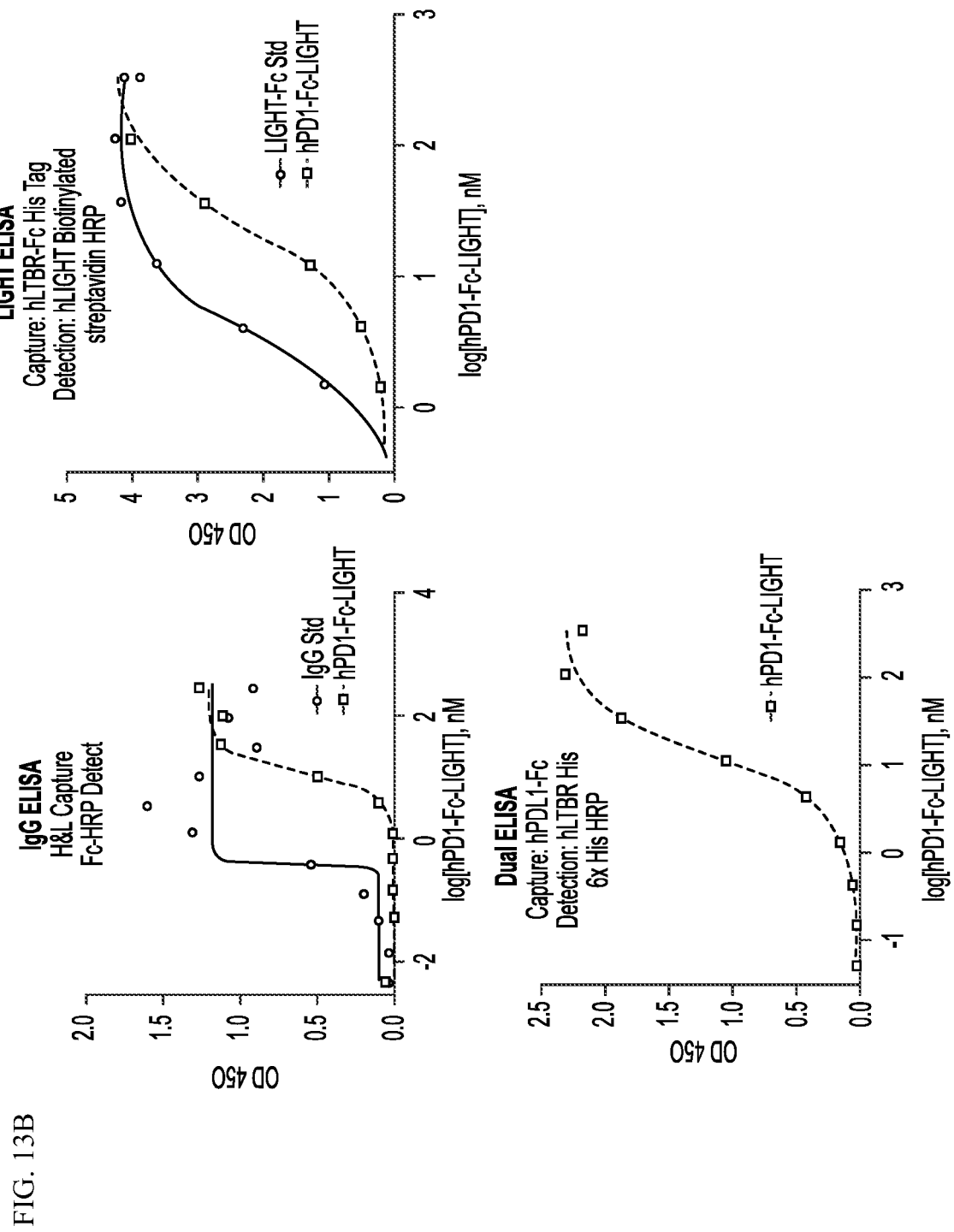
FIG. 13B are graphs showing ELISAs of human PD-1-Fc-LIGHT chimeric proteins performed under the following conditions: Heavy+Light Chain captured and detected with Fc-HRP (left), hLTBR-Fc His captured and detected with biotinylated hLIGHT (middle), and hPDL1-Fc captured and detected with hLTBR-His/6×His-HRP (right).

The binding capabilities of the mPD-1-Fc-LIGHT chimeric proteins and hPD-1-Fc-LIGHT chimeric proteins were then assayed. For each chimeric protein ELISAs were performed under the following conditions: Heavy+Light Chain captured and detected with Fc-HRP (FIG. 13A and FIG. 13B, top left), a murine LTBR-His captured and detected with an antibody directed to murine LIGHT (FIG. 13A, top right) or human LTBR-His captured and detected with biotinylated human LIGHT (FIG. 13B, top right), and mPD-L1 captured and detected with an antibody directed to mLIGHT (FIG. 13A, bottom left; "Dual ELISA") or hPDL1-Fc captured and detected with hLTBR-His/6×His-HRP (FIG. 13A, bottom left; "Dual ELISA"). These data indicate that the mPD-1-Fc-LIGHT chimeric protein and the hPD-1-Fc-LIGHT chimeric proteins bind each of their targets and can bind both targets contemporaneously.

Additional analyses were carried out to determine whether the murine PD-1-Fc-LIGHT chimeric protein (FIG. 14A) or human PD-1-Fc-LIGHT chimeric protein (FIG. 14A) can bind its targets on the surface of living cells. CHO-K1 cells expressing murine mPD-L1 (FIG. 14A, left), CHO-K1 cells expressing murine LTbR (FIG. 14A, right) and CHO-K1 cells expressing human mPD-L1 (FIG. 14B, left), were prepared.

Figure 14A:
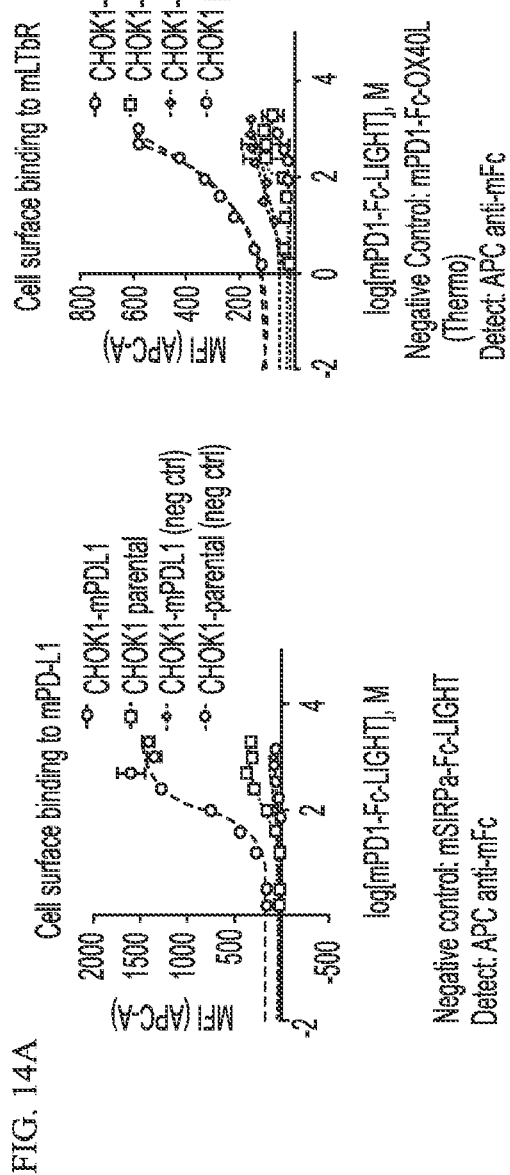
FIG. 14A are graphs showing binding of mouse PD-1-Fc-LIGHT to CHO-K1 cells expressing mouse PD-L1 (left) or to CHO-K1 cells expressing mouse LTbR (right).
Figure 14B:
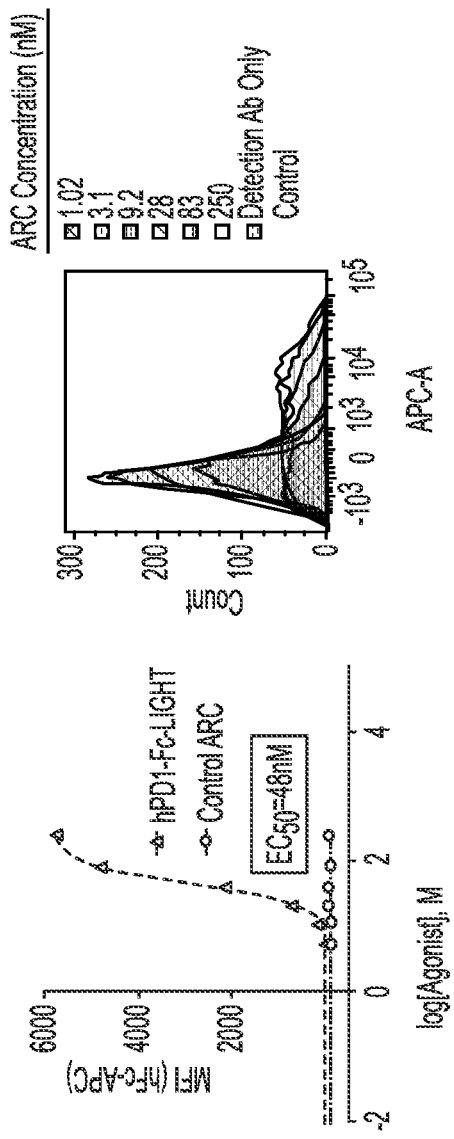
FIG. 14B are graphs showing binding of human PD-1-Fc-LIGHT to CHO-K1 cells expressing human PD-L1.

The mPD-1-Fc-LIGHT chimeric protein was incubated with the parental and over-expressing cell lines for 2 hours. Cells were collected, washed, and stained with antibodies for the detection of the chimeric protein binding by flow cytometry. As shown in FIG. 14A (left and right), and as expected, the mPD-1-Fc-LIGHT chimeric protein did not bind the parental cell lines and at any concentration of chimeric protein. However, the mPD-1-Fc-LIGHT bound the mPD-L1 engineered cell line (FIG. 14A, left) and the mLTbR engineered cell line (FIG. 14A, right) in concentration-dependent manners. Additionally, hPD-1-Fc-LIGHT chimeric protein was incubated with the hPD-L1 over-expressing cell line. The hPD-1-Fc-LIGHT bound the hPD-L1 engineered cell line (FIG. 14B) in a concentration-dependent manner; based on this data an $EC_{50}$ value of 48 nM was calculated. These data indicate that the different components of the chimeric protein are each capable of binding its respective receptor/ligands on living cells.

Example 4: Characterization of TIGIT-Fc-LIGHT Chimeric Proteins

In this example, chimeric proteins comprising TIGIT and LIGHT domains were biochemically and functionally characterized.

Figure 15A:
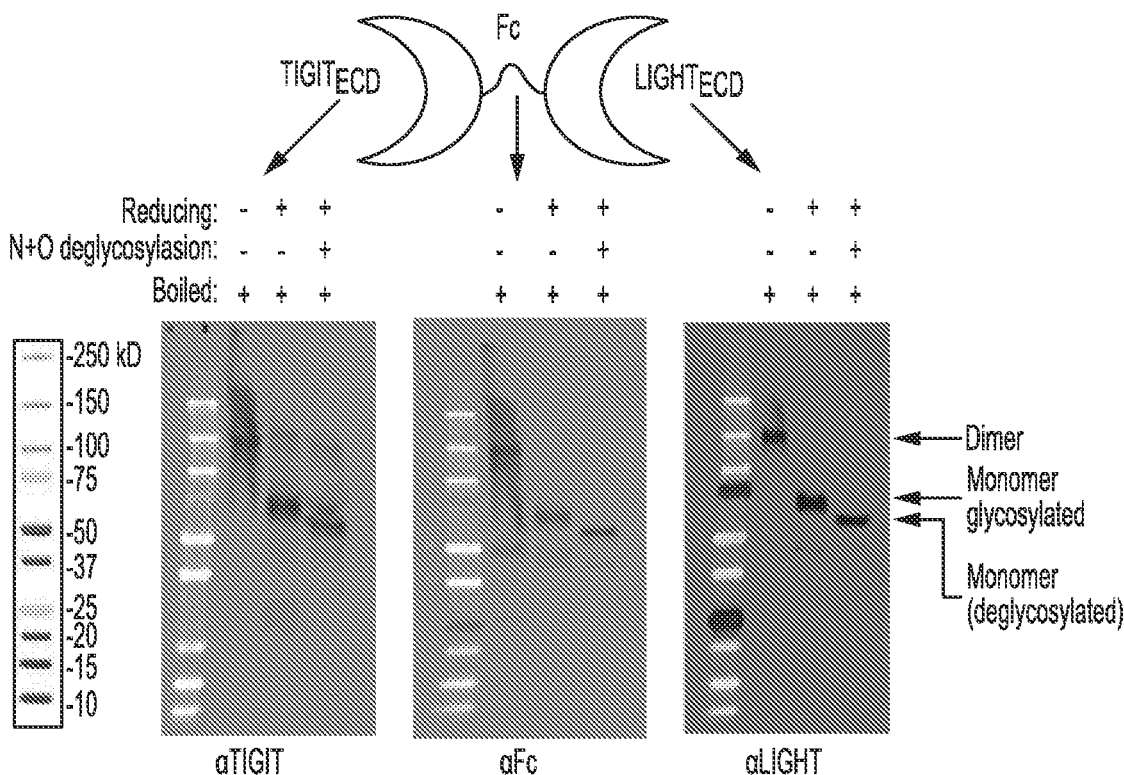
FIG. 15A shows Western blots of murine TIGIT-Fc-LIGHT chimeric proteins run on SDS-PAGE under reducing conditions, following treatment with N+O deglycosylating enzyme, and/or after boiling.
Figure 15B:
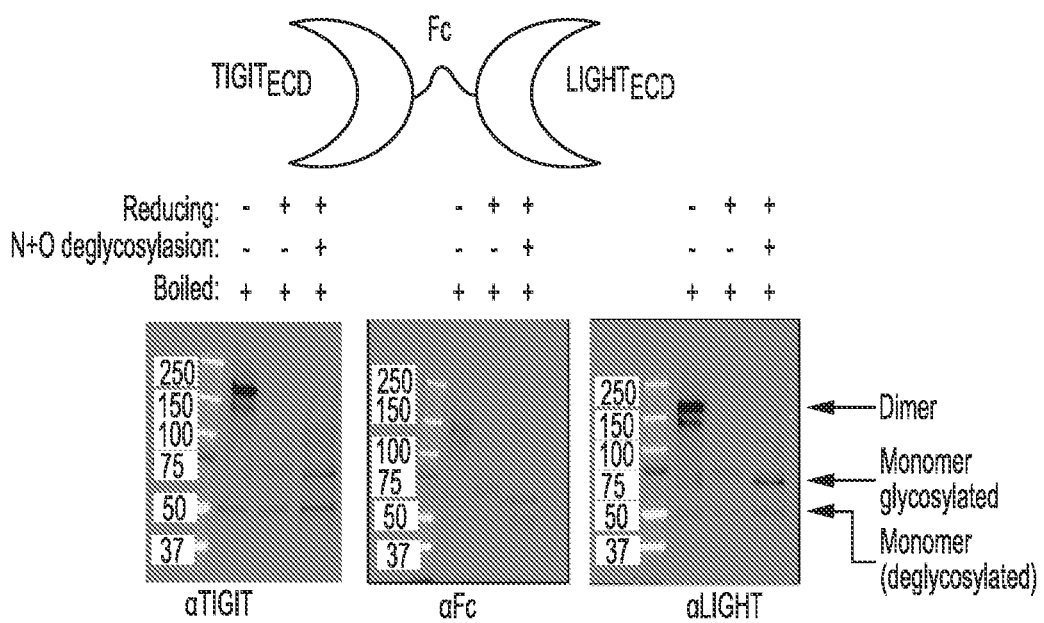
FIG. 15B shows Western blots of human TIGIT-Fc-LIGHT chimeric proteins run on SDS-PAGE under reducing conditions, following treatment with N+O deglycosylating enzyme, and/or after boiling.

Murine TIGIT-Fc-LIGHT chimeric proteins and human TIGIT-Fc-LIGHT chimeric proteins were prepared; their schematics are shown at the top of FIG. 15A and FIG. 15B. The mTIGIT-Fc-LIGHT and hTIGIT-Fc-LIGHT chimeric proteins were run on SDS-PAGE under reducing conditions, following treatment with N+O deglycosylating enzyme, and/or after boiling. The Western blots of the mTIGIT-Fc-LIGHT and hTIGIT-Fc-LIGHT chimeric proteins indicated the presence of a dominant dimeric band in the non-reduced lanes (FIG. 15A and FIG. 15B, lane 2 in each blot), which was reduced to a glycosylated monomeric band in the presence of the reducing agent, 3-mercaptoethanol (FIG. 15A and FIG. 15B, lane 3 each blot). As shown in FIGS. 15A and 15B, lane 3 in each bot, the chimeric protein ran as a monomer in the presence of both a reducing agent (3-mercaptoethanol) and an endoglycosidase (PNGase).

Figure 16A:
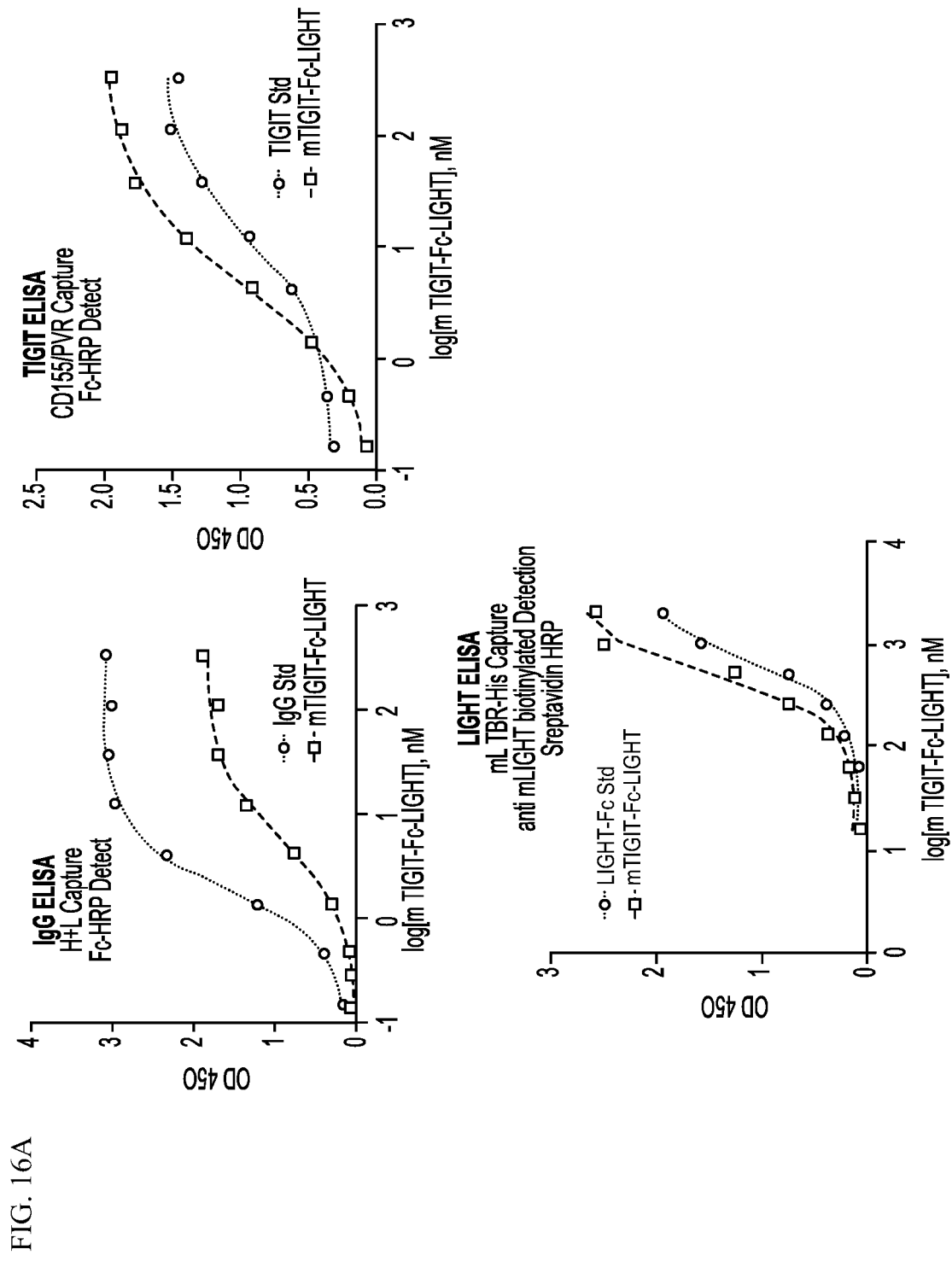
FIG. 16A are graphs showing ELISAs of murine TIGIT-Fc-LIGHT chimeric proteins performed under the following conditions: Heavy+Light Chain captured and detected with Fc-HRP (left), CD155/PVR captured and detected with Fc-HRP (middle), and mLTBR-His captured and detected with an antibody directed to mLIGHT (right).
Figure 16B:
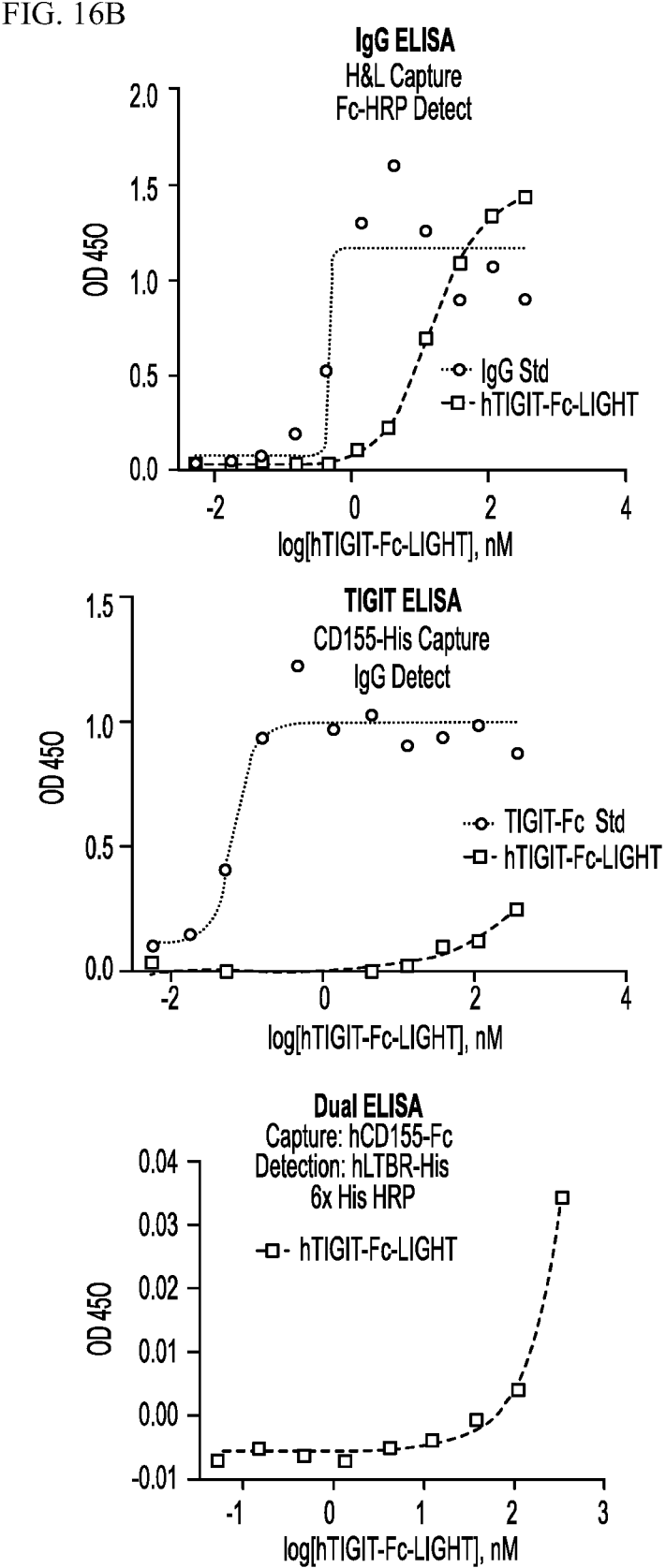
FIG. 16B are graphs showing ELISAs of human TIGIT-Fc-LIGHT chimeric proteins performed under the following conditions: Heavy+Light Chain captured and detected with Fc-HRP (left), CD155-His captured and detected IgG (middle), and hCD155-Fc captured and detected with hLTBR-His/6×His-HRP (right).

The binding capabilities of the mTIGIT-1-Fc-LIGHT chimeric proteins and hTIGIT-1-Fc-LIGHT chimeric proteins were then assayed. For each chimeric protein ELISAs were performed under the following conditions: Heavy+ Light Chain captured and detected with Fc-HRP (FIG. 16A and FIG. 16B, top left), CD155/PVR captured and detected with Fc-HRP (FIG. 16A, top right) or CD155-His captured and detected with (FIG. 16B, top right), and mLTBR-His captured and detected with an antibody directed to mLIGHT (FIG. 16A, bottom left) or hCD155-Fc captured and detected with hLTBR-His/6xHis-HRP (FIG. 16B, bottom left; "Dual ELISA"). These data indicate that the mTIGIT-1-Fc-LIGHT chimeric protein and the hTIGIT-1-Fc-LIGHT chimeric proteins bind each of their targets and, at least the hTIGIT-1-Fc-LIGHT can bind both targets contemporaneously.

Figure 17:
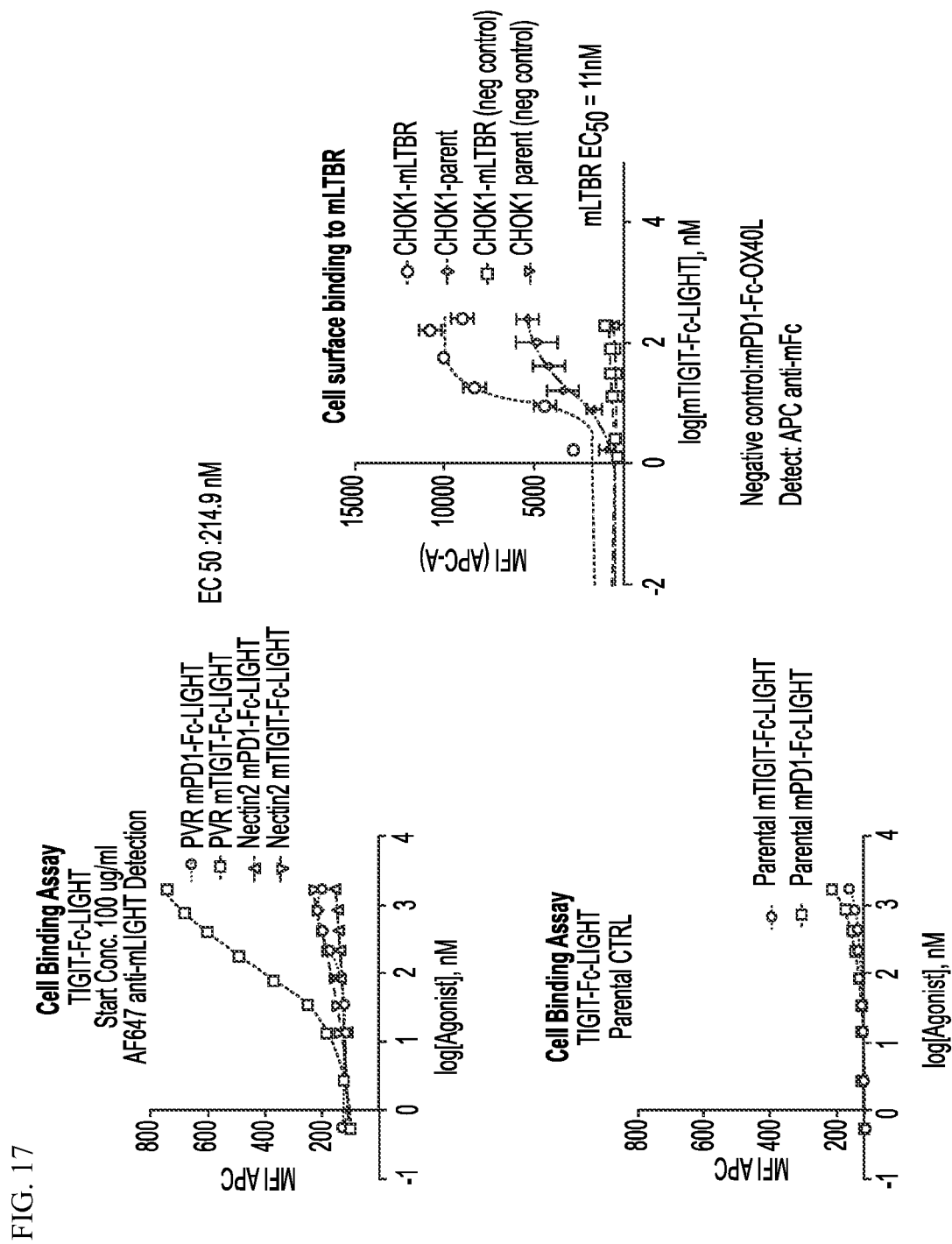
FIG. 17 are graphs showing binding of mouse TIGIT-Fc-LIGHT to CHO-K1 cells expressing mouse PVR (left) or to CHO-K1 cells expressing mouse LTbR (right).

Additional analyses were carried out to determine whether the murine TIGIT-1-Fc-LIGHT chimeric protein (FIG. 17) can bind its targets on the surface of living cells. mTIGIT-1-Fc-LIGHT chimeric protein or mPD-1-Fc-LIGHT chimeric protein was incubated CHO-K1 cells expressing murine PVR or expressing murine Nectin-2 (FIG. 17, left top), CHO-K1 cells expressing murine LTbR (FIG. 17A, right), or parental CHO-K1 cells (FIG. 17, right and left bottom).

As shown in FIG. 17 (bottom left), and as expected, neither the mTIGIT-1-Fc-LIGHT chimeric protein nor the mPD-1-Fc-LIGHT chimeric protein bound the parental cell lines, except at the highest concentration of chimeric protein. However, the mTIGIT-1-Fc-LIGHT bound the mPVR engineered cell line in concentration-dependent manner; based on this data an $EC_{50}$ value of 214.9 nM was calculated (FIG. 17, left top). The mTIGIT-1-Fc-LIGHT also bound the mLTbR engineered cell line in concentration-dependent manner; based on this data an $EC_{50}$ value of 11 nM was calculated (FIG. 17, right). These data indicate that the different components of the chimeric protein are each capable of binding its respective receptor/ligands on living cells.

Example 5: Further Characterization of Chimeric Proteins

In this example, further experiments were performed with the human TIGIT-Fc-LIGHT, human CD172a(SIRPα)-Fc-LIGHT, human PD-1-Fc-LIGHT, murine PD-1-Fc-LIGHT, human TIGIT-Fc-OX40L, human TIGIT-Fc-LIGHT, human CD172a(SIRPα)-Fc-LIGHT chimeric proteins.

Figure 18A:
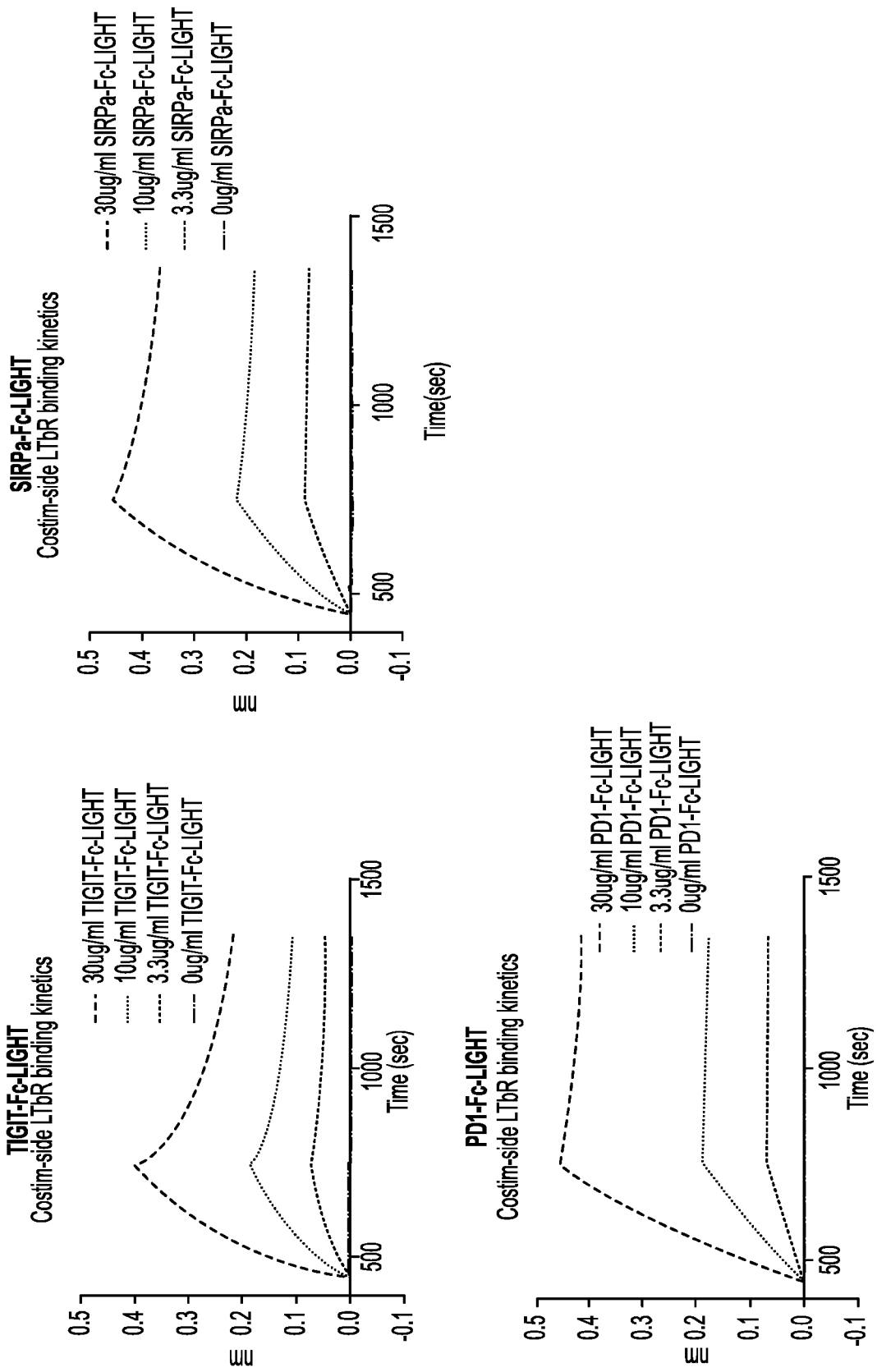
FIG. 18A are graphs showing binding affinity measurements collected by biolayer interferometry using an Octet system demonstrating binding of TIGIT-Fc-LIGHT, CD172a(SIRPα)-Fc-LIGHT and PD-1-Fc-LIGHT to human LTbR (all panels, top to bottom: 30, 10, 3.3, 0).
Figure 18B:
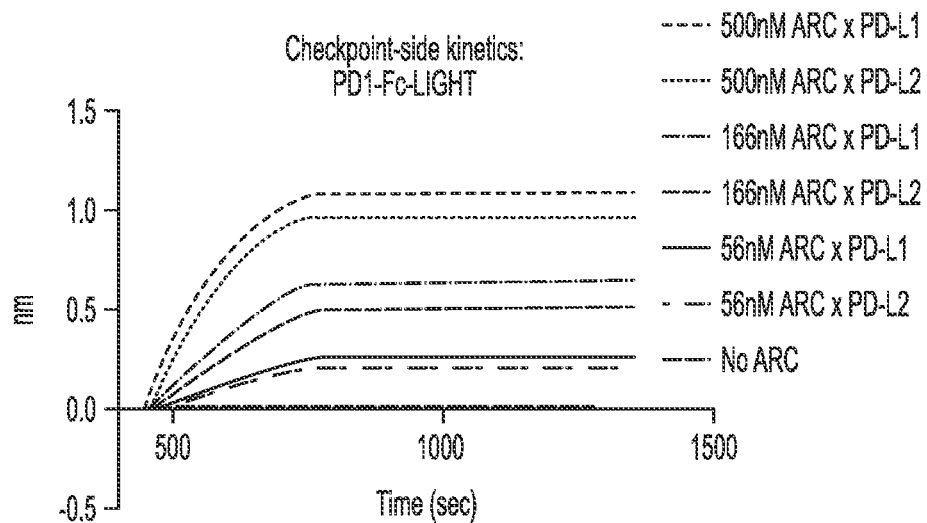
FIG. 18B are binding affinity measurements collected by biolayer interferometry using an Octet system demonstrating binding of human PD-1-Fc-LIGHT to recombinant human PD-L1 and PD-L2 across a range of concentrations (top to bottom: 500 nM ARC×PD-L1, 500 nM ARC×PD-L2, 166 nM ARC×PD-L1, 166 nM ARC×PD-L2, 56 nM ARC×PD-L1, 56 nM ARC×PD-L2, No ARC).

Binding affinity measurements for human TIGIT-Fc-LIGHT, CD172a(SIRPα)-Fc-LIGHT, or PD-1-Fc-LIGHT to human LTbR was collected by biolayer interferometry using an Octet system (see, FIG. 18A, all panels). Binding affinity measurements for human PD-1-Fc-LIGHT to recombinant human PD-L1 or PD-L2 across a range of concentrations was collected by biolayer interferometry using an Octet system (see, FIG. 18B).

Figure 19A:
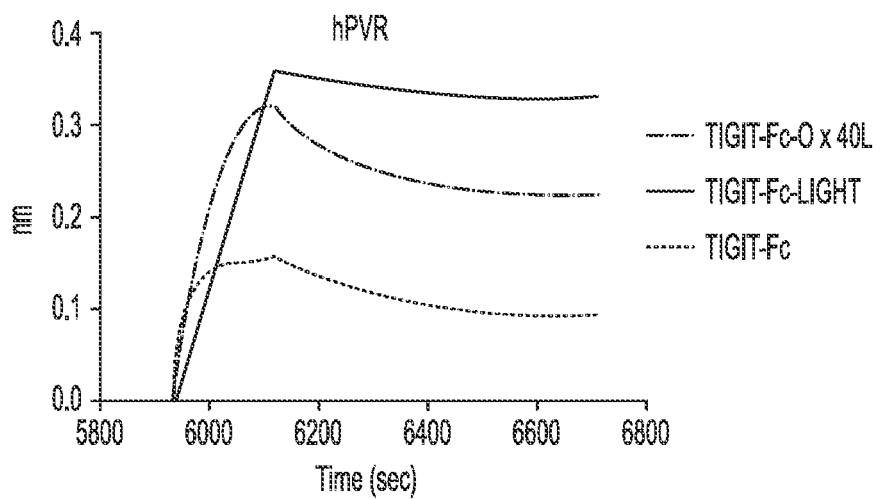
FIG. 19A are graphs showing binding affinity measurements collected by biolayer interferometry using an Octet system demonstrating binding of human TIGIT-Fc-OX40L and TIGIT-Fc-LIGHT to recombinant human CD155/PVR as compared to a one-sided TIGIT-Fc fusion protein control (top to bottom: TIGIT-Fc-LIGHT, TIGIT-Fc-Ox40L, TIGIT-Fc).
Figure 19B:
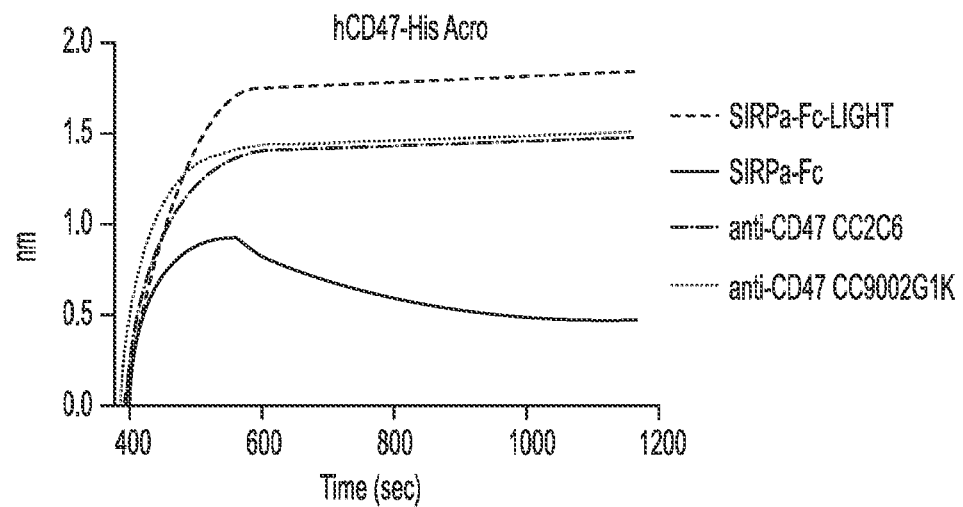
FIG. 19B are binding affinity measurements collected by biolayer interferometry using an Octet system demonstrating binding of human CD172a(SIRPα)-Fc-LIGHT to recombinant human CD47 as compared to a single-sided CD172a(SIRPα)-Fc control, or one of the two CD47 specific antibody controls (top to bottom: SIRPα-Fc-LIGHT, anti-CD47, anti-CD47 CC2C6, and SIRP-Fc).
Figure 19C:
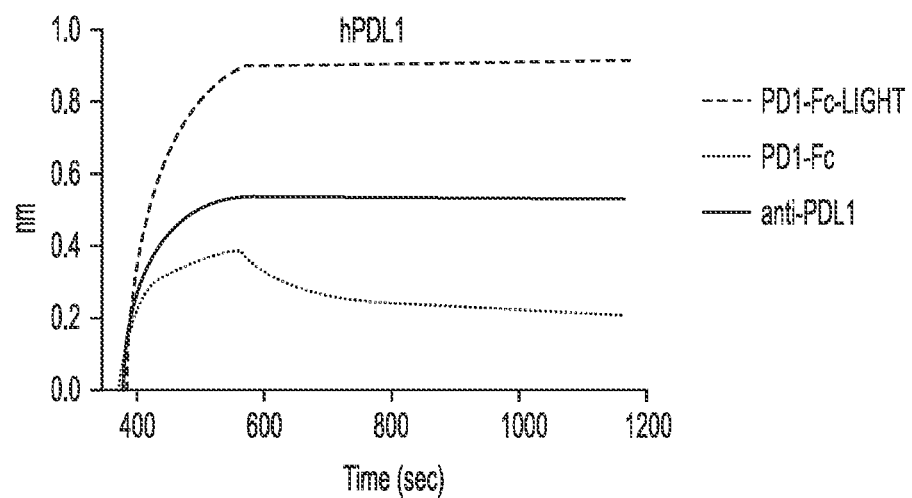
FIG. 19C are binding affinity measurements collected by biolayer interferometry using an Octet system demonstrating binding of human PD-1-Fc-LIGHT to recombinant human PD-L1 as compared to a single-sided PD-1-Fc control or an anti-PD-L1 control (Atezolizumab) (top to bottom: PD-1-Fc-LIGHT, anti-PDL1, and PD-1-Fc).
Figure 19D:
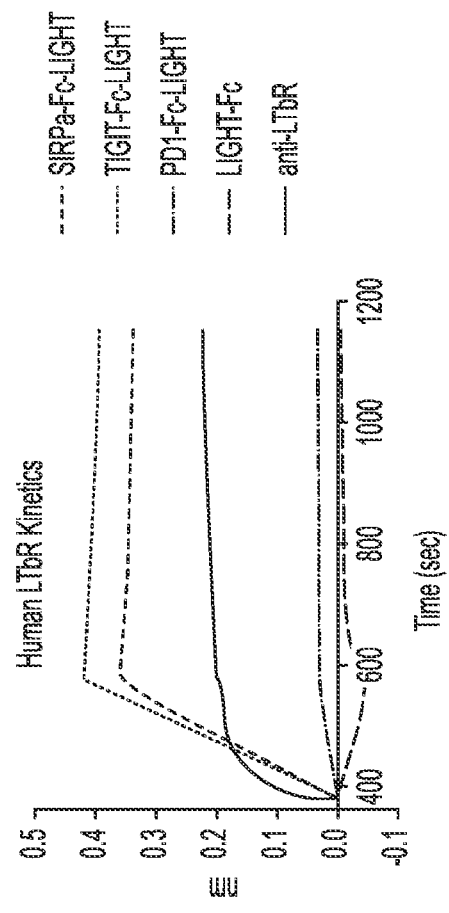
FIG. 19D are binding affinity measurements collected by biolayer interferometry using an Octet system demonstrating binding of human CD172a (SIRPα)-Fc-LIGHT, TIGIT-Fc-LIGHT or PD-1-Fc-LIGHT to recombinant human LTbR as compared to a single-sided LIGHT-Fc fusion protein control or an anti-LTbR antibody (top to bottom: TIGIT-Fc-LIGHT, Sirp1a-Fc-LIGHT, anti-LTbR, PD-1-Fc-LIGHT, and LIGHT-Fc).

Binding affinity measurements of human TIGIT-Fc-OX40L and TIGIT-Fc-LIGHT to recombinant human CD155/PVR (as compared to a one-sided TIGIT-Fc fusion protein control) was collected by biolayer interferometry using an Octet system (see, FIG. 19A) Binding affinity measurements of human CD172a(SIRPα)-Fc-LIGHT to recombinant human CD47 (as compared to a single-sided CD172a(SIRPα)-Fc control, or one of the two CD47 specific antibody controls) was collected by biolayer interferometry using an Octet system (see, FIG. 19B). Binding affinity measurements of human PD-1-Fc-LIGHT to recombinant human PD-L1 (as compared to a single-sided PD-1-Fc control or an anti-PD-L1 control: Atezolizumab) was collected by biolayer interferometry using an Octet system (see, FIG. 19C). Binding affinity measurements of human CD172a(SIRPα)-Fc-LIGHT, TIGIT-Fc-LIGHT, or PD-1-Fc-LIGHT to recombinant human LTbR (as compared to a single-sided LIGHT-Fc fusion protein control or an anti-LTbR antibody) was collected by biolayer interferometry using an Octet system (see, FIG. 19D).

A functional ability of the LIGHT domain-containing chimeric proteins or TIGIT domain-containing chimeric proteins was determined in a superantigen cytokine release assay. Here, increasing concentrations of *staphylococcus* enterotoxin B (SEB) were used to activate human peripheral blood leukocytes in the presence of various test agents. The quantity of IL-2 (FIG. 20A) or TNFα (FIG. 20B) secreted into the culture supernatant was monitored as a functional readout of the ability of test agents to either block suppressive signaling events or co-stimulate immune activating signals.

Figure 20A:
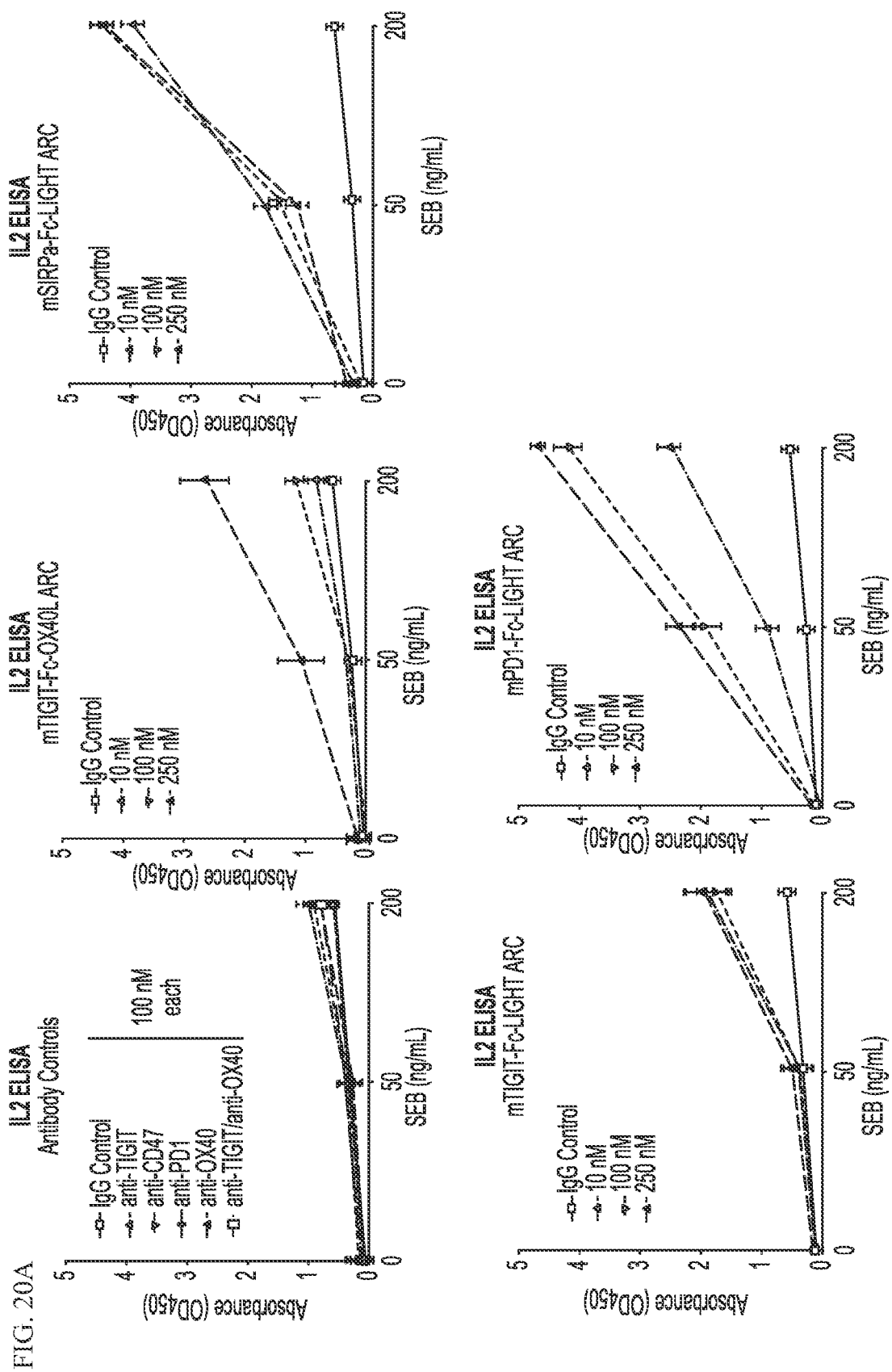
FIG. 20A and FIG. 20B show superantigen cytokine release assays which demonstrate the effects of the various antibodies, mouse TIGIT-Fc-OX40L, mouse CD172a (SIRPα)-Fc-LIGHT, mouse TIGIT-Fc-LIGHT, and mouse PD-1-Fc-LIGHT chimeric proteins on mouse peripheral blood leukocytes activated by *staphylococcus* enterotoxin B (SEB).
Figure 20B:
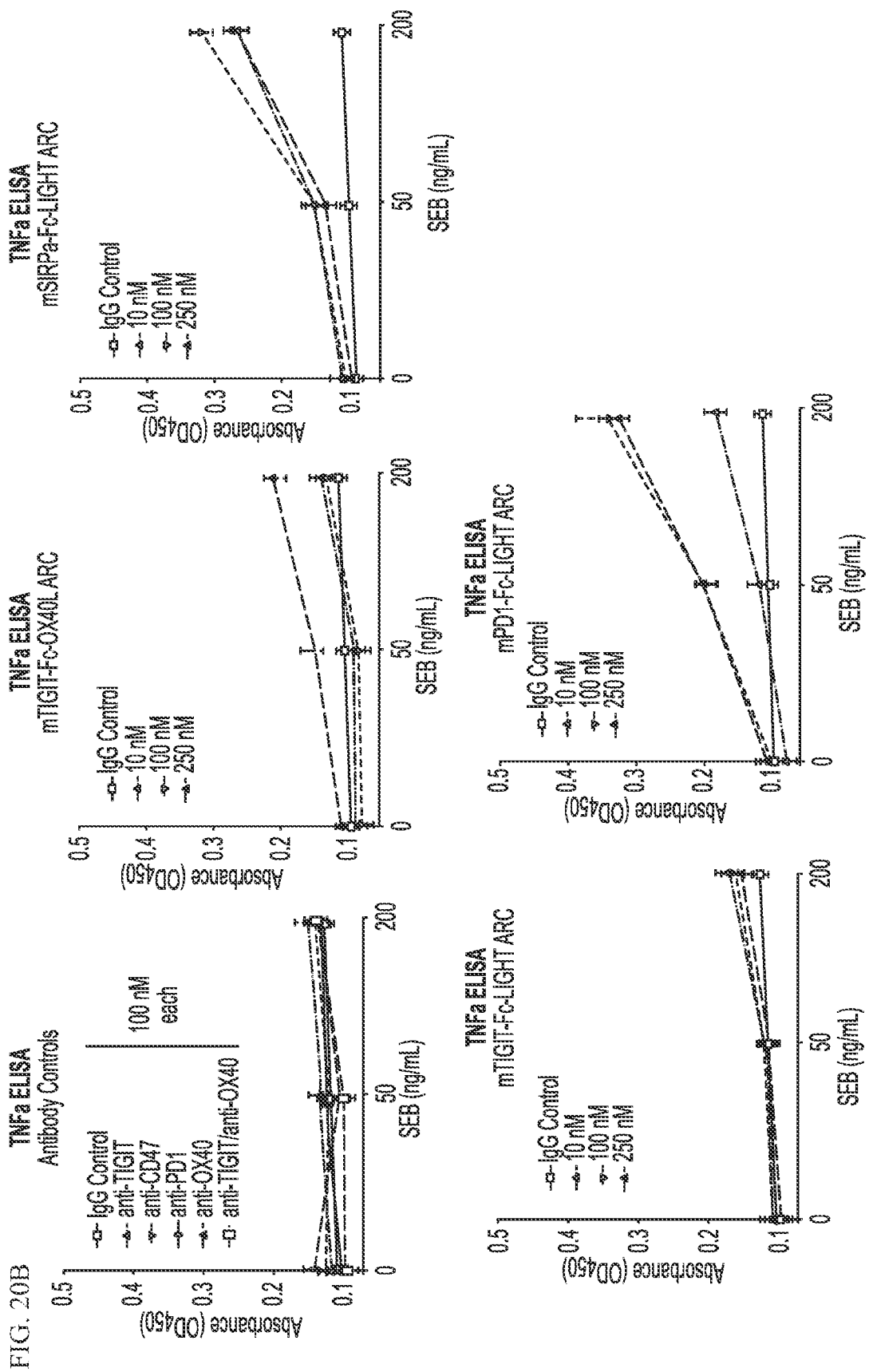
Figure 20C:
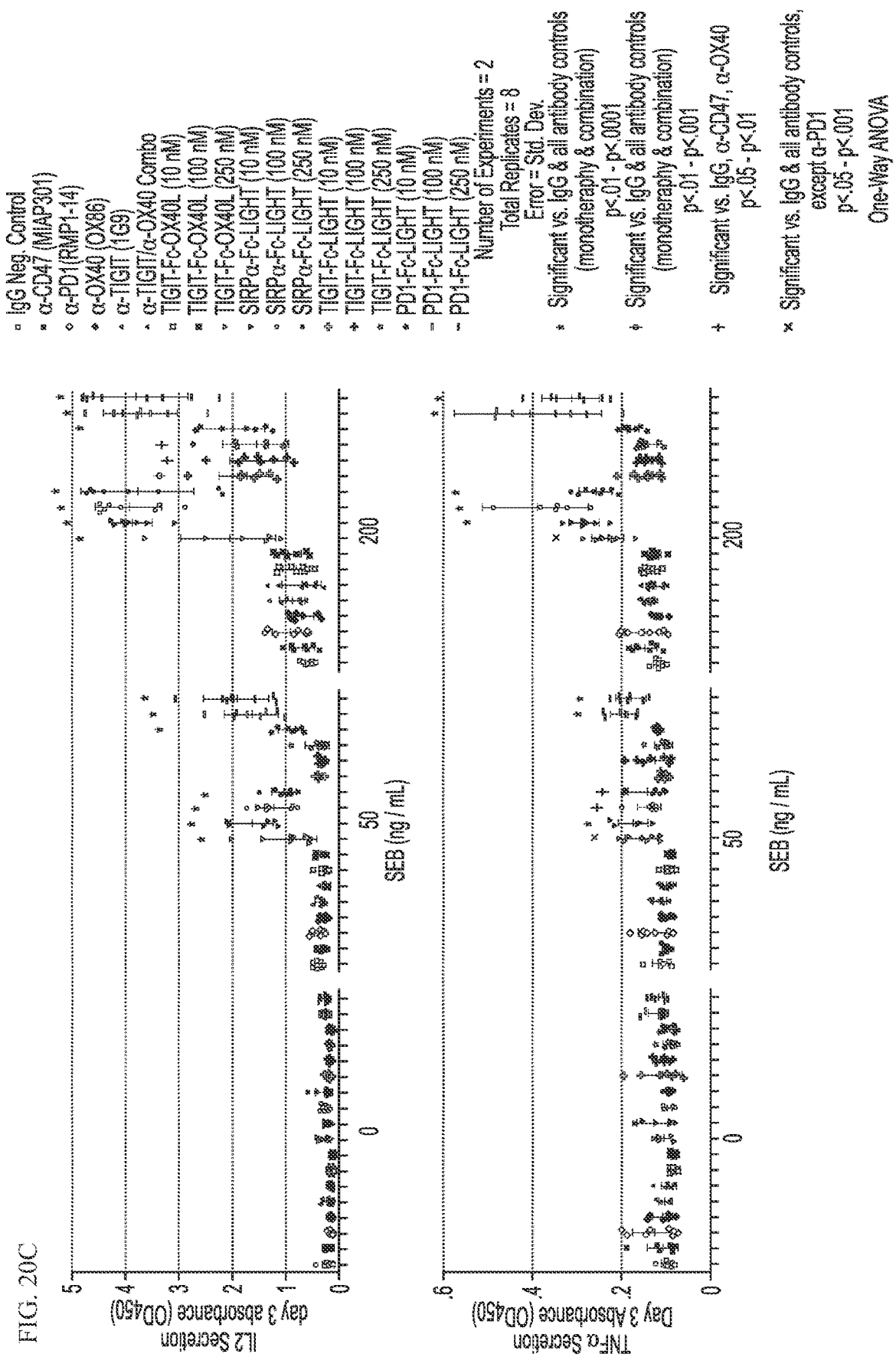
FIG. 20C shows a compilation of the data across multiple superantigen (SEB) concentrations (again, the order of conditions for each concentration of SEB mirrors from left to right, the conditions listed in the legends from top to bottom).

FIG. 20A and FIG. 20B show superantigen cytokine release assays which demonstrate the effects of the various antibodies, murine TIGIT-Fc-OX40L, murine CD172a (SIRPα)-Fc-LIGHT, murine TIGIT-Fc-LIGHT, or murine PD-1-Fc-LIGHT chimeric proteins on murine peripheral blood leukocytes activated by SEB. FIG. 20C shows a compilation of the data across multiple superantigen (SEB) concentrations. As shown in FIG. 20A and FIG. 20C, when 50 and 200 ng/ml SEB was administered, each of the three concentrations (10 nM, 100 nM, and 250 nM) for the mCD172a(SIRPα)-Fc-LIGHT and the mPD-1-Fc-LIGHT provided significantly greater secretion of IL2 than all the antibody controls. As shown in FIG. 20B, when 50 and 200 ng/ml SEB was administered, at 100 nm or 250 nm concentrations, the mPD-1-Fc-LIGHT provided significantly greater secretion of TNFα than all the antibody controls; when 200 ng/ml SEB was administered, all three concentrations of mCD172a(SIRPα)-Fc-LIGHT, provided significantly greater secretion of TNFα than all the antibody controls.

Figure 21A:
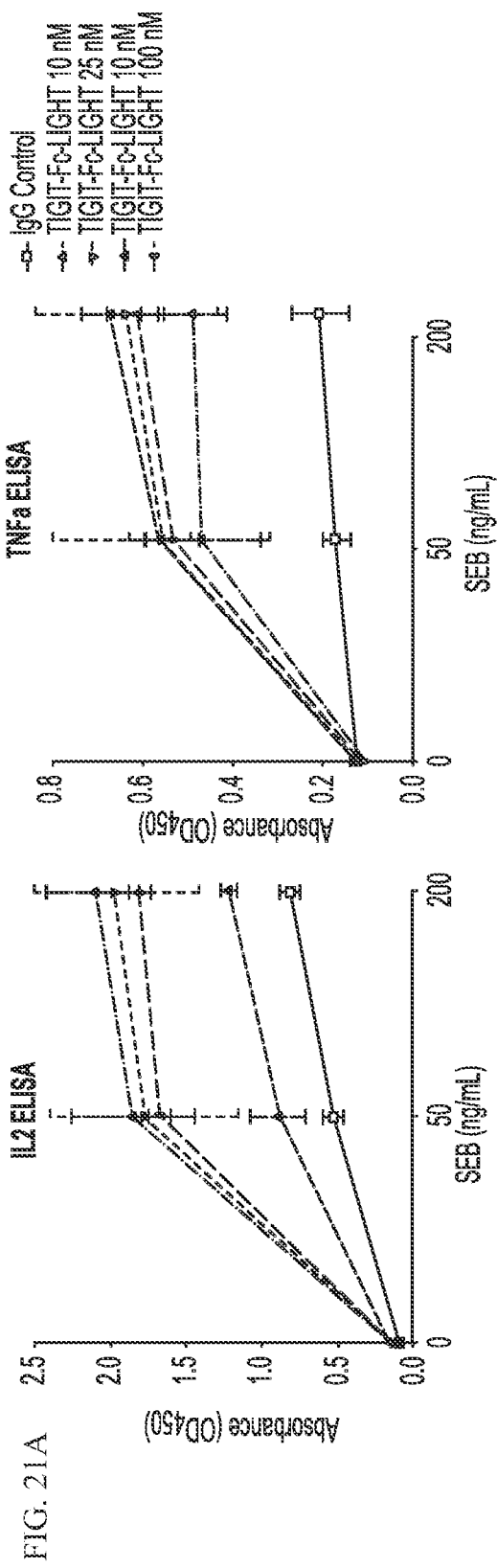
FIG. 21A to FIG. 21C show superantigen cytokine release assays which demonstrate the effects of the various antibodies, human TIGIT-Fc-LIGHT (FIG. 21A), human TIGIT-Fc-OX40L (FIG. 21B), human PD-1-Fc-LIGHT, and human CD172a(SIRPα)-Fc-LIGHT (FIG. 21C) chimeric proteins on human peripheral blood leukocytes activated by *staphylococcus* enterotoxin B (SEB).
Figure 21B:
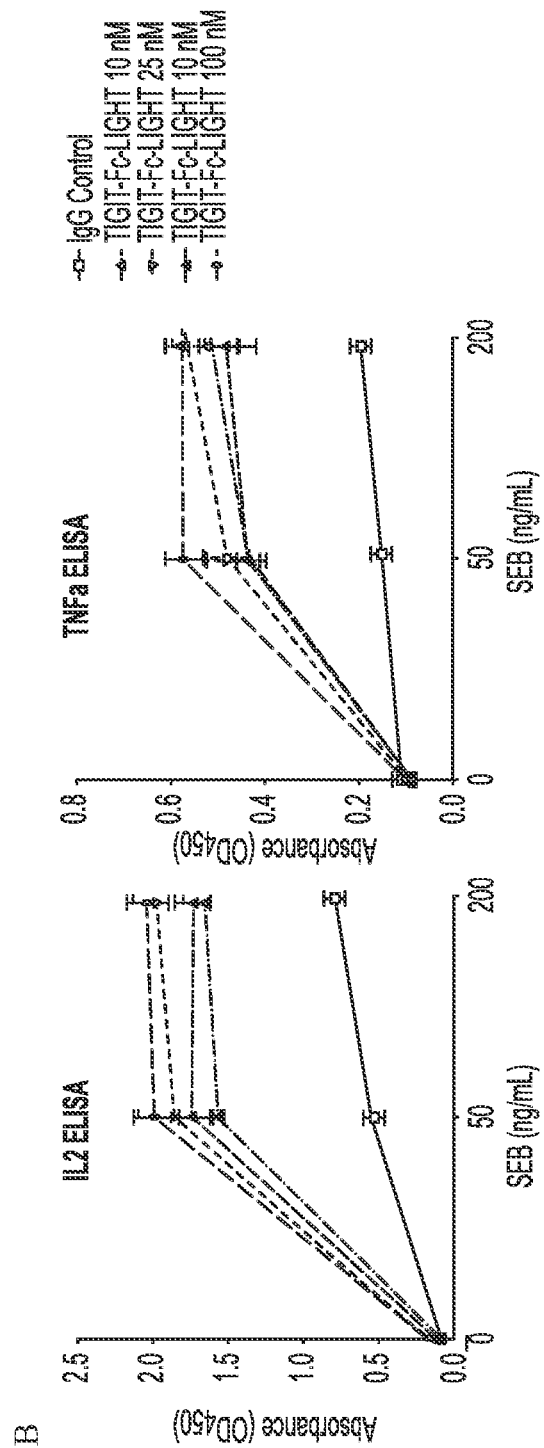
Figure 21C:
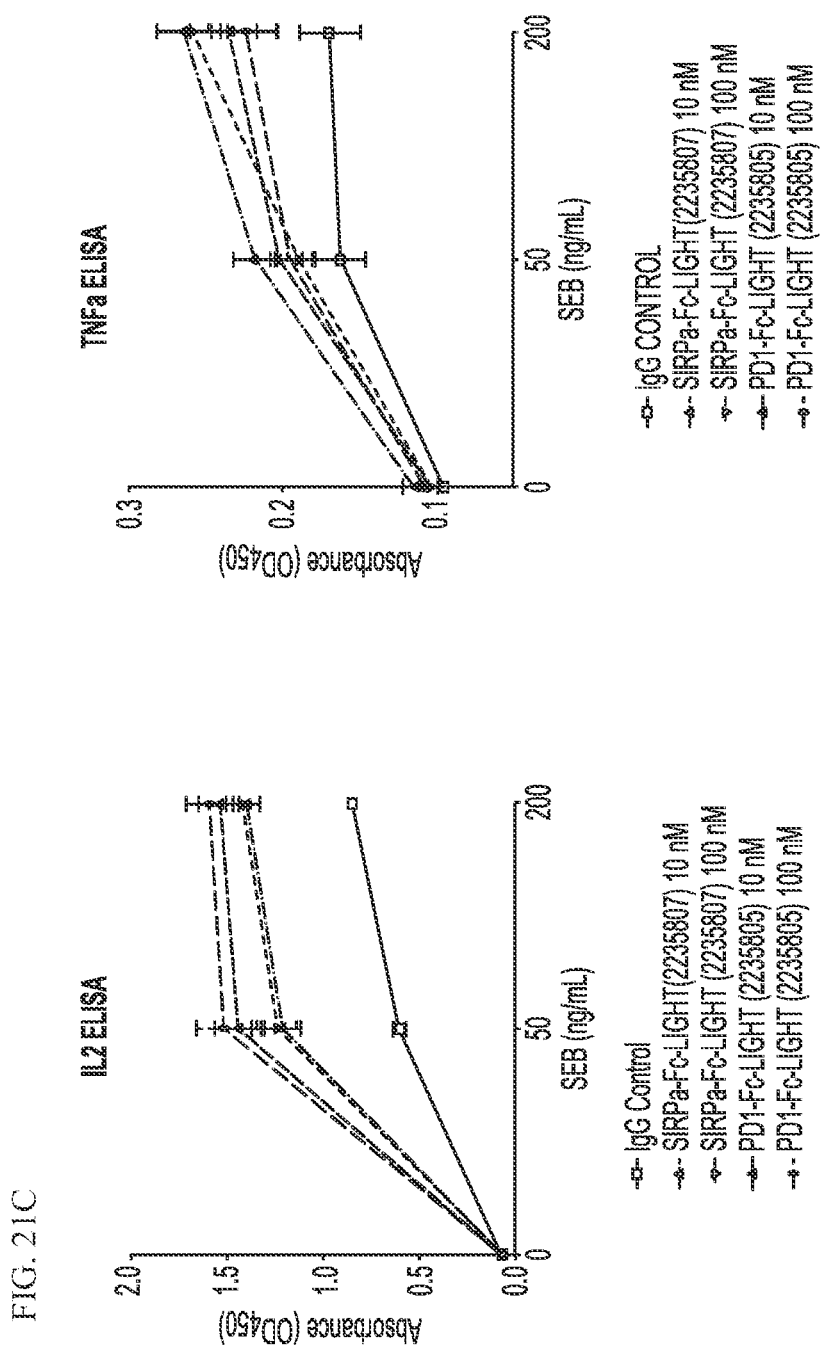

Moreover, FIG. 21A to FIG. 21C show superantigen cytokine release assays which demonstrate the effects of the various antibodies, human TIGIT-Fc-LIGHT (FIG. 21A), human TIGIT-Fc-OX40L (FIG. 21B), human PD-1-Fc-LIGHT, and human CD172a(SIRPα)-Fc-LIGHT (FIG. 21C) chimeric proteins on human peripheral blood leukocytes activated by SEB.

Accordingly, the above data demonstrates LIGHT domain-containing chimeric proteins and TIGIT domain-containing chimeric proteins as described herein are capable of binding each of its three binding partners; they functionally activate primary human leukocytes cells in vitro.

Example 6: Improved Tumor Killing and Increased Survival from Treatments with Chimeric Proteins The in vivo anti-tumor activity of the murine TIGIT-Fc-OX40L, murine CD172a(SIRPα)-Fc-LIGHT, murine TIGIT-Fc-LIGHT, and murine PD-1-Fc-LIGHT chimeric protein was analyzed using the CT26 mouse colorectal tumor model. In one set of experiments, Balb/c mice were inoculated with CT26 tumor. When tumors reached a diameter of 4 to 5 mm, mice were treated with the mTIGIT-Fc-OX40L, mCD172a(SIRPα)-Fc-LIGHT, mTIGIT-Fc-LIGHT, and mPD-1-Fc-LIGHT chimeric protein or an anti-TIGIT, anti-CD47, anti-OX40, or anti-PD-1 antibody or a combination of anti-TIGIT and anti-OX40 antibodies.

The tumor growth for each treatment group was assessed as shown in FIG. 22A (left and right panels). Specifically, the untreated mice developed tumors quickly and treatment with an antibody or antibodies appeared to slightly delay the development of tumors. In contrast, treating mice with the mTIGIT-Fc-OX40L, mCD172a(SIRPα)-Fc-LIGHT, mTIGIT-Fc-LIGHT, or mPD-1-Fc-LIGHT chimeric protein significantly inhibited growth and/or delayed the development of tumors.

The overall survival percentage of mice through forty days after tumor inoculation was also assessed. All of the untreated mice died within twenty days after tumor inoculation and none of the antibody or antibodies treated mice had a 40-day survival percentage greater than 25%; see FIG. 22B, left panel. Significantly, all the mice treated with the mTIGIT-Fc-OX40L, mCD172a(SIRPα)-Fc-LIGHT, mTIGIT-Fc-LIGHT, or mPD-1-Fc-LIGHT chimeric protein survived past forty days after tumor inoculation; see FIG. 22B, right panel.

These data indicate that in vivo treatments with a TIGIT-Fc-OX40L, CD172a(SIRPα)-Fc-LIGHT, TIGIT-Fc-LIGHT, or PD-1-Fc-LIGHT chimeric protein inhibits tumor growth and improves survival.

Example 7: Characterization of the Contribution of an Fc Domain in a Linker to Functionality of Chimeric Proteins In this example, the contribution of an Fc domain in a linker to functionality of chimeric proteins of the present invention was assayed. Here, a PD-1-Fc-OX40L was used as a model for Fc-containing chimeric proteins. Thus, the data presented below is relevant to chimeric proteins of the present invention.

Figure 23:
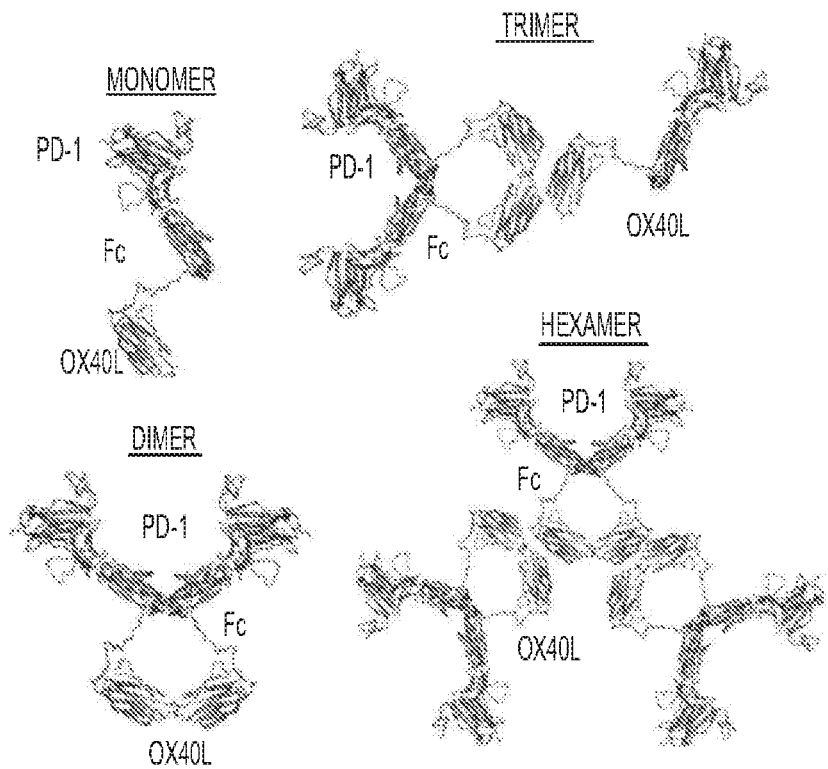
FIG. 23 shows, without wishing to be bound by theory, four potential configurations of PD-1-Fc-OX40L chimeric proteins.

In its native state, PD-1 exists as monomer whereas OX40Ls tend to dimerize due to electrostatic interactions between the OX40L domains; Fc domains associate with each other via disulfide bonds, e.g., via their cysteine residue(s). Together, several inter-molecular interactions may contribute to the quaternary structure of PD-1-Fc-OX40L. There are, at least, four potential configurations of PD-1-Fc-OX40L, with the chimeric protein existing as a monomer, a dimer, a trimer, or a hexamer. See, FIG. 23.

Figure 24:
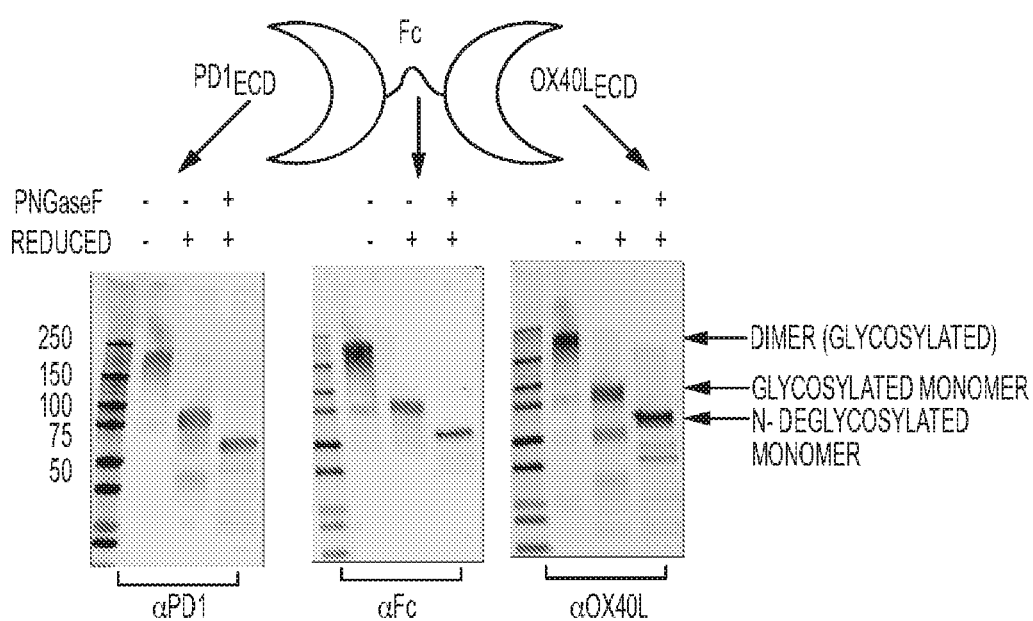
FIG. 24 shows Western blots of PD-1-Fc-OX40L chimeric proteins run on SDS-PAGE under a non-reducing condition, a reducing condition, and a reducing condition and following treatment with Peptide-N-Glycosidase F (PN-GaseF).

The existence of monomeric and dimeric configurations of the chimeric protein was tested by exposing chimeric proteins to reducing and non-reducing conditions and then running the proteins on SDS-PAGE. Under non-reducing conditions (Reduced: "−"), the chimeric protein migrated in SDS-PAGE at about 200 kDa. Here, Western blots were probed with antibodies directed against PD-1, Fc, or OX40L in, respectively, the left, middle, and right blots shown in FIG. 24. Since, the predicted monomeric molecular weight of the chimeric protein is 57.6 kDa, the 200 kDa species was expected to be, at least a dimer. However, under reduced conditions (Reduced: "−"), which reduces disulfide bonds (e.g., between Fc domains), the chimeric protein migrated in SDS-PAGE at about 100 kDa. Since the 100 kDa species was heavier than expected, it was predicted that the extra mass was due to glycosylation. Finally, chimeric proteins were treated with Peptide-N-Glycosidase F (PNGaseF "+") and run on SDS-PAGE under reduced conditions. Under these conditions, the chimeric protein migrated at about 57.6 kDa. These data suggest that the chimeric protein is glycosylated and exists naturally, at least, as a dimer; with dimerization likely due to disulfide bonding between Fc domains e.g., via their cysteine residue(s).

Figure 25:
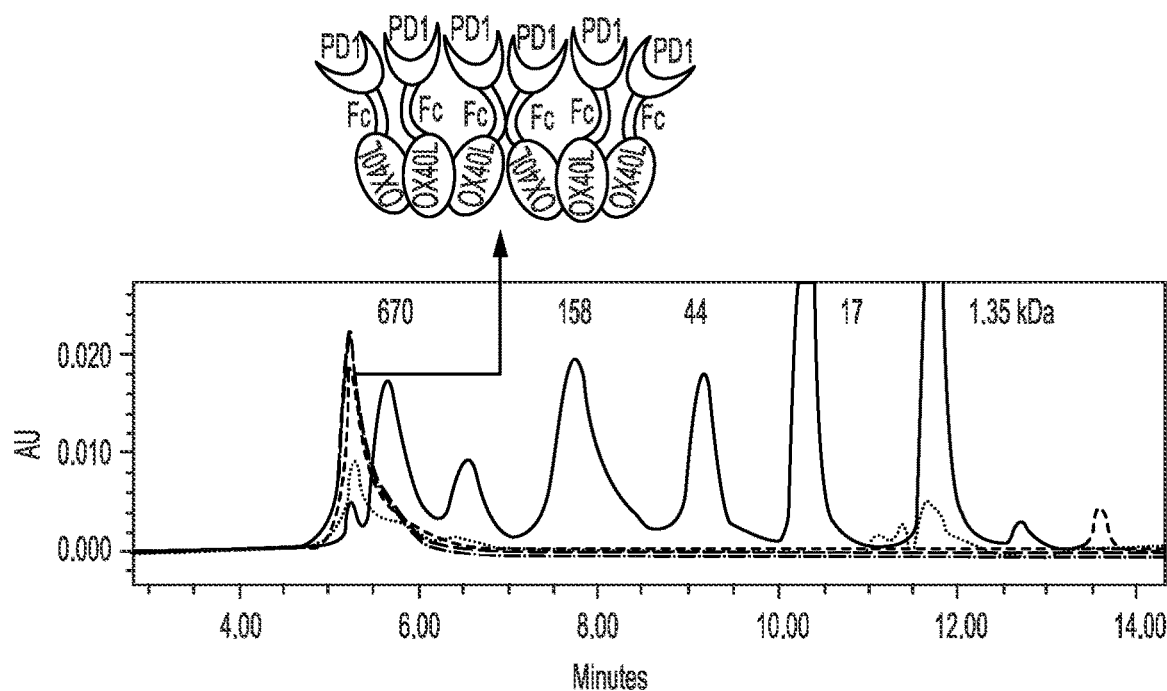
FIG. 25 shows a chromatograph for PD-1-Fc-OX40L chimeric proteins run on Size Exclusion Chromatography (SEC).

SDS-PAGE gel methods do not accurately predict the molecular weight for highly charged and/or large molecular weight proteins. Thus, chimeric proteins were next characterized using Size Exclusion Chromatography (SEC). Unlike SDS-PAGE, in which the negatively-charged SDS reduces charge-based interactions between peptides, SEC does not use detergents or reducing agents. When the PD-1-Fc-OX40L chimeric protein was run on SEC, none of the peaks were around 200 kDa. This suggests, that natively, the chimeric protein does not exist as a dimer. Instead, a peak having a size greater than 670 kDa was detected. See, FIG. 25. This and the prior data suggests that the PD-1-Fc-OX40L chimeric protein exists as a hexamer in its native state.

Figure 26:
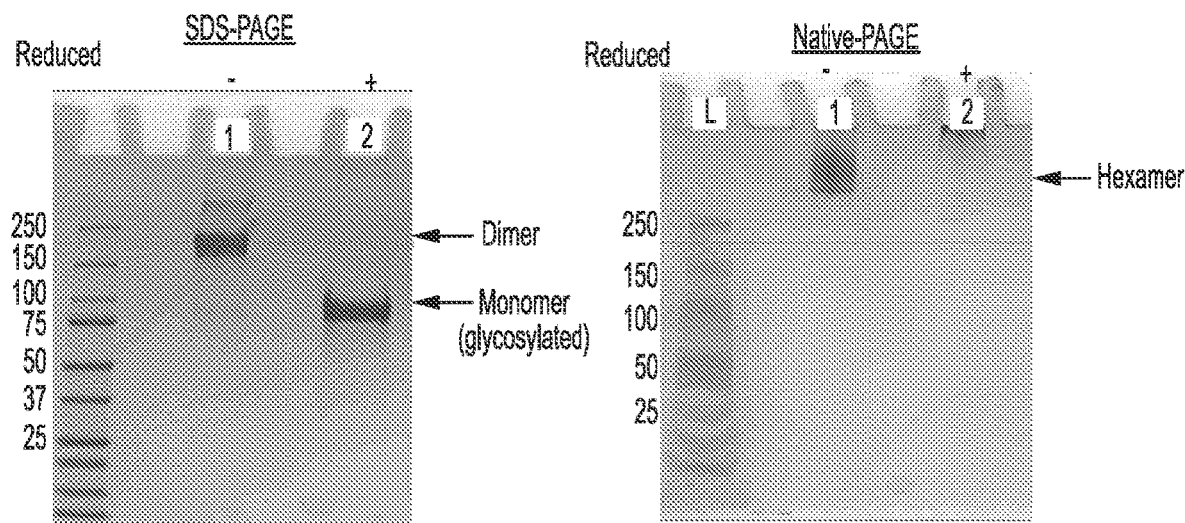
FIG. 26 shows SDS-PAGE and native (non-SDS) PAGE gels for PD-1-Fc-OX40L chimeric proteins run under a non-reducing condition ("−") or a reducing condition ("+").

As shown above, when run on SDS-PAGE under non-reducing conditions or under reducing conditions, SDS in the sample and/or running buffer converts the hexameric PD-1-Fc-OX40L chimeric protein into a predominant dimer or monomer, respectively, in the absence and presence of a reducing agent. See, FIG. 26 (left gel). When run on native PAGE, which lacks SDS, and in the absence of a reducing agent, the chimeric protein exists as a hexamer. However, when run on native PAGE and in the presence of a reducing agent (which reduces disulfide bonds) the chimeric protein migrated heavier than expected; as shown in FIG. 26 (right gel, lane 2), with the chimeric protein failed to substantially migrate out of the loading well. This data suggests that the chimeric protein oligomerized into a higher-order protein. Thus, in chimeric proteins, disulfide bonding appears to be important for controlling higher-order oligomerization.

Figure 27:
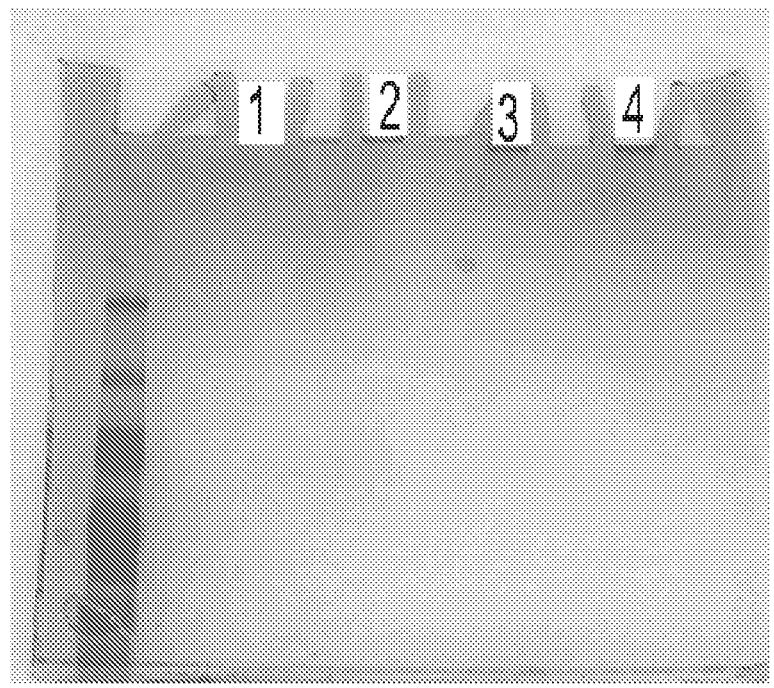
FIG. 27 shows a native (non-SDS) PAGE gel for PD-1-No Fc-OX40L chimeric proteins which lack a Fc domain.
Figure 28:
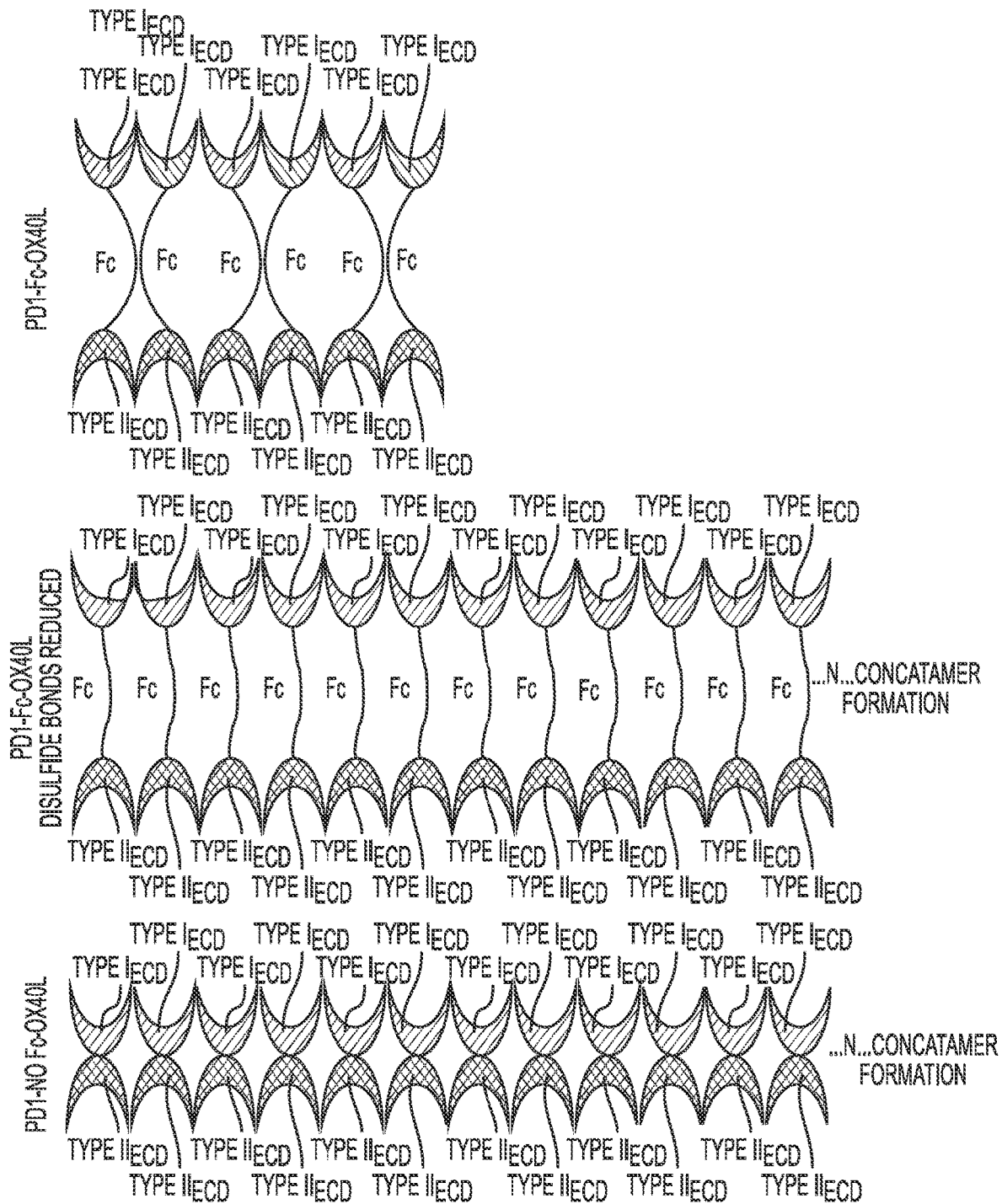
FIG. 28 shows, without wishing to be bound by theory, a model for how a hexamer and concatemers form from chimeric proteins of the present invention.

To further confirm this, chimeric proteins lacking an Fc domain were constructed, e.g., "PD-1-No Fc-OX40L". Such chimeric proteins will not have the disulfide bonding which occurs between Fc domains in the chimeric proteins described previously. As shown in FIG. 27, when chimeric proteins lacking Fc domains are run on native PAGE, none of the protein substantially migrated out of its loading well; again, suggesting that the "No Fc" chimeric proteins have formed a concatemer-like complex comprising numerous proteins. Thus, omission of the Fc domain in a chimeric protein leads to formation of protein aggregates. These data indicate that disulfide bonding, e.g., between Fc domains on different chimeric proteins, stabilizes the chimeric proteins and ensures that they each exist as a hexamer and not as a higher-order protein/concatemer. In other words, the Fc domain surprisingly puts order to chimeric protein complexes. Lanes 1 to 4 respectively include 2.5 µg, of PD-1-No Fc-OX40L, 5 µg of PD-1-No Fc-OX40L, 2.5 µg of PD-1-No Fc-OX40L, and 5 µg of PD-1-No Fc-OX40L Shown in FIG. 28 is a model summarizing the above data and showing how a hexamer and concatamers form from chimeric proteins of the present invention. The illustrative chimeric protein (PD-1-Fc-OX40L) naturally forms into a hexamer (due to electrostatic interactions between the OX40L domains and dimerization by Fc domains). However, in the absence of the controlling effects off disulfide bonding between Fc domains, under reduced conditions for the PD-1-Fc-OX40L protein and due to the absence of Fc domains in the PD-1-No Fc-OX40L, these latter chimeric proteins form concatamers.

Additionally, chimeric proteins were constructed in which the Fc domain (as described herein) was replaced with Ficolin (which lacks cysteine residues necessary for disulfide bonding between chimeric proteins). As with the No Fc chimeric proteins and chimeric proteins comprising an Fc and run on native PAGE and in the presence of a reducing agent (both of which formed aggregates that do not migrate into a gel) chimeric proteins comprising Ficolin appear to also form higher-order lattices which did not migrate into a gel. These data reinforce the conclusion that disulfide binding is important for proper folding and function of chimeric proteins of the present invention.

Finally, chimeric proteins were prepared using coiled Fc domains (CCDFc). Very little purified protein was delivered under functional evaluation.

Accordingly, including an Fc domain in a linker of a chimeric protein (which is capable of forming disulfide bonds between chimeric proteins), helps avoid formation of insoluble and, likely, non-functional protein concatamers and/or aggregates.

Example 8: Characterization of Different Joining Linker Sequences for the Chimeric Proteins Different unique joining linker sequences (17 linkers) were identified with varying characteristics (length, solubility, charge and flexibility). Constructs were then synthesized incorporating each of those 17 joining linker sequences into the 'linker 2' position, where the configuration of chimeric protein:

ECD 1-Joining Linker 1-Fc-Joining Linker 2-ECD 2

The production levels for those 17 constructs were tested in CHO cells. The following table provides a summary for the different joining linker sequences, characteristics of those joining linkers, the production level (by A280), and the binding values ($EC_{50}$) based on FACS analysis to PD-L1 or OX40. Some variations in production levels and activity between certain joining linker sequences were determined.

TABLE 2

Summary for optional joining linker sequences

| Protein Name | Protein conc. A280 | CHO-PD-L1 EC50 (nM) | HeLa-OX40 EC50 (nM) | Joining Linker 2 Sequence | Characteristics |
|---|---|---|---|---|---|
| PD-1_IgG4_OX40L (1) | 0.17 | 27 | 6 | IEGRMD (SEQ ID NO: 52) | Linker |
| PD-1_IgG4_OX40L (2) | 0.12 | 23 | 67 | SKYGPPCPPCP (SEQ ID NO: 50) | IgG4 Hinge Region |
| PD-1_IgG4_OX40L (3) | 0.15 | 25 | 140 | GGGSGGGS (SEQ ID NO: 55) | Flexible |
| PD-1_IgG4_OX40L (4) | 0.11 | 36 | 125 | GGGSGGGGSGGG (SEQ ID NO: 56) | Flexible |
| PD-1_IgG4_OX40L (5) | 0.22 | 25 | 41 | EGKSSGSGSESKST (SEQ ID NO: 57) | Flexible + soluble |
| PD-1_IgG4_OX40L (6) | 0.12 | 26 | 171 | GGSG (SEQ ID NO: 58) | Flexible |
| PD-1_IgG4_OX40L (7) | 0.11 | 27 | 195 | GGSGGGSGGSG (SEQ ID NO: 59) | Flexible |

TABLE 2-continued

Summary for optional joining linker sequences

| Protein Name | Protein conc. A280 | CHO-PD-L1 EC50 (nM) | HeLa-OX40 EC50 (nM) | Joining Linker 2 Sequence | Characteristics |
|---|---|---|---|---|---|
| PD-1_IgG4_OX40L (8) | 0.21 | 20 | 48 | EAAAKEAAAKAAAK (SEQ ID NO: 60) | Rigid Alpha Helix |
| PD-1_IgG4_OX40L (9) | 0.23 | 45 | 87 | EAAAREAAAREAAAREAAAR (SEQ ID NO: 61) | Rigid Alpha Helix |
| PD-1_IgG4_OX40L (10) | 0.13 | 52 | 62 | GGGGSGGGGSGGGGSAS (SEQ ID NO: 62) | Flexible |
| PD-1_IgG4_OX40L (11) | 0.07 | 25 | 100 | GGGVPRDCG (SEQ ID NO: 53) | Flexible |
| PD-1_IgG4_OX40L (12) | 0.11 | 33 | 70 | GGGGAGGGG (SEQ ID NO: 63) | Flexible |
| PD-1_IgG4_OX40L (13) | 0.12 | 38 | 60 | GS (SEQ ID NO: 64) | Highly flexible |
| PD-1_IgG4_OX40L (14) | 0.18 | 25 | 70 | GSGSGS (SEQ ID NO: 65) | Highly flexible |
| PD-1_IgG4_OX40L (15) | 0.19 | 24 | 67 | GSGSGSGSGS (SEQ ID NO: 66) | Highly flexible |
| PD-1_IgG4_OX40L (16) | 0.11 | 34 | 77 | GGGGSAS (SEQ ID NO: 67) | Flexible |
| PD-1_IgG4_OX40L (17) | 0.19 | 32 | 44 | APAPAPAPAPAPAPAPAP (SEQ ID NO: 68) | Rigid |

Figure 29A:
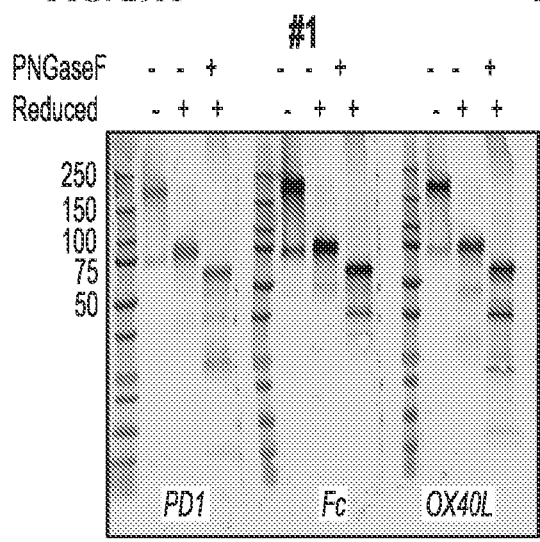
FIG. 29A to FIG. 29Q show characterization of PD-1-Fc-OX40L chimeric proteins with different joining linker sequences by Western blot analysis. Sequences of the different joining linkers are provided below in the Examples section. Specifically, each individual domain of the fusion construct was probed using an α-PD-1, α-Fc, or α-OX40L antibody. In each figure, untreated samples of the PD-1-Fc-OX40L chimeric protein, e.g. control, were loaded into lane 1 in all the blots (no 3-mercaptoethanol or PNGase). Samples in lane 2 were treated with the reducing agent, 3-mercaptoethanol, while samples in lane 3 were treated with PNGase.
Figure 29B:
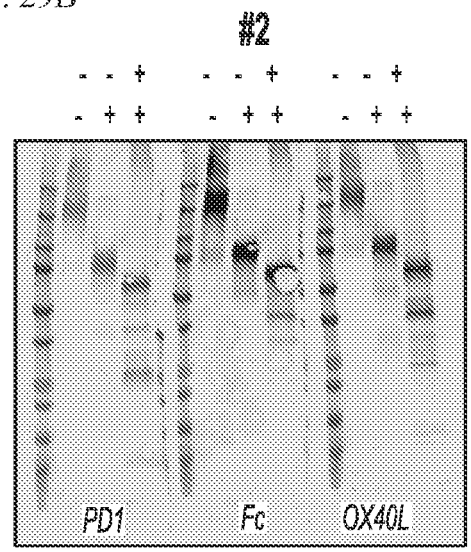
Figure 29C:
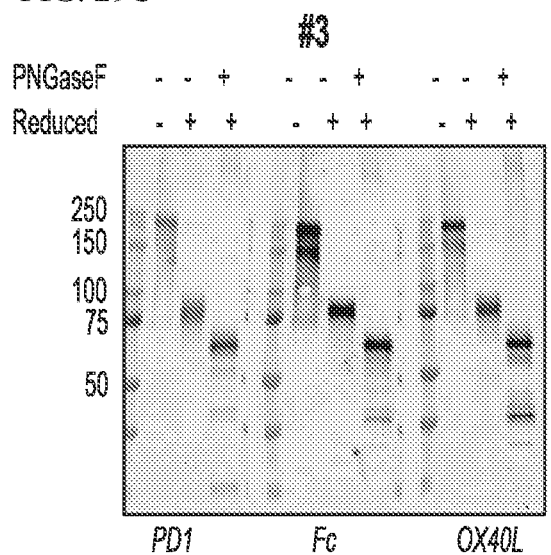
Figure 29D:
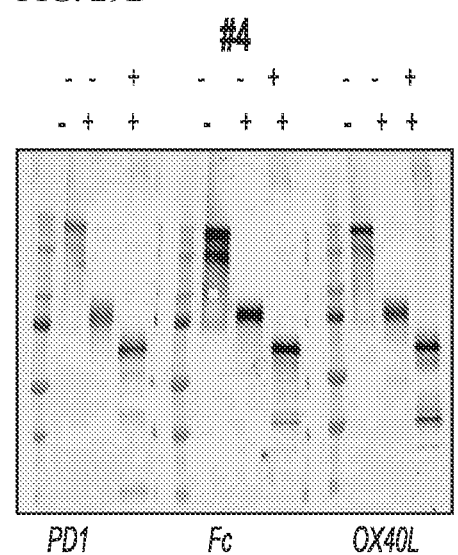
Figure 29E:
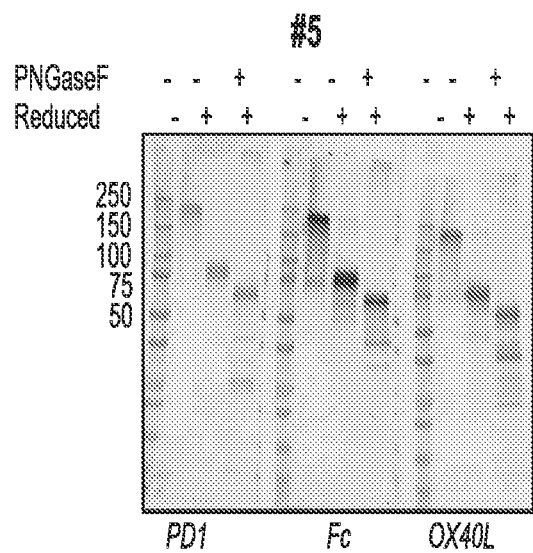
Figure 29F:
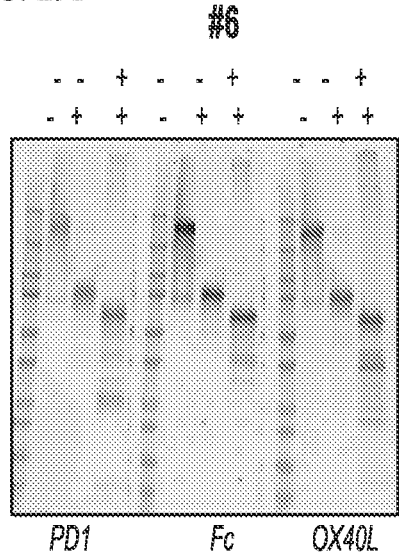
Figure 29G:
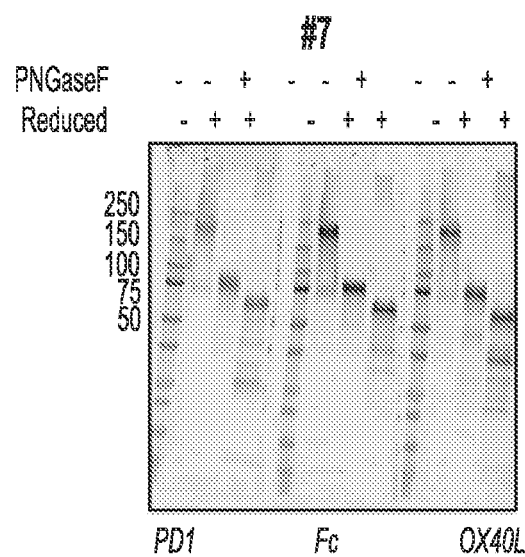
Figure 29H:
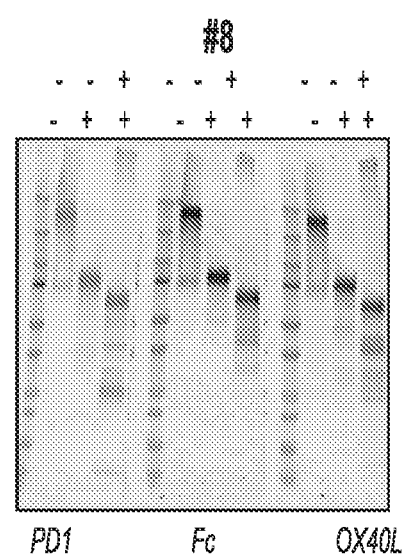
Figure 29I:
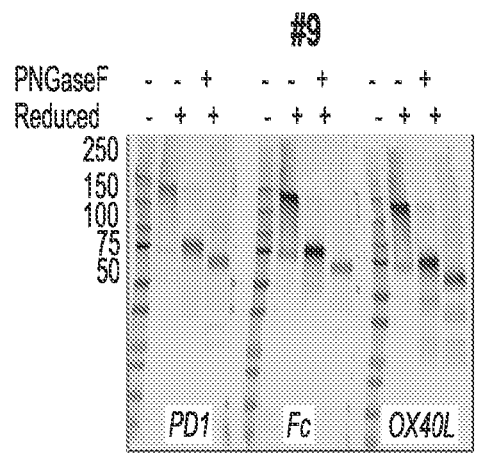
Figure 29J:
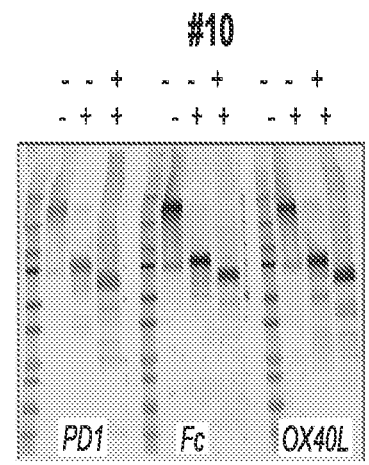
Figure 29K:
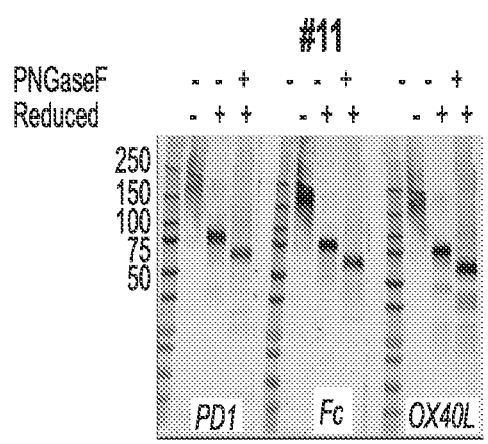
Figure 29L:
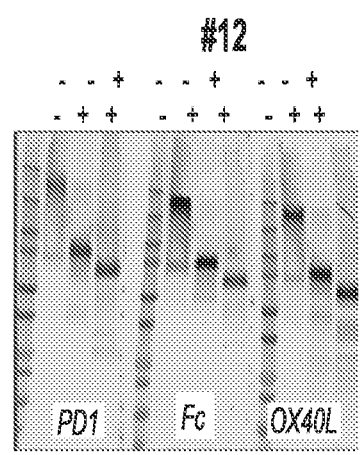
Figure 29M:
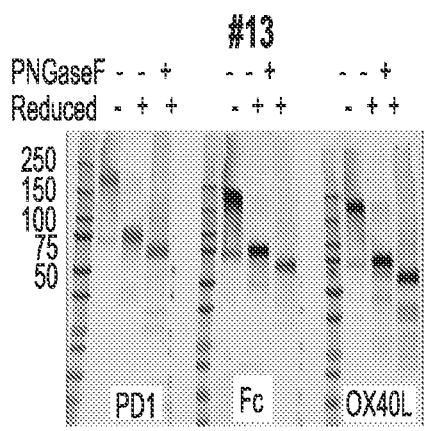
Figure 29N:
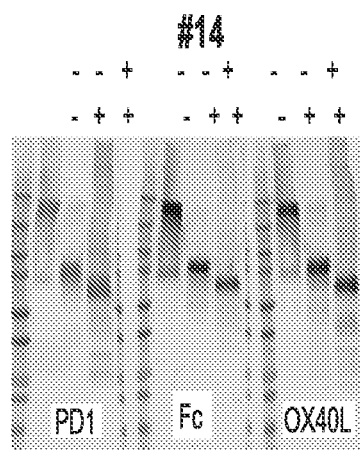
Figure 29O:
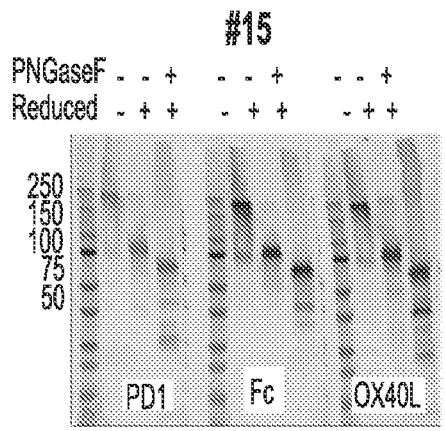
Figure 29P:
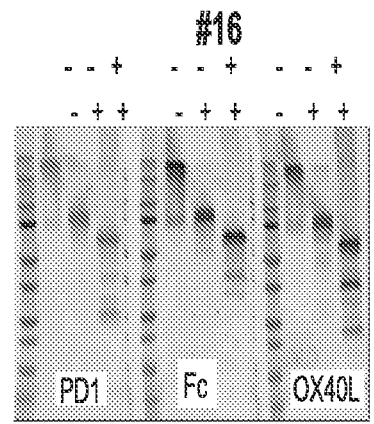
Figure 29Q:
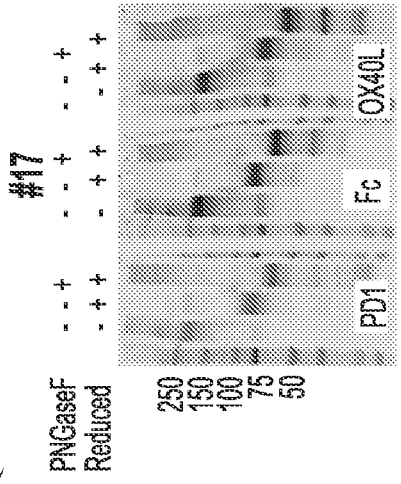

Characterization of PD-1-IgG4-OX40L chimeric proteins with different joining linker sequences (17 linkers) by Western blot analysis is shown in FIG. 29A to FIG. 29Q. Specifically, each individual domain of the fusion construct was probed using an anti-PD-1, anti-Fc, or anti-OX40L antibody. Results showed similar performance across each chimeric protein suggesting that all of the candidate joining linker sequences were functional.

Figure 30:
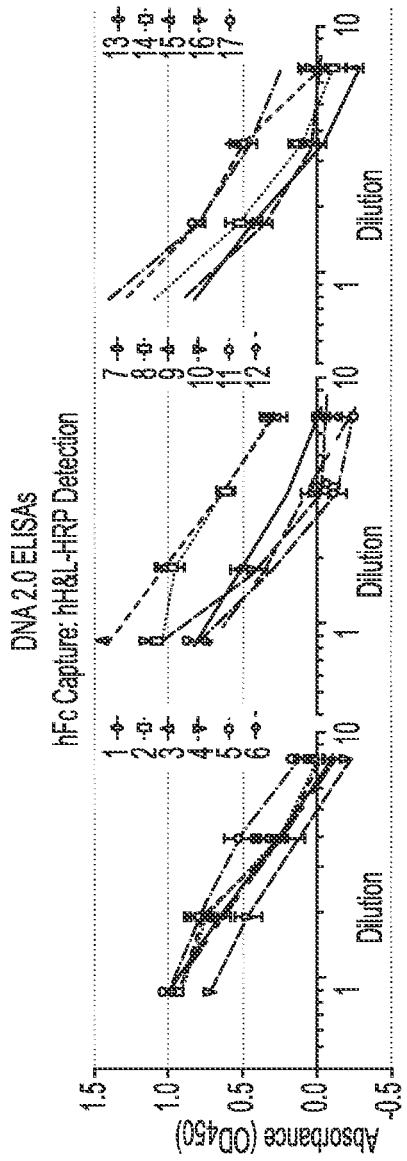
FIG. 30 shows characterization of PD-1-Fc-OX40L chimeric proteins with different joining linker sequences by ELISA-based capture and detection assay against the central Fc region of the protein. The protein concentration of each PD-1-Fc-OX40L chimeric protein with different joining linker sequence (#1 to #17) was determined.
Figure 31A:
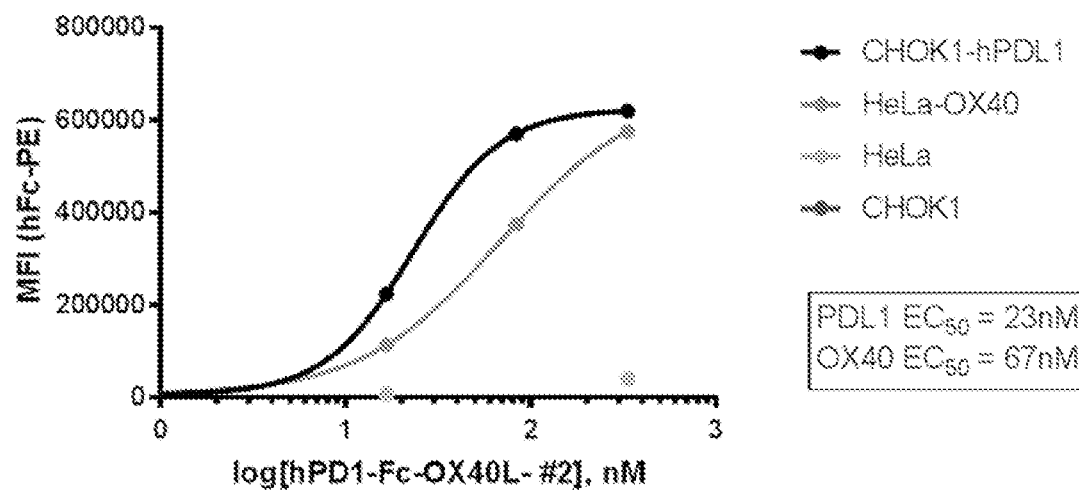
FIG. 31A to FIG. 31P show the flow cytometry profiles of PD-1-Fc-OX40L chimeric proteins with different joining linker sequences by FACS analysis to PD-L1 or OX40. The $EC_{50}$ values were calculated for each PD-1-Fc-OX40L chimeric protein with different joining linker sequence (#2 to #17—see X-axis label and chart in the Examples below for linker identity).
Figure 31B:
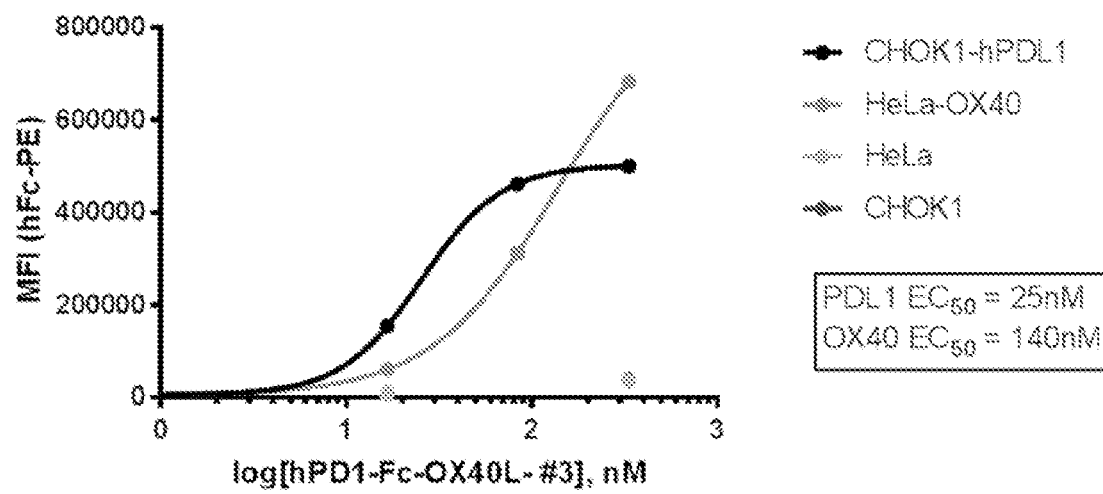
Figure 31C:
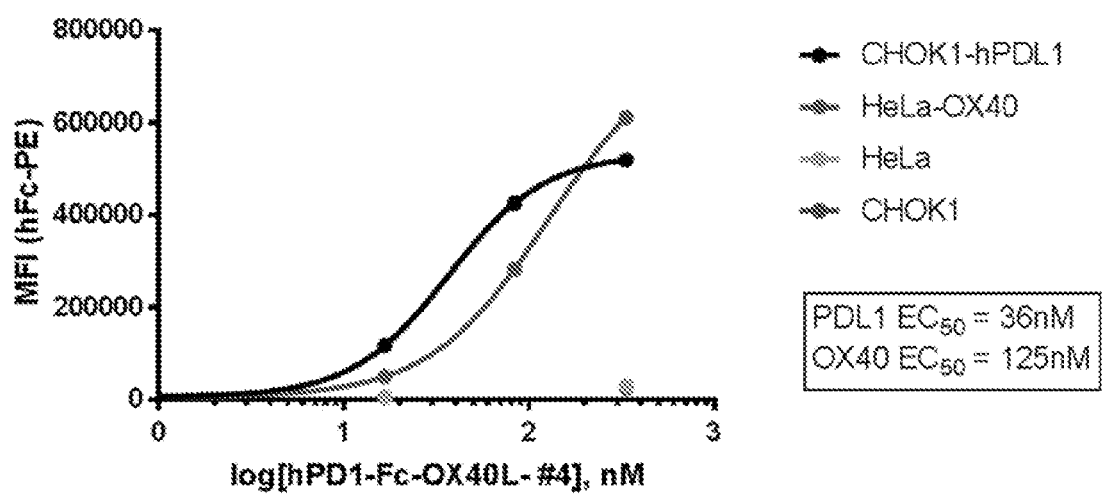
Figure 31D:
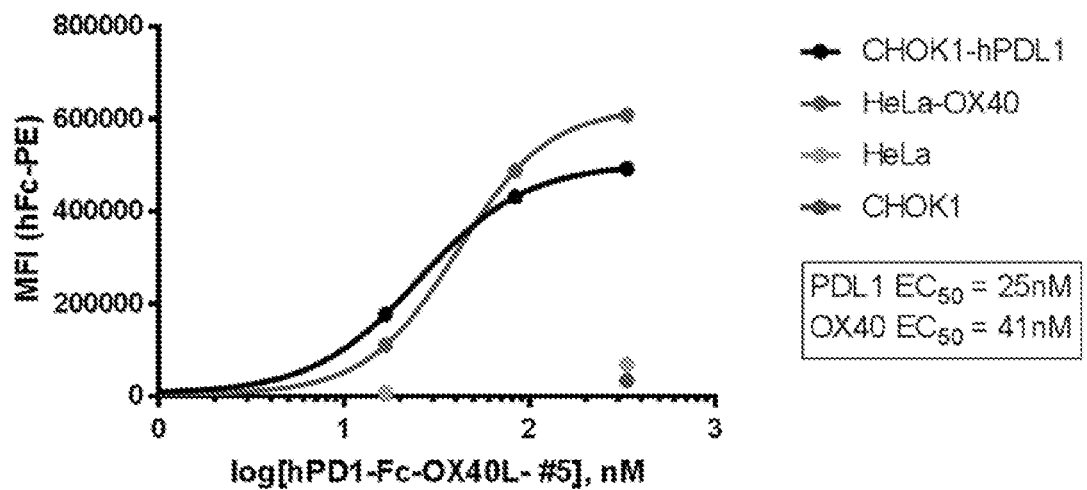
Figure 31E:
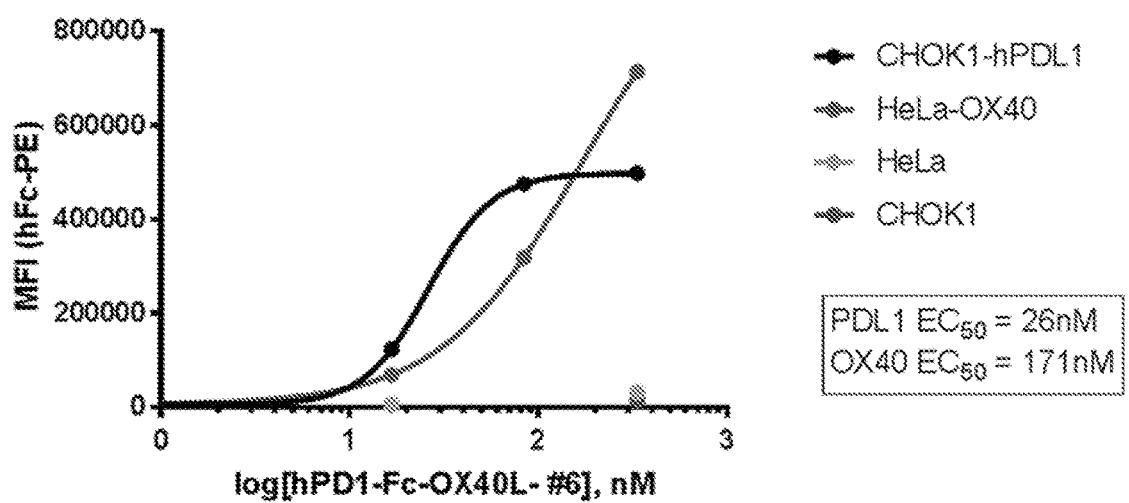
Figure 31F:
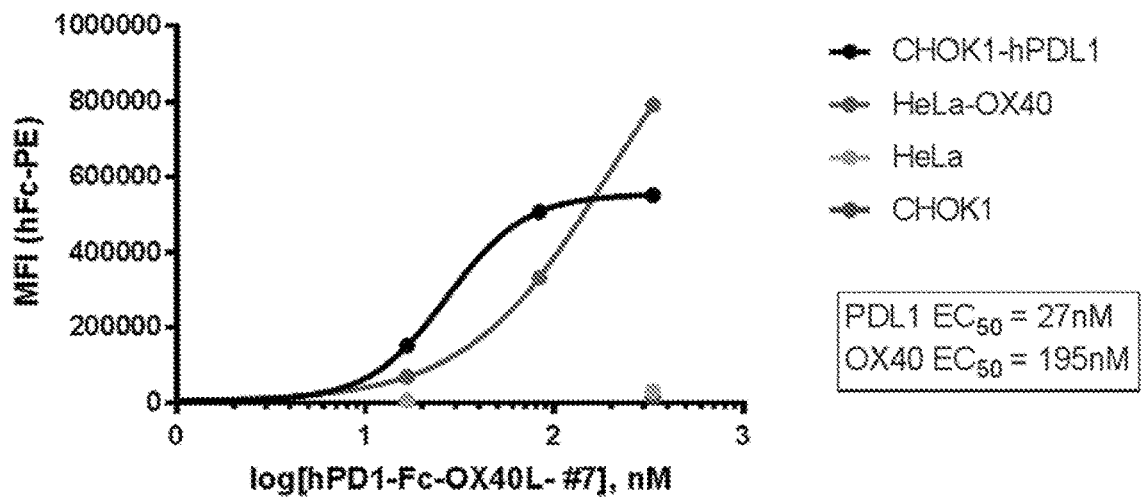
Figure 31G:
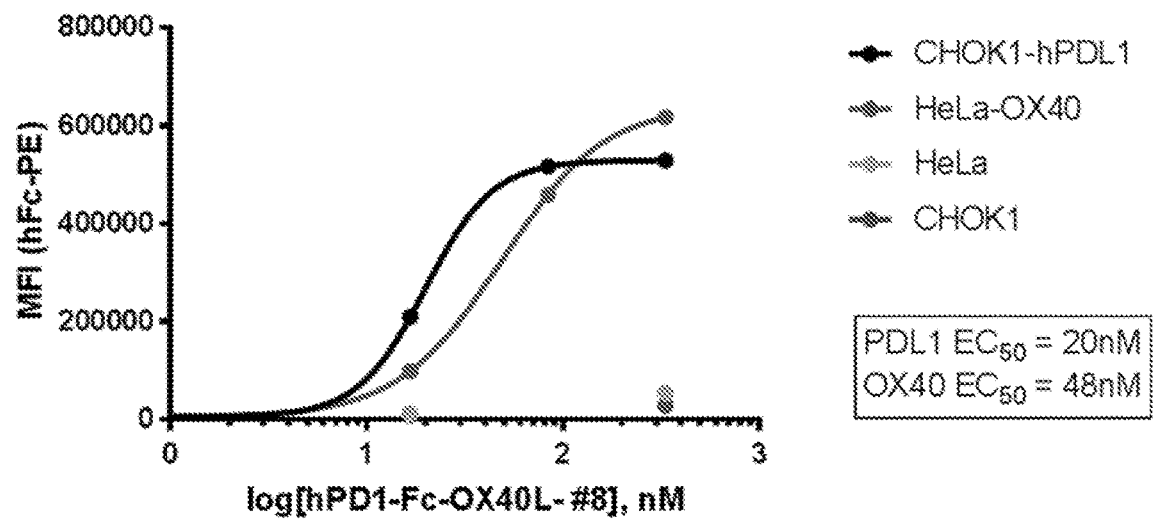
Figure 31H:
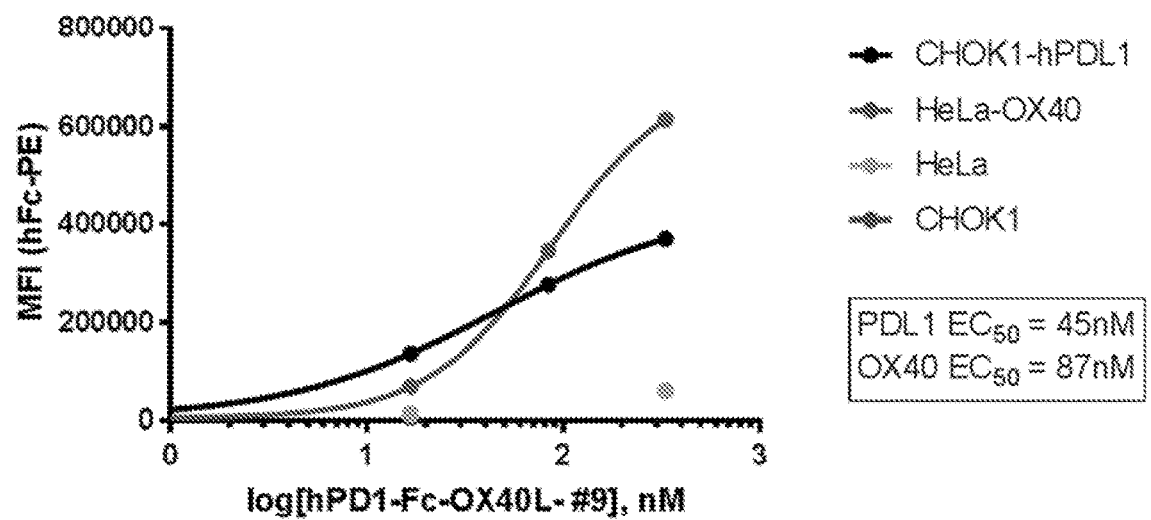
Figure 31I:
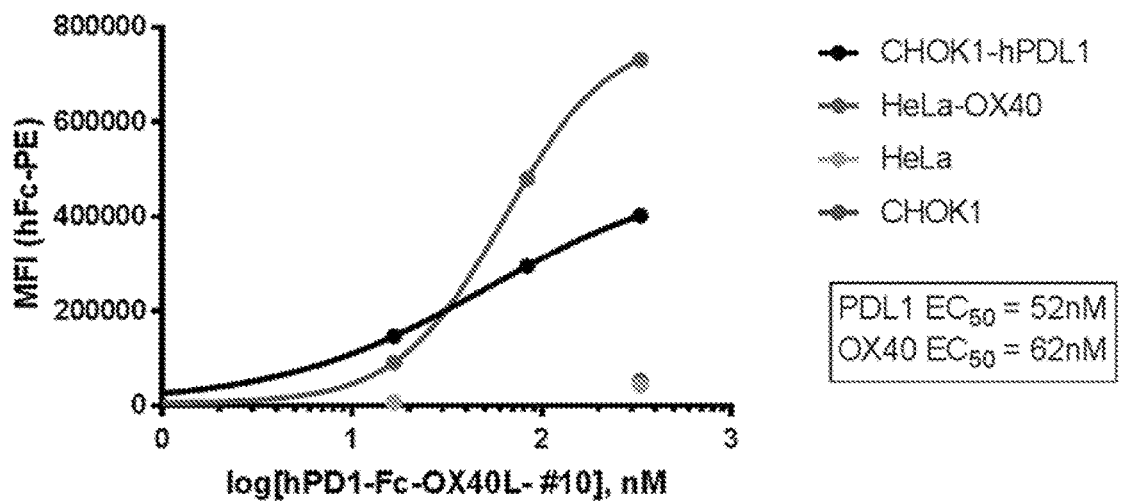
Figure 31J:
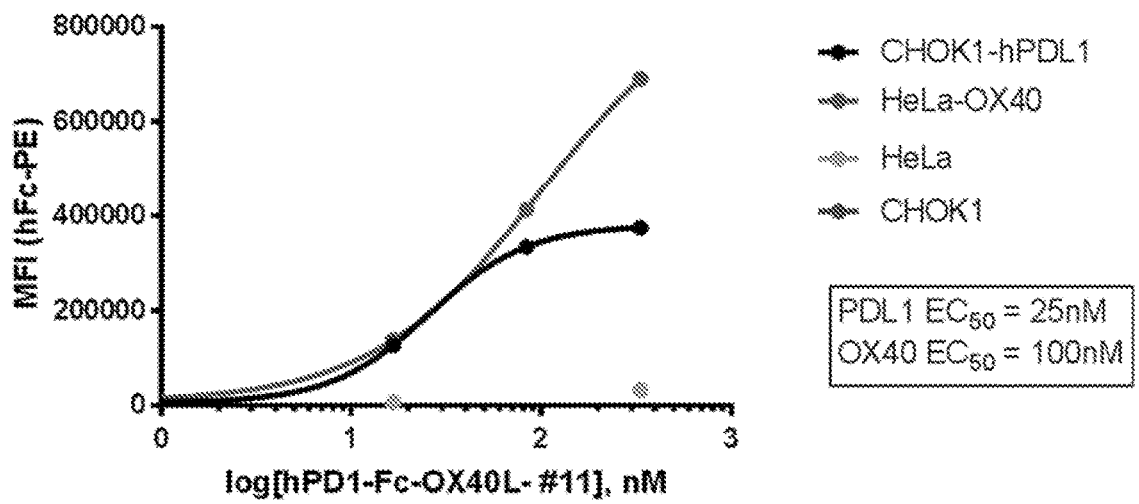
Figure 31K:
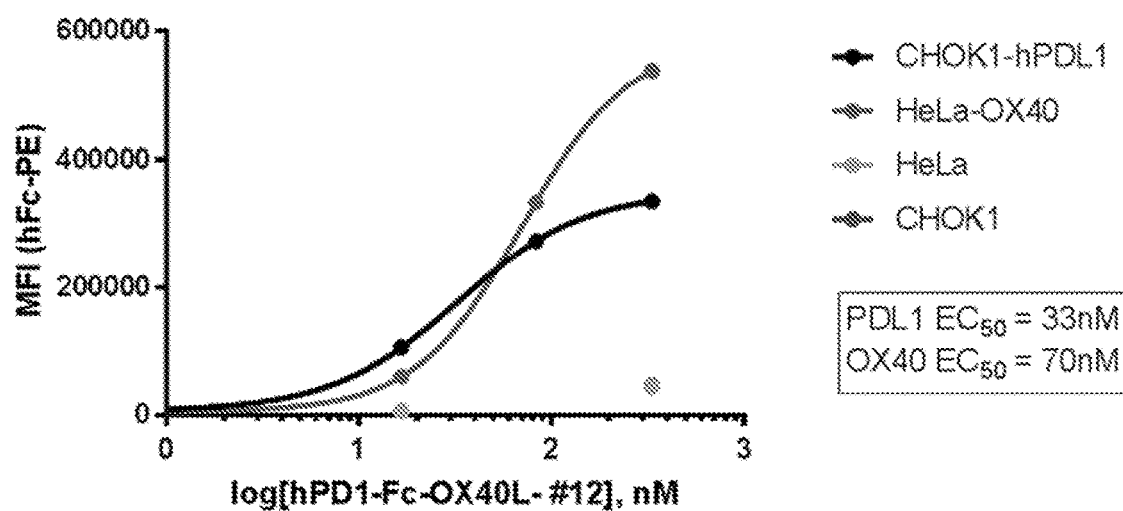
Figure 31L:
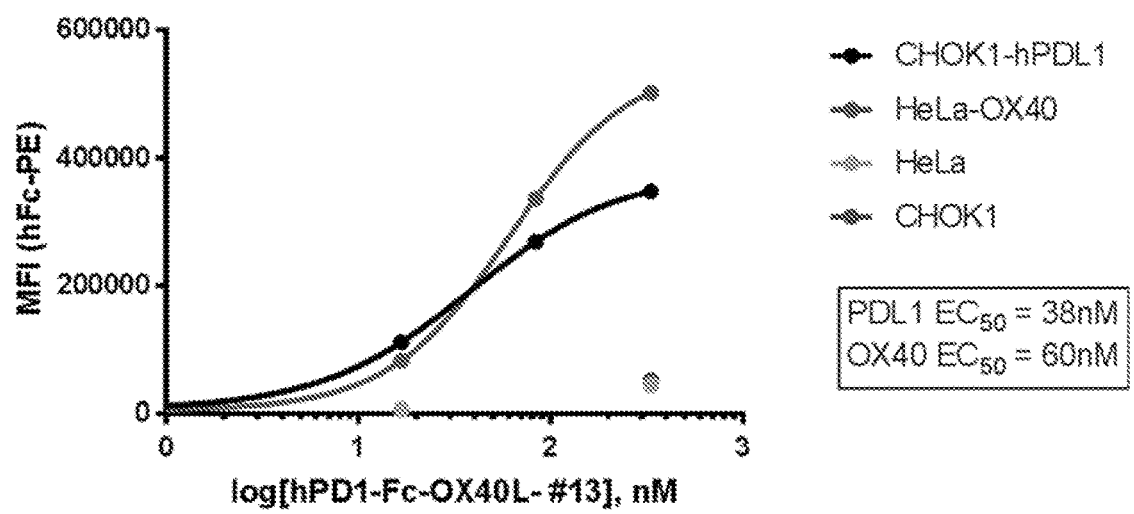
Figure 31M:
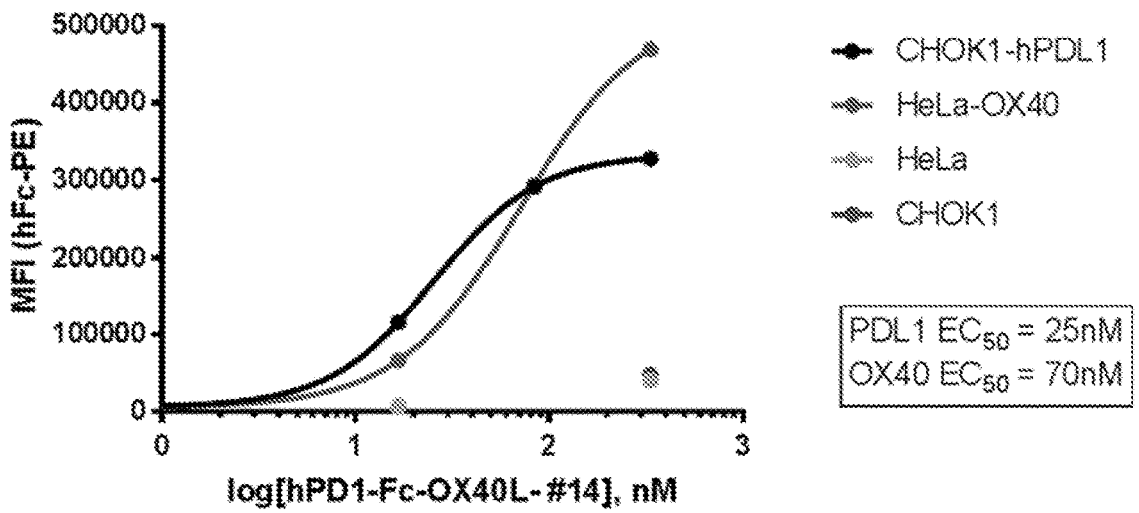
Figure 31N:
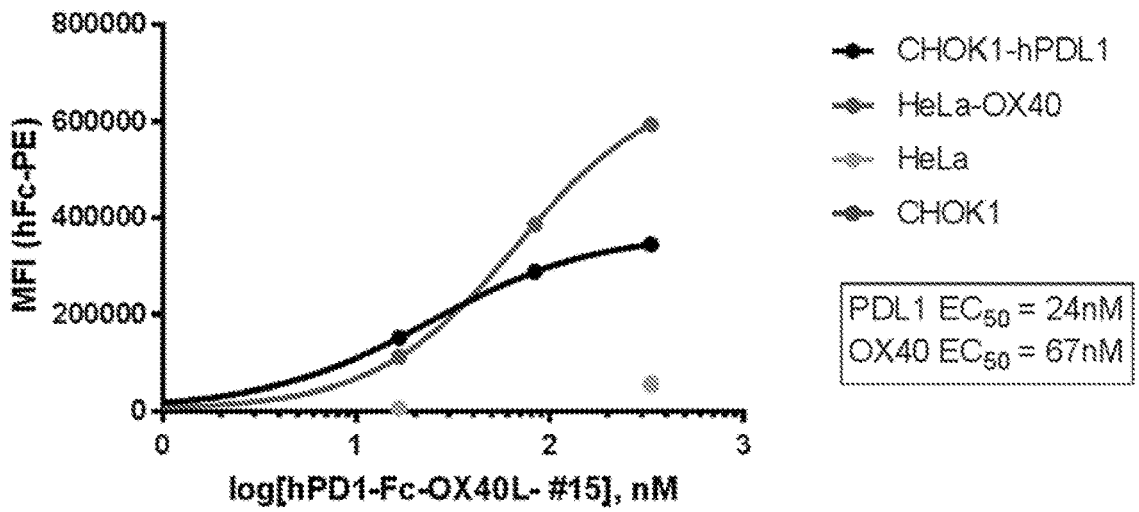
Figure 31O:
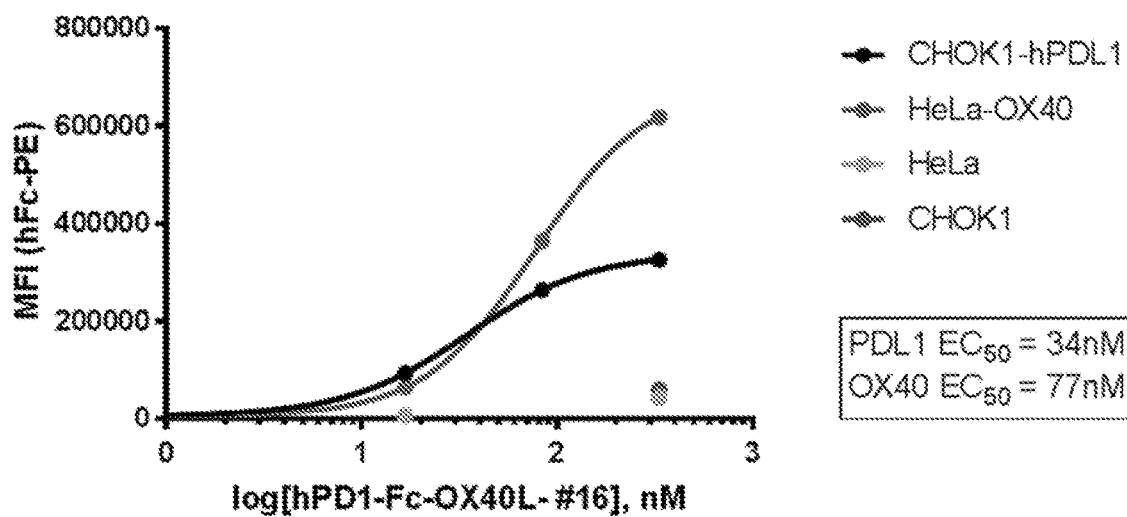
Figure 31P:
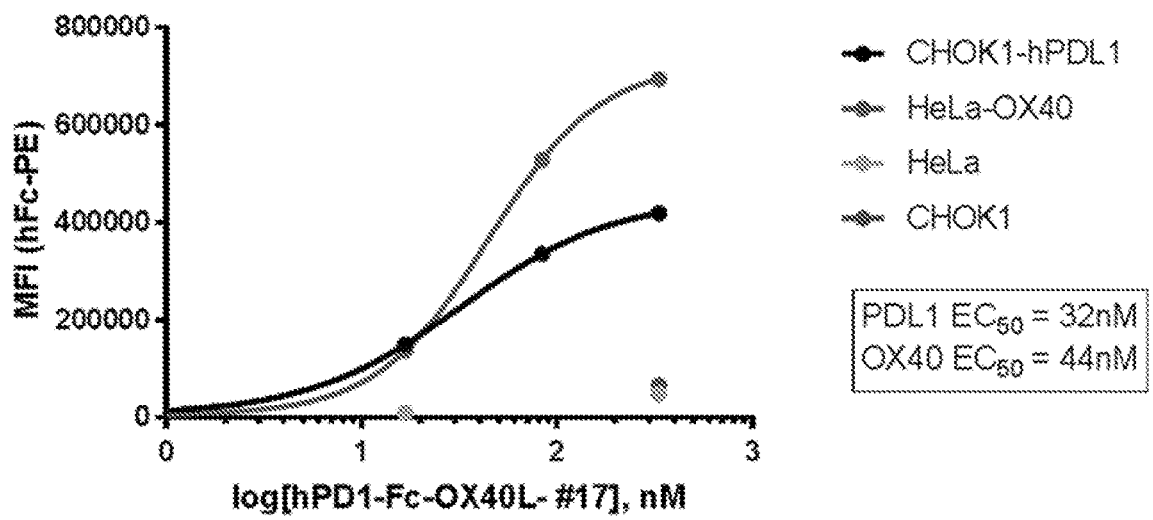

Additionally, each purified protein with different linker sequences was also characterized by binding to PD-L1 or OX40 in ELISA assays (FIG. 30), as well as cell-based flow cytometry assays (FIG. 31A to FIG. 31P).

Example 9: Production of Additional TIGIT-Containing Chimeric Proteins Comprising Extracellular Domains of Other Type II Proteins In this example, additional chimeric proteins of the present invention are described. Such additional chimeric proteins will be made similar to how the TIGIT-Fc-OX40L, TIGIT-Fc-CD40L, or TIGIT-Fc-LIGHT chimeric proteins were made, e.g., as described above in the Detailed Description and in the present application's priority document: U.S. 62/464,002.

These additional chimeric proteins will have the general formula: ECD 1-Joining Linker 1-Fc Domain-Joining Linker 2-ECD 2, in which ECD 1 is the extracellular domain of TIGIT and ECD 2 is the extracellular domain of a Type II protein, other than CD40L, OX40L, or LIGHT. Exemplary Type II proteins include 4-1BBL, CD30L, FasL, GITRL, TL1A, and TRAIL. These chimeric proteins may lack one or both of the joining linkers. Exemplary Joining Linker 1s, Fc Domains, and Joining Linker 2s are described above in Table 1; modular linkers useful for forming chimeric proteins and comprising specific Joining Linker 1s, Fc Domains, and Joining Linker 2s are shown in FIG. 32.

Alternately, the additional chimeric proteins will be fusion proteins having the general formula: N terminus-(a)-(b)-(c)-C terminus, in which (a) is TIGIT, (b) is a linker comprising at least a portion of a Fc domain, and (c) is the extracellular domain of a Type II protein other than CD40L, OX40L, or LIGHT. Exemplary Type II proteins include 4-1BBL, CD30L, FasL, GITRL, TL1A, and TRAIL. Exemplary linkers are described above in Table 1; modular linkers useful for forming chimeric proteins and comprising specific Joining Linker 1s, Fc Domains, and Joining Linker 2s are shown in FIG. 32.

The amino acid sequence for 4-1BBL, CD30L, FasL, GITRL, TL1A, and TRAIL, respectively, comprises SEQ ID NO: 12, 26, 30, 15, 18, and 40. The amino acid sequence for extracellular domain of 4-1BBL, CD30L, FasL, GITRL, TL1A, and TRAIL, respectively, comprises SEQ ID NO: 13, 27, 31, 16, 19, and 41. The amino acid sequence for TIGIT comprises SEQ ID NO: 9 and the extracellular domain of TIGIT comprises SEQ ID NO: 10. The chimeric proteins may comprise a variant of the above-mentioned sequences, e.g., at least about 95% identical to an above-mentioned sequence.

According, the present invention further includes the following additional chimeric proteins and methods using the additional chimeric proteins (e.g., in treating a cancer and/or treating an inflammatory disease): TIGIT-Fc-4-

1BBL, TIGIT-Fc-CD30L, TIGIT-Fc-FasL, TIGIT-Fc-GITRL, TIGIT-Fc-TL1A, and TIGIT-Fc-TRAIL.

The additional chimeric proteins will be characterized as described above for TIGIT-Fc-OX40L, TIGIT-Fc-CD40L, or TIGIT-Fc-LIGHT in Examples 1 to 8, albeit with reagents (e.g., binding partners, recombinant target cells, and cancer cell/tumor types) that are specific to the additional chimeric proteins rather than as needed for characterizing TIGIT-Fc-OX40L, TIGIT-Fc-CD40L, or TIGIT-Fc-LIGHT. Thus, using TIGIT-Fc-4-1BBL and TIGIT-Fc-CD40L as examples, characterizations of TIGIT-Fc-4-1BBL akin to Example 1 can be performed using anti-TIGIT, anti-Fc, and anti-4-1BBL antibodies rather than the anti-TIGIT, anti-Fc, and anti-CD40L antibodies needed for TIGIT-Fc-CD40L.

As with the TIGIT-Fc-OX40L, TIGIT-Fc-CD40L, or TIGIT-Fc-LIGHT chimeric proteins, the additional chimeric proteins will be effective in treating a cancer and/or treating an inflammatory disease by blocking TIGIT (which inhibits the transmission of an immune inhibitory signal) and enhancing, increasing, and/or stimulating the transmission of an immune stimulatory signal via activating the receptor/ligand of one of 4-1BBL, CD30L, FasL, GITRL, TL1A, and TRAIL. Moreover, the additional chimeric proteins will be effective in treating a cancer and/or an inflammatory disease yet without the toxicity resulting and undesirable side-effects, e.g., GI complications, from treatments comprising a plurality of antibodies, e.g., a blocking antibody and an agonist antibody for the receptor/ligand of one of 4-1BBL, CD30L, FasL, GITRL, and TRAIL.

Example 10: Production of Additional LIGHT-Containing Chimeric Proteins Comprising Extracellular Domains of Other Type I Proteins In this example, additional chimeric proteins of the present invention are described. Such additional chimeric proteins will be made similar to how the CD172a(SIRPα)-Fc-LIGHT, TIGIT-Fc-LIGHT, or PD-1-Fc-LIGHT chimeric proteins were made, e.g., as described above in the Detailed Description and in the present application's priority document: U.S. 62/464,002.

These additional chimeric proteins will have the general formula: ECD 1-Joining Linker 1-Fc Domain-Joining Linker 2-ECD 2, in which ECD 1 is the extracellular domain of a Type I protein other than CD172a(SIRPα), TIGIT, or PD-1 and ECD 2 is the extracellular domain of a LIGHT. Exemplary Type I proteins include TIM3 and BTLA. These chimeric proteins may lack one or both of the joining linkers. Exemplary Joining Linker 1s, Fc Domains, and Joining Linker 2s are described above in Table 1; modular linkers useful for forming chimeric proteins and comprising specific Joining Linker 1s, Fc Domains, and Joining Linker 2s are shown in FIG. 32.

Alternately, the additional chimeric proteins will be fusion proteins having the general formula: N terminus-(a)-(b)-(c)-C terminus, in which (a) is the extracellular domain of a Type I protein other than CD172a(SIRPα), TIGIT, or PD-1, (b) is a linker comprising at least a portion of a Fc domain, and (c) is the extracellular domain of LIGHT. Exemplary Type I proteins include TIM3 and BTLA. Exemplary linkers are described above in Table 1; modular linkers useful for forming chimeric proteins and comprising specific Joining Linker 1s, Fc Domains, and Joining Linker 2s are shown in FIG. 32.

The amino acid sequence for TIM3 and BTLA respectively, comprises SEQ ID NO: 36 and 24. The amino acid sequence for extracellular domain of TIM3 and BTLA, respectively, comprises SEQ ID NO: 37 and 25. The amino acid sequence for LIGHT comprises SEQ ID NO: 1 and the extracellular domain of LIGHT comprises SEQ ID NO: 2. The chimeric proteins may comprise a variant of the above-mentioned sequences, e.g., at least about 95% identical to an above-mentioned sequence.

According, the present invention further includes the following additional chimeric proteins and methods using the additional chimeric proteins (e.g., in treating a cancer and/or treating an inflammatory disease): TIM3-Fc-LIGHT and BTLA-Fc-LIGHT. The additional chimeric proteins will be characterized as described above for CD172a(SIRPα)-Fc-LIGHT, TIGIT-Fc-LIGHT, or PD-1-Fc-LIGHT in Examples 1 to 8, albeit with reagents (e.g., binding partners, recombinant target cells, and cancer cell/tumor types) that are specific to the additional chimeric proteins rather than as needed for characterizing TIM3-Fc-LIGHT and BTLA-Fc-LIGHT; as examples, characterizations of TIM3-Fc-LIGHT akin to Example 2 can be performed using anti-LIGHT, anti-Fc, and anti-TIM3 antibodies rather than the anti-LIGHT, anti-Fc, and anti-CD172a(SIRPα) antibodies needed for CD172a(SIRPα)-Fc-LIGHT.

As with the CD172a(SIRPα)-Fc-LIGHT, TIGIT-Fc-LIGHT, or PD-1-Fc-LIGHT chimeric proteins, the additional chimeric proteins will be effective in treating a cancer and/or treating an inflammatory disease by blocking TIM3 and LIGHT (which inhibits the transmission of an immune inhibitory signal) and enhancing, increasing, and/or stimulating the transmission of an immune stimulatory signal via activating the receptor/ligand by LIGHT. Moreover, the additional chimeric proteins will be effective in treating a cancer and/or an inflammatory disease yet without the toxicity resulting and undesirable side-effects, e.g., GI complications, from treatments comprising a plurality of antibodies, e.g., a blocking antibody and an agonist antibody for the receptor/ligand of one of TIM3 and LIGHT.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A chimeric protein of a general structure of:

N terminus-(a)-(b)-(c)-C terminus, wherein:
- (a) is a first domain comprising an extracellular domain of TIGIT,
- (b) is a linker comprising at least one cysteine residue capable of forming a disulfide bond, and
- (c) is a second domain comprising an extracellular domain of LIGHT, wherein the linker connects the first domain and the second domain, wherein said extracellular domain of TIGIT comprises an amino acid sequence that is at least 95% identical to the amino acid sequence of SEQ ID NO: 10, and wherein said extracellular domain of LIGHT comprises an amino acid sequence that is at least 95% identical to the amino acid sequence of SEQ ID NO: 2.

2. The chimeric protein of claim 1, wherein the first domain is capable of binding a TIGIT ligand selected from CD155/PVR, Nectin-2, Nectin-3, and Nectin-4.

3. The chimeric protein of claim 1, wherein the second domain is capable of binding a LIGHT ligand selected from LTBR, HVEM, and DcR3.

4. The chimeric protein of claim 1, wherein the linker is a polypeptide selected from a flexible amino acid sequence, an IgG hinge region, a hinge-CH2-CH3 Fc domain, or an antibody sequence.

5. The chimeric protein of claim 1, wherein the linker comprises hinge-CH2-CH3 Fc domain derived from IgG1 or IgG4.

6. The chimeric protein of claim 5, wherein the hinge-CH2-CH3 Fc domain is derived from human IgG1 or human IgG4.

7. The chimeric protein of claim 4, wherein the linker comprises an amino acid sequence that is at least 95% identical to the amino acid sequence of SEQ ID NO: 46, SEQ ID NO: 47, or SEQ ID NO: 48.

8. The chimeric protein of claim 1, wherein the linker comprises one or more joining linkers, such joining linkers being independently selected from SEQ ID NOs: 49-95.

9. The chimeric protein of claim 4, wherein the linker further comprises two or more joining linkers each joining linker independently selected from SEQ ID NOs: 49-95; wherein one joining linker is N terminal to the hinge-CH2-CH3 Fc domain and another joining linker is C terminal to the hinge-CH2-CH3 Fc domain.

10. The chimeric protein of claim 1, wherein the first domain comprises an amino acid sequence that is at least 98% identical to the amino acid sequence of SEQ ID NO: 10.

11. The chimeric protein of claim 1, wherein the second domain comprises an amino acid sequence that is at least 98% identical to the amino acid sequence of SEQ ID NO: 2.

12. The chimeric protein of claim 1, wherein:
(a) the first domain comprises the amino acid sequence that is at least 98% identical to the amino acid sequence of SEQ ID NO: 10,
(b) the second domain comprises the amino acid sequence that is at least 98% identical to the amino acid sequence of SEQ ID NO: 2, and
(c) the linker comprises an amino acid sequence that is at least 95% identical to the amino acid sequence of SEQ ID NO: 46, SEQ ID NO: 47, or SEQ ID NO: 48.

13. The chimeric protein of claim 12, wherein the linker further comprises one or more joining linkers, such joining linkers being independently selected from SEQ ID NOs: 49-95.

14. The chimeric protein of claim 1, wherein the chimeric protein has an amino acid sequence that is at least 95% identical to the amino acid sequence of SEQ ID NO: 11.

15. The chimeric protein of claim 1, wherein the chimeric protein is capable of forming a stable synapse between cells.

16. The chimeric protein of claim 15, wherein the stable synapse between cells provides spatial orientation that favors tumor reduction.

17. The chimeric protein of claim 16, wherein the spatial orientation positions T cells to attack tumor cells and/or sterically prevents a tumor cell from delivering negative signals, including negative signals beyond those masked by the chimeric protein of the invention.

18. The chimeric protein of claim 1, wherein binding of either or both of the extracellular domains to its respective binding partner occurs with slow off rates ($K_{off}$), which provides a long interaction of a receptor and its ligand.

19. The chimeric protein of claim 18, wherein the long interaction provides sustained negative signal masking effect.

20. The chimeric protein of claim 18, wherein the long interaction delivers a longer positive signal effect.

21. The chimeric protein of claim 20, wherein the longer positive signal effect allows an effector cell to be adequately stimulated for an anti-tumor effect.

22. The chimeric protein of claim 18, wherein the long interaction provides T cell proliferation and allows for anti-tumor attack.

23. The chimeric protein of claim 18, wherein the long interaction allows sufficient signal transmission to provide release of stimulatory signals.

24. The chimeric protein of claim 23, wherein the stimulatory signal is a cytokine.

25. The chimeric protein of claim 1, wherein the subject's T cells are activated.

26. A pharmaceutical composition comprising the chimeric protein of claim 1.

* * * * *